(12) United States Patent
Jiang et al.

(10) Patent No.: US 7,897,843 B2
(45) Date of Patent: *Mar. 1, 2011

(54) TRANSCRIPTIONAL REGULATION OF PLANT BIOMASS AND ABIOTIC STRESS TOLERANCE

(75) Inventors: Cai-Zhong Jiang, Fremont, CA (US); Jacqueline E. Heard, Stonington, CT (US); Oliver Ratcliffe, Oakland, CA (US); Neal I. Gutterson, Oakland, CA (US); Frederick D. Hempel, Albany, CA (US); Roderick W. Kumimoto, San Bruno, CA (US); James S. Keddie, San Mateo, CA (US); Bradley K. Sherman, Berkeley, CA (US); Jeffrey M. Libby, Cupertino, CA (US); Jindong Sun, Urbana, IL (US); Kimberly Faye Zobrist-Duff, Greenville, IL (US); Jingrui Wu, Chesterfield, MO (US); Changlin Fu, Chesterfield, MO (US); Stanton B. Dotson, Chesterfield, MO (US); Linda L. Lutfiyya, St. Louis, MO (US)

(73) Assignee: Mendel Biotechnology, Inc., Hayward, CA (US)

( * ) Notice: Subject to any disclaimer, the term of this patent is extended or adjusted under 35 U.S.C. 154(b) by 501 days.

This patent is subject to a terminal disclaimer.

(21) Appl. No.: 10/870,198

(22) Filed: Jun. 16, 2004

(65) Prior Publication Data

US 2005/0097638 A1 May 5, 2005

Related U.S. Application Data

(60) Continuation-in-part of application No. 10/714,887, filed on Nov. 13, 2003, and a continuation-in-part of application No. 10/669,824, filed on Sep. 23, 2003, which is a continuation-in-part of application No. 09/823,676, filed on Mar. 30, 2001, now Pat. No. 6,717,034, and a continuation-in-part of application No. 10/374,780, filed on Feb. 25, 2003, now Pat. No. 7,511,190, and a continuation-in-part of application No. 09/934,455, filed on Aug. 22, 2001, now abandoned, said application No. 10/669,824 is a continuation-in-part of application No. 10/412,699, filed on Apr. 10, 2003, now Pat. No. 7,345,217, and a continuation-in-part of application No. 09/713,994, filed on Nov. 16, 2000, now abandoned, and a continuation-in-part of application No. 09/533,029, filed on Mar. 22, 2000, now Pat. No. 6,664,446, said application No. 10/669,824 is a continuation-in-part of application No. 10/225,066, filed on Aug. 9, 2002, now Pat. No. 7,238,860, said application No. 10/669,824 is a continuation-in-part of application No. 10/225,067, filed on Aug. 9, 2002, now Pat. No. 7,135,616, application No. 10/870,198, which is a continuation-in-part of application No. 10/302,267, filed on Nov. 22, 2002, now Pat. No. 7,223,904, which is a division of application No. 09/506,720, filed on Feb. 17, 2000, now abandoned, application No. 10/870,198, which is a continuation-in-part of application No. 10/278,173, filed on Oct. 21, 2002, now abandoned, which is a division of application No. 09/533,392, filed on Mar. 22, 2000, now abandoned, application No. 10/870,198, which is a continuation-in-part of application No. 10/225,066, and a continuation-in-part of application No. 09/837,944, filed on Apr. 18, 2001, now abandoned, and a continuation-in-part of application No. 10/171,468, filed on Jun. 14, 2002, now abandoned, application No. 10/870,198, which is a continuation-in-part of application No. 10/225,067, and a continuation-in-part of application No. 09/837,944, and a continuation-in-part of application No. 10/171,468, application No. 10/870,198, which is a continuation-in-part of application No. 10/225,068, and a continuation-in-part of application No. 09/837,944, and a continuation-in-part of application No. 10/171,468.

(60) Provisional application No. 60/565,948, filed on Apr. 26, 2004, provisional application No. 60/527,658, filed on Dec. 5, 2003, provisional application No. 60/542,928, filed on Feb. 5, 2004, provisional application No. 60/227,439, filed on Aug. 22, 2000, provisional application No. 60/125,814, filed on Mar. 23, 1999, provisional application No. 60/336,049, filed on Nov. 19, 2001, provisional application No. 60/310,847, filed on Aug. 9, 2001, provisional application No. 60/338,692, filed on Dec. 11, 2001, provisional application No. 60/135,134, filed on May 20, 1999.

(51) Int. Cl.
*C12N 15/82* (2006.01)
*C12N 15/29* (2006.01)
(52) U.S. Cl. .................. 800/298; 800/266; 800/290
(58) Field of Classification Search .................. None
See application file for complete search history.

(56) References Cited

U.S. PATENT DOCUMENTS 5,689,049 A 11/1997 Cigan et al.

(Continued)

FOREIGN PATENT DOCUMENTS

CA 2271716 3/1999

(Continued)

OTHER PUBLICATIONS

Aravind et al 1998, Nucleic Acids Research 26(19): 4413-4421.*

(Continued)

*Primary Examiner*—David H Kruse
(74) *Attorney, Agent, or Firm*—Jeffrey M. Libby; Yifan Mao; Donna Scherer

(57) ABSTRACT

The invention relates to plant transcription factor polypeptides, polynucleotides that encode them, homologs from a variety of plant species, and methods of using the polynucleotides and polypeptides to produce transgenic plants having advantageous properties, including increased biomass or improved cold or other osmotic stress tolerance, as compared to wild-type or reference plants. The invention also pertains to expression systems that may be used to regulate these transcription factor polynucleotides, providing constitutive, transient, inducible and tissue-specific regulation.

27 Claims, 19 Drawing Sheets

U.S. PATENT DOCUMENTS

Figure 1:
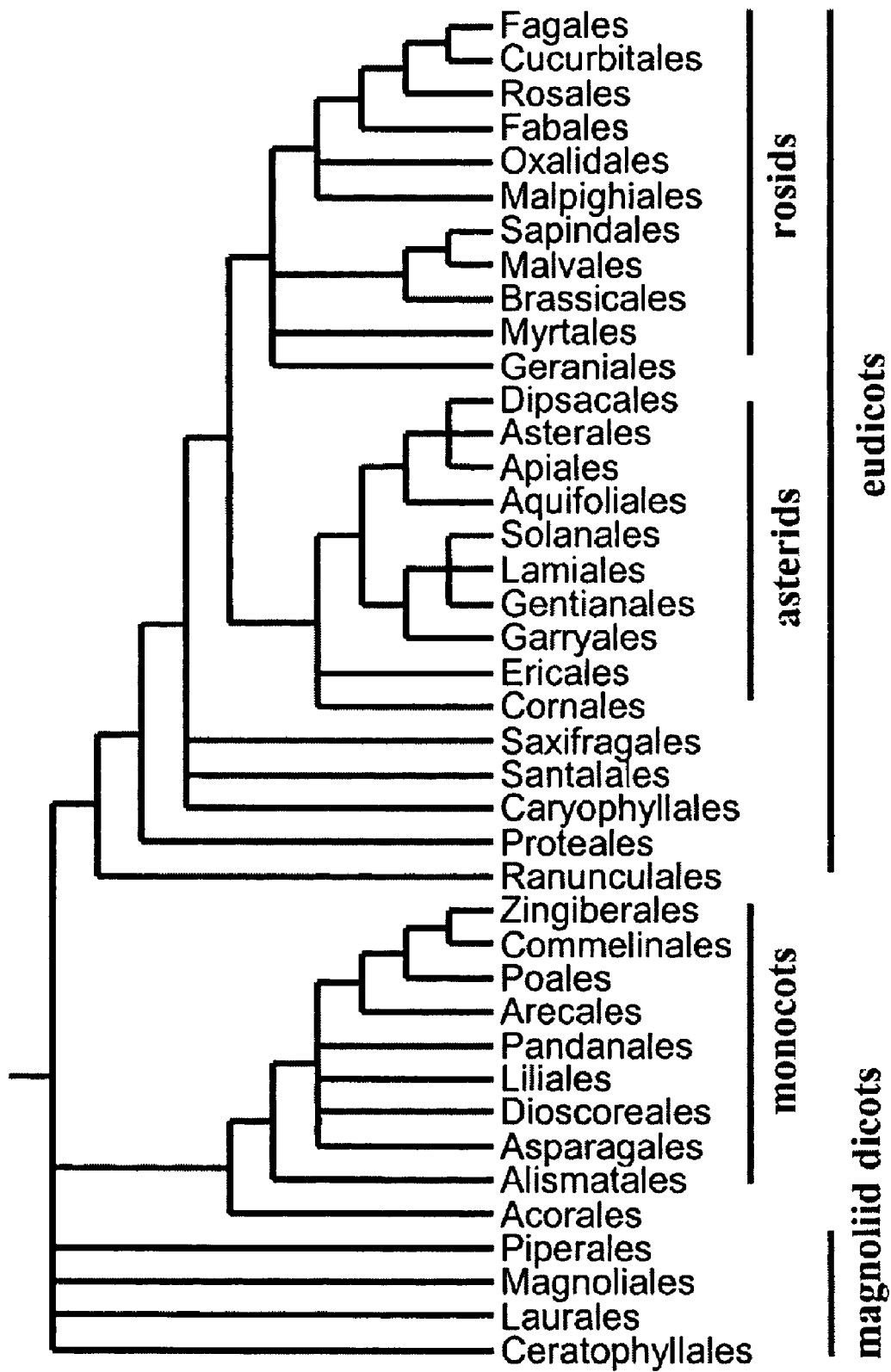

| | | | |
|---|---|---|---|
| 5,834,236 A * | 11/1998 | Lamb et al. | 435/69.1 |
| 6,057,492 A | 5/2000 | de Haan et al. | |
| 6,248,937 B1 | 6/2001 | Finkelstein et al. | |
| 6,717,034 B2 * | 4/2004 | Jiang | 800/290 |
| 2002/0160378 A1 | 10/2002 | Harper et al. | |
| 2003/0061637 A1 | 3/2003 | Jiang et al. | |
| 2003/0121070 A1 | 6/2003 | Adam et al. | |
| 2004/0009476 A9 | 1/2004 | Harper et al. | |
| 2004/0031072 A1 | 2/2004 | La Rosa et al. | |
| 2004/0034888 A1 | 2/2004 | Liu et al. | |
| 2004/0123340 A1 | 6/2004 | Deikman | |
| 2004/0123343 A1 | 6/2004 | La Rosa et al. | |
| 2004/0128712 A1 | 7/2004 | Jiang et al. | |
| 2004/0172684 A1 | 9/2004 | Kovalic | |
| 2004/0214272 A1 | 10/2004 | La Rosa et al. | |
| 2004/0216190 A1 | 10/2004 | Kovalic | |
| 2005/0097631 A1 * | 5/2005 | Sun et al. | 800/278 |
| 2005/0097638 A1 | 5/2005 | Jiang | |
| 2006/0183137 A1 | 8/2006 | Harper et al. | |

FOREIGN PATENT DOCUMENTS

| | | |
|---|---|---|
| CA | 2442496 | 3/2010 |
| EP | 1033405 | 9/2000 |
| JP | 2000041685 | 9/1996 |
| JP | 200041685 | 2/2000 |
| JP | 2000041685 | 2/2000 |
| WO | WO-99/41974 | 8/1999 |
| WO | WO-9941974 | 8/1999 |
| WO | WO-99/49046 | 9/1999 |
| WO | WO-9949046 | 9/1999 |
| WO | WO-01/26459 | 4/2001 |
| WO | WO-01/35698 | 5/2001 |
| WO | WO-01/36444 | 5/2001 |
| WO | WO-0135725 | 5/2001 |
| WO | WO-0136444 | 5/2001 |
| WO | WO-0185946 | 11/2001 |
| WO | WO-0216655 | 2/2002 |
| WO | WO-02/079403 | 10/2002 |
| WO | WO-03006622 | 1/2003 |
| WO | WO-03008540 | 1/2003 |
| WO | WO-03018627 | 3/2003 |

PUBLICATIONS

Reeves 2001 Gene 277: 63-81.*
Weigel et al Nov. 10, 1999 NCBI Accession No. AAF07197, National Library Of Medicine, USA, Bethesda Maryland.*
Weigel et al Apr. 2000, Plant Physiology 122: 1003-1013.*
Eisen 2007, Genome Research, 8: 163-167.*
Bevan et al Apr. 1998, Genbank Accession No. O65489, NCBI Database, National Library of Medicine, Bethesda, Maryland USA.*
Pilgrim, M. et al. (Jul. 2, 2002) "Arabidopsis transcription factor #86" Geneseq Database EBI accession No. AAU93048.
Sasaki, T. et al. (Mar. 1, 2003), DNA-binding protein-like from Oryza sativa, Uniprot Database EBI accession No. Q8GRR7.
EP Examination Report dated Jun. 20, 2007, for EP Application No. 04784569.8, filed Sep. 17, 2004, three pages.
Fourgoux-Nicol et al. (1999). "Isolation of rapeseed genes expressed early and specifically during development of the male gametophyte," Plant Molecular Biology 40:857-872.
Grasser et al. (2000). "Chromatin-associated HMG1, HMGI/Y and SSRP1 proteins of higher plants," Physiologia Plantarum, 110:427-435.
Nieto-Sotelo, J. et al. (1994) NCBI Accession No. AAA33914.
Meijer, A.H., and Hoge, J.H.C. (1997) NCBI Acc. No. S57459.
Meijer, A.H. et al. (1996) NCBI Accession No. CAA61277.
Meijer, A.H. et al. (1996) NCBI Accession No. CAA61276.
Lin, X. et al. (2002) NCBI Accession No. AAF04888.
Gupta, R. et al. (1998) NCBI Accession No. X99373.
Gupta, R. et al. (1998) NCBI Accession No. X99491.
Gupta, R. et al. (1997) NCBI Accession No. X99116.
Forzani, C. et al. (2001) J. Biol. Chem. 276: 16731-16738.
Bevan, M. et al. (2000) NCBI Accession No. CAB80256.
Bevan, M. et al. (1999) NCBI Accession No. CAA18730.
Nieto-Sotelo, J. et al. (1994) NCBI Acc. No. AAA32718.
NCBI acc. No. AAAA01000486 (gi: 19924795) (Apr. 4, 2002); Yu,J., et al. *Oryza sativa* (indica cultivar-group) scaffold000486, whole genome shotgun sequence; source: *Oryza sativa* (indica cultivar-group); Title: ""The Genomes of *Oryza sativa*: A History of Duplications"" (PLoS Biol. 3 (2), E38 (2005)).
AAAA01000935 "NCBI acc. No. AAAA01000935 (gi: 19925244) (Apr. 4, 2002); Yu,J., et al. *Oryza sativa* (indica cultivar-group) scaffold000935, whole genome shotgun sequence"; source: *Oryza sativa* (indica cultivar-group); Title: ""The Genomes of *Oryza sativa*: A History of Duplications""(PLoS Biol. 3 (2), E38 (2005)).
AAAA01003524 "NCBI acc. No. AAAA01003524 (gi: 19927833) (Apr. 4, 2002); Yu,J., et al. *Oryza sativa* (indica cultivar-group) scaffold003524, whole genome shotgun sequence"; source: *Oryza sativa* (indica cultivar-group); Title: ""The Genomes of *Oryza sativa*: A History of Duplications"" (PLoS Biol. 3 (2), E38 (2005)).
EP 1033405 A2 Seq ID No. 56797, Gene sequence, Oct. 18, 2000 (AAC48248 Database Geneseq, Acc. No. AAC48248).
EP 1033405 A2 Seq ID No. 34900, Gene sequence, Oct. 17, 2000 (AAG29345 Database Geneseq, Acc. No. AAG29345).
AAG51949 NCBI acc. No. AAG51949 (gi: 12323978) (Jan. 19, 2001); Lin,X., et al. "unknown protein; 41834-42742 [*Arabidopsis thaliana*]"; source: *Arabidopsis thaliana* (thale cress); Title: "*Arabidopsis thaliana* chromosome 1 BAC F14G6 genomic sequence" (Unpublished).
AAM62794 NCBI acc. No. AAM62794 (gi: 21553701) (Jun. 25, 2002); Haas,B.J., et al. "putative DNA-binding protein [*Arabidopsis thaliana*]"; source: *Arabidopsis thaliana* (thale cress); Title: "Full-length messenger RNA sequences greatly improve genome annotation" (Genome Biol. (2002) In press).
AAM65129 NCBI acc. No. AAM65129 (gi: 21593180) (Jun. 26, 2002); Haas,B.J., et al. "putative DNA-binding protein [*Arabidopsis thaliana*]"; source: *Arabidopsis thaliana* (thale cress); Title: "Full-length messenger RNA sequences greatly improve genome annotation" (Genome Biol. (2002) In press).
AC135209 "NCBI acc. No. AC135209 (gi: 23621897) (Oct. 9, 2002); Wing,R.A., et al. *Oryza sativa* (japonica cultivar-group) chromosome 3 clone OSJNBa0071M09, * Sequencing In Progress *, 4 ordered pieces"; source: *Oryza sativa* (japonica cultivar-group); Title: ""Rice Genomic Sequence"" (Unpublished).
AL366947 "NCBI acc. No. AL366947 (gi: 9666700) (Aug. 3, 2000); Journet,E.P., et al. MtBA11B10F1 MtBA *Medicago truncatula* cDNA clone MtBA11B10 T3, mRNA sequence"; source: *Medicago truncatula* (barrel medic); Title: ""*Medicago truncatula* ESTs from nitrogen-starved roots"" (Unpublished (2000)).
AL662981 NCBI acc. No. AL662981 (gi: 17998493) (Dec. 28, 2001); Han,B., et al. "*Oryza sativa* chromosome 4 clone OSJNBa0086O06, * Sequencing in Progress *"; source: *Oryza sativa*; Title: "Direct Submission" (Submitted (Dec. 27, 2001) Han Bin, National Center for Gene Research, Chinese Acad. Sciences.
AP003526 NCBI acc. No. AP003526 (gi: 13676546) (Apr. 18, 2001); Sasaki,T., et al. *Oryza sativa* chromosome 6 clone P0548D03, * Sequencing in Progress *; source: *Oryza sativa*; Title: "*Oryza sativa* nipponbare(GA3) genomic DNA, chromosome 6, PAC clone:P0548D03".
AP003891 NCBI acc. No. AP003891 (gi: 14646849) (Jul. 9, 2001); Sasaki,T., et al. *Oryza sativa* chromosome 8 clone OJ1314__F06, * Sequencing in Progress *; source: *Oryza sativa*; Title: "*Oryza sativa* nipponbare(GA3) genomic DNA, chromosome 8, BAC clone:OJ1314__F06".
AP004020 NCBI acc. No. AP004020 (gi: 15130682) (Aug. 9, 2001); Sasaki,T., et al. *Oryza sativa* chromosome 2 clone OJ1119__A01, * Sequencing in Progress *; source: *Oryza sativa*; Title: "*Oryza sativa* nipponbare(GA3) genomic DNA, chromosome 2, BAC clone:OJ1119__A01".
AP004165 NCBI acc. No. AP004165 (gi: 15594177) (Sep. 13, 2001); Sasaki,T., et al. *Oryza sativa* chromosome 2 clone OJ1479__B12, * Sequencing in Progress *; source: *Oryza sativa*; Title: "*Oryza sativa* nipponbare(GA3) genomic DNA, chromosome 2, BAC clone:OJ1479__B12".

AP004587 NCBI acc. No. AP004587 (gi: 18146734) (Jan. 14, 2002); Sasaki,T., et al. *Oryza sativa* chromosome 8 clone P0543D10, * Sequencing in Progress * ; source: *Oryza sativa*; Title: "*Oryza sativa* nipponbare(GA3) genomic DNA, chromosome 8, PAC clone:P0543D10" (Published Only in Database (2001)).

AP004635 NCBI acc. No. AP004635 (gi: 18182015) (Jan. 16, 2002); Sasaki,T., et al. *Oryza sativa* chromosome 8 clone P0672D01, * Sequencing in Progress *; source: *Oryza sativa*; Title: "*Oryza sativa* nipponbare(GA3) genomic DNA, chromosome 8, PAC clone:P0672D01" (Published Only in Database (2002)).

AP005477 NCBI acc. No. AP005477 (gi: 21624397) (Jun. 28, 2002); Sasaki,T., et al. *Oryza sativa* (japonica cultivar-group) chromosome 6 clone OSJNBb0039F24, * Sequencing in Progress *.

AP005653 NCBI acc. No. AP005653 (gi: 22415838) (Aug. 21, 2002); Sasaki,T., et al. *Oryza sativa* (japonica cultivar-group) chromosome 2 clone OSJNBb0075E08, * Sequencing in Progress *; source: *Oryza sativa* (japonica cultivar-group).

AP005755 NCBI acc. No. AP005755 (gi: 23200614) (Sep. 19, 2002); Sasaki,T., et al. *Oryza sativa* (japonica cultivar-group) chromosome 9 clone OSJNBb0019B14, * Sequencing in Progress *; source: *Oryza sativa* (japonica cultivar-group).

AW560824 NCBI acc. No. AW560824 (gi: 7206250) (Mar. 7, 2000); Fedorova,M., et al. EST315872 DSIR *Medicago truncatula* cDNA clone pDSIR-30G7, mRNA sequence; source: *Medicago truncatula* (barrel medic); Title: "ESTs from roots of *Medicago truncatula* after inoculation with *Phytophthora medicaginis*".

AW720668 NCBI acc. No. AW720668 (gi: 7615218) (Apr. 19, 2000); Colebatch,G., et al. LjNEST14h9rc *Lotus japonicus* nodule library 5 and 7 week-old *Lotus japonicus* cDNA 5', mRNA sequence; source: *Lotus japonicus*; Title: "*Lotus japonicus* root nodule ESTs: tools for functional genomics" (Unpublished (2000)).

AW774484 NCBI acc. No. AW774484 (gi: 7718401) (May 8, 2000); VandenBosch,K., et al. EST333635 KV3 *Medicago truncatula* cDNA clone pKV3-22P11, mRNA sequence; source: *Medicago truncatula* (barrel medic); Title: "ESTs from roots of *Medicago truncatula* after Rhizobium inoculation" (Unpublished (1999)).

BG134451 NCBI acc. No. BG134451 (gi: 12634639) (Jan. 31, 2001); van der Hoeven,R., et al. "EST467343 tomato crown gall *Lycopersicon esculentum* cDNA clone cTOE16I16 5' sequence, mRNA sequence".

BG581882 NCBI acc. No. BG581882 (gi: 13596946) (Apr. 11, 2001); Fedorova,M., et al. "EST483618 GVN *Medicago truncatula* cDNA clone pGVN-66K1 5' end, mRNA sequence"; source: *Medicago truncatula* (barrel medic).

BG646893 NCBI acc. No. BG646893 (gi: 13782005) (Apr. 24, 2001); Hahn,M.G., et al. "EST508512 HOGA *Medicago truncatula* cDNA clone pHOGA-15I11 5' end, mRNA sequence"; source: *Medicago truncatula* (barrel medic).

BG647027 NCBI acc. No. BG647027 (gi: 13782139) (Apr. 24, 2001); Hahn,M.G., et al. "EST508646 HOGA *Medicago truncatula* cDNA clone pHOGA-15O24 5' end, mRNA sequence"; source: *Medicago truncatula* (barrel medic).

BG647144 NCBI acc. No. BG647144 (gi: 13782256) (Apr. 24, 2001); Hahn,M.G., et al. "EST508763 HOGA *Medicago truncatula* cDNA clone pHOGA-15F24 5' end, mRNA sequence"; source: *Medicago truncatula* (barrel medic).

BI426899 NCBI acc. No. BI426899 (gi: 15204131) (Aug. 16, 2001); Shoemaker,R., et al. "sag08g12.y1 Gm-c1080 *Glycine max* cDNA clone Genome Systems Clone ID: Gm-c1080-696 5' similar to TR:O22130 O22130 Putative PD1-Like DNA-Binding Protein. ;, mRNA sequence."

BI701170 NCBI acc. No. BI701170 (gi: 15663799) (Sep. 18, 2001); Shoemaker,R., et al. "sag55e11.y1 Gm-c1082 *Glycine max* cDNA clone Genome Systems Clone ID: Gm-c1082-597 5' similar to TR:O23620 O23620 Hypothetical 29.7 KD Protein. ;, mRNA sequence."

BQ785950 NCBI acc. No. BQ785950 (gi: 21994422) (Jul. 26, 2002); Shoemaker,R., et al. "saq61f09.y1 Gm-c1076 *Glycine max* cDNA clone Soybean Clone ID: Gm-c1076-4481 5' similar to TR:Q9SR17 Q9SR17 F7O18.4 Protein. ;, mRNA sequence"; source: *Glycine max* (soybean).

AAF07197 NCBI acc. No. AAF07197 (gi: 6319180) (Nov. 10, 1999); Weigel,D., et al. "ESCAROLA [*Arabidopsis thaliana*]"; source: *Arabidopsis thaliana* (thale cress); Title: "Activation Tagging in *Arabidopsis*" (Unpublished).

AC015450 NCBI acc. No. AC015450 (gi: 6437539) (Nov. 16, 1999); Lin,X., et al. "*Arabidopsis thaliana* chromosome I clone IGF-F14G6, * Sequencing in Progress *, 4 unordered pieces"; source: *Arabidopsis thaliana* (thale cress).

AC011437 NCBI acc. No. AC011437 (gi: 6013612) (Oct. 6, 1999); Lin,X., et al. "*Arabidopsis thaliana* chromosome III clone IGF-F7O18, * Sequencing in Progress *, 5 unordered pieces"; source: *Arabidopsis thaliana* (thale cress).

AC007369 NCBI acc. No. AC007369 (gi: 4678189) (Apr. 24, 1999); Federspiel,N.A., et al. "*Arabidopsis thaliania* chromosome I clone F9H16; * Sequencing in Progress *, 3 unordered pieces"; source: *Arabidopsis thaliania*; Title: "Direct Submission" (Unpublished).

AC006931 NCBI acc. No. AC006931 (gi: 4309684) (Mar. 1, 1999); Lin,X., et al. "*Arabidopsis thaliana* clone F7D19, * Sequencing in Progress *, 6 unordered pieces"; source: *Arabidopsis thaliana* (thale cress).

AC006580 NCBI acc. No. AC006580 (gi: 4263589) (Feb. 24, 1999); Lin,X., et al. "*Arabidopsis thaliana* clone F23E6, * Sequencing in Progress *, 6 unordered pieces"; source: *Arabidopsis thaliana* (thale cress).

AC004667 NCBI acc. No. AC004667 (gi: 3115341) (May 6, 1998); Rounsley,S.D., et al. "*Arabidopsis thaliana* clone T4C15, * Sequencing in Progress *, 9 unordered pieces"; source: *Arabidopsis thaliana* (thale cress).

AC002387 NCBI acc. No. AC002387 (gi: 2281079) (Jul. 25, 1997); Rounsley,S.D., et al. "*Arabidopsis thaliana* clone F04L23, * Sequencing in Progress *, 5 unordered pieces"; source: *Arabidopsis thaliana* (thale cress).

AI736668 "NCBI acc. No. AI736668 (gi: 5058192) (Jun. 14, 1999); Shoemaker,R., et al. sb32a03.y1 Gm-c1012 *Glycine max* cDNA clone Genome Systems Clone ID: Gm-c1012-101 5' similar to TR:O23620 O23620 Hypothetical 29.7 KD Protein. ;, mRNA sequence"; source: *Glycine max* (soybean).

AL022604 Database EMBL, acc No. AL022604, Apr. 22, 1998, *Arabidopsis thaliana* DNA chromosome 4, BAC clone F23E12; NCBI acc. No. AL022604 (gi: 3080406) (Apr. 24, 1998); Bevan,M., et al. "*Arabidopsis thaliana* DNA chromosome 4, BAC clone F23E12 (ESSAII project)"; source: *Arabidopsis thaliana* (thale cress).

AL162295 NCBI acc. No. AL162295 (gi: 7329669) (Mar. 26, 2000); Choisne,N., et al. "*Arabidopsis thaliana* DNA chromosome 3, BAC clone T4C21"; source: *Arabidopsis thaliana* (thale cress); Title: "Direct Submission" (Unpublished).

AL161533 NCBI acc. No. AL161533 (gi: 7267889) (Mar. 20, 2000); Hilbert,H., et al. "*Arabidopsis thaliana* DNA chromosome 4, contig fragment No. 33"; source: *Arabidopsis thaliana* (thale cress); Title: "Direct Submission" (Unpublished).

AL132975 NCBI acc. No. AL132975 (gi: 6434228) (Nov. 15, 1999); Benes,V., et al. "*Arabidopsis thaliana* DNA chromosome 3, BAC clone T22E16"; source: *Arabidopsis thaliana* (thale cress); Title: "Direct Submission" (Unpublished).

AL021635 NCBI acc. No. AL021635 (gi: 2827538) (Feb. 1, 1998); Bevan,M., et al. "*Arabidopsis thaliana* DNA chromosome 4, BAC clone T12H17 (ESSAII project)"; source: *Arabidopsis thaliana* (thale cress); Title: "Direct Submission" (Unpublished).

AW574000 NCBI acc. No. AW574000 (gi: 7238733) (Mar. 13, 2000); Fedorova,M., et al. EST316591 GVN *Medicago truncatula* cDNA clone pGVN-50F8, mRNA sequence; source: *Medicago truncatula* (barrel medic); Title: "ESTs from one month old nitrogen-fixing root nodules of *Medicago truncatula*" (Unpublished (2000)).

AW349284 NCBI acc. No. AW349284 (gi: 6846994) (Feb. 1, 2000); Vodkin,L., et al. GM210004B21H7 Gm-r1021 *Glycine max* cDNA clone Gm-r1021-1526 3', mRNA sequence; source: *Glycine max* (soybean); Title: "A Functional Genomics Program for Soybean (NSF 9872565)" (Unpublished (1999)).

CAB82691 NCBI acc. No. CAB82691 (gi: 7329697) (Mar. 26, 2000); Choisne,N., et al. "putative protein [*Arabidopsis thaliana*]"; source: *Arabidopsis thaliana* (thale cress); Title: "Direct Submission" (Unpublished).

CAB78783 NCBI acc. No. CAB78783 (gi: 7268533) (Mar. 20, 2000); EU *Arabidopsis* sequencing,project., et al. "hypothetical protein [*Arabidopsis thaliana*]"; source: *Arabidopsis thaliana* (thale cress).

T43108 NCBI acc. No. T43108 (gi: 635696) (Jan. 25, 1995); Newman,T., et al. "6371 Lambda-PRL2 *Arabidopsis thaliana* cDNA clone 11515T7, mRNA sequence"; source: *Arabidopsis thaliana* (thale cress).

Z97344 NCBI acc. No. Z97344 (gi: 2245126) (Jul. 6, 1997); Bevan,M., et al. "*Arabidopsis thaliana* DNA chromosome 4, ESSA I contig fragment No. 9"; source: *Arabidopsis thaliana* (thale cress); Title: "Direct Submission" (Unpublished).

065489 Database EMBL, EBI acc No. 065489, Aug. 1, 1998, Hypothetical protein F23E12.50 (AT4g35390).

Q8GRR7 Database UniProt Online, Database acc No. Q8GRR7, Mar. 1, 2003.

T06118 Database PIR, Accession No. T06118, Bevan et al., Gene Sequence, Apr. 1990.

Aravind and Landsman. (Oct. 1, 1998) "AT-hook motifs identified in a wide variety of DNA-binding proteins" Nucl. Acids Res. (Oct. 1998) vol. 26, No. 19 pp. 4413-4421.

Lin, et al. (Dec. 16, 1999) "Sequence and analysis of chromosome 2 of the plant *Arabidopsis thaliana*" Nature (1999), 402(6763), 761-768.

Bevan, et al. (Jan. 29, 1998) "Sequence of 1.9 Mb contiguous region from chromosome 4 of *Arabidopsis thaliana*" Nature (1998), 391(6666), 485-488.

Mayer, et al. (Dec. 16, 1999) "Sequence and analysis of chromosome 4 of the plant *Arabidopsis thaliana*" Nature (1999), 402(6763), 769-777.

Hofmann, et al. (2000). Isolation of Two cDNAs Encoding AT-Hook DNA-Binding Proteins, SAP1 and HMR1, from an Antirrhinum majus L. Inflorescence Expression Library. Plant Physiol. 122, 292-292.

Martinez-Garcia, J.F., and Quail, P.H. (Apr. 1999). The HMG-I/Y protein PF1 stimulates binding of the transcriptional activator GT-2 to the PHYA gene promoter. Plant J 18, 173-183.

Meijer, Annemarie, (Jun. 1996) "Novel members of a family of AT hook-continaing DNA-binding proteins from rice are identified through their in vitro intereaction with consensus target sites of plant and animal homeodomain proteins" Plant Molecular Biology, vol. 31, No. 3, 1996, pp. 607-618.

Nieto-Sotelo, et al. (Feb. 1994). PF1: an A-T hook-containing DNA binding protein from rice that interacts with a functionally defined d (AT) -rich element in the oat phytochrome A3 gene promoter. Plant Cell 6 (2), 287-301.

Nieto-Sotelo, et al. (Mar. 25, 1994). Positive Factor 1 (PF1) from oat is an HMGY- and H1 histone-like protein that binds a functionally defined AT-rich DNA element in the oat phytochrome A gene (PHYA3) promoter. Nucleic Acids Res. 22 (6), 1115-1116.

Reeves and Nissen (1990) J. Biol. Chem. 265: 8573-8582.

Reeves & Beckerbauer (2001) Biochim.Biophys.Acta 1519:13-29.

Weigel, D. et al. (2000) Plant Physiol. 122: 1003-1013.

U.S. Appl. No. 10/155,881, filed May 22, 2002, for David Kovalic.

U.S. Appl. No. 10/679,063, unpublished.

Database EMBL EBI Accession No. 065489, last updated Jul. 24, 2004. located at <http://srs.ebi.ac.uk/srsbin/cgi-bin/wgetz?-e+[UNIPROT:O65489_ARATH]+-newld> visited on Oct. 26, 2007. (2 pages).

GenBank Accession No. AAA32718, last updated Apr. 25, 1994, located at <http://www.ncbi.nlm.nih.gov/entrez/viewer.fcgi?db=protein&id=454279> visited on Oct. 26, 2007. (2 pages).

GenBank Accession No. AAA33914, last updated Mar. 11, 1994, located at <http://www.ncbi.nlm.nih.gov/entrez/viewer.fcgi?db=protein&id=453692> visited on Oct. 26, 2007. (2 pages).

GenBank Accession No. AAD21715, last updated Mar. 11, 2002, located at <http://www.ncbi.nlm.nih.gov/entrez/viewer.fcgi?db=protein&id=4512661> visited on Oct. 26, 2007. (2 pages).

GenBank Accession No. AAF04888, last updated Oct. 30, 2002, located at <http://www.ncbi.nlm.nih.gov/entrez/viewer.fcgi?db=protein&id=6175162> visited on Oct. 26, 2007. (2 pages).

GenBank Accession No. AAF07197, last updated Nov. 10, 1999, located at <http://www.ncbi.nlm.nih.gov/entrez/viewer.fcgi?db=protein&id=6319180> visited on Oct. 26, 2007. (2 pages).

Database EMBL EBI Accession No. AB016472, last updated Apr. 14, 2005, located at <http://srs.ebi.ac.uk/srsbin/cgi-bin/wgetz?-e+[EMBL:AB016472]+-newld> visited on Oct. 26, 2007. (4 pages).

GenBank Accession No. AB025613 , last updated Feb. 14, 2004, located at <http://www.ncbi.nlm.nih.gov/entrez/viewer.fcgi?db=nuccore&id=4589419> visited on Oct. 26, 2007. (27 pages).

GenBank Accession No. AC002387, last updated Mar. 11, 1992, located at <http://www.ncbi.nlm.nih.gov/entrez/viewer.fcgi?db=nuccore&val=AC002387> visited on Oct. 26, 2007. (47 pages).

GenBank Accession No. AC004667, last updated Feb. 27, 2002, located at <http://www.ncbi.nlm.nih.gov/entrez/viewer.fcgi?db=nuccore&val=AC004667> visited on Oct. 26, 2007. (37 pages).

GenBank Accession No. AC006580, last updated Mar. 11, 2002, located at <http://www.ncbi.nlm.nih.gov/entrez/viewer.fcgi?db=nuccore&id=20197861> visited on Oct. 26, 2007. (16 pages).

GenBank Accession No. AC006931, last updated Mar. 11, 2002, located at <http://www.ncbi.nlm.nih.gov/entrez/viewer.fcgi?db=nuccore&id=20197957> visited on Oct. 26, 2007. (47 pages).

GenBank Accession No. AC007369, last updated Oct. 30, 2002, located at <http://www.ncbi.nlm.nih.gov/entrez/viewer.fcgi?db=nuccore&id=4757678> visited on Oct. 26, 2007. (37 pages).

GenBank Accession No. AC007789 , last updated on Oct. 30, 2002, located at <http://www.ncbi.nlm.nih.gov/entrez/viewer.fcgi?db=nuccore&id=5042437> visited on Oct. 26, 2007. (78 pages).

GenBank Accession No. AC011437, last updated Oct. 30, 2002, located at <http://www.ncbi.nlm.nih.gov/entrez/viewer.fcgi?db=nuccore&id=12408724> visited on Oct. 26, 2007. (42 pages).

GenBank Accession No. AC012188, last updated Mar. 18, 2000, located at <http://www.ncbi.nlm.nih.gov/entrez/viewer.fcgi?db=nuccore&id=6554463> visited on Oct. 26, 2007. (44 pages).

GenBank Accession No. AC015450, last updated on Jun. 15, 2001, located at <http://www.ncbi.nlm.nih.gov/entrez/viewer.fcgi?db=nuccore&id=12323968> visited on Oct. 26, 2007. (38 pages).

Database EMBL EBI Accession No. AF003101, last updated Apr. 15, 2005, located at <http://srs.ebi.ac.uk/srsbin/cgi-bin/wgetz?-e+[EMBL:AF003101]+-newld>visited on Oct. 26, 2007. ( 3 pages).

GenBank Accession No. AI443215 , last updated Jul. 23, 2004, located at <http://www.ncbi.nlm.nih.gov/entrez/viewer.fcgi?db=nucest&id=4301610 >visited on Oct. 26, 2007. (2 pages).

GenBank Accession No. AI494847, last updated Jul. 24, 2004, located at <http://www.ncbi.nlm.nih.gov/entrez/viewer.fcgi?db=nucest&id=4395850> visited on Oct. 26, 2007. (3 pages).

GenBank Accession No. AI522913, last updated Jul. 24, 2004, located at <http://www.ncbi.nlm.nih.gov/entrez/viewer.fcgi?db=nucest&id=4437048> visited on Oct. 26, 2007. (2 pages).

GenBank Accession No. AI522924, last updated Jul. 24, 2004, located at <http://www.ncbi.nlm.nih.gov/entrez/viewer.fcgi?db=nucest&id=4437059> visited on Oct. 26, 2007. (3 pages).

GenBank Accession No. AI736668, last updated Jul. 12, 2004, located at <http://www.ncbi.nlm.nih.gov/entrez/viewer.fcgi?db=nucest&id=5058192> visited on Oct. 26, 2007. (2 pages).

GenBank Accession No. AI960613, last updated Jul. 12, 2004, located at <http://www.ncbi.nlm.nih.gov/entrez/viewer.fcgi?db=nucest&id=5753326> visited on Oct. 262007. (2 pages).

GenBank Accession No. AI965992, last updated Jul. 12, 2004, located at <http://www.ncbi.nlm.nih.gov/entrez/viewer.fcgi?db=nucest&id=5760629> visited on Oct. 26, 2007. (2 pages).

GenBank Accession No. AJ005196, last updated Apr. 15, 2005, located at <http://www.ncbi.nlm.nih.gov/entrez/viewer.fcgi?db=nuccore&id=3549642> visited on Oct. 26, 2007. (2 pages).

GenBank Accession No. AL021635, last updated Nov. 14, 2006, located at <http://www.ncbi.nlm.nih.gov/entrez/viewer.fcgi?db=nuccore&id=2827538> visited on Oct. 26, 2007. (43 pages).

Database EMBL EBI Accession No. AL022604, last updated Nov. 14, 2006, located at <http://srs.ebi.ac.uk/srsbin/cgi-bin/wgetz?-e+[EMBL:AL022604]+-newld> visited on Oct. 26, 2007. (19 pages).

GenBank Accession No. AL132975, last updated Nov. 14, 2006, located at <http://www.ncbi.nlm.nih.gov/entrez/viewer.fcgi?db=nuccore&id=6434228> visited on Oct. 26, 2007. (52 pages).

GenBank Accession No. AL161533, last updated Nov. 14, 2006, located at <http://www.ncbi.nlm.nih.gov/entrez/viewer.fcgi?db=nuccore&id=7267889> visited on Oct. 26, 2007. (95 pages).

GenBank Accession No. AL162295, last updated Nov. 14, 2006, located at <http://www.ncbi.nlm.nih.gov/entrez/viewer.fcgi?db=nuccore&id=7329669> visited on Oct. 26, 2007. (57 pages).

GenBank Accession No. AJ132349, last updated Feb. 24, 2003, located at <http://www.ncbi.nlm.nih.gov/entrez/viewer.fcgi?db=nuccore&id=4165182> visited on Oct. 26, 2007. (2 pages).

GenBank Accession No. AW066510, last updated Oct. 12, 1999, located at <http://www.ncbi.nlm.nih.gov/entrez/viewer.fcgi?db=nucest&id=6021582> visited on Oct. 26, 2007. (2 pages).

GenBank Accession No. AW099294, last updated Jul. 24, 2004, located at <http://www.ncbi.nlm.nih.gov/entrez/viewer.fcgi?db=nucest&id=6069638> visited on Oct. 26, 2007. (2 pages).

GenBank Accession No. AW132605, last updated on Jul. 8, 2004, located at <http://www.ncbi.nlm.nih.gov/entrez/viewer.fcgi?db=nucest&id=6134212> visited on Oct. 26, 2007. (2 pages).

GenBank Accession No. AW278127, last updated Jul. 24, 2004, located at <http://www.ncbi.nlm.nih.gov/entrez/viewer.fcgi?db=nucest&id=6666668> visited on Oct. 26, 2007. (2 pages).

GenBank Accession No. AW309814, last updated Jul. 16, 2004, located at <http://www.ncbi.nlm.nih.gov/entrez/viewer.fcgi?db=nucest&id=6725415> visited on Oct. 26, 2007. (2 pages).

GenBank Accession No. AW310124, last updated Jul. 16, 2004, located at <http://www.ncbi.nlm.nih.gov/entrez/viewer.fcgi?db=nucest&id=6725725> visited on Oct. 26, 2007. (2 pages).

GenBank Accession No. AW349284, last updated Oct. 4, 2000, located at <http://www.ncbi.nlm.nih.gov/entrez/viewer.fcgi?db=nucest&id=6846994> visited on Oct. 26, 2007. (2 pages).

GenBank Accession No. AW349908, last updated Oct. 4, 2000, located at <http://www.ncbi.nlm.nih.gov/entrez/viewer.fcgi?db=nucest&id=6847618> visited on Oct. 26, 2007. (2 pages).

GenBank Accession No. AW350603, last updated Oct. 4, 2000, located at <http://www.ncbi.nlm.nih.gov/entrez/viewer.fcgi?db=nucest&id=6848313> visited on Oct. 26, 2007. (2 pages).

GenBank Accession No. AW448258, last updated Jan. 3, 2001, located at <http://www.ncbi.nlm.nih.gov/entrez/viewer.fcgi?db=nucest&id=12018686> visited on Oct. 26, 2007. (2 pages).

GenBank Accession No. AW455702, last updated Feb. 20, 2000, located at <http://www.ncbi.nlm.nih.gov/entrez/viewer.fcgi?db=nucest&id=7009437> visited on Oct. 26, 2007. (2 pages).

GenBank Accession No. AW574000, last updated Sep. 7, 2000, located at <http://www.ncbi.nlm.nih.gov/entrez/viewer.fcgi?db=nucest&id=7238733> visited on Oct. 26, 2007. (2 pages).

GenBank Accession No. AW596434, last updated Jul. 14, 2004, located at <http://www.ncbi.nlm.nih.gov/entrez/viewer.fcgi?db=nucest&id=7283832> visited on Oct. 26, 2007. (2 pages).

GenBank Accession No. AW596625, last updated Jul. 14, 2004, located at <http://www.ncbi.nlm.nih.gov/entrez/viewer.fcgi?db=nucest&id=7284025> visited on Oct. 26, 2007. (2 pages).

GenBank Accession No. CAA18730, last updated Nov. 14, 2006, located at <http://www.ncbi.nlm.nih.gov/entrez/viewer.fcgi?db=protein&id=3080411> visited on Oct. 26, 2007. (2 pages).

GenBank Accession No. CAA61276, last updated Apr. 18, 2005, located at <http://www.ncbi.nlm.nih.gov/entrez/viewer.fcgi?db=protein&id=871496> visited on Oct. 26, 2007. (2 pages).

GenBank Accession No. CAA61277, last updated Oct. 7, 1996, located at <http://www.ncbi.nlm.nih.gov/entrez/viewer.fcgi?db=protein&id=871498> visited on Oct. 26, 2007. (2 pages).

GenBank Accession No. CAB75914, last updated Nov. 14, 2006, located at <http://www.ncbi.nlm.nih.gov/entrez/viewer.fcgi?db=protein&id=7076799> visited on Oct. 26, 2007. (2 pages).

GenBank Accession No. CAB78783, last updated Nov. 14, 2006, located at <http://www.ncbi.nlm.nih.gov/entrez/viewer.fcgi?db=protein&id=7268533> visited on Oct. 26, 2007. (2 pages).

GenBank Accession No. CAB80256, last updated Nov. 14, 2006, located at <http://www.ncbi.nlm.nih.gov/entrez/viewer.fcgi?db=protein&id=7270491> visited on Oct. 26, 2007. (2 pages).

GenBank Accession No. CAB82691, last updated Nov. 14, 2006, located at <http://www.ncbi.nlm.nih.gov/entrez/viewer.fcgi?db=protein&id=7329697> visited on Oct. 26, 2007. (2 pages).

GenBank Accession No. D42950, last updated Dec. 7, 2004, located at <http://www.ncbi.nlm.nih.gov/entrez/viewer.fcgi?db=nucest&id=3107210> visited on Oct. 26, 2007. (2 pages).

GenBank Accession No. S57459, last updated May 7, 1993, located at <http://www.ncbi.nlm.nih.gov/entrez/viewer.fcgi?db=nuccore&id=235870> visited on Oct. 26, 2007. (2 pages).

GenBank Accession No. T43108, last updated Nov. 6, 1997, located at <http://www.ncbi.nlm.nih.gov/entrez/viewer.fcgi?db=nucest&id=2597674> visited on Oct. 26, 2007. (2 pages).

GenBank Accession No. W43561, last updated Jan. 5, 1998, located at <http://www.ncbi.nlm.nih.gov/entrez/viewer.fcgi?db=nucest&id=2748865> visited on Oct. 26, 2007. (2 pages).

GenBank Accession No. X98738, last updated Dec. 3, 2004, located at <http://www.ncbi.nlm.nih.gov/entrez/viewer.fcgi?db=nuccore&id=2213535> visited on Oct. 26, 2007. (2 pages).

GenBank Accession No. X98739, last updated Dec. 3, 2004, located at <http://www.ncbi.nlm.nih.gov/entrez/viewer.fcgi?db=nuccore&id=2213533> visited on Oct. 26, 2007. (2 pages).

GenBank Accession No. X99116, last updated Apr. 18, 2005, located at <http://www.ncbi.nlm.nih.gov/entrez/viewer.fcgi?db=nuccore&id=1592673> visited on Oct. 26, 2007. (2 pages).

GenBank Accession No. X99373, last updated Nov. 14, 2006, located at <http://www.ncbi.nlm.nih.gov/entrez/viewer.fcgi?db=nuccore&id=1435174> visited on Oct. 26, 2007. (2 pages).

GenBank Accession No. X99491, last updated Apr. 18, 2005, located at <http://www.ncbi.nlm.nih.gov/entrez/viewer.fcgi?db=nuccore&id=1460087> visited on Oct. 26, 2007. (2 pages).

GenBank Accession No. Z97344, last updated Nov. 14, 2006, located at <http://www.ncbi.nlm.nih.gov/entrez/viewer.fcgi?db=nuccore&id=5281025> visited on Oct. 26, 2007. (37 pages).

Abel et al. (Jan. 1994). "Early Auxin-induced Genes Encode Short-lived Nuclear Proteins," *Proc Natl Acad Sci USA* (91): 326-330.

Ainley et al. (Apr. 1993). "Regulatable Endogenous Production of Cytokinins Up to 'Toxic' Levels in Transgenic Plants and Plant Tissues," *Plant Mol. Biol.* 22: 13-23.

Aoyama et al. (Nov. 1995). "Ectopic Expression of the *Arabidopsis* Transcriptional Activator Athb-1 alters Leaf Cell Fate in Tobacco," *Plant Cell* 7: 1773-1785.

Aravind et al. (1998). "AT-hook motifs Identified in a Wide Variety of DNA-binding Proteins," *Nucleic Acids Research* 26(19):4413-4421.

Baerson et al. (Dec. 1994). "Identification of Domains in an *Arabidopsis* Acyl Carrier Protein Gene Promoter Required for Maximal Organ-specific Expression," *Plant Mol. Biol.* 20: 1947-1959.

Baumann et al. (Mar. 1999). "The DNA Binding Site of the Dof Protein NtBBF1 is Essential for Tissue-specific and Auxin-regulated Expression of the RolB Oncogene in Plants," *Plant Cell* 11: 323-333.

Bevan et al. (Jan. 1998). "Sequence of 1.9 Mb Contiguous Region from Chromosome 4 of *Arabidopsis thaliana*," *Nature* 391 (6666): 485-488.

Bird et al. (1988). "The Tomato Polygalacturonase Gene and Ripening-Specific Expression in Transgenic Plants," *Plant Mol. Biol.* 11: 651-662.

Buchel et al. (1999). "Mutation of GT-1 Binding Sites in the Pr-1A Promoter Influences the Level of Inducible Gene Expression In Vivo," *Plant Mol. Biol.* 40: 387-396.

Cubas et al. (Apr. 1999). "The TCP Domain: a Motif Found in Proteins Regulating Plant Growth and Development," *Plant J.* 18: 215-222.

Da Costa E Silva et al. (Jul. 1993). "BPF-1, a Pathogen-Induced DNA-binding Protein Involved in the Plant Defense Response," *Plant J.* 4: 125-135.

Falvo et al. (Dec. 1995). "Reversal of Intrinsic DNA Bends in the IFN Beta Gene Enhancer by Transcription Factors and the Architectural Protein HMG I(Y)," *Cell* 83: 1101-1111.

Forsburg et al. (Aug. 1989). "Identification and Characterization of HAP4: a Third Component of the CCAAT-bound HAP2/HAP3 Heteromer," *Genes Develop.* 3: 1166-1178.

Foster et al. (Feb. 1994). "Plant bZIP Proteins Gather at ACGT Elements," *FASEB J.* 8: 192-200.

Gan et al. (Dec. 1995). "Inhibition of Leaf Senescence by Autoregulated Production of Cytokinin," *Science* 270: 1986-1989.

Gatz et al. (Jun. 1997). "Chemical Control of Gene Expression," *Annu. Rev. Plant Physiol. Plant Mol. Biol.* (1997) 48: 89-108.

Giniger et al. (Dec. 1987). "Transcription in Yeast Activated by a Putative Amphipathic Alpha Helix Linked to a DNA Binding Unit," *Nature* 330: 670-672.

Glover et al. (Sep. 1998). "Development of Several Epidermal Cell Types Can be Specified by the Same MYB-Related Plant Transcription Factor," *Development* 125: 3497-3508.

Grasser. (Feb. 1995). "Plant Chromosomal High Mobility Group (HMG) Proteins," *Plant J.* 7: 185-192.

Guevara-Garacia et al. (Nov. 1998. "A 42 Bp Fragment of the Pmas1' Promoter Containing an Ocs-like Element Confers a Developmental, Wound- and Chemically Inducible Expression Pattern," *Plant Mol. Biol.* 38: 743-753.

Hall et al. (Jun. 1998). "GOLDEN2: a Novel Transcriptional Regulator of Cellular Differentiation in the Maize Leaf," *Plant Cell* 10: 925-936.

Hofmann, et al. (2000). "Isolation of Two cDNAs Encoding AT-Hook DNA-Binding Proteins, SAP1 and HMR1, from an *Antirrhinum majus* L. Inflorescence Expression Library," *Plant Physiol.* 122: 292-292.

Ishiguro et al. (1994). "Characterization of a cDNA Encoding a Novel DNA-binding Protein, SPF1, that Recognizes SP8 Sequences in the 5' Upstream Regions of Genes Coding for Sporamin and β-amylase from Sweet Potato," *Mol. Gen. Genet.* 244: 563-571.

Kaiser et al. (May 1995). "Cis-acting Elements of the CHS1 gene from White Mustard Controlling Promoter Activity and Spatial Patterns of Expression," *Plant Mol. Biol.* 28: 231-243.

Kim et al. (Jun. 1997). "Isolation of a Novel Class of bZIP Transcription Factors that Interact with ABA-responsive and Embryo-specification Elements in the Dc3 Promoter Using a Modified Yeast One-hybrid System," *Plant J.* 11: 1237-1251.

Klein et al. (Jan. 15, 1996). "A New Family of DNA Binding Proteins Includes Putative Transcriptional Regulators of the *Antirrhinum majus* Floral Meristem Identify Gene *squamosa*," *Mol. Gen. Genet.* 250: 7-16.

Klug et al. (May 1995). "Protein motifs 5. Zinc Fingers," *FASEB J.* 9, 597-604.

Kuhlemeier et al., (Apr. 1989). "The Pea rbcS-3A Promoter Mediates Light Responsiveness but not Organ Specificity," *Plant Cell* 1: 471-478.

Leyser et al. (Sep. 1996). "Mutations in the AXR3 gene of *Arabidopsis* Result in Altered Auxin Response Including Ectopic Expression from the SAUR-AC1 Promoter," *Plant J.* 10: 403-413.

Lin et al. (Dec. 16, 1999). "Sequence and Analysis of Chromosome 2 of the Plant *Arabidopsis thaliana*," *Nature* 402(6763): 761-768.

Lincoln et al. (Nov. 1990). "Growth and Development of the Axr1 Mutants of *Arabidopsis*," *Plant Cell* 2: 1071-1080.

Littlewood et al. (1994). "Transcription Factors 2: Helix-loop-helix," *Protein Profile* 1: 639-709.

Lohrmann et al. (Sep. 1999) "Differential Expression and Nuclear Localization of Response Regulator-like Proteins from *Arabidopsis thaliana*," *Plant Biol.* 1: 495-505.

Ma et al. (Oct. 1987). "A New Class of Yeast Transcriptional Activators," *Cell* 51: 113-119.

Manners et al. (Dec. 1998). "The Promoter of the Plant Defensin Gene PDF1.2 from *Arabidopsis* is Systemically Activated by Fungal Pathogens and Responds to Methyl Jasmonate but not to Salicylic Acid," *Plant Mot. Biol.* 38: 1071-1080.

Martin et al. (Feb. 1997). "MYB Transcription Factors in Plants," *Trends Genet.* 13: 67-73.

Martinez-Garcia et al. (Apr. 1999). "The HMG-I/Y protein PF1 Stimulates Binding of the Transcriptional Activator GT-2 to the PHYA Gene Promoter," *Plant J.* 18(2): 173-183.

Mayer et al. (Dec. 1999). "Sequence and Analysis of Chromosome 4 of the Plant *Arabidopsis thaliana*," *Nature*: 402(6763), 769-777.

Meijer et al. (Jun. 1996). "Novel Members of a Family of AT Hook-containing DNA-binding Proteins from Rice are Identified through their In Vitro Interaction with Consensus Target Sites of Plant and Animal Homeodomain Proteins," *Plant Molec. Biol.* 31:607-618.

Meissner et al. (Oct. 1999). "Function search in a Large Transcription Factor Gene Family in *Arabidopsis*: Assessing the Potential of Reverse Genetics to Identify Insertional Mutations in R2R3 MYB Genes," *Plant Cell* 11: 1827-1840.

Mizukami et al. (Jan. 2000). "Plant Organ Size Control: AINTEGUMENTA Regulates Growth and Cell numbers during Organogenesis," *Proc. Natl. Acad. Sci. U S A* 97:942-947.

Moore et al.,(Jan. 1998). "A Transcription Activation System for Regulated Gene Expression in Transgenic plants," *Proc. Nat'l Acad. Sci. USA* 95: 376-381.

Newman et al. (Dec. 1994). "Genes Galore: a Summary of Methods for Accessing Results Form Large Scale Partial Sequencing of Anonymous *Arabidopsis* cDNA Clones.," *Plant Physiol.* 106: 1241-1255.

Nieto-Sotelo et al. (Feb. 1994). "PF1: an A-T hook-containing DNA Binding Protein from Rice that Interacts with a Functionally Defined (AT) -rich Element in the Oat Phytochrome A3 gene Promoter," *Plant Cell* 6:287-301.

Nieto-Sotelo et al. (Mar. 1994). "Positive Factor 1 (PF1) from Oat is an HMGY- and H1 Histone-like Protein that Binds a Functionally Defined AT-rich DNA Element in the Oat Phytochrome A gene (PHYA3) Promoter," *Nucleic Acids Res.* 22 (6):1115-1116.

Odell et al. (Oct. 1994). "Seed-specific gene Activation Mediated by the Cre/lox Site-specific Recombination Systems," *Plant Physiol.* 106: 447-458.

Okamuro et al. (Jun. 1997). "The AP2 Domain of APETALA2 Defines a Large New Family of DNA Binding Proteins in *Arabidopsis*," *Proc. Natl. Acad. Sci. USA* 94: 7076-7081.

Onate et al. (May 1994). "The DNA-bending Protein HMG-1 Enhances Progesterone Receptor Binding to its Target DNA Sequences," *Mol. Cell Biol.* 14: 3376-3391.

Reeves et al. (May 25, 1990). "The A.T-DNA-binding Domain of Mammalian High Mobility Group I Chromosomal Proteins. A Novel Peptide Motif for Recognizing DNA Structure,"*J Biol Chem* 265: 8573-8582.

Riechmann et al. (Jun. 1998). "The AP2/EREBP Family of Plant Transcription Factors," *Biol. Chem.* 379: 633-640.

Riechmann et al. (Oct. 1997). "MADS Domain Proteins in Plant Development," *Biol. Chem.* 378: 1079-1101.

Ringli et al. (Aug. 1998). "Specific Interaction of the Tomato bZIP Transcription Factor VSF-1 with a Non-palindromic DNA Sequence that Controls Vascular Gene Expression," *Plant Mol. Biol.* 37: 977-988.

Rouse et al. (Feb. 1998). "Changes in Auxin Response from Mutations in an AUX/IAA Gene," *Science* 279: 1371-1373.

Sakai et al., (Nov. 1998). "Two-component Response Regulators from *Arabidopsis rhaliana* Contain a Putative DNA Binding Motif," *Plant Cell Physiol.* 39: 1232-1239.

Schaffner et al. (Sep. 1991). "Maize rbcS Promoter Activity Depends on Sequence Elements not Found in Dicot rbcS Promoters," *Plant Cell* 3: 997-1012.

Seo et al. (Feb. 1998). "Higher Activity of an Aldehyde Oxidase in the Auxin-overproducing Superroot1 Mutant of *Arabidopsis thaliana*," *Plant Physiol.* 116: 687-693.

Shi et al. (Dec. 1998). "Gibberellin and Abscisic Acid Regulate GAST1 Expression at the Level of Transcription," *Plant Mol. Biol.* 38: 1053-1060.

Siebertz et al. (Oct. 1989). "Cis-analysis of the Wound-inducible Promoter wun1 in Transgenic Tobacco Plants and Histochemical Localization of Its Expression," *Plant Cell* 1: 961-968.

Stemmer et al. (Aug. 1994). "Rapid Evolution of a Protein In Vitro by DNA Shuffling," *Nature* 370: 389-391.

Stemmer et al. (Oct. 1994). "DNA Shuffling by Random Fragmentation and Reassembly: In Vitro Recombination for Molecular Evolution," *Proc. Nat'l Acad. Sci. USA* 91: 10747-10751.

Tucker et al. (Jul. 1994). "Crystal Structure of the Adenovirus DNA Binding Protein Reveals a Hook-on Model for Cooperative DNA Binding," *EMBO J.* 13: 2994-3002.

Van Der Kop et al., (Mar. 1999). "Selection of *Arabidopsis* Mutantas Overexpressing Genes Driven by the Promoter of an Auxin-inducible Glutathione S-transferase Gene," *Plant Mol. Biol.* 39: 979-990.

Waterston. (Dec. 1998). "Genome Sequence of the Nematode *C. elegans*: a Platform for Investigating Biology *C. elegans* Sequencing Consortium," *Science* 282 (5396): 2012-2018.

Weigel et al. (Oct. 1995). "A Developmental Switch Sufficient for Flower Initiation in Diverse Plants," *Nature* 377: 495-500.

Willmott et al. (Nov. 1998). "DNase1 Footprints Suggest the Involvement of at Least Three Types of Transcription Factors in the Regulation of Alpha-Amy2/A by Gibbereilin." *Plant Mol. Biol.* 38: 817-825.

Zhang et al. (Dec. 1992). "Expression of Antisense or Sense RNA of an Ankyrin Repeat-containing Gene Blocks Chloroplast Differentiation in *Arabidopsis*," *Plant Cell* 4: 1575-1588.

Crawford et. al (2004). "Cincinnata Controls Both Cell Differentiation and Growth in Petal Lobes and Leaves of Antirrhinum," *Plant Physiol.* 135:244-253.

Gardiner et al. (2004). "Anchoring 9,371 Maize Expressed Sequence Tagged Unigenes to the Bacterial Artificial Chromosome Contig Map by Two-Dimensional Overgo Hybridization," *Plant Physiology* 134:1317-1326.

Grasser. (2003). "Chromatin-associated HMGA and HMGB Proteins: Versatile Co-regulators of DNA-dependent Processes," *Plant Molecular Biology* 53:281-295.

Hu et al. (2003). "The *Arabidopsis* Auxin-Inducible Gene ARGOS Controls Lateral Organ Size," *The Plant Cell* 15:1951-1961.

Knox et al. (2003). "AXR3 and SHY2 Interact to Regulate Root Hair Development," *Development* 130(23):5769-5777.

Raval et al. (2004). "A Database Analysis of Jacalin-like Lectins: Sequence-structure-function Relationships," *Glycobiology* 14(12):1247-1263.

NCBI Accession No. AL022604 (Apr. 24, 1998). *Arabidopsis thaliana* DNA chromosome 4, BAC clone F23E12 (ESSAII project).

* cited by examiner

```
G2789  (84)  ----MDEVS----------------------------RSHTPQFLSSD-HQ-------------HYHHQNA----GR
G596   (89)  ----MDQVS----------------------------RSLPPFLSRDLHL-------------HPHHQFQ----HQ
G1070  (48)  ---MDPVQSHGSQ------------------------SSLPPFHARDFQL-------------HLQQQQEFFLHHHQ
G3405  (28)  ---MDPVTASIHG------------------------HHLPPPFNTRDFHH-------------HLQQQQH----QL
G3404  (32)  ---MDPVTAAAHGGGHHHHHHHFGAPPVAAFHHH---------------------------PFHHGGAHYPAAFQ
G1075  (52)  ---MAGIDLGTTS------------------------RYVHNV-DGGGGG-------------QFTTDNHHEDDG-GA
G1076  (54)  ---MAGIDLGTAF------------------------RYVNHQ-LHRPDL-------------HLHHNSSSDDVTPGA
G3460  (18)  ---MAGIDLGSAS------------------------RFVQN--LHLPDL-------------HLQQNYQQPR---HK
G3459  (16)  ---MAGIDLGSAS------------------------RFVQN--LHRPDL-------------HLQQNFQQHQDQHQ
G3458  (24)  ---MAGIDLGSAS------------------------HFVHHR-LERPDL-------------EDDENQQDQDNNLNN
G3406  (26)  ---MAGIDLGTAAT-----------------------RYVHQLHHLHPDL-------------QLQHSYAKQHEPSDD
G3407  (12)  ---MAGIDLGTSYL-----------------------HHHQSLHLRHDDG-------------GAGSDDGGHDDLSPG
G1069  (42)  ---MANPWTNQSGLAGMVDHSVSSGH-----------------------------------HQN-HHHQSL---LT
G2153  (6)   ---MANPWTGQVNLSGLETTPPGSSQ---------------------------------LKKPDLHISMNMAMD
G3456  (14)  ------------------------------------MASKE-PSGD-----------------MKKPDLGFSMN---E
G3401  (38)  ---------------------------------------MGLPEQPSGSS------------------------
G3403  (22)  ---MANPWWVGNVAIGGVESPVTSSAPSLHHRNS--------------------------GPKAELPVAKE--PE
G2157  (88)  ---MANRWWAGNVGMIREQELMENSN-----------NN------------------------NNNPPTMTRSDPRL
G3462  (36)  ---MGSIDGHSLQQHQG-----------------------------------------NNNNATTTTPTTRS
G3556  (40)
G1067  (4)   ---MEGGYEQGGASRYFHNLFRPEIHHQQLQP-------------------------QGGINLIDQHHHQHQ
G2156  (8)   ---MDGGYDQSGGASRYFHNLFRPELHH-QLQP-------------------------QPQLHPLPQ---PQP
G3400  (30)  ---MAGMDPTGGGGGGVAAHYLHMLRAQQHQPLS--------------------------PAGDVKAERSMLSP
G2157  ...   MAGMDPGGGGAGAGSSRYFHHLLRPQQPSPLSPL-----------------------SPTSHVKMEHSKMSP
G3399  (10)
G1073  (2)   ---------------------------------MELNRSE-----------------------ADEAKAET---

G1945  (44)  ---MKGEYREQKSNEMF-------------------SKLPHH------------------QQQQQQQQQHSLTS
G2155  (46)  ---ML-----------------SKLPTQ---------R-
G3408  (20)  -MSFCERDMNKESMYQERDDMAGIRFATPPLPQQ-------------QQQQQLVECFSDEVD
BAB64709 (90) --MADEGSSRAELIEAS-------------------------
G1071  (91)  --MDRRDAMGLSG-SGSYYIHRG---LSGSGPPTFHGSPQQQGLRHLPNQNSPFGSGS
T06584 (92)  --MDGREAMAFSGGPGSYLHRGGVEAAGSGSGGFQVPP----GFRALPNNGIIAQPNV
CAA10643 (93) --MEQPNNDGNNG--------------------------GSCYR------------PQLPNQSPPANGVP
AAK00433 (94) --MEAKDVSPLVTVPPAPAAAAPPAAAAPAPPPSQPPPPPLPFAQQAPPAANPAAAPM
G1072  (95)  --METSDR---ISPGGGIGAEVPSAY-----------------HMAPRPSDSPANQFM
G1068  (96)  ---MDSREIHHQQQQQQQQQQQQQQQHLQ-------------------QQQQPPGMLMSHHN
```

FIG. 5A

```
G2789  (84)  QKRGR----EEEG---------------------------------VE---PN---NIGEDLA
G596   (89)  QQQQQ---QNHGHDIDQHRIGGLKRDRDADID----------------------PNEHSSAGKDQS
G1070  (48)  QQRNQTDGDQQGGSGGNRQIKMDREETSDNIDN-IANNSGSEGKDID
G3405  (28)  HLKTED---DQGGGTPGVFGSRGTKRDHDDDENSGNGHGSGGDGGDLA
G3404  (32)  QFQEEQ---QQLVAAAAAGGMAKQELVDESNNTINSGGSNGSGGEEQ
G1075  (52)  GGNHH---------------------------HHHHNHHQGLDLIASN
G1076  (54)  GMGHFT-----------------------VDDEDNNNNHQGLDLASGG
G3460  (18)  RDSEE-----------------------------QETPPNPGTALAPFDND
G3459  (16)  RDLEE-----------------------------QKTPPNHRMG-APFDDD
G3458  (24)  HEGLD---------------------------------LVTP
G3406  (26)  DPNGS-----------------------GGGGNSNGGPYGDHDGGS
G3407  (12)  SGGGG
G1069  (42)  KGDLG-------------------------IAMNQSQDNDQDEED
G2153  (6)   SGHNN-------------------------HHHHQEVDNNNNDDDRD
G3456  (14)  STVTG-------------------------NHIGEE-DEDRENSD
G3401  (38)  ------------------------------HDHEMNGTSAGGG
G3403  (22)  ASPTG-------------------------GAAADHADENNESGGG
G2157  (88)  DHDFT-------------------------TNNSGSPNTQTQSQEEQ
G3462  (36)  NSNTN-------------------------ANTNTNTEEEVSRDNG
G3556  (40)  -YSHG-------------------------GGAGGSNEEEEASPPPG
G1067  (4)   QHQQQQQPSDDS------------------RESDHSNKD
G2156  (8)   QPQPQQQNSDD-------------------ESD-SNKD
G3400  (30)  DESPGADAD--------------------LGSDH-PTSSAM
G3399  (10)  DKSPVGEGDHAGG-----------------SGSGGVGGDHQPSSSAM
G1073  (2)   -TPTGG---------------------------ATSSA
G1945  (44)  HFHLSS----------------------------TVTPTV
G2155  (46)  HLHLSP----------------------------SSP
G3408  (20)  SRGSGG----------------------------EMKDAVGS
BAB64709 (90) -PAPAL----------------------------DLP
G1071  (91)  TGFGSPSLHGDPSLATAAGGAGALPHHIGVNMIAPPPPSETPMKRK----RGRPRK
T06584 (92)  RAQGG---NGDTSSMFSLEPQSHADFNHDISVGASSGAPSSEPVKKK----RGRPRK
CAA10643(93) NSTTTN---------------------------STHSPPNESVKRK----RGRPRK
AAK00433(94) RLSFDQMAGKAPGGEQQHHHHPGPMLYAAAPAGGAAPPPQGGNVMGMGELMRKKRGRPRK
G1072  (95)  GLSLPPME-------------------------APMPSSGEASGK----KRRGRPRK
G1068  (96)  SYNRNPNAAAAVLMGHNTSTSQAMHQRLPFGGSMSPHQPQQHQYHHPQQQIDQKTLES
```

FIG. 5E  Second Conserved domain

```
G2789   (84)  GSVVGPLTASSPVVVMAASFGNASYERLPLEEEETER----------EIDGNAARAIG
G596    (89)  GSVVGPLMASGPVVIMAASFGNAAYERLPLEEDDQEEQTA----GAVANNIDGNATMGGG
G1070   (48)  GSVVGPLLCAGPVVIMAASFSNAAYERLPLEEDEMQTP------VHGGGGGSL
G3405   (28)  GSVVGALTAAGPVVIMAASFANAVYERLPLEDDELLAAQG----QADSAGLLAAG
G3404   (32)  GTVAGPLIAVGPVVIMAASFGNAVYERLPLEDDEPPQH------MAGGGQSSPP
G1075   (52)  GNVVGELMAAGPVMVMAASFTNVAYERLPLDEHEEHLQS-----GGGG---GG
G1076   (54)  GSVVGELTAAGPVIVIAASFTNVAYERLPLEEDEQQQQL-----GGGSN---GG
G3460   (18)  GNVVGELTAAGPVIVIAASFTNVAYERLPLEEDEQQQQQ-----LQIQSPATTSS--QG
G3459   (16)  GNVIGELTAAGPVLVIAASFTNVAYERLPLEEDEQQQQQ-----QLQIQPPATTSS--QG
G3458   (24)  GNVVGPLVASGPVIVIASSFTNVAYERLPLDEDESMQMQ-----QGQSSAGDGSGDHG
G3406   (26)  GNVVGALYAAGPVIVIAASFANVAYERLPLEEEAPPPQA-----GLQMQQPGGGAD--AG
G3407   (12)  GSVAGALIAAGPVVVVAASFSNVAYERLPLEDGDEVVPPA----PAGSDQGGGGSG--GM
G1069   (42)  GSVVGPLLAIGSVMVIAATFSNATYERLPMEEEEDGGG------SRQIHGGGDSP
G2153   (6)   GSVVGPLMAAGPVMLIAATFSNATYERLPLEEEAAER-------GGGGGSGGVVP
G3456   (14)  GGVVGPLVAAGPVLVMAATFSNATYERLPLEDDDQEQH------GGG-GGGGSPQ
G3401   (38)  GSVVGTLTAAGPVMVIASTFANATYERLPLEEEEG---------AAAGGMMAPPP
G2157   (22)  GSVVGSLIAAGPVIASGTFANATYERLPIEEEQ--QQE------SGPPMPGGAEP
G3403   (88)  GGVAGPLIASGPVVMVIAATFCNATYERLPICNATYERLPIEEEQ--QQE------QPLQLEDGKKQ
G2157   (36)  GNVAGSLVASGPVMVIAATFANATYERLPLEDDQGEEE------MQVQQQQQQQ
G3462   (40)  GSVMGELIASGPVMVIAATFGNATYERLPLDQEG--EEG-----AVLSGSEGAAA
G3556   (4)   GSVVAPLIASAPVILMAASFSNAVFERLPIEEEEEE--------GGGGG--GGGGGPPQ
G1067   (8)   GNVVAPLVASGPVILMAASFSNATFERLPLDEGGE---------GGEGGEVGEGGGEGG
G2156   (30)  GSVAGQLIAAGPVFLMAASFANAVYERLPLDGEDPEAEAA----AATPPGDAAQPTGPPP
G3400   (10)  GSVVGPLVAAGPVVLMAASFANAVYERLPLEGEEEVAAP-----AAGGEAQDVAQSAGP
G3399   (2)   GNVAGSLIASGPVVLMAASFANAVYDRLPLEEEETPPPRT----TGVQQQPEASQSSEV
G1073

G1945   (44)  GFVAGPLISAGTVYVIAASFNNPSYHRLPAEEEQ----------KHSAGTGEREG
G2155   (46)  GFVAGPLVAAGTVYFVATSFKNPSYHRLPATEEE----------QRNSAEGEEEG
G3408   (20)  GAVAGPLYAATTVVVVAAAFTNPTFHRLPADDDASVSVSVSLSGSGDADEHRGHQHKPEP
BAB64709 (90) GTLAGEMTTADGLVVVAATFGSAEVHRLPADEDD----------EATGSRGGEER
G1071   (91)  GAIGGPLIAASPVQVIVGSFIWAAPKIKSKREE-----------ASEVVQETDDHHV
T06584  (92)  GSVA-MLIAGSPIQLVVCSFVYGG---GSKVKTKQ---------GMITNGESSEPHN
CAA10643 (93) GGVGGPLTAAATIQVIVGTFVVETKKDANVEAAAS---------GKSPSPNGGASAP
AAK00433 (94) GCVAGMLMAATPVQVVVASFIAEGKKSKPVETRKV---------EPMSAPPQMATYV
G1072   (95)  GGVAGLLIAATPIQVVVGSFITSDQQD-HQKPRKQ---------RVEHAPAAVMSVP
G1068   (96)  GCVDGMLVAGSQVQVIVGSFVPDGRKQKQSAGRAQNTP------EPASAPANMLSFG
```

FIG. 5F

FIG. 5G

| | | |
|---|---|---|
| G2789 | (84) | GEAYWGTQ--------RPS-F------------------ |
| G596 | (89) | AEAYWGTP--------RPS-F------------------ |
| G1070 | (48) | DQSYWSTG--------RPP-Y------------------ |
| G3405 | (28) | EAAYGWNPGAGGG-RPAPF------------------ |
| G3404 | (32) | DAAYGWTSGGGGGRAAPY------------------ |
| G1075 | (52) | IGVESWQGNH-AGAGRAPF------------------ |
| G1076 | (54) | LPVEGWPGNS-G--GRGPF------------------ |
| G3460 | (18) | LP-------------PF------------------ |
| G3459 | (16) | LPVEGWAVNP-AS-RPQPF------------------ |
| G3458 | (24) | LPVDGWAGNS-GG-R-QSY------------------ |
| G3406 | (26) | LPPGADGHGW-AG-ARPPF------------------ |
| G3407 | (12) | MPVDGHAGWPGAGVGRPPFS----------------- |
| G1069 | (42) | GHEPYT--W---VHARPPY------------------ |
| G2153 | (6)  | GQEAYG--W---AQARSGF------------------ |
| G3456 | (14) | NHEAYSSPWGHSPHARPPF------------------ |
| G3401 | (38) | -HHARP--------PPPPY------------------ |
| G3403 | (22) | -GDGFPW--------AAHPRPPY--------------- |
| G2157 | (88) | QHDVYWGG-------PPPRAPP-SY------------- |
| G3462 | (36) | -HDVFWG--------APPRPPP-SF------------- |
| G3556 | (40) | PHDMFGQWG-HAAVARPPPTSF---------------- |
| G1067 | (4)  | HLL-GWGAG-----TPSRPPF------------------ |
| G2156 | (8)  | HLL-GWGAAAAAAPPRPAF------------------ |
| G3400 | (30) | FG--SWSGS----IRPPPF------------------ |
| G3399 | (10) | FG--GWSGAGAGGVR-PPF------------------ |
| G1073 | (2)  | YGMSGGSGGGGGATRPAF------------------ |
| G1945 | (44) | IWA--PTARAP-----PPY------------------ |
| G2155 | (46) | IWD---PNAKAP----SPY------------------ |
| G3408 | (20) | MWP--PPARTPHPPPPPY------------------ |
| BAB64709 | (90) | LWAQSPGSVGPAHPATSRY------------------ |
| G1071 | (91) | -GSRQMDMR--HAHADIDLMRG--------------- |
| T06584 | (92) | -GSQPSDMKSAPAHTGIDLTRG--------------- |
| CAA10643 | (93) | IGSADHGMHQSPENGDYDHIPD--------------- |
| AAK00433 | (94) | NHSGQQQQHQQHMPPAYASGGWSLSAHHQNRHDSDMKMMSN |
| G1072 | (95) | WTNGQD----MPRNSAT-----DINISLPVD---- |
| G1068 | (96) | NNSNNHGIFGNSTPQPLHQIPMQMYQNLWPGNSPQ---- |

FIG. 5H

TRANSCRIPTIONAL REGULATION OF PLANT BIOMASS AND ABIOTIC STRESS TOLERANCE

RELATIONSHIP TO COPENDING APPLICATIONS

This application (the "instant application") claims the benefit of U.S. Provisional Application No. 60/565,948, filed Apr. 26, 2004 (pending), hereby incorporated by reference in its entirety; and, the instant application claims the benefit of U.S. Provisional Application No. 60/527,658, filed Dec. 5, 2003 (pending); and, the instant application claims the benefit of U.S. Provisional Application No. 60/542,928, filed Feb. 5, 2004 (pending); and, the instant application is a continuation-in-part of prior application Ser. No. 10/302,267, filed Nov. 22, 2002 (pending), hereby incorporated by reference in its entirety, which is a divisional of prior application Ser. No. 09/506,720, filed Feb. 17, 2000 (abandoned), hereby incorporated by reference in its entirety, which claims the benefit of U.S. Provisional Application No. 60/135,134, filed May 20, 1999 (expired), hereby incorporated by reference, and, the instant application is a continuation-in-part of prior application Ser. No. 10/278,173, filed Oct. 21, 2002 (pending), hereby incorporated by reference in its entirety, which is a divisional of prior application Ser. No. 09/533,392, filed Mar. 22, 2000 (abandoned), hereby incorporated by reference in its entirety, which claims the benefit of U.S. Provisional Application No. 60/125,814, filed Mar. 23, 1999 (expired), hereby incorporated by reference; and, the instant application is a continuation-in-part of prior application Ser. No. 10/714,887, filed Nov. 13, 2003 (pending); and, the instant application is a continuation-in-part of prior application Ser. No. 10/669,824, filed Sep. 23, 2003 (pending), hereby incorporated by reference in its entirety, which is a continuation-in-part of prior application Ser. No. 09/934,455, filed Aug. 22, 2001 (abandoned), hereby incorporated by reference in its entirety, which claims the benefit of U.S. Provisional Application No. 60/227,439, filed Aug. 22, 2000 (expired), hereby incorporated by reference in its entirety; and, application Ser. No. 10/669,824 (supra) is a continuation-in-part of prior application Ser. No. 09/533,029, filed Mar. 22, 2000 (now U.S. Pat. No. 6,664,446 B2, issued Dec. 16, 2003), hereby incorporated by reference in its entirety, which claims the benefit of U.S. Provisional Application No. 60/125,814, filed Mar. 23, 1999 (supra), hereby incorporated by reference; and, application Ser. No. 10/669,824 (supra) is a continuation-in-part of prior application Ser. No. 09/823,676, filed Mar. 30, 2001 (now U.S. Pat. No. 6,717,034, issued on Apr. 6, 2004), hereby incorporated by reference in its entirety; and 10/669,824 (supra) is a continuation-in-part of prior application Ser. No. 10/374,780, filed Feb. 25, 2003 (pending), hereby incorporated by reference in its entirety; and, application Ser. No. 10/669,824 (supra) is a continuation-in-part of prior application Ser. No. 10/412,699, filed Apr. 10, 2003 (pending), hereby incorporated by reference in its entirety, which is a continuation-in-part of prior application Ser. No. 09/713,994, filed Nov. 16, 2000 (abandoned), hereby incorporated by reference in its entirety; and, application Ser. No. 10/669,824 (supra) is a continuation-in-part of prior application Ser. No. 10/225,066 (pending), prior application Ser. No. 10/225,067 (pending), and prior application Ser. No. 10/225,068 (pending), all three of which were filed on Aug. 9, 2002, and all three hereby incorporated by reference in their entirety, and all three of which are continuations-in-part of prior application Ser. No. 09/837,944, filed Apr. 18, 2001 (abandoned), and prior application Ser. No. 10/171,468, filed Jun. 14, 2002 (abandoned), and all three of which claim the benefit of U.S. Provisional Application No. 60/336,049, filed Nov. 19, 2001 (expired), hereby incorporated by reference in its entirety, U.S. Provisional Application No. 60/310,847, filed Aug. 9, 2001 (expired), hereby incorporated by reference in its entirety, and U.S. Provisional Application No. 60/338,692, filed Dec. 11, 2001 (expired), hereby incorporated by reference in its entirety.

The claimed invention, in the field of functional genomics and the characterization of plant genes for the improvement of plants, was made by or on behalf of Mendel Biotechnology, Inc, and Monsanto Company as a result of activities undertaken within the scope of a joint research agreement, in effect on or before the date the claimed invention was made.

FIELD OF THE INVENTION

The present invention relates to increasing a plant's size or biomass, the yield that may be obtained from such a plant, and increasing tolerance to abiotic stresses including cold and osmotic stresses.

BACKGROUND OF THE INVENTION

Studies from a diversity of prokaryotic and eukaryotic organisms suggest a gradual evolution of biochemical and physiological mechanisms and metabolic pathways. Despite different evolutionary pressures, proteins that regulate the cell cycle in yeast, plant, nematode, fly, rat, and man have common chemical or structural features and modulate the same general cellular activity. A comparison of gene sequences with known structure and/or function from one plant species, for example, *Arabidopsis thaliana*, with those from other plants, allows researchers to develop models for manipulating a plant's traits and developing varieties with valuable properties.

A plant's traits may be controlled through a number of cellular processes. One important way to manipulate that control is through transcription factors proteins that influence the expression of a particular gene or sets of genes. Because transcription factors are key controlling elements of biological pathways, altering the expression levels of one or more transcription factors can change entire biological pathways in an organism. Strategies for manipulating a plant's biochemical, developmental, or phenotypic characteristics by altering a transcription factor expression can result in plants and crops with new and/or improved commercially valuable properties, including traits that improve yield under non-stressed conditions, or survival and yield during periods of abiotic stress. Examples of the latter include, for example, germination in cold conditions, and osmotic stresses such as desiccation, drought, excessive heat, and salt stress.

Desirability of increasing biomass. The ability to increase the biomass or size of a plant would have several important commercial applications. Crop species may be generated that produce larger cultivars, generating higher yield in, for example, plants in which the vegetative portion of the plant is edible.

Increased leaf size may be of particular interest. Increasing leaf biomass can be used to increase production of plant-derived pharmaceutical or industrial products. An increase in total plant photosynthesis is typically achieved by increasing leaf area of the plant. Additional photosynthetic capacity may be used to increase the yield derived from particular plant tissue, including the leaves, roots, fruits or seed, or permit the growth of a plant under decreased light intensity or under high light intensity.

Modification of the biomass of another tissue, such as root tissue, may be useful to improve a plant's ability to grow under harsh environmental conditions, including drought or nutrient deprivation, because larger roots may better reach water or nutrients or take up water or nutrients.

For some ornamental plants, the ability to provide larger varieties would be highly desirable. For many plants, including fruit-bearing trees, trees that are used for lumber production, or trees and shrubs that serve as view or wind screens, increased stature provides improved benefits in the forms of greater yield or improved screening.

Problems associated with drought. A drought is a period of abnormally dry weather that persists long enough to produce a serious hydrologic imbalance (for example crop damage, water supply shortage, etc.). In severe cases, drought can last for many years and have devastating effects on agriculture. Drought is the primary weather-related problem in agriculture and also ranks as one of the major natural disasters of all time, causing not only economic damage, but also loss of human lives. For example, losses from the US drought of 1988 exceeded $40 billion, exceeding those caused by Hurricane Andrew in 1992, the Mississippi River floods of 1993, and the San Francisco earthquake in 1989. The 1984-1985 drought in the Horn of Africa led to a famine that killed 750,000 people.

Problems for plants caused by low water availability include mechanical stresses caused by the withdrawal of cellular water. Drought also causes plants to become more susceptible to various diseases (Simpson (1981) in *Water Stress on Plants*, (Simpson, G. M., ed.), Praeger, N.Y., pp. 235-265). The most important factor in drought resistance is the ability of the plant to maintain high water status and turgidity, while maintaining carbon fixation. Various adaptive mechanisms influence this ability, including increasing root surface area or depth, osmotic adjustment, and the accumulation of hydrophilic proteins. ABA is also an essential regulatory component of many of these protective features.

Maintaining reproductive performance is another component of yield stability that has been studied in maize. Grain yield is known to be correlated with the kernel number per unit area rather than the weight per kernel. Yield losses in maize due to drought are particularly prevalent when the stress occurs at the transition from vegetative to reproductive growth. A consequence of the growth of maize under drought stress conditions is the delay in silking in relation to pollen shed, adversely affecting kernel set (Edmeades et al. (2000) in *Physiology and Modeling Kernel Set in Maize*, M. E. Westgate and K. J. Boote, eds (Crop Sci. Soc. America and Amer. Soc. Agron., Madison, Wis.) and reproductive performance. Kernel set is also adversely affected when the grain sink size exceeds the nitrogen uptake capacity from dry soil (Chapman and Edmeades (1999) *Crop Sci.* 39: 1315-1324). Varieties that were selected for improved yield under drought stress at flowering showed similar performance gains under conditions of low nitrogen, suggesting a common mechanism of tolerance to the two stresses (Beck et al. (1996) in 51st Annual Corn and Sorghum Research Conference, D. Wilkinson, ed (Chicago: ASTA), pp. 85-111; Banzinger et al. (1999) *Crop Sci.* 39: 1035-1040). When a drought stress occurs between flowering and seed fill of soybeans, total seed yield is reduced due to a reduction in branch growth and thus seed number per branch (Frederick et al. (2001) *Crop Sci.* 41: 759-763).

Physiological changes occurring in maize plants during drought include:
(a) accumulation of abscisic acid (ABA);
(b) inhibition of cell expansion, resulting in reduced leaf area, reduced silk growth, reduced stem elongation, and reduced root growth;
(c) inhibition of cell division resulting in reduced organ size;
(d) cellular osmotic adjustment (this is more apparent in sorghum and rice and less apparent in maize (Bolanos and Edmeades, 1991)); and
(e) accumulation of proline (during severe drought).

In addition to the many land regions of the world that are too arid for most, if not all, crop plants, overuse and overutilization of available water is resulting in an increasing loss of agriculturally-usable land, a process which, in the extreme, results in desertification. The problem is further compounded by increasing salt accumulation in soils, which adds to the loss of available water in soils.

Problems associated with high salt levels. One in five hectares of irrigated land is damaged by salt, an important historical factor in the decline of ancient agrarian societies. This condition is expected to worsen, further reducing the availability of arable land and crop production, since none of the top five food crops—wheat, corn, rice, potatoes, and soybean—can tolerate excessive salt.

Detrimental effects of salt on plants are a consequence of both water deficit resulting in osmotic stress (similar to drought stress) and the effects of excess sodium ions on critical biochemical processes. As with freezing and drought, high saline causes water deficit. The presence of high salt makes it difficult for plant roots to extract water from their environment (Buchanan et al. (2000) in *Biochemistry and Molecular Biology of Plants*, American Society of Plant Physiologists, Rockville, Md.). Soil salinity is thus one of the more important variables that determines where a plant may thrive. In many parts of the world, sizable land areas are uncultivable due to naturally high soil salinity. To compound the problem, salination of soils that are used for agricultural production is a significant and increasing problem in regions that rely heavily on agriculture. The latter is compounded by over-utilization, over-fertilization and water shortage, typically caused by climatic change and the demands of increasing population. Salt tolerance is of particular importance early in a plant's lifecycle, since evaporation from the soil surface causes upward water movement, and salt accumulates in the upper soil layer where the seeds are placed. Thus, germination normally takes place at a salt concentration much higher than the mean salt level in the whole soil profile.

Problems associated with excessive heat. Germination of many crops is very sensitive to temperature. A transcription factor that would enhance germination in hot conditions would be useful for crops that are planted late in the season or in hot climates. Seedlings and mature plants that are exposed to excess heat may experience heat shock, which may arise in various organs including leaves and particularly fruit, when transpiration is insufficient to overcome heat stress. Heat also damages cellular structures, including organelles and cytoskeleton, and impairs membrane function (Buchanan et al. (2000) supra).

Heat shock may produce a decrease in overall protein synthesis, accompanied by expression of heat shock proteins. Heat shock proteins function as chaperones and are involved in refolding proteins denatured by heat.

Heat stress often accompanies conditions of low water availability. Heat itself is seen as an interacting stress and adds to the detrimental effects caused by water deficit conditions. Evaporative demand exhibits near exponential increases with increases in daytime temperatures, and can result in high transpiration rates and low plant water potentials (Hall et al. (2000) *Plant Physiol.* 123: 1449-1458). High-temperature damage to pollen almost always occurs in conjunction with drought stress, and rarely occurs under well-watered conditions. It may be difficult to separate the effects of heat and drought stress on pollination and plant metabolism, and thus an understanding of the interaction between these and other stresses may be important when developing strategies to enhance stress tolerance by genetic manipulation.

Problems associated with excessive cold or chilling conditions. The term "chilling sensitivity" has been used to describe many types of physiological damage produced at low, but above freezing, temperatures. Most crops of tropical origins such as soybean, rice, maize and cotton are easily damaged by chilling. Typical cold damage includes wilting, necrosis, chlorosis or leakage of ions from cell membranes. The underlying mechanisms of chilling sensitivity are not completely understood yet, but probably involve the level of membrane saturation and other physiological deficiencies. For example, photoinhibition of photosynthesis (disruption of photosynthesis due to high light intensities) often occurs under clear atmospheric conditions subsequent to cold late summer/autumn nights. Chilling may lead to yield losses and lower product quality through the delayed ripening of maize. Another consequence of poor growth is the rather poor ground cover of maize fields in spring, often resulting in soil erosion, increased occurrence of weeds, and reduced uptake of nutrients. A retarded uptake of mineral nitrogen could also lead to increased losses of nitrate into the ground water. By some estimates, chilling accounts for monetary losses in the United States (US) behind only to drought and flooding.

Desirability of altered sugar sensing. Sugars are key regulatory molecules that affect diverse processes in higher plants including germination, growth, flowering, senescence, sugar metabolism and photosynthesis. Sucrose, for example, is the major transport form of photosynthate and its flux through cells has been shown to affect gene expression and alter storage compound accumulation in seeds (source-sink relationships). Glucose-specific hexose-sensing has also been described in plants and is implicated in cell division and repression of "famine" genes (photosynthetic or glyoxylate cycles).

Water deficit is a common component of many plant stresses. Water deficit occurs in plant cells when the whole plant transpiration rate exceeds the water uptake. In addition to drought, other stresses, such as salinity and low temperature, produce cellular dehydration (McCue and Hanson (1990) *Trends Biotechnol.* 8: 358-362).

Salt and drought stress signal transduction consist of ionic and osmotic homeostasis signaling pathways. The ionic aspect of salt stress is signaled via the SOS pathway where a calcium-responsive SOS3-SOS2 protein kinase complex controls the expression and activity of ion transporters such as SOS1. The pathway regulating ion homeostasis in response to salt stress has been reviewed recently by Xiong and Zhu (Xiong and Zhu (2002) *Plant Cell Environ.* 25: 131-139).

The osmotic component of salt stress involves complex plant reactions that overlap with drought and/or cold stress responses.

Common aspects of drought, cold and salt stress response have been reviewed recently by Xiong and Zhu (2002) supra. Those include:

(a) transient changes in the cytoplasmic calcium levels very early in the signaling event (Knight, (2000) *Int. Rev. Cytol.* 195: 269-324; Sanders et al. (1999) *Plant Cell* 11: 691-706);

(b) signal transduction via mitogen-activated and/or calcium dependent protein kinases (CDPKs; see Xiong and Zhu (2002) supra) and protein phosphatases (Merlot et al. (2001) *Plant J.* 25: 295-303; Tähtiharju and Palva (2001) *Plant J.* 26: 461-470);

(c) increases in ABA levels in response to stress triggering a subset of responses (Xiong and Zhu (2002) supra, and references therein);

(d) inositol phosphates as signal molecules (at least for a subset of the stress responsive transcriptional changes (Xiong et al. (2001) *Genes Dev.* 15: 1971-1984));

(e) activation of phospholipases which in turn generate a diverse array of second messenger molecules, some of which might regulate the activity of stress responsive kinases (phospholipase D functions in an ABA independent pathway, Frank et al. (2000) *Plant Cell* 12: 111-124);

(f) induction of late embryogenesis abundant (LEA) type genes including the CRT/DRE-containing COR/RD genes (Xiong and Zhu (2002) supra);

(g) increased levels of antioxidants and compatible osmolytes such as proline and soluble sugars (Hasegawa et al. (2000) *Annu. Rev. Plant Mol. Plant Physiol.* 51: 463-499);

(h) accumulation of reactive oxygen species such as superoxide, hydrogen peroxide, and hydroxyl radicals (Hasegawa et al. (2000) supra).

ABA biosynthesis is regulated by osmotic stress at multiple steps. Both ABA-dependent and ABA-independent osmotic stress signaling first modify constitutively expressed transcription factors, leading to the expression of early response transcriptional activators, which then activate downstream stress tolerance effector genes.

Based on the commonality of many aspects of cold, drought and salt stress responses, it can be concluded that genes that increase tolerance to cold or salt stress can also improve drought stress protection. In fact, this has already been demonstrated for transcription factors (in the case of AtCBF/DREB1) and for other genes such as OsCDPK7 (Saijo et al. (2000) *Plant J.* 23: 319-327), or AVP1 (a vacuolar pyrophosphatase-proton-pump; Gaxiola et al. (2001) *Proc. Natl. Acad. Sci. USA* 98: 11444-11449).

The present invention relates to methods and compositions for producing transgenic plants with modified traits, particularly traits that address agricultural and food needs. These traits, including increased biomass, altered sugar sensing, and tolerance to abiotic stress, may provide significant value in that greater yield may be achieved, and/or the plant can then thrive in hostile environments, where, for example, high or low temperature, low water availability or high salinity may limit or prevent growth of non-transgenic plants.

We have identified polynucleotides encoding transcription factors, including G1073 (atHRC1), and equivalogs in the G1073 clade of transcription factor polypeptides, developed numerous transgenic plants using these polynucleotides, and have analyzed the plants for their biomass and tolerance to abiotic stresses. In so doing, we have identified important polynucleotide and polypeptide sequences for producing commercially valuable plants and crops as well as the methods for making them and using them. Other aspects and embodiments of the invention are described below and can be derived from the teachings of this disclosure as a whole.

SUMMARY OF THE INVENTION

The invention pertains to a method for increasing a plant's biomass and tolerance to abiotic stresses. This is accomplished by providing a vector, plasmid or other nucleic acid construct that contains a transcription factor polynucleotide and regulatory elements for transcriptional regulation of the polynucleotide. The polynucleotide is a sequence that encodes a member of the G1073 clade of transcription factor polypeptides, which are derived from a common polypeptide ancestor (FIG. 4), and which comprise an AT-hook domain and a second conserved domain. The G1073 clade member sequences that have been successfully used to confer increased tolerance to abiotic stress derive from a number of diverse species, including dicots such as *Arabidopsis* and soy, and monocots such as rice. The G1073 clade member polypeptides comprise an AT-hook domain and a second conserved domain, which in turn comprise the sequences SEQ ID NO: 79 (in the At-hook domain) and either SEQ ID NO: 80 or SEQ ID NO: 81 (in the second conserved domain). The vector, plasmid or nucleic acid construct may also contain a regulatory element. This may be a constitutive, inducible or tissue-specific promoter that controls expression of the polynucleotide sequence. The vector, plasmid or nucleic acid construct is then introduced into a target plant (a plant that has not yet been transformed with the vector, plasmid or nucleic acid construct), thus transforming the plant into one that has increased biomass and/or tolerance to an abiotic stress, relative to control plants. Inducible promoters may include, for example, the DREB2A and RD29A promoters. The RD29A promoter has been successfully used to regulate expression of the G1073 polynucleotide and confer increased abiotic stress tolerance. Examples of tissue-specific promoters that have been used in this manner include the ARSK1 (root specific) promoter, the CUT1 (epidermis-specific) promoter, the RBSC3 (leaf specific) promoter, and the SUC2 (vascular specific) promoter. Use of tissue-specific or inducible promoters mitigates undesirable morphological effects that may be associated with constitutive overexpression of G1073 clade members (e.g., when increased size is undesirable).

The method also pertains to increasing a plant's biomass and/or tolerance to abiotic stress with a multiple vector approach. In this case, a first vector that comprises a promoter cloned in front of a LexA DNA binding domain fused to a GAL4 activation domain is introduced into the plant. A second vector is then introduced into the same plant; this second vector comprises a polynucleotide sequence encoding a G1073 polypeptide clade member. The plant is then allowed to overexpress the G1073 member polypeptide, which increases the plant's biomass and/or tolerance to abiotic stress. The promoter cloned in front of a LexA DNA binding domain may be, for example, the RD29A promoter, although other promoters that function in a similar capacity and that may be expressed in an inducible or tissue-specific manner are readily envisioned and also encompassed by the present invention.

The methods encompassed by the invention may also be extended to propagation techniques used to generate plants. For example, a target plant that has been transformed with a polynucleotide encoding a G1073 polypeptide clade member and that has greater biomass and/or abiotic stress tolerance than to a wild-type or non-transformed control may be "selfed" (i.e., self-pollinated) or crossed with another plant to produce seed. Progeny plants may be grown from this seed, thus generating transformed progeny plants with increased tolerance to abiotic stress than control plants.

Transgenic plants (and seed from these transgenic plants) produced by the present methods are also encompassed by the invention.

BRIEF DESCRIPTION OF THE SEQUENCE LISTING AND DRAWINGS

The Sequence Listing provides exemplary polynucleotide and polypeptide sequences of the invention. The traits associated with the use of the sequences are included in the Examples.

CD-ROM1 and CD-ROM2 are read-only memory computer-readable compact discs. Each contains a copy of the Sequence Listing in ASCII text format. The Sequence Listing is named "MBI0068CIP.ST25.txt", the Sequence Listing was created on Jun. 15, 2004, and is 167 kilobytes in size. The copies of the Sequence Listing on the CD-ROM discs are hereby incorporated by reference in their entirety.

FIG. 1 shows a conservative estimate of phylogenetic relationships among the orders of flowering plants (modified from Angiosperm Phylogeny Group (1998) *Ann. Missouri Bot. Gard.* 84: 1-49). Those plants with a single cotyledon (monocots) are a monophyletic clade nested within at least two major lineages of dicots; the eudicots are further divided into rosids and asterids. *Arabidopsis* is a rosid eudicot classified within the order Brassicales; rice is a member of the monocot order Poales. FIG. 1 was adapted from Daly et al. (2001) *Plant Physiol.* 127: 1328-1333.

Figure 2:
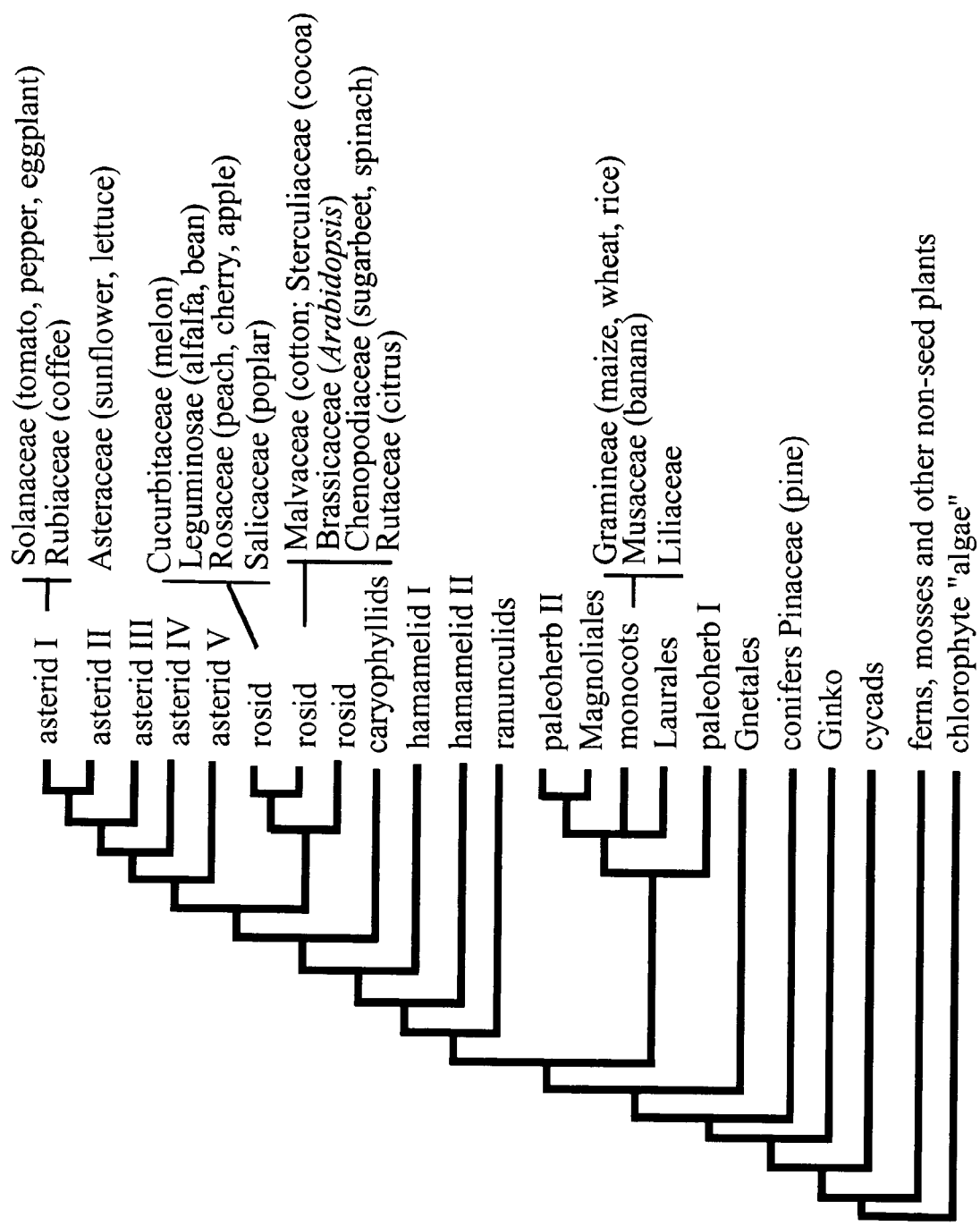

FIG. 2 shows a phylogenic dendogram depicting phylogenetic relationships of higher plant taxa, including clades containing tomato and *Arabidopsis*; adapted from Ku et al. (2000) *Proc. Natl. Acad. Sci. USA* 97: 9121-9126; and Chase et al. (1993) *Ann. Missouri Bot. Gard.* 80: 528-580.

Figure 3:
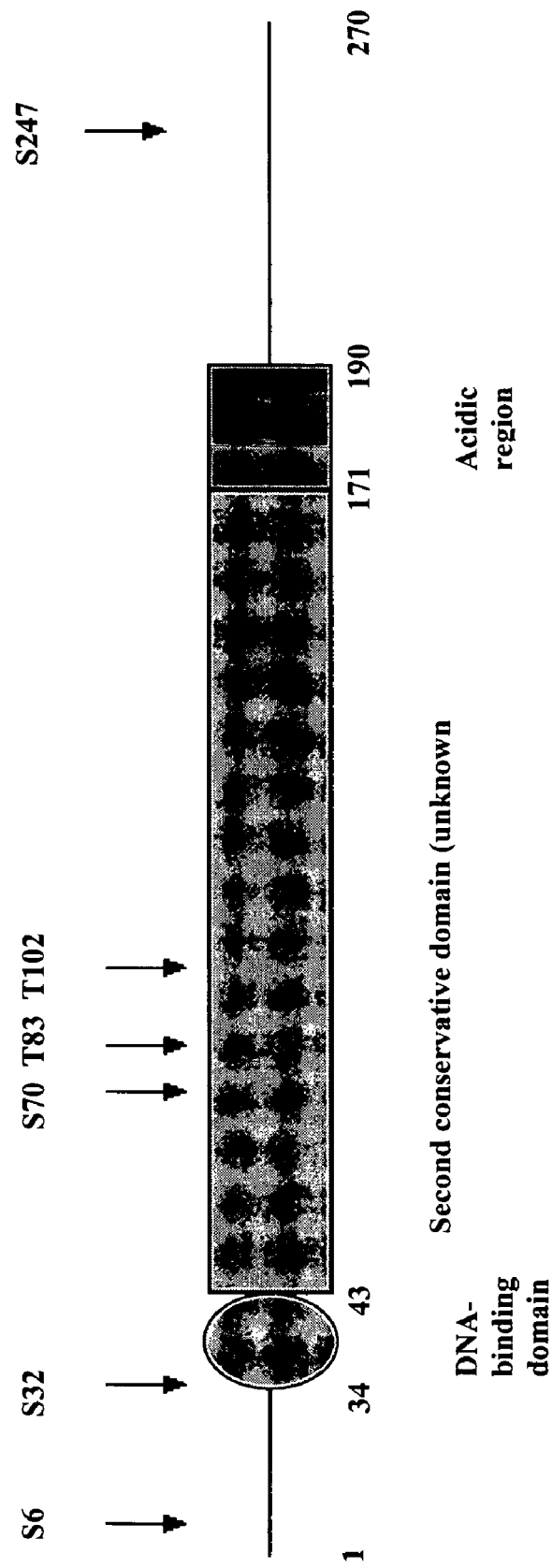

FIG. 3 depicts the domain structure of AT-hook proteins, represented by a schematic representation of the G1073 (AtHRC1) protein. Arrows indicate potential CK2 and PKC phosphorylation sites. A conservative DNA binding domain is located at positions 34 through 42.

Figure 4:
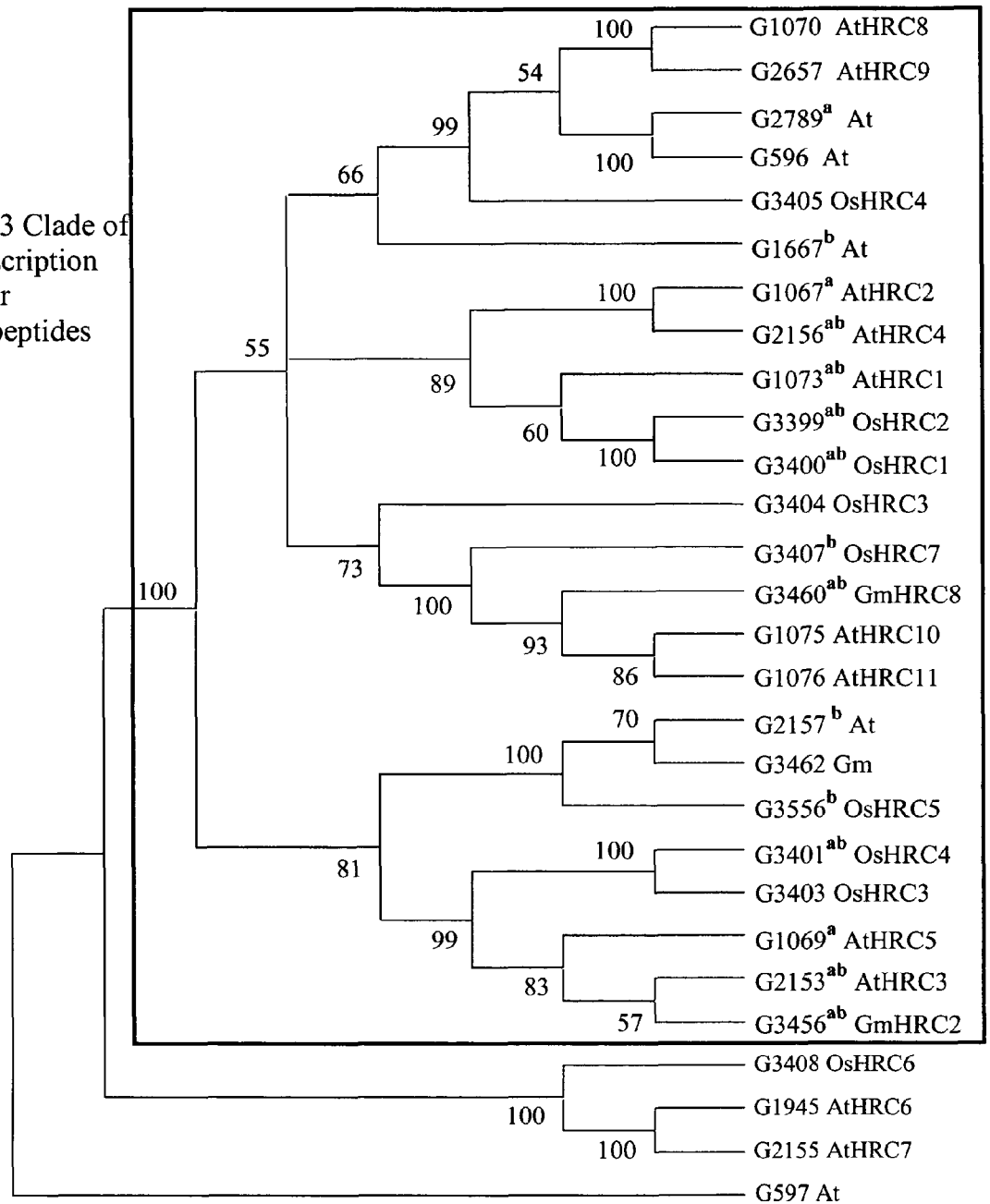

FIG. 4 shows crop orthologs that were identified through BLAST analysis of proprietary and public data sources. A phylogeny tree was then generated using ClustalX based on whole protein sequences. Sequences that are annotated with a "GID" number" beginning with capital letter "G" followed by "At" refer to *Arabidopsis* sequences; sequences with "Gm" are soy sequences, and "Os" are rice sequences. A representative number of G1073 clade members confer advantageous properties to plants when overexpressed; sequences that appear with a superscript "a" have been shown to confer increased tolerance to abiotic stress increased, and sequences that appear with a superscript "b" have been shown to confer increased biomass. Many of the remaining sequences have not yet been tested in overexpressing plants. Several G1073 clade member sequences that have also been shown to confer abiotic stress in plants are not shown in FIG. 4, but are disclosed in Example VIII.

In FIGS. 5A-5H, the alignments of a number of AT-hook proteins identified in FIG. 4 are shown, and include Glade members from *Arabidopsis* (G1067, G1069, G1073, G1667, G2153, G2156, G2789), soy G3456, G3459, G3460), and rice (G3399, G3400, G3401, G3407) that have been shown to confer similar traits in plants when overexpressed the G1073 clade of transcription factor polypeptides is indicated by the large box). Also shown are the AT-hook conserved domains (FIG. 5C) and the second conserved domains spanning FIGS. 5D through 5F).

Figure 6B:
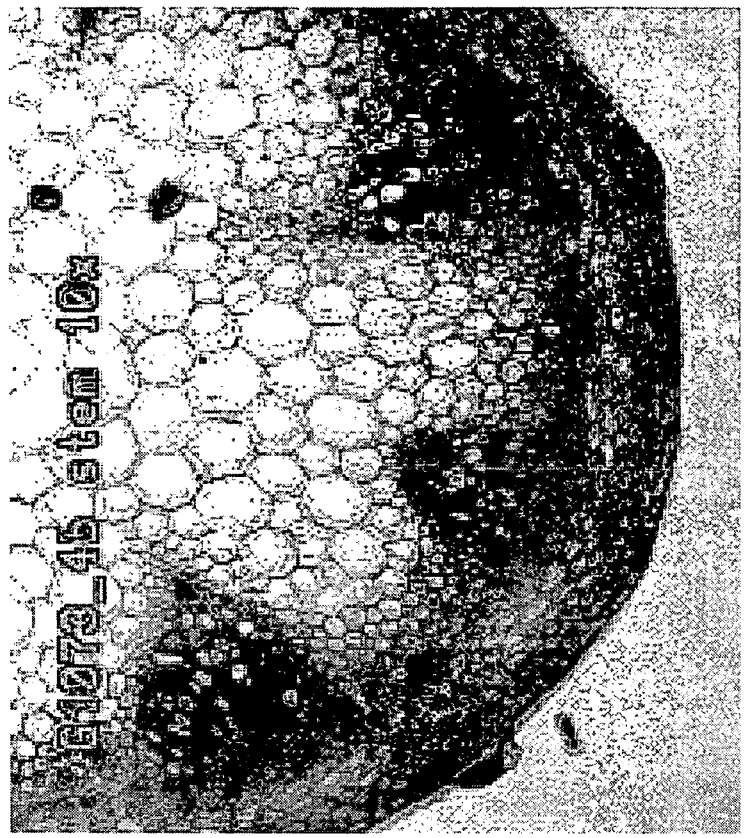
Figure 6A:

FIGS. 6A and 6B show wild-type (left) and G1073-overexpressing (right) *Arabidopsis* stem cross-sections. In the stem from the G1073-overexpressing plant, the vascular bundles are larger (containing more cells in the phloem and xylem areas) and the cells of the cortex are enlarged.

Figure 7A:
Figure 7B:
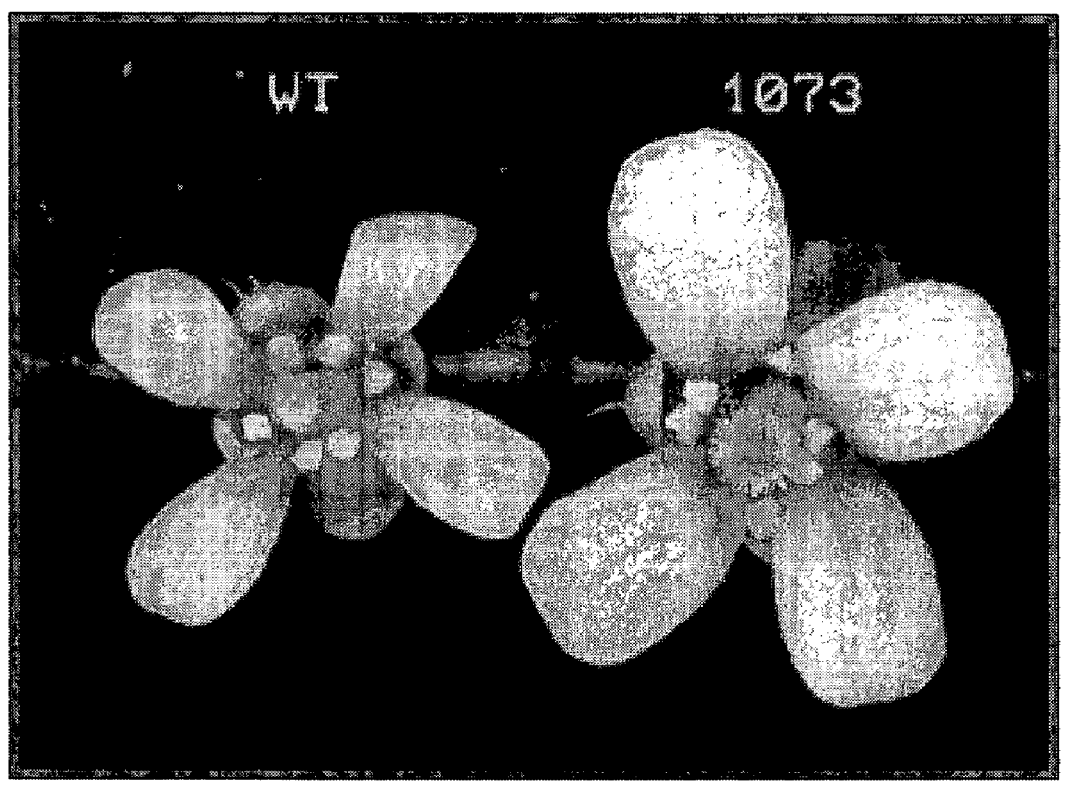

Many *Arabidopsis* plants that overexpress G1073 (FIG. 7A, example on right) are larger than wild-type control plants (FIG. 7A, left). This distinction also holds true for the floral organs, which, as seen in FIG. 7B, are significantly larger in the G1073-overexpressing plant on the right than in that from the wild-type plant on the left.

Figure 8:
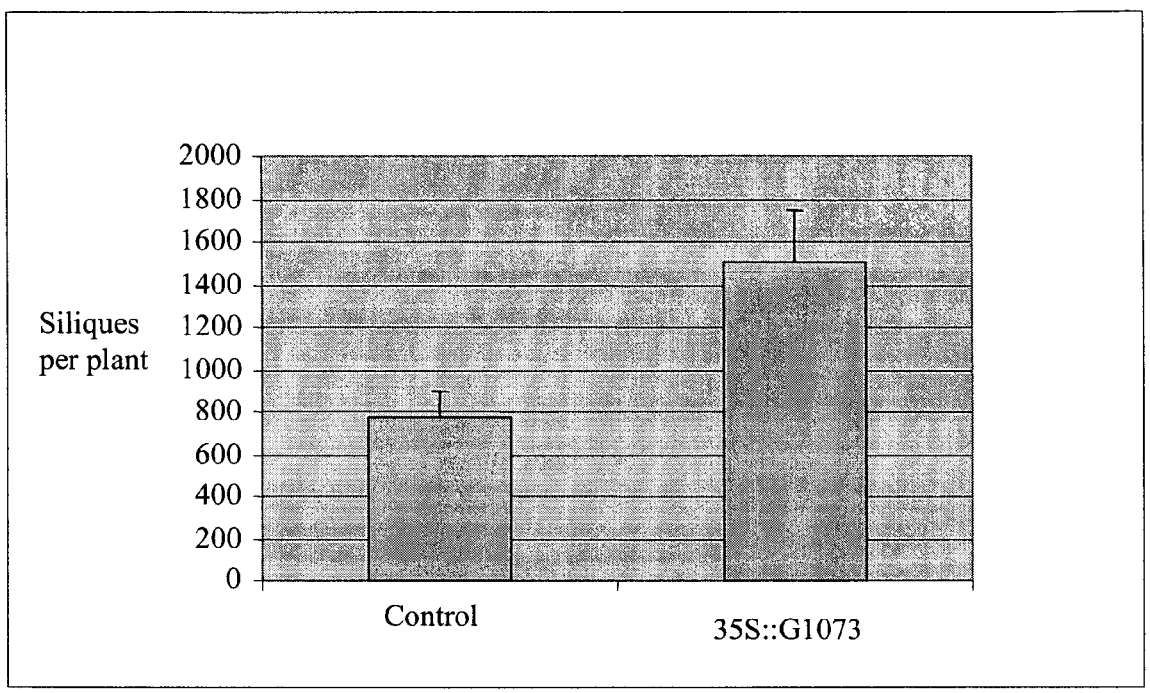

FIG. 8 is a graph comparing silique number in control (wild type) and 35S::G1073 plants indicating how seed number is associated with the increased number of siliques per plant seen in the overexpressing lines.

Figure 9A:
Figure 9B:

As seen in FIGS. 9A and 9B, G1073 functions in both soybean and tomato to increase biomass. In FIG. 9A, the larger soybean plant on the right is overexpressing G1073. Tomato leaves of a number of G1073 overexpressor lines were much larger than those of wild-type tomato plants, as seen in FIG. 9B by comparing the leaves of the overexpressor plant on the left and that from a wild-type plant on the right.

Figure 10A:
Figure 10B:
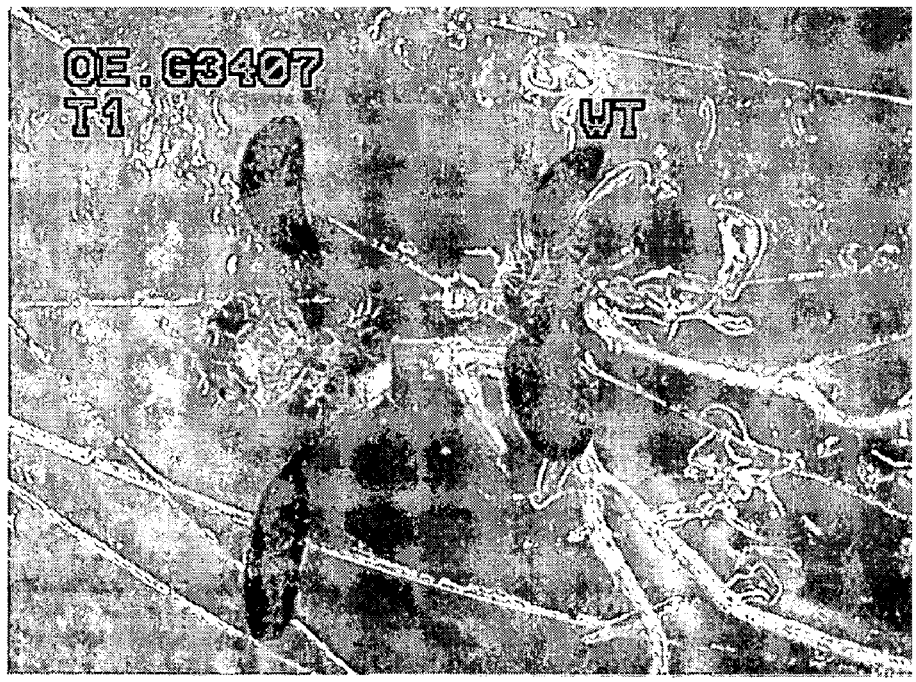

FIG. 10A is a photograph of an *Arabidopsis* plant overexpressing the monocot gene G3399, a rice ortholog of G1073. The phenotype of increased size and mass is the same as the phenotype conferred by *Arabidopsis* G1073 and its paralog sequences G1067, G2153 and G2157. FIG. 10B similarly shows the effects of another rice ortholog, G3407, at seven days. The overexpressor on the left is approximately 50% larger than the control plant on the right.

Figure 11:
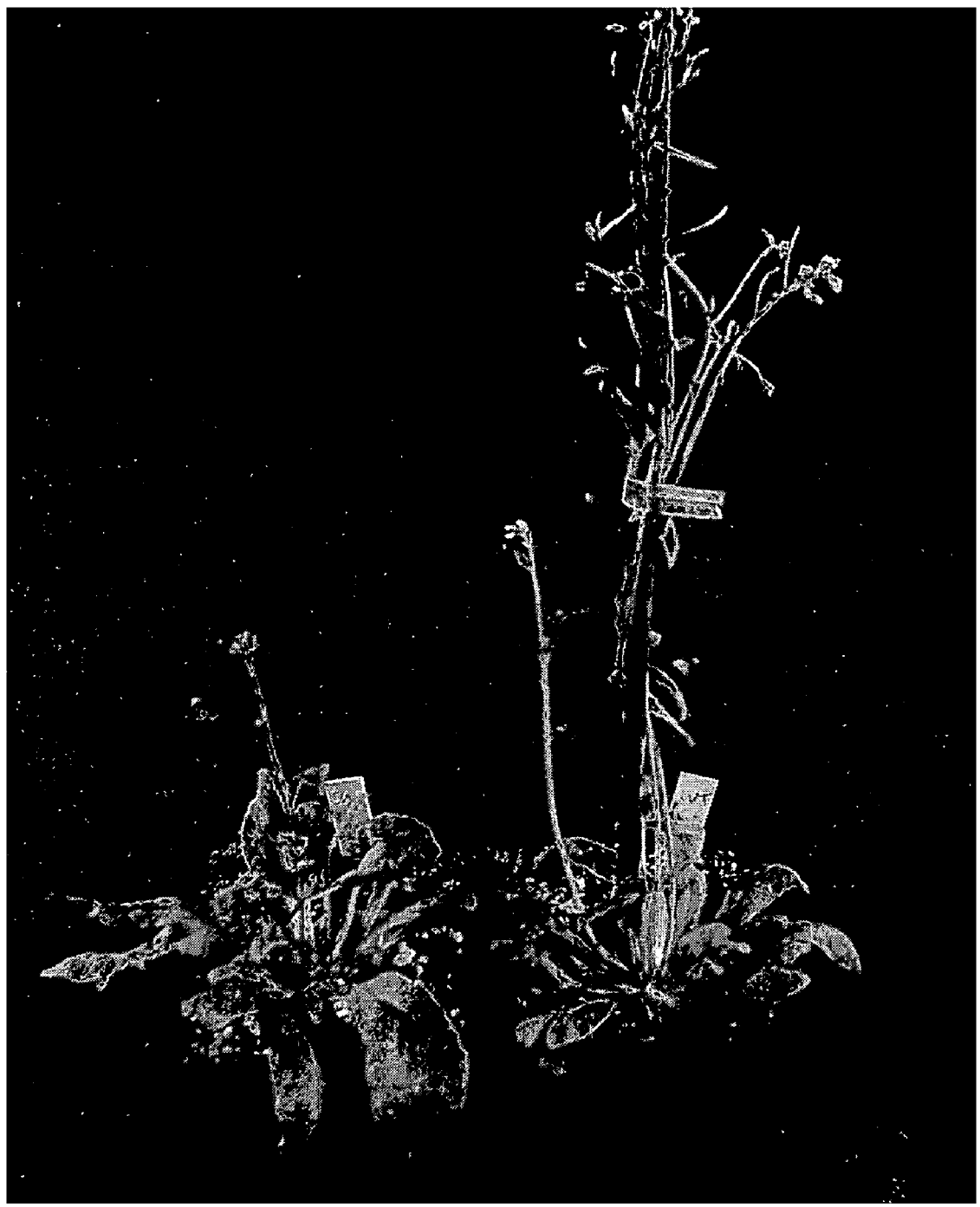

FIG. 11 shows the effects of overexpression of G3460, a soy ortholog of G1073, on plant morphology. Thirty-eight days after planting, the overexpressor on the left has significantly broader and more massive leaves than the control plant on the right. The overexpressor also demonstrates late development, a characteristic also seen when G1073 or its paralogs are overexpressed.

Figure 12:
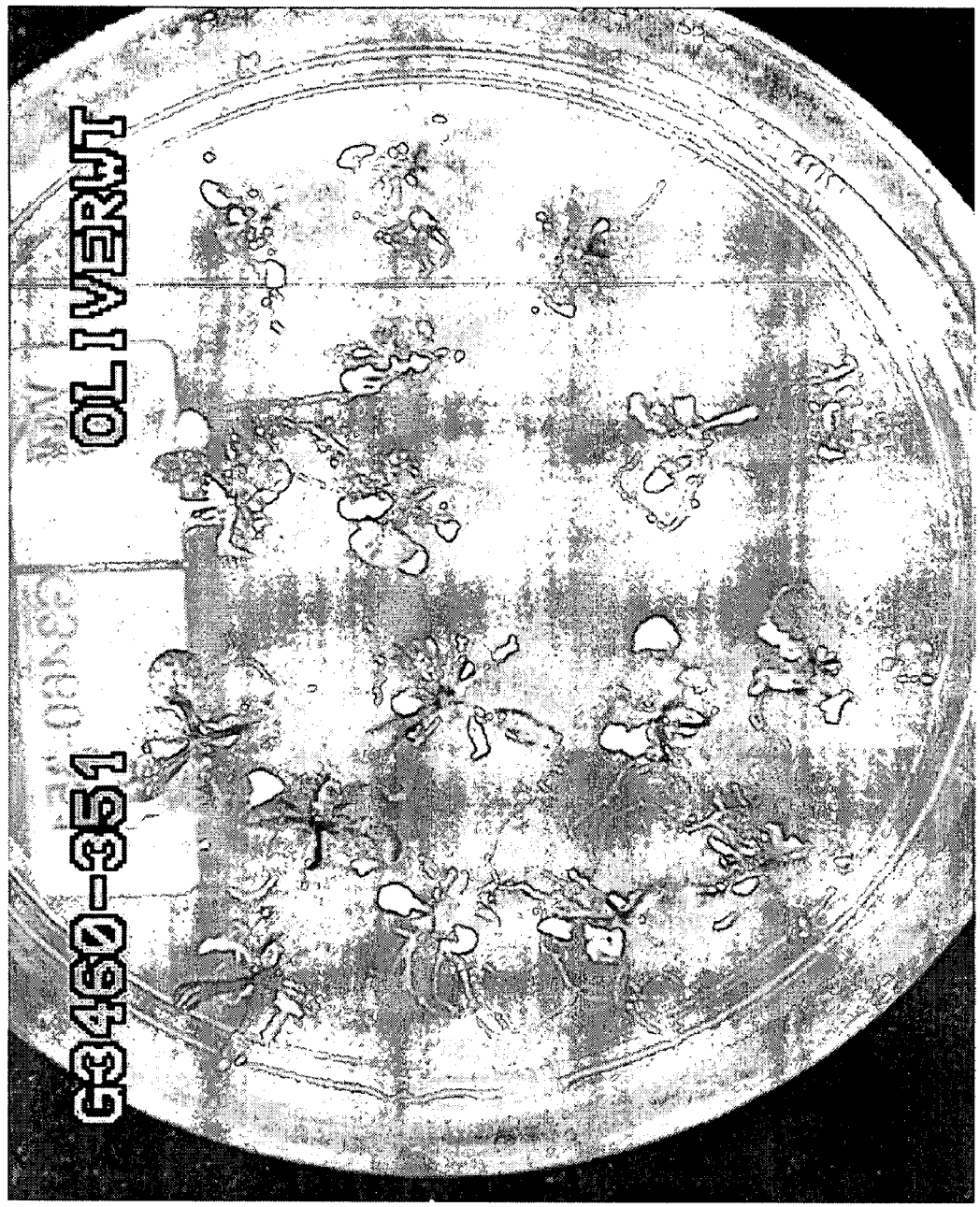

FIG. 12 shows the effects of overexpression of G3460, a soy ortholog of G1073, in *Arabidopsis* plants subjected to a plate-based desiccation assay. The seedlings overexpressing G3460 are more tolerant to the desiccation treatment, as evidenced by the larger size, greater root mass, and greener color of the plants on the left than the control plants on the right.

DETAILED DESCRIPTION

The present invention relates to polynucleotides and polypeptides for modifying phenotypes of plants, particularly those associated with increased biomass and/or abiotic stress tolerance. Throughout this disclosure, various information sources are referred to and/or are specifically incorporated. The information sources include scientific journal articles, patent documents, textbooks, and World Wide Web browser-inactive page addresses. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the invention.

As used herein and in the appended claims, the singular forms "a", "an", and "the" include the plural reference unless the context clearly dictates otherwise. Thus, for example, a reference to "a host cell" includes a plurality of such host cells, and a reference to "a stress" is a reference to one or more stresses and equivalents thereof known to those skilled in the art, and so forth.

Definitions

"Nucleic acid molecule" refers to an oligonucleotide, polynucleotide or any fragment thereof. It may be DNA or RNA of genomic or synthetic origin, double-stranded or single-stranded, and combined with carbohydrate, lipids, protein, or other materials to perform a particular activity such as transformation or form a useful composition such as a peptide nucleic acid (PNA).

"Polynucleotide" is a nucleic acid molecule comprising a plurality of polymerized nucleotides, e.g., at least about 15 consecutive polymerized nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single-stranded or double-stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single-stranded.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found with an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and that may be used to determine the limits of the genetically active unit (Rieger et al. (1976) *Glossary of Genetics and Cytogenetics; Classical and Molecular.* 4th ed., Springer Verlag, Berlin). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

An "isolated polynucleotide" is a polynucleotide, whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

A "polypeptide" is an amino acid sequence comprising a plurality of consecutive polymerized amino acid residues e.g., at least about 15 consecutive polymerized amino acid residues. In many instances, a polypeptide comprises a polymerized amino acid residue sequence that is a transcription factor or a domain or portion or fragment thereof. Additionally, the polypeptide may comprise: (i) a localization domain; (ii) an activation domain; (iii) a repression domain; (iv) an oligomerization domain; (v) a DNA-binding domain; or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide or portions thereof whether naturally occurring or synthetic.

"Portion", as used herein, refers to any part of a protein used for any purpose, but especially for the screening of a library of molecules which specifically bind to that portion or for the production of antibodies.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value therebetween. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical, matching or corresponding nucleotides at positions shared by the polynucleotide sequences. A degree of identity of polypeptide sequences is a function of the number of identical amino acids at corresponding positions shared by the polypeptide sequences. A degree of homology or similarity of polypeptide sequences is a function of the number of amino acids at corresponding positions shared by the polypeptide sequences.

"Alignment" refers to a number of nucleotide bases or amino acid residue sequences aligned by lengthwise comparison so that components in common (i.e., nucleotide bases or amino acid residues at corresponding positions) may be visually and readily identified. The fraction or percentage of components in common is related to the homology or identity between the sequences. Alignments such as those of FIGS. 5A-5H may be used to identify conserved domains and relatedness within these domains. An alignment may suitably be determined by means of computer programs known in the art, such as MACVECTOR software (1999) (Accelrys, Inc., San Diego, Calif.).

A "conserved domain" or "conserved region" as used herein refers to a region in heterologous polynucleotide or polypeptide sequences where there is a relatively high degree of sequence identity between the distinct sequences. An "AT-hook" domain", such as is found in a polypeptide member of AT-hook transcription factor family, is an example of a conserved domain. With respect to polynucleotides encoding presently disclosed transcription factors, a conserved domain is preferably at least nine base pairs (bp) in length. A "conserved domain", with respect to presently disclosed AT-hook polypeptides refers to a domain within a transcription factor family that exhibits a higher degree of sequence homology, such as at least about 62% sequence identity including conservative substitutions, or at least about 63%, or at least about 65%, or at least about 67%, or at least about 68%, or at least about 69%, or at least about 71%, or at least about 78%, %, or at least about 89% amino acid residue sequence identity to the conserved domain. Sequences that possess or encode for conserved domains that meet these criteria of percentage identity, and that have comparable biological activity to the present transcription factor sequences, thus being members of the G1073 clade of transcription factor polypeptides, are encompassed by the invention. A fragment or domain can be referred to as outside a conserved domain, outside a consensus sequence, or outside a consensus DNA-binding site that is known to exist or that exists for a particular transcription factor class, family, or sub-family. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

As one of ordinary skill in the art recognizes, conserved domains may be identified as regions or domains of identity to a specific consensus sequence (see, for example, Riechmann et al. (2000) *Science* 290: 2105-2110). Thus, by using alignment methods well known in the art, the conserved domains of the plant transcription factors for the AT-hook proteins (Reeves and Beckerbauer (2001) *Biochim. Biophys. Acta* 1519: 13-29; and Reeves (2001) *Gene* 277: 63-81) may be determined.

The conserved domains for SEQ ID NO: 2, 4, 6, 8, 10, 12, 14, 16, 18, 26, 30, 38, 40, 42, 84 and 86 are listed in Table 1. Also, the polypeptides of Table 1 have AT-hook and second conserved domains specifically indicated by start and stop sites. A comparison of the regions of the polypeptides in SEQ ID NO: 2, 4, 6, 8, 10, 12, 14, 16, 18, 26, 30, 38, 40 and 42 allows one of skill in the art (see, for example, Reeves and Nisson (1995) *Biol. Chem.* 265: 8573-8582) to identify AT-hook domains or conserved domains for any of the polypeptides listed or referred to in this disclosure.

"Complementary" refers to the natural hydrogen bonding by base pairing between purines and pyrimidines. For example, the sequence A-C-G-T (5'->3') forms hydrogen bonds with its complements A-C-G-T (5'->3') or A-C-G-U (5'->3'). Two single-stranded molecules may be considered partially complementary, if only some of the nucleotides bond, or "completely complementary" if all of the nucleotides bond. The degree of complementarity between nucleic acid strands affects the efficiency and strength of hybridization and amplification reactions. "Fully complementary" refers to the case where bonding occurs between every base pair and its complement in a pair of sequences, and the two sequences have the same number of nucleotides.

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the polynucleotides of the present invention may be, for example, variants of the disclosed polynucleotide sequences, including allelic or splice variants, or sequences that encode orthologs or paralogs of presently disclosed polypeptides. Nucleic acid hybridization methods are disclosed in detail by Kashima et al. (1985) *Nature* 313:402-404, Sambrook et al. (1989) *Molecular Cloning: A Laboratory Manual,* 2nd Ed., Cold Spring Harbor Laboratory, Cold Spring Harbor, N.Y. ("Sambrook"), and by Haymes et al. "*Nucleic Acid Hybridization: A Practical Approach*", IRL Press, Washington, D.C. (1985), which references are incorporated herein by reference.

In general, stringency is determined by the temperature, ionic strength, and concentration of denaturing agents (e.g., formamide) used in a hybridization and washing procedure (for a more detailed description of establishing and determining stringency, see the section "Identifying Polynucleotides or Nucleic Acids by Hybridization", below). The degree to which two nucleic acids hybridize under various conditions of stringency is correlated with the extent of their similarity. Thus, similar nucleic acid sequences from a variety of sources, such as within a plant's genome (as in the case of paralogs) or from another plant (as in the case of orthologs) that may perform similar functions can be isolated on the basis of their ability to hybridize with known transcription factor sequences. Numerous variations are possible in the conditions and means by which nucleic acid hybridization can be performed to isolate transcription factor sequences having similarity to transcription factor sequences known in the art and are not limited to those explicitly disclosed herein. Such an approach may be used to isolate polynucleotide sequences having various degrees of similarity with disclosed transcription factor sequences, such as, for example, encoded transcription factors having 62% or greater identity with the AT-hook domain of disclosed transcription factors.

The terms "paralog" and "ortholog" are defined below in the section entitled "Orthologs and Paralogs". In brief, orthologs and paralogs are evolutionarily related genes that have similar sequences and functions. Orthologs are structurally related genes in different species that are derived by a speciation event. Paralogs are structurally related genes within a single species that are derived by a duplication event.

The term "equivalog" describes members of a set of homologous proteins that are conserved with respect to function since their last common ancestor. Related proteins are grouped into equivalog families, and otherwise into protein families with other hierarchically defined homology types. This definition is provided at the Institute for Genomic Research (TIGR) World Wide Web (www) website, "tigr.org" under the heading "Terms associated with TIGRFAMs".

The term "variant", as used herein, may refer to polynucleotides or polypeptides, that differ from the presently disclosed polynucleotides or polypeptides, respectively, in sequence from each other, and as set forth below.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations may result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Also within the scope of the invention is a variant of a transcription factor nucleic acid listed in the Sequence Listing, that is, one having a sequence that differs from the one of the polynucleotide sequences in the Sequence Listing, or a complementary sequence, that encodes a functionally equivalent polypeptide (i.e., a polypeptide having some degree of equivalent or similar biological activity) but differs in sequence from the sequence in the Sequence Listing, due to degeneracy in the genetic code. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide.

"Allelic variant" or "polynucleotide allelic variant" refers to any of two or more alternative forms of a gene occupying the same chromosomal locus. Allelic variation arises naturally through mutation, and may result in phenotypic polymorphism within populations. Gene mutations may be "silent" or may encode polypeptides having altered amino acid sequence. "Allelic variant" and "polypeptide allelic variant" may also be used with respect to polypeptides, and in this case the term refer to a polypeptide encoded by an allelic variant of a gene.

"Splice variant" or "polynucleotide splice variant" as used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. Thus, splice variants may encode polypeptides having different amino acid sequences, which may or may not have similar functions in the organism. "Splice variant" or "polypeptide splice variant" may also refer to a polypeptide encoded by a splice variant of a transcribed mRNA.

As used herein, "polynucleotide variants" may also refer to polynucleotide sequences that encode paralogs and orthologs of the presently disclosed polypeptide sequences. "Polypeptide variants" may refer to polypeptide sequences that are paralogs and orthologs of the presently disclosed polypeptide sequences.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in a functionally equivalent transcription factor. Thus, it will be readily appreciated by those of skill in the art, that any of a variety of polynucleotide sequences is capable of encoding the transcription factors and transcription factor homolog polypeptides of the invention. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as a significant amount of the functional or biological activity of the transcription factor is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine (for more detail on conservative substitutions, see Table 3). More rarely, a variant may have "non-conservative" changes, e.g., replacement of a glycine with a tryptophan. Similar minor variations may also include amino acid deletions or insertions, or both. Related polypeptides may comprise, for example, additions and/or deletions of one or more N-linked or O-linked glycosylation sites, or an addition and/or a deletion of one or more cysteine residues. Guidance in determining which and how many amino acid residues may be substituted, inserted or deleted without abolishing functional or biological activity may be found using computer programs well known in the art, for example, DNASTAR software (see U.S. Pat. No. 5,840,544).

"Fragment", with respect to a polynucleotide, refers to a clone or any part of a polynucleotide molecule that retains a usable, functional characteristic. Useful fragments include oligonucleotides and polynucleotides that may be used in hybridization or amplification technologies or in the regulation of replication, transcription or translation. A polynucleotide fragment" refers to any subsequence of a polynucleotide, typically, of at least about 9 consecutive nucleotides, preferably at least about 30 nucleotides, more preferably at least about 50 nucleotides, of any of the sequences provided herein. Exemplary polynucleotide fragments are the first sixty consecutive nucleotides of the transcription factor polynucleotides listed in the Sequence Listing. Exemplary fragments also include fragments that comprise a region that encodes an AT-hook domain of a transcription factor. Exemplary fragments also include fragments that comprise a conserved domain of a transcription factor. Exemplary fragments include fragments that comprise an AT-hook or second conserved domain of an AT-hook transcription factor, for example, amino acid residues 34-42 and 73-175 of G1073 (AtHRC1; SEQ ID NO: 2), as noted in Table 1.

Fragments may also include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, but are preferably at least about 30 amino acid residues in length and more preferably at least about 60 amino acid residues in length.

The invention also encompasses production of DNA sequences that encode transcription factors and transcription factor derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding transcription factors or any fragment thereof.

"Derivative" refers to the chemical modification of a nucleic acid molecule or amino acid sequence. Chemical modifications can include replacement of hydrogen by an alkyl, acyl, or amino group or glycosylation, pegylation, or any similar process that retains or enhances biological activity or lifespan of the molecule or sequence.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae (see for example, FIG. 1, adapted from Daly et al. (2001) *Plant Physiol.* 127: 1328-1333; FIG. 2, adapted from Ku et al. (2000) *Proc. Natl. Acad. Sci. USA* 97: 9121-9126; and see also Tudge in *The Variety of Life*, Oxford University Press, New York, N.Y. (2000) pp. 547-606).

A "transgenic plant" refers to a plant that contains genetic material not found in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding sequence operably linked (i.e., under regulatory control of) to appropriate inducible or constitutive regulatory sequences that allow for the controlled expression of polypeptide. The expression cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which a transcription factor expression is altered, e.g., in that it has been knocked out, overexpressed, or ectopically expressed.

A "control plant" as used in the present invention refers to a plant cell, seed, plant component, plant tissue, plant organ or whole plant used to compare against transgenic or genetically modified plant for the purpose of identifying an enhanced phenotype in the transgenic or genetically modified plant. A control plant may in some cases be a transgenic plant line that comprises an empty vector or marker gene, but does not contain the recombinant polynucleotide of the present invention that is expressed in the transgenic or genetically modified plant being evaluated. In general, a control plant is a plant of the same line or variety as the transgenic or genetically modified plant being tested. A suitable control plant would include a genetically unaltered or non-transgenic plant of the parental line used to generate a transgenic plant herein.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, e.g., by employing Northern analysis, RT-PCR, microarray gene expression assays, or reporter gene expression systems, or by agricultural observations such as osmotic stress tolerance or yield. Any technique can be used to measure the amount of, comparative level of, or difference in any selected chemical compound or macromolecule in the transgenic plants, however.

"Trait modification" refers to a detectable difference in a characteristic in a plant ectopically expressing a polynucleotide or polypeptide of the present invention relative to a plant not doing so, such as a wild-type plant. In some cases, the trait modification can be evaluated quantitatively. For example, the trait modification can entail at least about a 2% increase or decrease, or an even greater difference, in an observed trait as compared with a control or wild-type plant. It is known that there can be a natural variation in the modified trait. Therefore, the trait modification observed entails a change of the normal distribution and magnitude of the trait in the plants as compared to control or wild-type plants.

When two or more plants have "similar morphologies", "substantially similar morphologies", "a morphology that is substantially similar", or are "morphologically similar", the plants have comparable forms or appearances, including analogous features such as overall dimensions, height, width, mass, root mass, shape, glossiness, color, stem diameter, leaf size, leaf dimension, leaf density, internode distance, branching, root branching, number and form of inflorescences, and other macroscopic characteristics, and the individual plants are not readily distinguishable based on morphological characteristics alone.

"Modulates" refers to a change in activity (biological, chemical, or immunological) or lifespan resulting from specific binding between a molecule and either a nucleic acid molecule or a protein.

The term "transcript profile" refers to the expression levels of a set of genes in a cell in a particular state, particularly by comparison with the expression levels of that same set of genes in a cell of the same type in a reference state. For example, the transcript profile of a particular transcription factor in a suspension cell is the expression levels of a set of genes in a cell knocking out or overexpressing that transcription factor compared with the expression levels of that same set of genes in a suspension cell that has normal levels of that transcription factor. The transcript profile can be presented as a list of those genes whose expression level is significantly different between the two treatments, and the difference ratios. Differences and similarities between expression levels may also be evaluated and calculated using statistical and clustering methods.

"Ectopic expression or altered expression" in reference to a polynucleotide indicates that the pattern of expression in, e.g., a transgenic plant or plant tissue, is different from the expression pattern in a wild-type plant or a reference plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more transcription factors are under the control of a strong promoter (e.g., the cauliflower mosaic virus 35S transcription initiation region). Overexpression may also under the control of an inducible or tissue specific promoter. Thus, overexpression may occur throughout a plant, in specific tissues of the plant, or in the presence or absence of particular environmental signals, depending on the promoter used.

Overexpression may take place in plant cells normally lacking expression of polypeptides functionally equivalent or identical to the present transcription factors. Overexpression may also occur in plant cells where endogenous expression of the present transcription factors or functionally equivalent molecules normally occurs, but such normal expression is at a lower level. Overexpression thus results in a greater than normal production, or "overproduction" of the transcription factor in the plant, cell or tissue.

The term "transcription regulating region" refers to a DNA regulatory sequence that regulates expression of one or more genes in a plant when a transcription factor having one or more specific binding domains binds to the DNA regulatory sequence. Transcription factors of the present invention possess an AT-hook domain and a second conserved domain. Examples of similar AT-hook and second conserved domain of the sequences of the invention may be found in Table 1. The transcription factors of the invention also comprise an amino acid subsequence that forms a transcription activation domain that regulates expression of one or more abiotic stress tolerance genes in a plant when the transcription factor binds to the regulating region.

DESCRIPTION OF THE SPECIFIC EMBODIMENTS

Transcription Factors Modify Expression of Endogenous Genes

A transcription factor may include, but is not limited to, any polypeptide that can activate or repress transcription of a single gene or a number of genes. As one of ordinary skill in the art recognizes, transcription factors can be identified by the presence of a region or domain of structural similarity or identity to a specific consensus sequence or the presence of a specific consensus DNA-binding site or DNA-binding site motif (see, for example, Riechmann et al. (2000) supra). The plant transcription factors of the present invention belong to the AT-hook transcription factor family (Reeves and Beckerbauer (2001) supra; and Reeves (2001) supra).

Generally, the transcription factors encoded by the present sequences are involved in cell differentiation and proliferation and the regulation of growth. Accordingly, one skilled in the art would recognize that by expressing the present sequences in a plant, one may change the expression of autologous genes or induce the expression of introduced genes. By affecting the expression of similar autologous sequences in a plant that have the biological activity of the present sequences, or by introducing the present sequences into a plant, one may alter a plant's phenotype to one with improved traits related to osmotic stresses. The sequences of the invention may also be used to transform a plant and introduce desirable traits not found in the wild-type cultivar or strain. Plants may then be selected for those that produce the most desirable degree of over- or under-expression of target genes of interest and coincident trait improvement.

The sequences of the present invention may be from any species, particularly plant species, in a naturally occurring form or from any source whether natural, synthetic, semi-synthetic or recombinant. The sequences of the invention may also include fragments of the present amino acid sequences. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

In addition to methods for modifying a plant phenotype by employing one or more polynucleotides and polypeptides of the invention described herein, the polynucleotides and polypeptides of the invention have a variety of additional uses. These uses include their use in the recombinant production (i.e., expression) of proteins; as regulators of plant gene expression, as diagnostic probes for the presence of complementary or partially complementary nucleic acids (including for detection of natural coding nucleic acids); as substrates for further reactions, e.g., mutation reactions, PCR reactions, or the like; as substrates for cloning e.g., including digestion or ligation reactions; and for identifying exogenous or endogenous modulators of the transcription factors. The polynucleotide can be, e.g., genomic DNA or RNA, a transcript (such as an mRNA), a cDNA, a PCR product, a cloned DNA, a synthetic DNA or RNA, or the like. The polynucleotide can comprise a sequence in either sense or antisense orientations.

Expression of genes that encode transcription factors that modify expression of endogenous genes, polynucleotides, and proteins are well known in the art. In addition, transgenic plants comprising isolated polynucleotides encoding transcription factors may also modify expression of endogenous genes, polynucleotides, and proteins. Examples include Peng et al. (1997) *Genes Development* 11: 3194-3205) and Peng et al. (1999) *Nature,* 400: 256-261). In addition, many others have demonstrated that an *Arabidopsis* transcription factor expressed in an exogenous plant species elicits the same or very similar phenotypic response. See, for example, Fu et al. (2001) *Plant Cell* 13: 1791-1802); Nandi et al. (2000) *Curr. Biol.* 10: 215-218); Coupland (1995) *Nature* 377: 482-483); and Weigel and Nilsson (1995) *Nature* 377: 482-500).

In another example, Mandel et al. (1992) *Cell* 71-133-143, and Suzuki et al. (2001) *Plant J.* 28: 409-418, teach that a transcription factor expressed in another plant species elicits the same or very similar phenotypic response of the endogenous sequence, as often predicted in earlier studies of *Arabidopsis* transcription factors in *Arabidopsis* (see Mandel et al. (1992) supra; Suzuki et al. (2001) supra). Other examples include Müller et al. (2001) *Plant J.* 28: 169-179; Kim et al. (2001) *Plant J.* 25: 247-259; Kyozuka and Shimamoto (2002) *Plant Cell Physiol.* 43: 130-135; Boss and Thomas (2002) *Nature,* 416: 847-850; He et al. (2000) *Transgenic Res.* 9: 223-227; and Robson et al. (2001) *Plant J.* 28: 619-631.

In yet another example, Gilmour et al. (1998) *Plant J.* 16: 433-442) teach an *Arabidopsis* AP2 transcription factor, CBF1 (SEQ ID NO: 70), which, when overexpressed in transgenic plants, increases plant freezing tolerance. Jaglo et al. (2001) *Plant Physiol.* 127: 910-917, further identified sequences in *Brassica napus* which encode CBF-like genes and that transcripts for these genes accumulated rapidly in response to low temperature. Transcripts encoding CBF-like proteins were also found to accumulate rapidly in response to low temperature in wheat, as well as in tomato. An alignment of the CBF proteins from *Arabidopsis, B. napus,* wheat, rye, and tomato revealed the presence of conserved consecutive amino acid residues, PKK/RPAGRxKFxETRHP and DSAWR, that bracket the AP2/EREBP DNA binding domains of the proteins and distinguish them from other members of the AP2/EREBP protein family. (Jaglo et al. (2001) supra).

Transcription factors mediate cellular responses and control traits through altered expression of genes containing cis-acting nucleotide sequences that are targets of the introduced transcription factor. It is well appreciated in the art that the effect of a transcription factor on cellular responses or a cellular trait is determined by the particular genes whose expression is either directly or indirectly (e.g., by a cascade of transcription factor binding events and transcriptional changes) altered by transcription factor binding. In a global analysis of transcription comparing a standard condition with one in which a transcription factor is overexpressed, the resulting transcript profile associated with transcription factor overexpression is related to the trait or cellular process controlled by that transcription factor. For example, the PAP2 gene (and other genes in the MYB family) have been shown to control anthocyanin biosynthesis through regulation of the expression of genes known to be involved in the anthocyanin biosynthetic pathway (Bruce et al. (2000) *Plant Cell* 12: 65-79; and Borevitz et al. (2000) *Plant Cell* 12: 2383-2393). Further, global transcript profiles have been used successfully as diagnostic tools for specific cellular states (e.g., cancerous vs. non-cancerous; Bhattacharjee et al. (2001) *Proc. Natl. Acad. Sci. USA* 98: 13790-13795; and Xu et al. (2001) *Proc Natl Acad Sci, USA* 98: 15089-15094). Consequently, it is evident to one skilled in the art that similarity of transcript profile upon overexpression of different transcription factors would indicate similarity of transcription factor function.

Polypeptides and Polynucleotides of the Invention

The present invention provides, among other things, transcription factors (TFs), and transcription factor homolog polypeptides, and isolated or recombinant polynucleotides encoding the polypeptides, or novel sequence variant polypeptides or polynucleotides encoding novel variants of transcription factors derived from the specific sequences provided in the Sequence Listing. Also provided are methods for modifying a plant's biomass by modifying the size or number of leaves or seed of a plant by controlling a number of cellular processes, and for increasing a plant's tolerance to abiotic stresses. These methods are based on the ability to alter the expression of critical regulatory molecules that may be conserved between diverse plant species. Related conserved regulatory molecules may be originally discovered in a model system such as *Arabidopsis* and homologous, functional molecules then discovered in other plant species. The latter may then be used to confer increased biomass or abiotic stress tolerance in diverse plant species.

Exemplary polynucleotides encoding the polypeptides of the invention were identified in the *Arabidopsis thaliana* GenBank database using publicly available sequence analysis programs and parameters. Sequences initially identified were then further characterized to identify sequences comprising specified sequence strings corresponding to sequence motifs present in families of known transcription factors. In addition, further exemplary polynucleotides encoding the polypeptides of the invention were identified in the plant GenBank database using publicly available sequence analysis programs and parameters. Sequences initially identified were then further characterized to identify sequences comprising specified sequence strings corresponding to sequence motifs present in families of known transcription factors. Polynucleotide sequences meeting such criteria were confirmed as transcription factors.

Additional polynucleotides of the invention were identified by screening *Arabidopsis thaliana* and/or other plant cDNA libraries with probes corresponding to known transcription factors under low stringency hybridization conditions. Additional sequences, including full length coding sequences, were subsequently recovered by the rapid amplification of cDNA ends (RACE) procedure using a commercially available kit according to the manufacturer's instructions. Where necessary, multiple rounds of RACE are performed to isolate 5' and 3' ends. The full-length cDNA was then recovered by a routine end-to-end polymerase chain reaction (PCR) using primers specific to the isolated 5' and 3' ends. Exemplary sequences are provided in the Sequence Listing.

The polypeptide and polynucleotide sequences of G1067 were previously identified in U.S. Provisional Patent Application 60/135,134, filed May 20, 1999. The polypeptide and polynucleotide sequences of G1073 were previously identified in U.S. Provisional Patent Application 60/125,814, filed Mar. 23, 1999. The function of G1073 in increasing biomass was disclosed in U.S. Provisional Application No. 60/227,439, filed Aug. 22, 2000, and the utility for increased drought tolerance observed in 35S::G1073 transgenic lines was disclosed in U.S. Non-Provisional application Ser. No. 10/374,780, filed Feb. 25, 2003. The polypeptide and polynucleotide sequences of G2153 and G2156 were previously identified in U.S. Provisional Patent Application No. 60/338,692, filed Dec. 11, 2001, and in U.S. Non-provisional patent application Ser. Nos. 10/225,066 and 10/225,068, both of which were filed Aug. 9, 2002. The altered sugar sensing and osmotic stress tolerance phenotype conferred by G2153 overexpression was disclosed in these filings. At the time each of the above applications were filed, these sequences were identified as encoding or being transcription factors, which were defined as polypeptides having the ability to effect transcription of a target gene. Sequences that have gene-regulating activity have been determined to have specific and substantial utility by the U.S. Patent and Trademark Office (*Federal Register* (2001) 66(4): 1095).

These sequences and others derived from diverse species and found in the sequence listing have been ectopically expressed in overexpressor plants. The changes in the characteristic(s) or trait(s) of the plants were then observed and found to confer increased biomass or abiotic stress tolerance. Therefore, the polynucleotides and polypeptides can be used to improve desirable characteristics of plants.

The polynucleotides of the invention were also ectopically expressed in overexpressor plant cells and the changes in the expression levels of a number of genes, polynucleotides, and/or proteins of the plant cells observed. Therefore, the polynucleotides and polypeptides can be used to change expression levels of a genes, polynucleotides, and/or proteins of plants or plant cells.

The AT-Hook Transcription Factor Family

In higher organisms, genomic DNA is assembled into multilevel complexes with a range of DNA-binding proteins, including the well-known histones and non-histone proteins such as the high mobility group (HMG) proteins. HMG proteins are classified into different groups based on their DNA-binding motifs, and one such group is the HMG-I(Y) subgroup (recently renamed as HMGA). Proteins in this group have been shown to bind to the minor groove of DNA via a conserved nine amino acid peptide (KRPRGRPKK; SEQ ID NO: 97) called the AT-hook motif (Reeves and Nisson (1995) supra). At the center of this AT-hook motif is a short, strongly conserved tripeptide of glycine-arginine-proline (GRP). This simple AT-hook motif can be present in a variable number of copies (1-15) in a given AT-hook protein. For example, the mammalian HMGA1 protein has three copies of this motif. The mammalian HMGA proteins participate in a wide variety of nuclear processes ranging from chromosome and chromatin remodeling, to acting as architectural transcription factors that regulate the expression of numerous genes in vivo. As a result, these proteins influence a diverse array of cellular processes including growth, proliferation, differentiation and death through the protein-DNA and protein-protein interactions (for reviews, see Reeves and Beckerbauer (2001) supra;

and Reeves (2001) supra). It has been shown that HMGA proteins specifically interact with a large number of other proteins, most of which are transcription factors (Reeves (2001) supra). They are also subject to many types of post-translational modification. One example is phosphorylation, which markedly influences their ability to interact with DNA substrates, other proteins, and chromatin (Onate et al. (1994) Mol. Cell. Biol. 14: 3376-3391; Falvo et al. (1995) Cell 83: 1101-1111; Reeves and Nissen (1995) supra; Huth et al. (1997) Nat. Struct. Biol. 4, 657-665; and Girard et al. (1998) EMBO J. 17: 2079-2085).

In plants, a protein with AT-hook DNA-binding motifs was identified in oat (Nieto-Sotelo and Quail (1994) *Biochem. Soc. Symp.* 60, 265-275). This protein binds to the PE1 region in the oat phytochrome A3 gene promoter, and may be involved in positive regulation of PHYA3 gene expression (Nieto-Sotelo and Quail (1994) supra). DNA-binding proteins containing AT-hook domains have also been identified in a variety of plant species, including rice, pea and *Arabidopsis* (Meijer et al. (1996) *Plant Mol. Biol.* 31: 607-618; and Gupta et al (1997a) *Plant Mol. Biol.* 35: 987-992). The rice AT-hook genes are predominantly expressed in young and meristematic tissues, suggesting that AT-hook proteins may affect the expression of genes that determine the differentiation status of cells. The pea AT-hook gene is expressed in all organs including roots, stems, leaves, flowers, tendrils and developing seeds (Gupta et al. (1997a) supra). Northern blot analysis revealed that an *Arabidopsis* AT-hook gene was expressed in all organs with the highest expression in flowers and developing siliques (Gupta et al. (1997b) *Plant Mol. Biol.* 34: 529-536).

Recently, it has also been shown that expression of a maize AT-hook protein in yeast cells produces better growth on a medium containing high nickel concentrations.

Novel AT-Hook Transcription Factor Genes and Binding Motifs in *Arabidopsis* and Other Diverse Species We have identified at least thirty-four *Arabidopsis* genes that code for proteins with AT-hook DNA-binding motifs. Of these, there are twenty-two genes encoding a single AT-hook DNA-binding motif; eight genes encoding two AT-hook DNA-binding motifs; three genes (G280, G1367 and G2787, SEQ ID NOs: 55, 57 and 59, respectively) encoding four AT-hook DNA-binding motifs and a single gene (G3045, SEQ ID NO: 61) encoding three AT-hook DNA-binding motifs.

G1073 (AtHRC1; SEQ ID NO: 2), for example, contains a single typical AT-hook DNA-binding motif (RRPRGRPAG; SEQ ID NO: 98) corresponding to positions 34 to 42 within the protein. A highly conserved 129 amino acid residue domain with unknown function (henceforth referred to as the "second conserved domain") can be identified in the single AT-hook domain subgroup, the "G1073 clade of transcription factor polypeptides", or more simply the "G1073 clade". Following this region, a potential acidic domain spans from position 172 to 190. Additionally, analysis of the protein using PROSITE reveals three potential protein kinase C phosphorylation sites at Ser32, Thr83 and Thr102, and three potential casein kinase II phosphorylation sites at Ser6, Ser70 and Ser247 (FIG. 3). Compared to many other AT-hook proteins, the G1073 protein contains a shorter N-terminus (FIGS. 5A-5C).

Figure 5G:
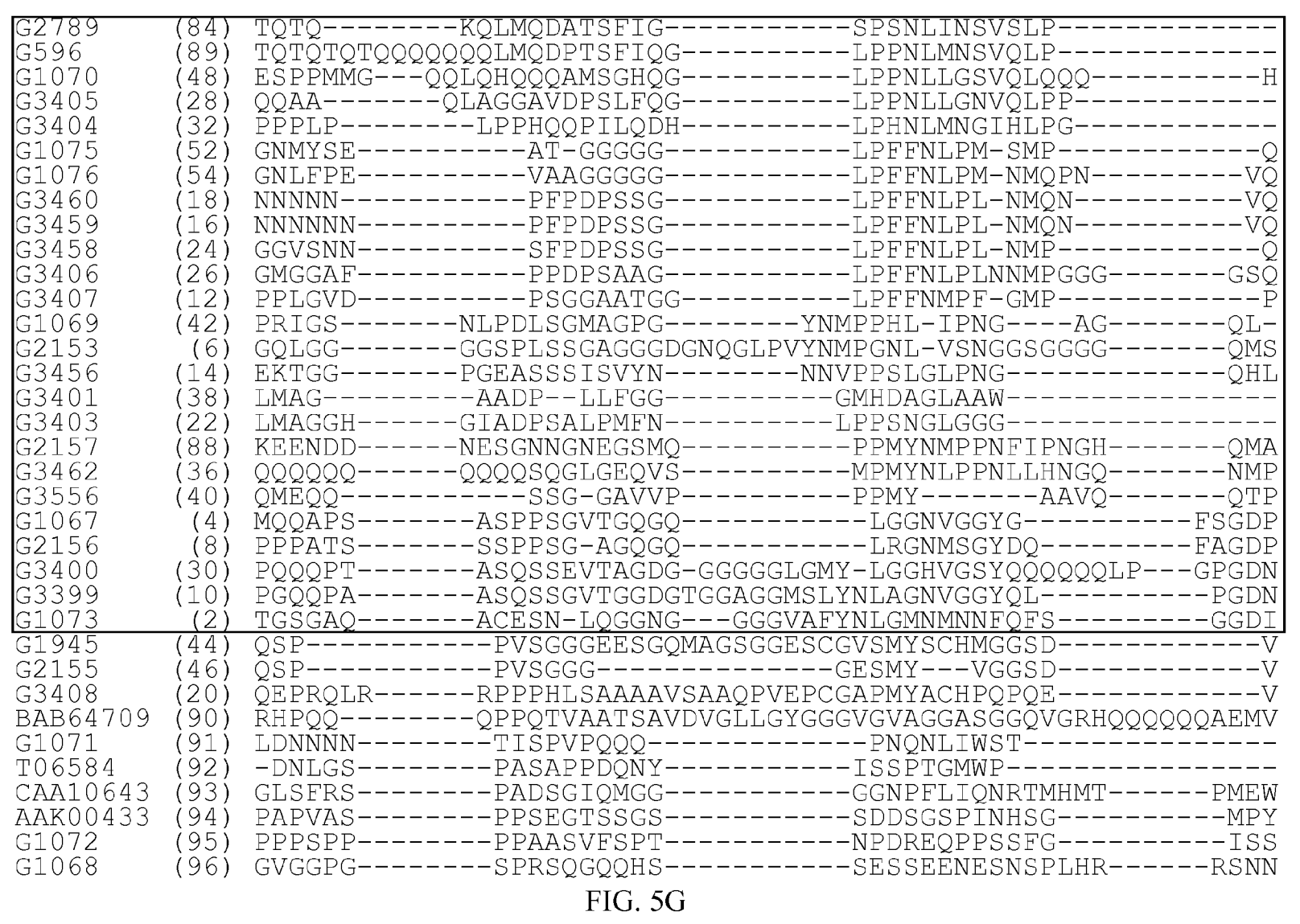

Members of the G1073 clade are structurally distinct from other AT-hook-related proteins, as may be seen in FIGS. 5E-5G, comparing G1073 and above sequences that are comprised within the G1073 clade, and those sequences including and below G1945 representing AT-hook sequences falling outside of the clade.

Table 1 shows the polypeptides identified by: polypeptide SEQ ID NO (first column); Gene ID or "GID" No. (second column); the amino acid residue coordinates for the AT-hook and second conserved domain (third column); AT-hook sequences of the respective polypeptides (fourth column); the identity in percentage terms to the AT-hook domain of G1073 (fifth column); second conserved domain sequences of the respective polypeptides (sixth column); and the identity in percentage terms to the second conserved domain of G1073 (seventh column). Many of these sequences have been shown to confer abiotic stress tolerant phenotypes when overexpressed in plants, as indicated in the penultimate column of Table 1. The last column indicates the sequences that have been observed to increase plant biomass in overexpressing lines relative to wild-type controls. The polypeptide sequences that show significant ability to confer abiotic stress tolerance and increased biomass include At-hook and second conserved domains with 78% and 62% or greater identity to the At-hook and second conserved domains of G1073, respectively.

TABLE 1

Gene families and binding domains

| SEQ ID NO: | GID No. | AT-hook and Second Conserved Domains in AA Coordinates and Base Coordinates | AT-hook domain | % ID to First Domain of G1073 | Second Conserved Domain | % ID to Second Conserved Domain of G1073 | Abiotic Stress Tolerant | Greater Biomass |
|---|---|---|---|---|---|---|---|---|
| 2 | G1073 AtHRC1 | Polypeptide coordinates: 34-42; 78-175 | RRPRGRPAG | 100% | VSTYATRRGCGVCIISGTGAV TNVTIRQPAAPAGGGVITLHG RFDILSLTGTALPPPAPPGAG GLTVYLAGGQGQVVGGNVAGS LIASGPVVLMAASF | 100% | Yes | Yes |
| 26 | G3406 | Polypeptide coordinates: 82-90, 126-222 | RRPRGRPPG | 89% | VSTYARRQRGVCVLSGSGVV TNVTLRQPSAPAGAVVSLHGR FEILSLSGSFLPPPAPPGATS LTIFLAGGQGQVVGGNVVGAL YAAGPVIVIAASF | 71% | Yes | No |

TABLE 1-continued

Gene families and binding domains

| SEQ ID NO: | GID No. | AT-hook and Second Conserved Domains in AA Coordinates and Base Coordinates | AT-hook domain | % ID to First Domain of G1073 | Second Conserved Domain | % ID to Second Conserved Domain of G1073 | Abiotic Stress Tolerant | Greater Biomass |
|---|---|---|---|---|---|---|---|---|
| 10 | G3399 | Polypeptide coordinates: 99-107, 143-240 | RRPRGRPPG | 89% | VAEYARRRGRGVCVLSGGGAV VNVALRQPGASPPGSMVATLR GRFEILSLTGTVLPPPAPPGA SGLTVFLSGGQGQVIGGSVVG PLVAAGPVVLMAAS | 71% | Yes | Yes |
| 4 | G1067 AtHRC2 | Polypeptide coordinates: 86-94, 130-235 | KRPRGRPPG | 78% | VSTYARRRGRGVSVLGGNGTV SNVTLRQPVTPGNGGGVSGGG GVVTLHGRFEILSLTGTVLPP PAPPGAGGLSIFLAGGQGQVV GGSVVAPLIASAPVILMAASF | 69% | No data | No |
| 16 | G3459 | Polypeptide coordinates: 76-84, 121-216 | RRPRGRPPG | 89% | VTAYARRRQRGICVLSGSGTV TNVSLRQPAAAGAVVTLHGRF EILSLSGSFLPPPAPPGATSL TIYLAGGQGQVVGGNVIGELT AAGPVIVIAASF | 68% | Yes | Yes |
| 30 | G3400 | Polypeptide coordinates: 83-91, 127-225 | RRPRGRPLG | 89% | VCEFARRRGRGVSVLSGGGAV ANVALRQPGASPPGSLVATMR GQFEILSLTGTVLPPPAPPSA SGLTVFLSGGQGQVVGGSVAG QLIAAGPVFLMAASF | 68% | Yes | Yes |
| 84 | G2789 | Polypeptide coordinates: 59-67; 103-196 | RRPRGRPAG | 100% | LAVFARRRQRGVCVLTGNGAV TNVTVRQPGGGVVSLHGRFEI LSLSGSFLPPPAPPAASGLKV YLAGGQGQVIGGSVVGPLTAS SPVVVMAASF | 67% | Yes | No |
| 18 | G3460 | Polypeptide coordinates: 74-82, 118-213 | RRPRGRPSG | 89% | VTAYARRRQRGICVLSGSGTV TNVSLRQPAAAGAVVRLHGRF EILSLSGSFLPPPAPPGATSL TIYLAGGQGQVVGGNVVGELT AAGPVIVIAASF | 67% | Yes | Yes |
| 86 | G1667 | Polypeptide coordinates: 53-61; 97-192 | KRPRGRPAG | 89% | LSDFARRKQRGLCILSANGCV TNVTLRQPASSGAIVTLHGRY EILSLLGSILPPPAPLGITGL TIYLAGPQGQVVGGGVVGGLI ASGPVVLMAASF | 66% | No | Yes |
| 8 | G2156 AtHRC4 | Polypeptide coordinates: 72-80, 116-220 | KRPRGRPPG | 78% | VTTYARRRGRGVSILSGNGTV ANVSLRQPATTAAHGANGGTG GVVALHGRFEILSLTGTVLPP PAPPGSGGLSIFLSGVQGQVI GGNVVAPLVASGPVILMAASF | 65% | Yes | Yes |
| 14 | G3456 | Polypeptide coordinates: 62-70, 106-201 | RRPRGRPPG | 89% | VAQFARRRQRGVSILSGSGTV VNVNLRQPTAPGAVMALHGRF DILSLTGSFLPGPSPPGATGL TIYLAGGQGQIVGGEVVGPLV AAGPVLVMAATF | 65% | Yes | Yes |
| 12 | G3407 | Polypeptide coordinates: 63-71, 106-208 | RRPRGRPPG | 89% | LTAYARRRQRGVCVLSAAGTV ANVTLRQPQSAQPGPASPAVA TLHGRFEILSLAGSFLPPPAP PGATSLAAFLAGGQGQVVGGS VAGALIAAGPVVVAASF | 63% | No data | Yes |
| 38 | G3401 | Polypeptide coordinates: 35-43, 79-174 | RRPRGRPPG | 89% | IAHFARRRQRGVCVLSGAGTV TDVALRQPAAPSAVVALRGRF EILSLTGTFLPGPAPPGSTGL TVYLAGGQGQVVGGSVVGTLT AAGPVMVIASTF | 63% | Yes | Yes |

TABLE 1-continued

Gene families and binding domains

| SEQ ID NO: | GID No. | AT-hook and Second Conserved Domains in AA Coordinates and Base Coordinates | AT-hook domain | % ID to First Domain of G1073 | Second Conserved Domain | % ID to Second Conserved Domain of G1073 | Abiotic Stress Tolerant | Greater Biomass |
|---|---|---|---|---|---|---|---|---|
| 6 | G2153 AtHRC3 | Polypeptide coordinates: 80-88, 124-227 | RRPRGRPPG | 100% | LATFARRRQRGICILSGNGTV ANVTLRQPSTAAVAAAPGGAA VLALQGRFEILSLTGSFLPGP APPGSTGLTIYLAGGQGQVVG GSVVGPLMAAGPVMLIAATF | 62% | Yes | Yes |
| 42 | G1069 | Polypeptide coordinates: 67-75, 111-206 | RRPRGRPPG | 89% | IAHFSRRRQRGVCVLSGTGSV ANVTLRQAAAPGGVVSLQGRF EILSLTGAFLPGPSPPGSTGL TVYLAGVQGQVVGGSVVGPLL AIGSVMVIAATF | 62% | Yes* | Yes |
| 40 | G3556 | Polypeptide coordinates: 45-53; 89-185 | RRPRGRPPG | 89% | IAGFSRRRQRGVSVLSGSGAV TNVTLRQPAGTGAAAVALRGR FEILSMSGAFLPAPAPPGATG LAVYLAGGQGQVVGGSVMGEL IASGPVMVIAATF | 62% | No | Yes |
| 88 | G2157 | 88-96, 132-228 | RRPRGRPPG | 89% | LNAFARRRGRGVSVLSGSGLV TNVTLRQPAASGGVVSLRGQF EILSMCGAFLPTSGSPAAAAG LTIYLAGAQGQVVGGGVAGPL IASGPVIVIAATF | 60% | No | Yes |

*results from previous studies, not shown

Within the G1073 clade of transcription factor polypeptides, the AT-hook domain comprises the consensus sequence:

RPRGRPXG (SEQ ID NO: 79)
Arg-Pro-Arg-Gly-Arg-Pro-Xaa-Gly where Xaa can be any of a number of amino acid residues; in the examples that have thus far been shown to confer abiotic stress tolerance, Xaa has been shown to represent an alanine, leucine, proline, or serine residue.

Also within the G1073 clade, the second conserved domain generally comprises the consensus sequence: Gly-Xaa-Phe-Xaa-Ile-Leu-Ser-(Xaa)$_2$-Gly-(Xaa)$_2$-Leu-Pro-(Xaa)$_3$-4-Pro-(Xaa)$_5$-Leu-(Xaa)$_2$-Tyr/Phe-(Xaa)$_2$-Gly-(Xaa)$_2$-Gly-Gln (SEQ ID NO: 99).

A smaller subsequence of interest in the G1073 clade sequences comprises:

Pro-(Xaa)$_5$-Leu-(Xaa)$_2$-Tyr-(Xaa)$_2$-Gly-(Xaa)$_2$-Gly-Gln (SEQ ID NO: 80); or

Pro-(Xaa)$_5$-Leu-(Xaa)$_2$-Phe-(Xaa)$_2$-Gly-(Xaa)$_2$-Gly-Gln (SEQ ID NO: 81).

The tenth position of SEQ ID NOs: 80 and 81 is an aromatic residue, specifically tyrosine or phenylalanine, in the G1073 sequences that have thus far been examined. Thus far, aromatic residues have not been found in the corresponding position in the At-hook transcription factors that are outside of the G1073 clade.

Thus, the transcription factors of the invention each possess an AT-hook domain and a second conserved domain, and include paralogs and orthologs of G1073 found by BLAST analysis, as described below. As shown in Table 1, the AT-hook domains of G1073 and related sequences are at least 78% identical to the At-Hook domains of G1073 and at least 62% identical to the second conserved domain found in G1073. These transcription factors rely on the binding specificity of their AT-hook domains; many have been shown to have similar or identical functions in plants by increasing the size and biomass of a plant (also see Example VIII, below).

Producing Polypeptides

The polynucleotides of the invention include sequences that encode transcription factors and transcription factor homolog polypeptides and sequences complementary thereto, as well as unique fragments of coding sequence, or sequence complementary thereto. Such polynucleotides can be, e.g., DNA or RNA, e.g., mRNA, cRNA, synthetic RNA, genomic DNA, cDNA synthetic DNA, oligonucleotides, etc. The polynucleotides are either double-stranded or single-stranded, and include either, or both sense (i.e., coding) sequences and antisense (i.e., non-coding, complementary) sequences. The polynucleotides include the coding sequence of a transcription factor, or transcription factor homolog polypeptide, in isolation, in combination with additional coding sequences (e.g., a purification tag, a localization signal, as a fusion-protein, as a pre-protein, or the like), in combination with non-coding sequences (e.g., introns or inteins, regulatory elements such as promoters, enhancers, terminators, and the like), and/or in a vector or host environment in which the polynucleotide encoding a transcription factor or transcription factor homolog polypeptide is an endogenous or exogenous gene.

A variety of methods exist for producing the polynucleotides of the invention. Procedures for identifying and isolating DNA clones are well known to those of skill in the art and are described in, e.g., Berger and Kimmel (1987), "Guide to Molecular Cloning Techniques", in *Methods in Enzymology*, vol. 152, Academic Press, Inc., San Diego, Calif. ("Berger"); Sambrook et al. (1989) *Molecular Cloning—A Laboratory Manual* (2nd Edition), Vol. 1-3, Cold Spring Harbor Laboratory, Cold Spring Harbor, N.Y., and *Current Protocols in*

*Molecular Biology*, Ausubel et al. editors, Current Protocols, Greene Publishing Associates, Inc. and John Wiley & Sons, Inc. (supplemented through 2000; "Ausubel").

Alternatively, polynucleotides of the invention, can be produced by a variety of in vitro amplification methods adapted to the present invention by appropriate selection of specific or degenerate primers. Examples of protocols sufficient to direct persons of skill through in vitro amplification methods, including the polymerase chain reaction (PCR) the ligase chain reaction (LCR), Qβ-replicase amplification and other RNA polymerase mediated techniques (e.g., NASBA), e.g., for the production of the homologous nucleic acids of the invention are found in Berger (1987) supra, Sambrook (1989) supra, and Ausubel (through 2000) supra, as well as Mullis et al. (1990) *PCR Protocols A Guide to Methods and Applications* (Innis et al., eds) Academic Press Inc. San Diego, Calif. Improved methods for cloning in vitro amplified nucleic acids are described in Wallace et al. U.S. Pat. No. 5,426,039. Improved methods for amplifying large nucleic acids by PCR are summarized in Cheng et al. (1994) *Nature* 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase (Berger (1987) supra; Sambrook (1989) supra; and Ausubel (through 2000) supra).

Alternatively, polynucleotides and oligonucleotides of the invention can be assembled from fragments produced by solid-phase synthesis methods. Typically, fragments of up to approximately 100 bases are individually synthesized and then enzymatically or chemically ligated to produce a desired sequence, e.g., a polynucleotide encoding all or part of a transcription factor. For example, chemical synthesis using the phosphoramidite method is described, e.g., by Beaucage et al. (1981) *Tetrahedron Letters* 22: 1859-1869; and Matthes et al. (1984) *EMBO J.* 3: 801-805. According to such methods, oligonucleotides are synthesized, purified, annealed to their complementary strand, ligated and then optionally cloned into suitable vectors. And if so desired, the polynucleotides and polypeptides of the invention can be custom ordered from any of a number of commercial suppliers.

Homologous Sequences

Sequences homologous to those provided in the Sequence Listing derived from *Arabidopsis thaliana* or from other plants of choice, are also an aspect of the invention. Homologous sequences can be derived from any plant including monocots and dicots and in particular agriculturally important plant species, including but not limited to, crops such as soybean, wheat, corn (maize), potato, cotton, rice, rape, oilseed rape (including canola), sunflower, alfalfa, clover, sugarcane, and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, tomatillo, watermelon, rosaceous fruits (such as apple, peach, pear, cherry and plum) and vegetable brassicas (such as broccoli, cabbage, cauliflower, Brussels sprouts, and kohlrabi). Other crops, including fruits and vegetables, whose phenotype can be changed and which comprise homologous sequences include barley; rye; millet; sorghum; currant; avocado; citrus fruits such as oranges, lemons, grapefruit and tangerines, artichoke, cherries; nuts such as the walnut and peanut; endive; leek; roots such as arrowroot, beet, cassava, turnip, radish, yam, and sweet potato; and beans. The homologous sequences may also be derived from woody species, such pine, poplar and eucalyptus, or mint or other labiates. In addition, homologous sequences may be derived from plants that are evolutionarily-related to crop plants, but which may not have yet been used as crop plants. Examples include deadly nightshade (*Atropa belladona*), related to tomato; jimson weed (*Datura strommium*), related to peyote; and teosinte (*Zea* species), related to corn (maize).

Orthologs and Paralogs

Homologous sequences as described above can comprise orthologous or paralogous sequences. Several different methods are known by those of skill in the art for identifying and defining these functionally homologous sequences. Three general methods for defining orthologs and paralogs are described; an ortholog or paralog, including equivalogs, may be identified by one or more of the methods described below.

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL (Thompson et al. (1994) *Nucleic Acids Res.* 22: 4673-4680; Higgins et al. (1996) *Methods Enzymol.* 266: 383-402). Groups of similar genes can also be identified with pair-wise BLAST analysis (Feng and Doolittle (1987) *J. Mol. Evol.* 25: 351-360). For example, a clade of very similar MADS domain transcription factors from *Arabidopsis* all share a common function in flowering time (Ratcliffe et al. (2001) *Plant Physiol.* 126: 122-132), and a group of very similar AP2 domain transcription factors from *Arabidopsis* are involved in tolerance of plants to freezing (Gilmour et al. (1998) *Plant J.* 16: 433-442). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount (2001), in *Bioinformatics: Sequence and Genome Analysis*, Cold Spring Harbor Laboratory Press, Cold Spring Harbor, N.Y., page 543).

Speciation, the production of new species from a parental species, can also give rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al. (1994) *Nucleic Acids Res.* 22: 4673-4680; Higgins et al. (1996) supra) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

Transcription factor gene sequences are conserved across diverse eukaryotic species lines (Goodrich et al. (1993) *Cell* 75: 519-530; Lin et al. (1991) *Nature* 353: 569-571; Sadowski et al. (1988) *Nature* 335: 563-564). Plants are no exception to this observation; diverse plant species possess transcription factors that have similar sequences and functions.

Orthologous genes from different organisms have highly conserved functions, and very often essentially identical functions (Lee et al. (2002) *Genome Res.* 12: 493-502; Remm et al. (2001) *J. Mol. Biol.* 314: 1041-1052). Paralogous genes, which have diverged through gene duplication, may retain similar functions of the encoded proteins. In such cases, paralogs can be used interchangeably with respect to certain embodiments of the instant invention (for example, transgenic expression of a coding sequence). An example of such highly related paralogs is the CBF family, with three well-defined members in *Arabidopsis* and at least one ortholog in *Brassica napus* (SEQ ID NOS: 69, 71, 73, or 75, respectively), all of which control pathways involved in both freezing and drought stress (Gilmour et al. (1998) *Plant J.* 16: 433-442; Jaglo et al. (1998) *Plant Physiol.* 127: 910-917).

The following references represent a small sampling of the many studies that demonstrate that conserved transcription factor genes from diverse species are likely to function similarly (i.e., regulate similar target sequences and control the same traits), and that transcription factors may be transformed into diverse species to confer or improve traits.

(1) The *Arabidopsis* NPR1 gene regulates systemic acquired resistance (SAR); over-expression of NPR1 leads to enhanced resistance in *Arabidopsis*. When either *Arabidopsis* NPR1 or the rice NPR1 ortholog was overexpressed in rice (which, as a monocot, is diverse from *Arabidopsis*), challenge with the rice bacterial blight pathogen *Xanthomonas oryzae* pv. *Oryzae*, the transgenic plants displayed enhanced resistance (Chem et al. (2001) *Plant J.* 27: 101-113). NPR1 acts through activation of expression of transcription factor genes, such as TGA2 (Fan and Dong (2002) *Plant Cell* 14: 1377-1389).

(2) E2F genes are involved in transcription of plant genes for proliferating cell nuclear antigen (PCNA). Plant E2Fs share a high degree of similarity in amino acid sequence between monocots and dicots, and are even similar to the conserved domains of the animal E2Fs. Such conservation indicates a functional similarity between plant and animal E2Fs. E2F transcription factors that regulate meristem development act through common cis-elements, and regulate related (PCNA) genes. (Kosugi and Ohashi, (2002) *Plant J.* 29: 45-59).

(3) The ABI5 gene (ABA insensitive 5) encodes a basic leucine zipper factor required for ABA response in the seed and vegetative tissues. Co-transformation experiments with ABI5 cDNA constructs in rice protoplasts resulted in specific transactivation of the ABA-inducible wheat, *Arabidopsis*, bean, and barley promoters. These results demonstrate that sequentially similar ABI5 transcription factors are key targets of a conserved ABA signaling pathway in diverse plants. (Gampala et al. (2001) *J. Biol. Chem.* 277: 1689-1694).

(4) Sequences of three *Arabidopsis* GAMYB-like genes were obtained on the basis of sequence similarity to GAMYB genes from barley, rice, and *L. temulentum*. These three *Arabidopsis* genes were determined to encode transcription factors (AtMYB33, AtMYB65, and AtMYB101) and could substitute for a barley GAMYB and control alpha-amylase expression. (Gocal et al. (2001) *Plant Physiol.* 127: 1682-1693).

(5) The floral control gene LEAFY from *Arabidopsis* can dramatically accelerate flowering in numerous dictoyledonous plants. Constitutive expression of *Arabidopsis* LEAFY also caused early flowering in transgenic rice (a monocot), with a heading date that was 26-34 days earlier than that of wild-type plants. These observations indicate that floral regulatory genes from *Arabidopsis* are useful tools for heading date improvement in cereal crops. (He et al. (2000) *Transgenic Res.* 9: 223-227).

(6) Bioactive gibberellins (GAs) are essential endogenous regulators of plant growth. GA signaling tends to be conserved across the plant kingdom. GA signaling is mediated via GAI, a nuclear member of the GRAS family of plant transcription factors. *Arabidopsis* GAI has been shown to function in rice to inhibit gibberellin response pathways. (Fu et al. (2001) *Plant Cell* 13: 1791-1802).

(7) The *Arabidopsis* gene SUPERMAN (SUP), encodes a putative transcription factor that maintains the boundary between stamens and carpels. By over-expressing *Arabidopsis* SUP in rice, the effect of the gene's presence on whorl boundaries was shown to be conserved. This demonstrated that SUP is a conserved regulator of floral whorl boundaries and affects cell proliferation. (Nandi et al. (2000) *Curr. Biol.* 10: 215-218.)

(8) Maize, petunia and *Arabidopsis* myb transcription factors that regulate flavonoid biosynthesis are very genetically similar and affect the same trait in their native species, therefore sequence and function of these myb transcription factors correlate with each other in these diverse species (Borevitz et al. (2000) *Plant Cell* 12: 2383-2394).

(9) Wheat reduced height-1 (Rht-B1/Rht-D1) and maize dwarf-8 (d8) genes are orthologs of the *Arabidopsis* gibberellin insensitive (GAI) gene. Both of these genes have been used to produce dwarf grain varieties that have improved grain yield. These genes encode proteins that resemble nuclear transcription factors and contain an SH2-like domain, indicating that phosphotyrosine may participate in gibberellin signaling. Transgenic rice plants containing a mutant GAI allele from *Arabidopsis* have been shown to produce reduced responses to gibberellin and are dwarfed, indicating that mutant GAI orthologs could be used to increase yield in a wide range of crop species. (Peng et al. (1999) *Nature* 400: 256-261.)

Transcription factors that are homologous to the listed AT-hook transcription factors will typically share at least about 78% and 62% amino acid sequence identity in their AT-hook and second conserved domains, respectively. More closely related transcription factors can share at least about 89% or about 100% identity in their AT-hook domains, and at least about 63%, 65%, 66%, 67%, 68%, 69%, 71%, or greater identity with the second conserved domain of G1073, as seen by the examples shown to confer abiotic stress tolerance in Table 1. Transcription factors that are homologous to the listed sequences should share at least about 50%, or at least about 75%, or at least about 80%, or at least about 90%, or at least about 95% amino acid sequence identity over the entire length of the polypeptide or the homolog.

At the nucleotide level, the sequences of the invention will typically share at least about 40% nucleotide sequence identity, preferably at least about 50%, about 60%, about 70% or about 80% sequence identity, and more preferably about 85%, about 90%, about 95% or about 97% or more sequence identity to one or more of the listed full-length sequences, or to a listed sequence but excluding or outside of the region(s) encoding a known consensus sequence or consensus DNA-binding site, or outside of the region(s) encoding one or all conserved domains. The degeneracy of the genetic code enables major variations in the nucleotide sequence of a polynucleotide while maintaining the amino acid sequence of the encoded protein.

Percent identity can be determined electronically, e.g., by using the MEGALIGN program (DNASTAR, Inc. Madison, Wis.). The MEGALIGN program can create alignments between two or more sequences according to different methods, for example, the clustal method (see, for example, Higgins and Sharp (1988) *Gene* 73: 237-244.) The clustal algorithm groups sequences into clusters by examining the distances between all pairs. The clusters are aligned pairwise and then in groups. Other alignment algorithms or programs may be used, including FASTA, BLAST, or ENTREZ, FASTA and BLAST, and which may be used to calculate percent similarity. These are available as a part of the GCG sequence analysis package (University of Wisconsin, Madison, Wis.), and can be used with or without default settings. ENTREZ is available through the National Center for Biotechnology Information. In one embodiment, the percent identity of two sequences can be determined by the GCG program with a gap weight of 1, e.g., each amino acid gap is weighted as if it were a single amino acid or nucleotide mismatch between the two sequences (see U.S. Pat. No. 6,262,333).

Other techniques for alignment are described in Methods in Enzymology, vol. 266, *Computer Methods for Macromolecular Sequence Analysis* (1996), ed. Doolittle, Academic Press, Inc., San Diego, Calif., USA. Preferably, an alignment program that permits gaps in the sequence is utilized to align the sequences. The Smith-Waterman is one type of algorithm that permits gaps in sequence alignments (see Shpaer (1997) *Methods Mol. Biol.* 70: 173-187). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The percentage similarity between two polypeptide sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between polynucleotide sequences can also be counted or calculated by other methods known in the art, e.g., the Jotun Hein method (see, for example, Hein (1990) *Methods Enzymol.* 183: 626-645.) Identity between sequences can also be determined by other methods known in the art, e.g., by varying hybridization conditions (see US Patent Application No. 20010010913).

Thus, the invention provides methods for identifying a sequence similar or paralogous or orthologous or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an internet or intranet) and a query is made against the sequence database using the relevant sequences herein and associated plant phenotypes or gene functions.

In addition, one or more polynucleotide sequences or one or more polypeptides encoded by the polynucleotide sequences may be used to search against a BLOCKS (Bairoch et al. (1997) *Nucleic Acids Res.* 25: 217-221), PFAM, and other databases which contain previously identified and annotated motifs, sequences and gene functions. Methods that search for primary sequence patterns with secondary structure gap penalties (Smith et al. (1992) *Protein Engineering* 5: 35-51) as well as algorithms such as Basic Local Alignment Search Tool (BLAST; Altschul (1993) *J. Mol. Evol.* 36: 290-300; Altschul et al. (1990) *J. Mol. Biol.* 215: 403-410), BLOCKS (Henikoff and Henikoff (1991) *Nucleic Acids Res.* 19: 6565-6572), Hidden Markov Models (HMM; Eddy (1996) *Curr. Opin. Str. Biol.* 6: 361-365; Sonnhammer et al. (1997) *Proteins* 28: 405-420), and the like, can be used to manipulate and analyze polynucleotide and polypeptide sequences encoded by polynucleotides. These databases, algorithms and other methods are well known in the art and are described in Ausubel et al. (1997) *Short Protocols in Molecular Biology*, John Wiley & Sons, New York, N.Y., unit 7.7, and in Meyers (1995) *Molecular Biology and Biotechnology*, Wiley VCH, New York, N.Y., p 856-853.

A further method for identifying or confirming that specific homologous sequences control the same function is by comparison of the transcript profile(s) obtained upon overexpression or knockout of two or more related transcription factors. Since transcript profiles are diagnostic for specific cellular states, one skilled in the art will appreciate that genes that have a highly similar transcript profile (e.g., with greater than 50% regulated transcripts in common, or with greater than 70% regulated transcripts in common, or with greater than 90% regulated transcripts in common) will have highly similar functions. Fowler et al. (2002) *Plant Cell* 14: 1675-1679, have shown that three paralogous AP2 family genes (CBF1, CBF2 and CBF3), each of which is induced upon cold treatment, and each of which can condition improved freezing tolerance, have highly similar transcript profiles. Once a transcription factor has been shown to provide a specific function, its transcript profile becomes a diagnostic tool to determine whether putative paralogs or orthologs have the same function.

Furthermore, methods using manual alignment of sequences similar or homologous to one or more polynucleotide sequences or one or more polypeptides encoded by the polynucleotide sequences may be used to identify regions of similarity and AT-hook domains. Such manual methods are well-known of those of skill in the art and can include, for example, comparisons of tertiary structure between a polypeptide sequence encoded by a polynucleotide that comprises a known function with a polypeptide sequence encoded by a polynucleotide sequence which has a function not yet determined. Such examples of tertiary structure may comprise predicted alpha helices, beta-sheets, amphipathic helices, leucine zipper motifs, zinc finger motifs, proline-rich regions, cysteine repeat motifs, and the like.

Orthologs and paralogs of presently disclosed transcription factors may be cloned using compositions provided by the present invention according to methods well known in the art. cDNAs can be cloned using mRNA from a plant cell or tissue that expresses one of the present transcription factors. Appropriate mRNA sources may be identified by interrogating Northern blots with probes designed from the present transcription factor sequences, after which a library is prepared from the mRNA obtained from a positive cell or tissue. Transcription factor-encoding cDNA is then isolated using, for example, PCR, using primers designed from a presently disclosed transcription factor gene sequence, or by probing with a partial or complete cDNA or with one or more sets of degenerate probes based on the disclosed sequences. The cDNA library may be used to transform plant cells. Expression of the cDNAs of interest is detected using, for example, methods disclosed herein such as microarrays, Northern blots, quantitative PCR, or any other technique for monitoring changes in expression. Genomic clones may be isolated using similar techniques to those.

Examples of orthologs of the *Arabidopsis* polypeptide sequences SEQ ID NOs: 2, 4, 6, 8, 42 and 86, include SEQ ID NOs: 10, 12, 14, 16, 18, 26, 30, 38, 40, and other functionally similar orthologs listed in the Sequence Listing. In addition to the sequences in the Sequence Listing, the invention encompasses isolated nucleotide sequences that are sequentially and structurally similar to G1073, G1067, G2153, G2156, G3399, G3407, G3456, G3459, G3460, G3406, G3400, G3401, G3556, G1069, G2789 and G1667 (SEQ ID NO: 1, 3, 5, 7, 9, 11, 13, 15, 17, 25, 29, 37, 39, 41, 85 and 86, respectively) and can function in a plant by increasing biomass and abiotic stress tolerance, particularly when overexpressed. These polypeptide sequences represent clade members that function similarly to G1073 by conferring abiotic stress tolerance, and show significant sequence similarity to G1073, particularly in their respective conserved domains, as identified in Table 1.

Since a representative number of these polynucleotide sequences in the G1073 clade of transcription factor polypeptides are phylogenetically (FIG. 4) and sequentially (FIG. 5A-5H) related and have been shown to increase a plant's biomass and abiotic stress tolerance, one skilled in the art would predict that other similar, phylogenetically related sequences falling within the G1073 clade would also increase a plant's biomass and abiotic stress tolerance when overexpressed.

Identifying Polynucleotides or Nucleic Acids by Hybridization

Polynucleotides homologous to the sequences illustrated in the Sequence Listing and tables can be identified, e.g., by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited below (e.g., Sambrook et al. (1989); Berger and Kimmel (1987); and Anderson and Young (1985)).

Encompassed by the invention are polynucleotide sequences that are capable of hybridizing to the claimed polynucleotide sequences, including any of the transcription factor polynucleotides within the Sequence Listing, and fragments thereof under various conditions of stringency (see, for example, Wahl and Berger (1987) *Methods Enzymol.* 152: 399-407; and Kimmel (1987) *Methods Enzymol.* 152: 507-511). In addition to the nucleotide sequences listed in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

With regard to hybridization, conditions that are highly stringent, and means for achieving them, are well known in the art. See, for example, Sambrook et al. (1989) "*Molecular Cloning: A Laboratory Manual*" (2nd ed., Cold Spring Harbor Laboratory); Berger (1987) supra, pages 467-469; and Anderson and Young (1985) "Quantitative Filter Hybridisation", In: Hames and Higgins, ed., *Nucleic Acid Hybridisation A Practical Approach.* Oxford, IRL Press, 73-111.

Stability of DNA duplexes is affected by such factors as base composition, length, and degree of base pair mismatch. Hybridization conditions may be adjusted to allow DNAs of different sequence relatedness to hybridize. The melting temperature ($T_m$) is defined as the temperature when 50% of the duplex molecules have dissociated into their constituent single strands. The melting temperature of a perfectly matched duplex, where the hybridization buffer contains formamide as a denaturing agent, may be estimated by the following equations:

(I) DNA-DNA:

$$T_m(°C.)=81.5+16.6(\log[Na+])+0.41(\%G+C)-0.62(\% \text{formamide})-500/L$$

(II) DNA-RNA:

$$T_m(°C.)=79.8+18.5(\log[Na+])+0.58(\%G+C)+0.12(\%G+C)^2-0.5(\% \text{formamide})-820/L$$

(III) RNA-RNA:

$$T_m(°C.)=79.8+18.5(\log[Na+])+0.58(\%G+C)+0.12(\%G+C)^2-0.35(\% \text{formamide})-820/L$$

where L is the length of the duplex formed, [Na+] is the molar concentration of the sodium ion in the hybridization or washing solution, and % G+C is the percentage of (guanine+cytosine) bases in the hybrid. For imperfectly matched hybrids, approximately 1° C. is required to reduce the melting temperature for each 1% mismatch.

Hybridization experiments are generally conducted in a buffer of pH between 6.8 to 7.4, although the rate of hybridization is nearly independent of pH at ionic strengths likely to be used in the hybridization buffer (Anderson and Young (1985) supra). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency (as described by the formula above). As a general guidelines high stringency is typically performed at $T_m$-5° C. to $T_m$-20° C., moderate stringency at $T_m$-20° C. to $T_m$-35° C. and low stringency at $T_m$-35° C. to $T_m$-50° C. for duplex>150 base pairs. Hybridization may be performed at low to moderate stringency (25-50° C. below $T_m$), followed by post-hybridization washes at increasing stringencies. Maximum rates of hybridization in solution are determined empirically to occur at $T_m$-25° C. for DNA-DNA duplex and $T_m$-15° C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or Northern blot for hybridization of complementary nucleic acids that have more than 100 complementary residues is about 5° C. to 20° C. lower than the thermal melting point ($T_m$) for the specific sequence at a defined ionic strength and pH. Conditions used for hybridization may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. More preferably, high stringency conditions are about 0.02 M sodium chloride, about 0.5% casein, about 0.02% SDS, about 0.001 M sodium citrate, at a temperature of about 50° C. Nucleic acid molecules that hybridize under stringent conditions will typically hybridize to a probe based on either the entire DNA molecule or selected portions, e.g., to a unique subsequence, of the DNA.

Stringent salt concentration will ordinarily be less than about 750 mM NaCl and 75 mM trisodium citrate. Increasingly stringent conditions may be obtained with less than about 500 mM NaCl and 50 mM trisodium citrate, to even greater stringency with less than about 250 mM NaCl and 25 mM trisodium citrate. Low stringency hybridization can be obtained in the absence of organic solvent, e.g., formamide, whereas high stringency hybridization may be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. with formamide present. Varying additional parameters, such as hybridization time, the concentration of detergent, e.g., sodium dodecyl sulfate (SDS) and ionic strength, are well known to those skilled in the art. Various levels of stringency are accomplished by combining these various conditions as needed.

The washing steps that follow hybridization may also vary in stringency; the post-hybridization wash steps primarily determine hybridization specificity, with the most critical factors being temperature and the ionic strength of the final wash solution. Wash stringency can be increased by decreasing salt concentration or by increasing temperature. Stringent salt concentration for the wash steps will preferably be less than about 30 mM NaCl and 3 mM trisodium citrate, and most preferably less than about 15 mM NaCl and 1.5 mM trisodium citrate.

Thus, hybridization and wash conditions that may be used to bind and remove polynucleotides with less than the desired homology to the nucleic acid sequences or their complements that encode the present transcription factors include, for example:

6×SSC at 65° C.;
50% formamide, 4×SSC at 42° C.; or
0.5×SSC, 0.1% SDS at 65° C.;
with, for example, two wash steps of 10-30 minutes each. Useful variations on these conditions will be readily apparent to those skilled in the art.

A person of skill in the art would not expect substantial variation among polynucleotide species encompassed within the scope of the present invention because the highly stringent conditions set forth in the above formulae yield structurally similar polynucleotides.

If desired, one may employ wash steps of even greater stringency, including about 0.2×SSC, 0.1% SDS at 65° C. and washing twice, each wash step being about 30 minutes, or about 0.1×SSC, 0.1% SDS at 65° C. and washing twice for 30 minutes. The temperature for the wash solutions will ordinarily be at least about 25° C., and for greater stringency at least about 42° C. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C. For identification of less closely related homologs, wash steps may be performed at a lower temperature, e.g., 50° C.

An example of a low stringency wash step employs a solution and conditions of at least 25° C. in 30 mM NaCl, 3 mM trisodium citrate, and 0.1% SDS over 30 minutes. Greater stringency may be obtained at 42° C. in 15 mM NaCl, with 1.5 mM trisodium citrate, and 0.1% SDS over 30 minutes. Even higher stringency wash conditions are obtained at 65° C.-68° C. in a solution of 15 mM NaCl, 1.5 mM trisodium citrate, and 0.1% SDS. Wash procedures will generally employ at least two final wash steps. Additional variations on these conditions will be readily apparent to those skilled in the art (see, for example, US Patent Application No. 20010010913).

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid encoding a transcription factor known as of the filing date of the application. It may be desirable to select conditions for a particular assay such that a higher signal to noise ratio, that is, about 15× or more, is obtained. Accordingly, a subject nucleic acid will hybridize to a unique coding oligonucleotide with at least a 2× or greater signal to noise ratio as compared to hybridization of the coding oligonucleotide to a nucleic acid encoding known polypeptide. The particular signal will depend on the label used in the relevant assay, e.g., a fluorescent label, a colorimetric label, a radioactive label, or the like. Labeled hybridization or PCR probes for detecting related polynucleotide sequences may be produced by oligolabeling, nick translation, end-labeling, or PCR amplification using a labeled nucleotide.

Encompassed by the invention are polynucleotide sequences that are capable of hybridizing to the claimed polynucleotide sequences, including any of the transcription factor polynucleotides within the Sequence Listing, and fragments thereof under various conditions of stringency (see, for example, Wahl and Berger (1987) supra, pages 399-407; and Kimmel (1987) *Methods Enzymol.* 152: 507-511). In addition to the nucleotide sequences in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

Identifying Polynucleotides or Nucleic Acids with Expression Libraries

In addition to hybridization methods, transcription factor homolog polypeptides can be obtained by screening an expression library using antibodies specific for one or more transcription factors. With the provision herein of the disclosed transcription factor, and transcription factor homolog nucleic acid sequences, the encoded polypeptide(s) can be expressed and purified in a heterologous expression system (for example, *E. coli*) and used to raise antibodies (monoclonal or polyclonal) specific for the polypeptide(s) in question. Antibodies can also be raised against synthetic peptides derived from transcription factor, or transcription factor homolog, amino acid sequences. Methods of raising antibodies are well known in the art and are described in Harlow and Lane (1988), *Antibodies: A Laboratory Manual*, Cold Spring Harbor Laboratory, New York. Such antibodies can then be used to screen an expression library produced from the plant from which it is desired to clone additional transcription factor homologs, using the methods described above. The selected cDNAs can be confirmed by sequencing and enzymatic activity.

Sequence Variations

It will readily be appreciated by those of skill in the art, that any of a variety of polynucleotide sequences are capable of encoding the transcription factors and transcription factor homolog polypeptides of the invention. Due to the degeneracy of the genetic code, many different polynucleotides can encode identical and/or substantially similar polypeptides in addition to those sequences illustrated in the Sequence Listing. Nucleic acids having a sequence that differs from the sequences shown in the Sequence Listing, or complementary sequences, that encode functionally equivalent peptides (i.e., peptides having some degree of equivalent or similar biological activity) but differ in sequence from the sequence shown in the Sequence Listing due to degeneracy in the genetic code, are also within the scope of the invention.

Altered polynucleotide sequences encoding polypeptides include those sequences with deletions, insertions, or substitutions of different nucleotides, resulting in a polynucleotide encoding a polypeptide with at least one functional characteristic of the instant polypeptides. Included within this definition are polymorphisms which may or may not be readily detectable using a particular oligonucleotide probe of the polynucleotide encoding the instant polypeptides, and improper or unexpected hybridization to allelic variants, with a locus other than the normal chromosomal locus for the polynucleotide sequence encoding the instant polypeptides.

Allelic variant refers to any of two or more alternative forms of a gene occupying the same chromosomal locus. Allelic variation arises naturally through mutation, and may result in phenotypic polymorphism within populations. Gene mutations can be silent (i.e., no change in the encoded polypeptide) or may encode polypeptides having altered amino acid sequence. The term allelic variant is also used herein to denote a protein encoded by an allelic variant of a gene. Splice variant refers to alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Those skilled in the art would recognize that, for example, G1073, SEQ ID NO: 2, represents a single transcription factor; allelic variation and alternative splicing may be expected to occur. Allelic variants of SEQ ID NO: 1 can be cloned by probing cDNA or genomic libraries from different individual organisms according to standard procedures. Allelic variants of the DNA sequence shown in SEQ ID NO: 1, including those containing silent mutations and those in which mutations result in amino acid sequence changes, are within the scope of the present invention, as are proteins which are allelic variants of SEQ ID NO: 2. cDNAs generated from alternatively spliced mRNAs, which retain the properties of the transcription factor are included within the scope of the present invention, as are polypeptides encoded by such cDNAs and mRNAs. Allelic variants and splice variants of these sequences can be cloned by probing cDNA or genomic libraries from different individual organisms or tissues according to standard procedures known in the art (see U.S. Pat. No. 6,388,064).

Thus, in addition to the sequences set forth in the Sequence Listing, the invention also encompasses related nucleic acid molecules that include allelic or splice variants, and sequences that are complementary. Related nucleic acid molecules also include nucleotide sequences encoding a polypeptide comprising a substitution, modification, addition and/or deletion of one or more amino acid residues. Such related polypeptides may comprise, for example, additions and/or deletions of one or more N-linked or O-linked glycosylation sites, or an addition and/or a deletion of one or more cysteine residues.

For example, Table 2 illustrates, for example, that the codons AGC, AGT, TCA, TCC, TCG, and TCT all encode the same amino acid: serine. Accordingly, at each position in the sequence where there is a codon encoding serine, any of the above trinucleotide sequences can be used without altering the encoded polypeptide.

TABLE 2

| Amino acid | | | Possible Codons | | | |
|---|---|---|---|---|---|---|
| Alanine | Ala | A | GCA | GCC | GCG | GCU |
| Cysteine | Cys | C | TGC | TGT | | |
| Aspartic acid | Asp | D | GAC | GAT | | |
| Glutamic acid | Glu | E | GAA | GAG | | |
| Phenylalanine | Phe | F | TTC | TTT | | |
| Glycine | Gly | G | GGA | GGC | GGG | GGT |
| Histidine | His | H | CAC | CAT | | |
| Isoleucine | Ile | I | ATA | ATC | ATT | |
| Lysine | Lys | K | AAA | AAG | | |
| Leucine | Leu | L | TTA | TTG | CTA | CTC | CTG | CTT |
| Methionine | Met | M | ATG | | | |
| Asparagine | Asn | N | AAC | AAT | | |
| Proline | Pro | P | CCA | CCC | CCG | CCT |
| Glutamine | Gln | Q | CAA | CAG | | |
| Arginine | Arg | R | AGA | AGG | CGA | CGC | CGG | CGT |
| Serine | Ser | S | AGC | AGT | TCA | TCC | TCG | TCT |
| Threonine | Thr | T | ACA | ACC | ACG | ACT |
| Valine | Val | V | GTA | GTC | GTG | GTT |
| Tryptophan | Trp | W | TGG | | | |
| Tyrosine | Tyr | Y | TAC | TAT | | |

Sequence alterations that do not change the amino acid sequence encoded by the polynucleotide are termed "silent" variations. With the exception of the codons ATG and TGG, encoding methionine and tryptophan, respectively, any of the possible codons for the same amino acid can be substituted by a variety of techniques, e.g., site-directed mutagenesis, available in the art. Accordingly, any and all such variations of a sequence selected from the above table are a feature of the invention.

In addition to silent variations, other conservative variations that alter one, or a few amino acids in the encoded polypeptide, can be made without altering the function of the polypeptide, these conservative variants are, likewise, a feature of the invention.

For example, substitutions, deletions and insertions introduced into the sequences provided in the Sequence Listing, are also envisioned by the invention. Such sequence modifications can be engineered into a sequence by site-directed mutagenesis (Wu, editor; *Methods Enzymol.* (1993) vol. 217, Academic Press) or the other methods noted below. Amino acid substitutions are typically of single residues; insertions usually will be on the order of about from 1 to 10 amino acid residues; and deletions will range about from 1 to 30 residues. In preferred embodiments, deletions or insertions are made in adjacent pairs, e.g., a deletion of two residues or insertion of two residues. Substitutions, deletions, insertions or any combination thereof can be combined to arrive at a sequence. The mutations that are made in the polynucleotide encoding the transcription factor should not place the sequence out of reading frame and should not create complementary regions that could produce secondary mRNA structure. Preferably, the polypeptide encoded by the DNA performs the desired function.

Conservative substitutions are those in which at least one residue in the amino acid sequence has been removed and a different residue inserted in its place. Such substitutions generally are made in accordance with the Table 3 when it is desired to maintain the activity of the protein. Table 3 shows amino acids which can be substituted for an amino acid in a protein and which are typically regarded as conservative substitutions. In one embodiment, transcriptions factors listed in the Sequence Listing may have up to 10 conservative substitutions and retain their function. In another embodiment, transcriptions factors listed in the Sequence Listing may have more than 10 conservative substitutions and still retain their function.

TABLE 3

| Residue | Conservative Substitutions |
|---------|---------------------------|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Similar substitutions are those in which at least one residue in the amino acid sequence has been removed and a different residue inserted in its place. Such substitutions generally are made in accordance with the Table 4 when it is desired to maintain the activity of the protein. Table 4 shows amino acids which can be substituted for an amino acid in a protein and which are typically regarded as structural and functional substitutions. For example, a residue in column 1 of Table 4 may be substituted with a residue in column 2; in addition, a residue in column 2 of Table 4 may be substituted with the residue of column 1.

TABLE 4

| Residue | Similar Substitutions |
|---------|----------------------|
| Ala | Ser; Thr; Gly; Val; Leu; Ile |
| Arg | Lys; His; Gly |
| Asn | Gln; His; Gly; Ser; Thr |
| Asp | Glu, Ser; Thr |
| Gln | Asn; Ala |
| Cys | Ser; Gly |
| Glu | Asp |
| Gly | Pro; Arg |
| His | Asn; Gln; Tyr; Phe; Lys; Arg |
| Ile | Ala; Leu; Val; Gly; Met |
| Leu | Ala; Ile; Val; Gly; Met |
| Lys | Arg; His; Gln; Gly; Pro |
| Met | Leu; Ile; Phe |
| Phe | Met; Leu; Tyr; Trp; His; Val; Ala |
| Ser | Thr; Gly; Asp; Ala; Val; Ile; His |
| Thr | Ser; Val; Ala; Gly |
| Trp | Tyr; Phe; His |
| Tyr | Trp; Phe; His |
| Val | Ala; Ile; Leu; Gly; Thr; Ser; Glu |

Substitutions that are less conservative than those in Table 4 can be selected by picking residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Further Modifying Sequences of the Invention by Mutation/Forced Evolution

In addition to generating silent or conservative substitutions as noted, above, the present invention optionally includes methods of modifying the sequences of the Sequence Listing. In the methods, nucleic acid or protein modification methods are used to alter the given sequences to produce new sequences and/or to chemically or enzymatically modify given sequences to change the properties of the nucleic acids or proteins.

Thus, in one embodiment, given nucleic acid sequences are modified, e.g., according to standard mutagenesis or artificial evolution methods to produce modified sequences. The modified sequences may be created using purified natural polynucleotides isolated from any organism or may be synthesized from purified compositions and chemicals using chemical means well known to those of skill in the art. For example, Ausubel (1997 and 2000; supra), provides additional details on mutagenesis methods. Artificial forced evolution methods are described, for example, by Stemmer (1994; *Nature* 370: 389-391), Stemmer (1994; *Proc. Natl. Acad. Sci. USA* 91: 10747-10751), and U.S. Pat. Nos. 5,811, 238, 5,837,500, and 6,242,568. Methods for engineering synthetic transcription factors and other polypeptides are described, for example, by Zhang et al. (2000) *J. Biol. Chem.*

275: 33850-33860, Liu et al. (2001) *J. Biol. Chem.* 276: 11323-11334, and Isalan et al. (2001) *Nature Biotechnol.* 19: 656-660. Many other mutation and evolution methods are also available and expected to be within the skill of the practitioner.

Similarly, chemical or enzymatic alteration of expressed nucleic acids and polypeptides can be performed by standard methods. For example, sequence can be modified by addition of lipids, sugars, peptides, organic or inorganic compounds, by the inclusion of modified nucleotides or amino acids, or the like. For example, protein modification techniques are illustrated in Ausubel (1997 and 2000; supra). Further details on chemical and enzymatic modifications can be found herein. These modification methods can be used to modify any given sequence, or to modify any sequence produced by the various mutation and artificial evolution modification methods noted herein.

Accordingly, the invention provides for modification of any given nucleic acid by mutation, evolution, chemical or enzymatic modification, or other available methods, as well as for the products produced by practicing such methods, e.g., using the sequences herein as a starting substrate for the various modification approaches.

For example, optimized coding sequence containing codons preferred by a particular prokaryotic or eukaryotic host can be used e.g., to increase the rate of translation or to produce recombinant RNA transcripts having desirable properties, such as a longer half-life, as compared with transcripts produced using a non-optimized sequence. Translation stop codons can also be modified to reflect host preference. For example, preferred stop codons for *Saccharomyces cerevisiae* and mammals are TAA and TGA, respectively. The preferred stop codon for monocotyledonous plants is TGA, whereas insects and *E. coli* prefer to use TAA as the stop codon.

The polynucleotide sequences of the present invention can also be engineered in order to alter a coding sequence for a variety of reasons, including but not limited to, alterations which modify the sequence to facilitate cloning, processing and/or expression of the gene product. For example, alterations are optionally introduced using techniques which are well known in the art, e.g., site-directed mutagenesis, to insert new restriction sites, to alter glycosylation patterns, to change codon preference, to introduce splice sites, etc.

Furthermore, a fragment or domain derived from any of the polypeptides of the invention can be combined with domains derived from other transcription factors or synthetic domains to modify the biological activity of a transcription factor. For instance, a DNA-binding domain derived from a transcription factor of the invention can be combined with the activation domain of another transcription factor or with a synthetic activation domain. A transcription activation domain assists in initiating transcription from a DNA-binding site. Examples include the transcription activation region of VP 16 or GAL4 (Moore et al. (1998) *Proc. Natl. Acad. Sci. USA* 95: 376-381; Aoyama et al. (1995) *Plant Cell* 7: 1773-1785), peptides derived from bacterial sequences (Ma and Ptashne (1987) *Cell* 51: 113-119) and synthetic peptides (Giniger and Ptashne (1987) *Nature* 330: 670-672).

Expression and Modification of Polypeptides

Typically, polynucleotide sequences of the invention are incorporated into recombinant DNA (or RNA) molecules that direct expression of polypeptides of the invention in appropriate host cells, transgenic plants, in vitro translation systems, or the like. Due to the inherent degeneracy of the genetic code, nucleic acid sequences which encode substantially the same or a functionally equivalent amino acid sequence can be substituted for any listed sequence to provide for cloning and expressing the relevant homolog.

The transgenic plants of the present invention comprising recombinant polynucleotide sequences are generally derived from parental plants, which may themselves be non-transformed (or non-transgenic) plants. These transgenic plants may either have a transcription factor gene "knocked out" (for example, with a genomic insertion by homologous recombination, an antisense or ribozyme construct) or expressed to a normal or wild-type extent. However, overexpressing transgenic "progeny" plants will exhibit greater mRNA levels, wherein the mRNA encodes a transcription factor, that is, a DNA-binding protein that is capable of binding to a DNA regulatory sequence and inducing transcription, and preferably, expression of a plant trait gene. Preferably, the mRNA expression level will be at least three-fold greater than that of the parental plant, or more preferably at least ten-fold greater mRNA levels compared to said parental plant, and most preferably at least fifty-fold greater compared to said parental plant.

Vectors Promoters, and Expression Systems

The present invention includes recombinant constructs comprising one or more of the nucleic acid sequences herein. The constructs typically comprise a vector, such as a plasmid, a cosmid, a phage, a virus (e.g., a plant virus), a bacterial artificial chromosome (BAC), a yeast artificial chromosome (YAC), or the like, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

General texts that describe molecular biological techniques useful herein, including the use and production of vectors, promoters and many other relevant topics, include Berger (1987) supra, Sambrook (1989), supra, and Ausubel (through 2000) supra. Any of the identified sequences can be incorporated into a cassette or vector, e.g., for expression in plants. A number of expression vectors suitable for stable transformation of plant cells or for the establishment of transgenic plants have been described including those described in Weissbach and Weissbach (1989) *Methods for Plant Molecular Biology*, Academic Press, and Gelvin et al. (1990) *Plant Molecular Biology Manual*, Kluwer Academic Publishers. Specific examples include those derived from a Ti plasmid of *Agrobacteriun tumefaciens*, as well as those disclosed by Herrera-Estrella et al. (1983) *Nature* 303: 209, Bevan (1984) *Nucleic Acids Res.* 12: 8711-8721, Klee (1985) *Bio/Technology* 3: 637-642, for dicotyledonous plants.

Alternatively, non-Ti vectors can be used to transfer the DNA into monocotyledonous plants and cells by using free DNA delivery techniques. Such methods can involve, for example, the use of liposomes, electroporation, microprojectile bombardment, silicon carbide whiskers, and viruses. By using these methods transgenic plants such as wheat, rice (Christou (1991) *Bio/Technology* 9: 957-962) and corn (Gordon-Kamm (1990) *Plant Cell* 2: 603-618) can be produced. An immature embryo can also be a good target tissue for monocots for direct DNA delivery techniques by using the particle gun (Weeks et al. (1993) *Plant Physiol.* 102: 1077-1084; Vasil (1993) *Bio/Technology* 10: 667-674; Wan and Lemeaux (1994) *Plant Physiol.* 104: 37-48, and for *Agrobacterium*-mediated DNA transfer (Ishida et al. (1996) *Nature Biotechnol.* 14: 745-750).

Typically, plant transformation vectors include one or more cloned plant coding sequences (genomic or cDNA) under the transcriptional control of 5' and 3' regulatory sequences and a dominant selectable marker. Such plant transformation vectors typically also contain a promoter (e.g., a regulatory region controlling inducible or constitutive, environmentally-or developmentally-regulated, or cell- or tissue-specific expression), a transcription initiation start site, an RNA processing signal (such as intron splice sites), a transcription termination site, and/or a polyadenylation signal.

A potential utility for the transcription factor polynucleotides disclosed herein is the isolation of promoter elements from these genes that can be used to program expression in plants of any genes. Each transcription factor gene disclosed herein is expressed in a unique fashion, as determined by promoter elements located upstream of the start of translation, and additionally within an intron of the transcription factor gene or downstream of the termination codon of the gene. As is well known in the art, for a significant portion of genes, the promoter sequences are located entirely in the region directly upstream of the start of translation. In such cases, typically the promoter sequences are located within 2.0 kb of the start of translation, or within 1.5 kb of the start of translation, frequently within 1.0 kb of the start of translation, and sometimes within 0.5 kb of the start of translation.

The promoter sequences can be isolated according to methods known to one skilled in the art.

Examples of constitutive plant promoters which can be useful for expressing the transcription factor sequence include: the cauliflower mosaic virus (CaMV) 35S promoter, which confers constitutive, high-level expression in most plant tissues (see, for example, Odell et al. (1985) *Nature* 313: 810-812); the nopaline synthase promoter (An et al. (1988) *Plant Physiol.* 88: 547-552); and the octopine synthase promoter (Fromm et al. (1989) *Plant Cell* 1: 977-984).

The transcription factors of the invention may be operably linked with a specific promoter that causes the transcription factor to be expressed in response to environmental, tissue-specific or temporal signals. A variety of plant gene promoters are known to regulate gene expression in response to environmental, hormonal, chemical, developmental signals, and in a tissue-active manner; many of these may be used for expression of a transcription factor sequence in plants. Choice of a promoter is based largely on the phenotype of interest and is determined by such factors as tissue (e.g., seed, fruit, root, pollen, vascular tissue, flower, carpel, etc.), inducibility (e.g., in response to wounding, heat, cold, drought, light, pathogens, etc.), timing, developmental stage, and the like. Numerous known promoters have been characterized and can favorably be employed to promote expression of a polynucleotide of the invention in a transgenic plant or cell of interest. For example, tissue specific promoters include: seed-specific promoters (such as the napin, phaseolin or DC3 promoter described in U.S. Pat. No. 5,773,697), fruit-specific promoters that are active during fruit ripening (such as the dru 1 promoter (U.S. Pat. No. 5,783,393), or the 2A11 promoter (U.S. Pat. No. 4,943,674) and the tomato polygalacturonase promoter (Bird et al. (1988) *Plant Mol. Biol.* 11: 651-662), root-specific promoters, such as ARSK1, and those disclosed in U.S. Pat. Nos. 5,618,988, 5,837,848 and 5,905,186, epidermis-specific promoters, including CUT1 (Kunst et al. (1999) *Biochem. Soc. Trans.* 28: 651-654), pollen-active promoters such as PTA29, PTA26 and PTA13 (U.S. Pat. No. 5,792,929), promoters active in vascular tissue (Ringli and Keller (1998) *Plant Mol. Biol.* 37: 977-988), flower-specific (Kaiser et al. (1995) *Plant Mol. Biol.* 28: 231-243), pollen (Baerson et al. (1994) *Plant Mol. Biol.* 26: 1947-1959), car- pels (Ohl et al. (1990) *Plant Cell* 2: 837-848), pollen and ovules (Baerson et al. (1993) *Plant Mol. Biol.* 22: 255-267), auxin-inducible promoters (such as that described in van der Kop et al. (1999) *Plant Mol. Biol.* 39: 979-990 or Baumann et al. (1999) *Plant Cell* 11: 323-334), cytokinin-inducible promoter (Guevara-Garcia (1998) *Plant Mol. Biol.* 38: 743-753), promoters responsive to gibberellin (Shi et al. (1998) *Plant Mol. Biol.* 38: 1053-1060, Willmott et al. (1998) *Plant Mol. Biol.* 38: 817-825) and the like. Additional promoters are those that elicit expression in response to heat (Ainley et al. (1993) *Plant Mol. Biol.* 22: 13-23), light (e.g., the pea rbcS-3A promoter, Kuhlemeier et al. (1989) *Plant Cell* 1: 471-478, and the maize rbcS promoter, Schaffner and Sheen (1991) *Plant Cell* 3: 997-1012); wounding (e.g., wun1, Siebertz et al. (1989) *Plant Cell* 1: 961-968); pathogens (such as the PR-1 promoter described in Buchel et al. (1999) *Plant Mol. Biol.* 40: 387-396, and the PDF1.2 promoter described in Manners et al. (1998) *Plant Mol. Biol.* 38: 1071-1080), and chemicals such as methyl jasmonate or salicylic acid (Gatz (1997) *Annu. Rev. Plant Physiol. Plant Mol. Biol.* 48: 89-108). In addition, the timing of the expression can be controlled by using promoters such as those acting at senescence (Gan and Amasino (1995) *Science* 270: 1986-1988); or late seed development (Odell et al. (1994) *Plant Physiol.* 106: 447-458).

Plant expression vectors can also include RNA processing signals that can be positioned within, upstream or downstream of the coding sequence. In addition, the expression vectors can include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Additional Expression Elements

Specific initiation signals can aid in efficient translation of coding sequences. These signals can include, e.g., the ATG initiation codon and adjacent sequences. In cases where a coding sequence, its initiation codon and upstream sequences are inserted into the appropriate expression vector, no additional translational control signals may be needed. However, in cases where only coding sequence (e.g., a mature protein coding sequence), or a portion thereof, is inserted, exogenous transcriptional control signals including the ATG initiation codon can be separately provided. The initiation codon is provided in the correct reading frame to facilitate transcription. Exogenous transcriptional elements and initiation codons can be of various origins, both natural and synthetic. The efficiency of expression can be enhanced by the inclusion of enhancers appropriate to the cell system in use.

Expression Hosts

The present invention also relates to host cells which are transduced with vectors of the invention, and the production of polypeptides of the invention (including fragments thereof) by recombinant techniques. Host cells are genetically engineered (i.e., nucleic acids are introduced, e.g., transduced, transformed or transfected) with the vectors of this invention, which may be, for example, a cloning vector or an expression vector comprising the relevant nucleic acids herein. The vector is optionally a plasmid, a viral particle, a phage, a naked nucleic acid, etc. The engineered host cells can be cultured in conventional nutrient media modified as appropriate for activating promoters, selecting transformants, or amplifying the relevant gene. The culture conditions, such as temperature, pH and the like, are those previously used with the host cell selected for expression, and will be apparent to those skilled in the art and in the references cited herein, including Sambrook (1989) supra, and Ausubel (through 2000) supra.

The host cell can be a eukaryotic cell, such as a yeast cell, or a plant cell, or the host cell can be a prokaryotic cell, such as a bacterial cell. Plant protoplasts are also suitable for some applications. For example, the DNA fragments are introduced into plant tissues, cultured plant cells or plant protoplasts by standard methods including electroporation (Fromm et al. (1985) *Proc. Natl. Acad. Sci. USA* 82: 5824-5828), infection by viral vectors such as cauliflower mosaic virus (CaMV) (Hohn et al. (1982) *Molecular Biology of Plant Tumors*, Academic Press, New York, N.Y., pp. 549-560; U.S. Pat. No. 4,407,956), high velocity ballistic penetration by small particles with the nucleic acid either within the matrix of small beads or particles, or on the surface (Klein et al. (1987) *Nature* 327: 70-73), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) *Science* 233: 496-498; Fraley et al. (1983) *Proc. Natl. Acad. Sci. USA* 80: 4803-4807).

The cell can include a nucleic acid of the invention that encodes a polypeptide, wherein the cell expresses a polypeptide of the invention. The cell can also include vector sequences, or the like. Furthermore, cells and transgenic plants that include any polypeptide or nucleic acid above or throughout this specification, e.g., produced by transduction of a vector of the invention, are an additional feature of the invention.

For long-term, high-yield production of recombinant proteins, stable expression can be used. Host cells transformed with a nucleotide sequence encoding a polypeptide of the invention are optionally cultured under conditions suitable for the expression and recovery of the encoded protein from cell culture. The protein or fragment thereof produced by a recombinant cell may be secreted, membrane-bound, or contained intracellularly, depending on the sequence and/or the vector used. As will be understood by those of skill in the art, expression vectors containing polynucleotides encoding mature proteins of the invention can be designed with signal sequences which direct secretion of the mature polypeptides through a prokaryotic or eukaryotic cell membrane.

Modified Amino Acid Residues

Polypeptides of the invention may contain one or more modified amino acid residues. The presence of modified amino acids may be advantageous in, for example, increasing polypeptide half-life, reducing polypeptide antigenicity or toxicity, increasing polypeptide storage stability, or the like. Amino acid residue(s) are modified, for example, co-translationally or post-translationally during recombinant production or modified by synthetic or chemical means.

Non-limiting examples of a modified amino acid residue include incorporation or other use of acetylated amino acids, glycosylated amino acids, sulfated amino acids, prenylated (e.g., farnesylated, geranylgeranylated) amino acids, PEG modified (for example, "PEGylated") amino acids, biotinylated amino acids, carboxylated amino acids, phosphorylated amino acids, etc. References adequate to guide one of skill in the modification of amino acid residues are replete throughout the literature.

The modified amino acid residues may prevent or increase affinity of the polypeptide for another molecule, including, but not limited to, polynucleotide, proteins, carbohydrates, lipids and lipid derivatives, and other organic or synthetic compounds.

Identification of Additional Protein Factors

A transcription factor provided by the present invention can also be used to identify additional endogenous or exogenous molecules that can affect a phentoype or trait of interest. Such molecules include endogenous molecules that are acted upon either at a transcriptional level by a transcription factor of the invention to modify a phenotype as desired. For example, the transcription factors can be employed to identify one or more downstream genes that are subject to a regulatory effect of the transcription factor. In one approach, a transcription factor or transcription factor homolog of the invention is expressed in a host cell, e.g., a transgenic plant cell, tissue or explant, and expression products, either RNA or protein, of likely or random targets are monitored, e.g., by hybridization to a microarray of nucleic acid probes corresponding to genes expressed in a tissue or cell type of interest, by two-dimensional gel electrophoresis of protein products, or by any other method known in the art for assessing expression of gene products at the level of RNA or protein. Alternatively, a transcription factor of the invention can be used to identify promoter sequences (such as binding sites on DNA sequences) involved in the regulation of a downstream target. After identifying a promoter sequence, interactions between the transcription factor and the promoter sequence can be modified by changing specific nucleotides in the promoter sequence or specific amino acids in the transcription factor that interact with the promoter sequence to alter a plant trait. Typically, transcription factor DNA-binding sites are identified by gel shift assays. After identifying the promoter regions, the promoter region sequences can be employed in double-stranded DNA arrays to identify molecules that affect the interactions of the transcription factors with their promoters (Bulyk et al. (1999) *Nature Biotechnol.* 17: 573-577).

The identified transcription factors are also useful to identify proteins that modify the activity of the transcription factor. Such modification can occur by covalent modification, such as by phosphorylation, or by protein-protein (homo or -heteropolymer) interactions. Any method suitable for detecting protein-protein interactions can be employed. Among the methods that can be employed are co-immunoprecipitation, cross-linking and co-purification through gradients or chromatographic columns, and the two-hybrid yeast system.

The two-hybrid system detects protein interactions in vivo and has been previously described (Chien et al. (1991) *Proc. Natl. Acad. Sci. USA* 88: 9578-9582), and is commercially available from Clontech (Palo Alto, Calif.). In such a system, plasmids are constructed that encode two hybrid proteins: one consists of the DNA-binding domain of a transcription activator protein fused to the transcription factor polypeptide and the other consists of the transcription activator protein's activation domain fused to an unknown protein that is encoded by a cDNA that has been recombined into the plasmid as part of a cDNA library. The DNA-binding domain fusion plasmid and the cDNA library are transformed into a strain of the yeast *Saccharomyces cerevisiae* that contains a reporter gene (e.g., lacZ) whose regulatory region contains the transcription activator's binding site. Either hybrid protein alone cannot activate transcription of the reporter gene. Interaction of the two hybrid proteins reconstitutes the functional activator protein and results in expression of the reporter gene, which is detected by an assay for the reporter gene product. Then, the library plasmids responsible for reporter gene expression are isolated and sequenced to identify the proteins encoded by the library plasmids. After identifying proteins that interact with the transcription factors, assays for compounds that interfere with the transcription factor protein-protein interactions can be performed.

Subsequences

Also contemplated are uses of polynucleotides, also referred to herein as oligonucleotides, typically having at least 12 bases, preferably at least 50 bases, which hybridize under stringent conditions to a polynucleotide sequence described above. The polynucleotides may be used as probes, primers, sense and antisense agents, and the like, according to methods as noted above.

Subsequences of the polynucleotides of the invention, including polynucleotide fragments and oligonucleotides are useful as nucleic acid probes and primers. An oligonucleotide suitable for use as a probe or primer is at least about 15 nucleotides in length, more often at least about 18 nucleotides, often at least about 21 nucleotides, frequently at least about 30 nucleotides, or about 40 nucleotides, or more in length. A nucleic acid probe is useful in hybridization protocols, for example, to identify additional polypeptide homologs of the invention, including protocols for microarray experiments. Primers can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods (Sambrook (1989) supra and Ausubel (through 2000) supra).

In addition, the invention includes an isolated or recombinant polypeptide including a subsequence of at least about 15 contiguous amino acids encoded by the recombinant or isolated polynucleotides of the invention. For example, such polypeptides, or domains or fragments thereof, can be used as immunogens, e.g., to produce antibodies specific for the polypeptide sequence, or as probes for detecting a sequence of interest. A subsequence can range in size from about 15 amino acids in length up to and including the full length of the polypeptide.

To be encompassed by the present invention, an expressed polypeptide which comprises such a polypeptide subsequence performs at least one biological function of the intact polypeptide in substantially the same manner, or to a similar extent, as does the intact polypeptide. For example, a polypeptide fragment can comprise a recognizable structural motif or functional domain such as a DNA binding domain that activates transcription, for example, by binding to a specific DNA promoter region an activation domain, or a domain for protein-protein interactions.

Production of Transgenic Plants

Modification of Traits

The polynucleotides of the invention are favorably employed to produce transgenic plants with various traits, or characteristics, that have been modified in a desirable manner, e.g., to improve the seed characteristics of a plant. For example, alteration of expression levels or patterns (e.g., spatial or temporal expression patterns) of one or more of the transcription factors (or transcription factor homologs) of the invention, as compared with the levels of the same protein found in a wild-type plant, can be used to modify a plant's traits. An illustrative example of trait modification, improved characteristics, by altering expression levels of a particular transcription factor is described further in the Examples and the Sequence Listing.

*Arabidopsis* as a Model System

*Arabidopsis thaliana* is the object of rapidly growing attention as a model for genetics and metabolism in plants. *Arabidopsis* has a small genome, and well-documented studies are available. It is easy to grow in large numbers and mutants defining important genetically controlled mechanisms are either available, or can readily be obtained. Various methods to introduce and express isolated homologous genes are available (see Koncz et al., editors, *Methods in Arabidopsis Research* (1992) World Scientific, New Jersey N.J., in "Preface"). Because of its small size, short life cycle, obligate autogamy and high fertility, *Arabidopsis* is also a choice organism for the isolation of mutants and studies in morphogenetic and development pathways, and control of these pathways by transcription factors (Koncz (1992) supra, p. 72). A number of studies introducing transcription factors into *A. thaliana* have demonstrated the utility of this plant for understanding the mechanisms of gene regulation and trait alteration in plants (see, for example, factors (Koncz (1992) supra, and U.S. Pat. No. 6,417,428).

*Arabidopsis* Genes in Transgenic Plants

Expression of genes which encode transcription factors modify expression of endogenous genes, polynucleotides, and proteins are well known in the art. In addition, transgenic plants comprising isolated polynucleotides encoding transcription factors may also modify expression of endogenous genes, polynucleotides, and proteins. Examples include Peng et al. (1997) et al. *Genes and Development* 11: 3194-3205, and Peng et al. (1999) *Nature* 400: 256-261. In addition, many others have demonstrated that an *Arabidopsis* transcription factor expressed in an exogenous plant species elicits the same or very similar phenotypic response. See, for example, Fu et al. (2001) *Plant Cell* 13: 1791-1802; Nandi et al. (2000) *Curr. Biol.* 10: 215-218; Coupland (1995) *Nature* 377: 482-483; and Weigel and Nilsson (1995) *Nature* 377: 482-500.

Homologous Genes Introduced into Transgenic Plants

Homologous genes that may be derived from any plant, or from any source whether natural, synthetic, semi-synthetic or recombinant, and that share significant sequence identity or similarity to those provided by the present invention, may be introduced into plants, for example, crop plants, to confer desirable or improved traits. Consequently, transgenic plants may be produced that comprise a recombinant expression vector or cassette with a promoter operably linked to one or more sequences homologous to presently disclosed sequences. The promoter may be, for example, a plant or viral promoter.

The invention thus provides for methods for preparing transgenic plants, and for modifying plant traits. These methods include introducing into a plant a recombinant expression vector or cassette comprising a functional promoter operably linked to one or more sequences homologous to presently disclosed sequences. Plants and kits for producing these plants that result from the application of these methods are also encompassed by the present invention.

Transcription Factors of Interest for the Modification of Plant Traits

Currently, the existence of a series of maturity groups for different latitudes represents a major barrier to the introduction of new valuable traits. Any trait (e.g. abiotic stress tolerance or increased biomass) has to be bred into each of the different maturity groups separately, a laborious and costly exercise. The availability of single strain, which could be grown at any latitude, would therefore greatly increase the potential for introducing new traits to crop species such as soybean and cotton.

For the specific effects, traits and utilities conferred to plants, one or more transcription factor genes of the present invention may be used to increase or decrease, or improve or prove deleterious to a given trait. For example, knocking out a transcription factor gene that naturally occurs in a plant, or suppressing the gene (with, for example, antisense suppression), may cause decreased tolerance to an osmotic stress relative to non-transformed or wild-type plants. By overexpressing this gene, the plant may experience increased tolerance to the same stress. More than one transcription factor gene may be introduced into a plant, either by transforming the plant with one or more vectors comprising two or more transcription factors, or by selective breeding of plants to yield hybrid crosses that comprise more than one introduced transcription factor.

Genes, Traits and Utilities that Affect Plant Characteristics

Plant transcription factors can modulate gene expression, and, in turn, be modulated by the environmental experience of a plant. Significant alterations in a plant's environment invariably result in a change in the plant's transcription factor gene expression pattern. Altered transcription factor expression patterns generally result in phenotypic changes in the plant. Transcription factor gene product(s) in transgenic plants then differ(s) in amounts or proportions from that found in wild-type or non-transformed plants, and those transcription factors likely represent polypeptides that are used to alter the response to the environmental change. By way of example, it is well accepted in the art that analytical methods based on altered expression patterns may be used to screen for phenotypic changes in a plant far more effectively than can be achieved using traditional methods.

I. Increased Biomass.

Plants overexpressing nine distinct related AT-hook transcription factors of the invention, including sequences from diverse species of monocots and dicots, such as *Arabidopsis thaliana* polypeptides G1073, G1067, G1667, G2153 and G2156, G2157, *Oryza sativa* polypeptides G3399, G3400, G3401, G3407, G3556, and *Glycine max* polypeptides G3456, G3459 and G3460, become larger than control or wild-type plants, and generally produced broader leaves than control or wild-type plants. For some ornamental plants, the ability to provide larger varieties with these genes or their equivalogs may be highly desirable. More significantly, crop species overexpressing these genes from diverse species would also produce larger cultivars, and thus higher yields, particularly in those plants which the vegetative portion of the plant is edible (e.g., lettuce, chard, etc.). This has already been observed in *Arabidopsis* and tomato plants. Tomato plants overexpressing the *A. thaliana* G2153 and G2157 polypeptides have been found to be significantly larger than wild-type control tomato plants. Numerous *Arabidopsis* lines that overexpress G3399, G3400, G3401, G3407, or G3556, which are rice genes, and G3456, G3459 or G3460, which are soy genes, develop significantly larger rosettes and leaves than wild-type *Arabidopsis* controls.

II. Increased Abiotic Stress Tolerance.

Overexpression of many of the transcription factors in the G1073 clade of transcription factor polypeptides confer increased stress tolerance when the sequences are overexpressed in plants. The increased biomass observed in many of these plants appears to be related to the particular mechanism of stress tolerance exhibited by these genes. The decision for a lateral organ to continue growth and expansion versus entering late development phases (growth cessation and senescence) is controlled genetically and hormonally, including regulation at an organ size checkpoint (e.g., Mizukami (2001) *Curr Opinion Plant Biol* 4: 533-39; Mizukami and Fisher (2000) *Proc. Natl. Acad. Sci. USA* 97: 942-947; Hu et al. 2003 *Plant Cell* 15: 1591). Organ size is controlled by the meristematic competence of organ cells, with increased meristematic competence leading to increased organ size (both leaves and stems). Plant hormones can impact plant organ size, with, for example, ethylene pathway overexpression leading to reduced organ size. There also suggestions that auxin plays a determinative role in organ size. Stress responses can impact hormone levels in plant tissues, including ABA and ethylene levels, thereby modifying meristematic competence and final organ size. Thus, overexpression of HRC genes alters environmental (e.g., stress) inputs to the organ size checkpoint, thus enhancing organ size under typical growth conditions.

Due to frequent exposure to stresses under typical plant growth conditions, the maximum genetically programmed organ size is infrequently achieved. It is well appreciated that increased leaf organ size can result in increased seed yield, through enhanced energy capture and source activity. Thus, a major strategy for yield optimization is altered characteristics of the sensor that integrates external environmental stress inputs to meristematic competence and organ size control. The HRC genes that are the subject of the instant invention represent one component of this control mechanism. Increased expression of HRC genes leads to diminished sensitivity of the environmental sensor for organ size control to those stress inputs. This increase in stress threshold for diminished meristematic competence results in increased vegetative and seed yield under typical plant growth conditions. AT-hook proteins are known to modulate gene expression through interactions with other proteins. Thus, the environmental integration mechanism for organ size control instantiated by HRC proteins will have additional components whose function will be recognized by the ability of the encoded proteins to participate in regulating gene sets that are regulated by HRC proteins. Identification of additional components of the integration can be achieved by identifying other transcription factors that bind to upstream regulatory regions, detecting proteins that directly interact with HRC proteins.

A. Responses to High Sugar Concentrations: Sugar Sensing.

In addition to their important role as an energy source and structural component of the plant cell, sugars are central regulatory molecules that control several aspects of plant physiology, metabolism and development (Hsieh et al. (1998) *Proc. Natl. Acad. Sci. USA* 95: 13965-13970). It is thought that this control is achieved by regulating gene expression and, in higher plants, sugars have been shown to repress or activate plant genes involved in many essential processes such as photosynthesis, glyoxylate metabolism, respiration, starch and sucrose synthesis and degradation, pathogen response, wounding response, cell cycle regulation, pigmentation, flowering and senescence. The mechanisms by which sugars control gene expression are not understood.

Several sugar sensing mutants have turned out to be allelic to ABA and ethylene mutants. ABA is found in all photosynthetic organisms and acts as a key regulator of transpiration, stress responses, embryogenesis, and seed germination. Most ABA effects are related to the compound acting as a signal of decreased water availability, whereby it triggers a reduction in water loss, slows growth, and mediates adaptive responses. However, ABA also influences plant growth and development via interactions with other phytohormones. Physiological and molecular studies indicate that maize and *Arabidopsis* have almost identical pathways with regard to ABA biosynthesis and signal transduction. For further review, see Finkelstein and Rock (2002) "Abscisic acid biosynthesis and response", in The *Arabidopsis* Book, Editors: Somerville and Meyerowitz (American Society of Plant Biologists, Rockville, Md.).

Thus, G1073, G2153, G2156 and related transcription factors are likely involved in hormone signaling based on the sucrose sugar sensing phenotype of 35S::G1073, 35S::G2153 and 35S::G2156 transgenic lines. On the other hand, the sucrose treatment used in these experiments (9.5% w/v) could also be an osmotic stress. Therefore, one could interpret these data as an indication that the 35S::G1073, 35S::G2153 and 35S::G2156 transgenic lines are more tolerant to osmotic stress. However, it is well known that plant responses to ABA, osmotic and other stress may be linked, and these different treatments may even act in a synergistic manner to increase the degree of a response. For example, Xiong, Ishitani, and Zhu ((1999) *Plant Physiol.* 119: 205-212) have shown that genetic and molecular studies may be used to show extensive interaction between osmotic stress, temperature stress, and ABA responses in plants. These investigators analyzed the expression of RD29A-L UC in response to various treatment regimes in *Arabidopsis*. The RD29A promoter contains both the ABA-responsive and the dehydration-responsive element—also termed the C-repeat—and can be activated by osmotic stress, low temperature, or ABA treatment; transcription of the RD29A gene in response to osmotic and cold stresses is mediated by both ABA-dependent and ABA-independent pathways (Xiong, Ishitani, and Zhu (1999) supra). LUC refers to the firefly luciferase coding sequence, which, in this case, was driven by the stress responsive RD29A promoter. The results revealed both positive and negative interactions, depending on the nature and duration of the treatments. Low temperature stress was found to impair osmotic signaling but moderate heat stress strongly enhanced osmotic stress induction, thus acting synergistically with osmotic signaling pathways. In this study, the authors reported that osmotic stress and ABA can act synergistically by showing that the treatments simultaneously induced transgene and endogenous gene expression. Similar results were reported by Bostock and Quatrano ((1992) *Plant Physiol.* 98: 1356-1363), who found that osmotic stress and ABA act synergistically and induce maize Em gene expression. Ishitani et al (1997) *Plant Cell* 9: 1935-1949) isolated a group of *Arabidopsis* single-gene mutations that confer enhanced responses to both osmotic stress and ABA. The nature of the recovery of these mutants from osmotic stress and ABA treatment suggested that although separate signaling pathways exist for osmotic stress and ABA, the pathways share a number of components; these common components may mediate synergistic interactions between osmotic stress and ABA. Thus, contrary to the previously-held belief that ABA-dependent and ABA-independent stress signaling pathways act in a parallel manner, our data reveal that these pathways crosstalk and converge to activate stress gene expression.

Because sugars are important signaling molecules, the ability to control either the concentration of a signaling sugar or how the plant perceives or responds to a signaling sugar could be used to control plant development, physiology or metabolism. For example, the flux of sucrose (a disaccharide sugar used for systemically transporting carbon and energy in most plants) has been shown to affect gene expression and alter storage compound accumulation in seeds. Manipulation of the sucrose signaling pathway in seeds may therefore cause seeds to have more protein, oil or carbohydrate, depending on the type of manipulation. Similarly, in tubers, sucrose is converted to starch which is used as an energy store. It is thought that sugar signaling pathways may partially determine the levels of starch synthesized in the tubers. The manipulation of sugar signaling in tubers could lead to tubers with a higher starch content.

Thus, the presently disclosed transcription factor genes that manipulate the sugar signal transduction pathway, including, for example, G1073 and G2156, along with their equivalogs, may lead to altered gene expression to produce plants with desirable traits. In particular, manipulation of sugar signal transduction pathways could be used to alter source-sink relationships in seeds, tubers, roots and other storage organs leading to increase in yield.

B. Responses to Osmotic Stresses (High Salt, Freezing, Dehydration and Drought)

Plants are subject to a range of environmental challenges. Several of these, including salt stress, general osmotic stress, drought stress and freezing stress, have the ability to impact whole plant and cellular water availability. Not surprisingly, then, plant responses to this collection of stresses are related. In a recent review, Zhu notes that "most studies on water stress signaling have focused on salt stress primarily because plant responses to salt and drought are closely related and the mechanisms overlap" (Zhu (2002) *Ann. Rev. Plant Biol.* 53: 247-273). Many examples of similar responses (i.e., genetic pathways to this set of stresses) have been documented. For example, the CBF transcription factors have been shown to condition resistance to salt, freezing and drought (Kasuga et al. (1999) *Nature Biotech.* 17: 287-291). The *Arabidopsis* rd29B gene is induced in response to both salt and dehydration stress, a process that is mediated largely through an ABA signal transduction process (Uno et al. (2000) *Proc. Natl. Acad. Sci. USA* 97: 11632-11637), resulting in altered activity of transcription factors that bind to an upstream element within the rd29B promoter. In *Mesembryanthemum crystallinum* (ice plant), Patharker and Cushman have shown that a calcium-dependent protein kinase (McCDPK1) is induced by exposure to both drought and salt stresses (Patharker and Cushman (2000) *Plant J.* 24: 679-691). The stress-induced kinase was also shown to phosphorylate a transcription factor, presumably altering its activity, although transcript levels of the target transcription factor are not altered in response to salt or drought stress. Similarly, Saijo et al. demonstrated that a rice salt/drought-induced calmodulin-dependent protein kinase (OsCDPK7) conferred increased salt and drought tolerance to rice when overexpressed (Saijo et al. (2000) *Plant J.* 23: 319-327).

Exposure to dehydration invokes similar survival strategies in plants as does freezing stress (see, for example, Yelenosky (1989) *Plant Physiol* 89: 444-451) and drought stress induces freezing tolerance (see, for example, Siminovitch et al. (1982) *Plant Physiol* 69: 250-255; and Guy et al. (1992) *Planta* 188: 265-270). In addition to the induction of cold-acclimation proteins, strategies that allow plants to survive in low water conditions may include, for example, reduced surface area, or surface oil or wax production. Plants overexpressing G1073, G1067 and G2156 have been shown to be more tolerant to dehydration in plate-based desiccation assays than wild-type control plants (as shown in tables in Examples VIII and IX). G1067, G1069 and G2789 have been shown to be more tolerant to drought in soil-based assays.

Consequently, one skilled in the art would expect that some pathways involved in resistance to one of these stresses, and hence regulated by an individual transcription factor, will also be involved in resistance to another of these stresses, regulated by the same or homologous transcription factors. Of course, the overall resistance pathways are related, not identical, and therefore not all transcription factors controlling resistance to one stress will control resistance to the other stresses. Nonetheless, if a transcription factor conditions resistance to one of these stresses, it would be apparent to one skilled in the art to test for resistance to these related stresses.

Thus, modifying the expression of G1073 clade members may be used to increase a plant's tolerance to low water conditions and provide the benefits of improved survival, increased yield and an extended geographic and temporal planting range.

A number of the G1073 clade sequences (G1073, G1067, G1069, G2153, G2156, G2657, G3401 and G3460) have been shown to have an altered osmotic stress tolerance phenotype by virtue of the improved germination of plants overexpressing these sequences on high sugar-containing media. Most of these genes have also been shown to confer increased salt stress or desiccation tolerance to overexpressing plants (all have been shown to increase osmotic stress tolerance in *Arabidopsis*, and G2153 has been shown to do the same for mature tomato plants). Thus, modification of the expression of these and other structurally related disclosed transcription factor genes may be used to increase germination rate or growth under adverse osmotic conditions, which could impact survival and yield of seeds and plants. Osmotic stresses may be regulated by specific molecular control mechanisms that include genes controlling water and ion movements, functional and structural stress-induced proteins, signal perception and transduction, and free radical scavenging, and many others (Wang et al. (2001) *Acta Hort.* (*ISHS*) 560: 285-292). Instigators of osmotic stress include freezing, drought and high salinity, each of which are discussed in more detail below.

In many ways, freezing, high salt and drought have similar effects on plants, not the least of which is the induction of common polypeptides that respond to these different stresses. For example, freezing is similar to water deficit in that freezing reduces the amount of water available to a plant. Exposure to freezing temperatures may lead to cellular dehydration as water leaves cells and forms ice crystals in intercellular spaces (Buchanan (2000) supra). As with high salt concentration and freezing, the problems for plants caused by low water availability include mechanical stresses caused by the withdrawal of cellular water. Thus, the incorporation of transcription factors that modify a plant's response to osmotic stress into, for example, a crop or ornamental plant, may be useful in reducing damage or loss. Specific effects caused by freezing, high salt and drought are addressed below.

The genes of the Sequence Listing, including, for example, G1073, G2153, G2156, G3401, G3456, G3459, and G3460, that provide tolerance to salt may be used to engineer salt tolerant crops and trees that can flourish in soils with high saline content or under drought conditions. In particular, increased salt tolerance during the germination stage of a plant enhances survival and yield. Presently disclosed transcription factor genes that provide increased salt tolerance during germination, the seedling stage, and throughout a plant's life cycle, would find particular value for imparting survival and yield in areas where a particular crop would not normally prosper.

C. Responses to Cold Stress

Enhanced chilling tolerance may extend the effective growth range of chilling sensitive crop species by allowing earlier planting or later harvest. Improved chilling tolerance may be conferred by increased expression of glycerol-3-phosphate acetyltransferase in chloroplasts (see, for example, Wolter et al. (1992) et al. *EMBO J.* 4685-4692, and Murata et al. (1992) *Nature* 356: 710-713).

Chilling tolerance could also serve as a model for understanding how plants adapt to water deficit. Both chilling and water stress share similar signal transduction pathways and tolerance/adaptation mechanisms. For example, acclimation to chilling temperatures can be induced by water stress or treatment with ABA. Genes induced by low temperature include dehydrins (or LEA proteins). Dehydrins are also induced by salinity, ABA, water stress, and during the late stages of embryogenesis.

Another large impact of chilling occurs during post-harvest storage. For example, some fruits and vegetables do not store well at low temperatures (for example, bananas, avocados, melons, and tomatoes). The normal ripening process of the tomato is impaired if it is exposed to cool temperatures. Transcription factor genes that confer resistance to chilling temperatures thus enhance tolerance during post-harvest storage. Several of the presently disclosed transcription factor genes have been shown to confer better germination and growth in cold conditions. For example, the improved germination in cold conditions seen with G1073, G2153 G2156, G3400, G3401, G3456, G3459, and G3460 indicates a role in regulation of cold responses by these genes and other members of the G1073 clade of transcription factor polypeptides. These genes thus can be overexpressed or otherwise engineered to manipulate the response to low temperature stress. Genes that would allow germination and seedling vigor in the cold would have highly significant utility in allowing seeds to be planted earlier in the season with a high rate of survival. Transcription factor genes that confer better survival in cooler climates allow a grower to move up planting time in the spring and extend the growing season further into autumn for higher crop yields. Germination of seeds and survival at temperatures significantly below that of the mean temperature required for germination of seeds and survival of non-transformed plants would increase the potential range of a crop plant into regions in which it would otherwise fail to thrive.

Increased Biomass

Overexpression of G1073 and a number of other members of the G1073 clade, including G1667, G2153, G2156, G3399, G3400, G3401, G3407, G3456, G3459, G3460, and G3556, has been shown to produce plants that are larger than control, particularly at later stages of growth. For some ornamental plants, the ability to provide larger varieties with these genes or their equivalogs may be highly desirable. For many plants, including fruit-bearing trees, trees that are used for lumber production, or trees and shrubs that serve as view or wind screens, increased stature provides improved benefits in the forms of greater yield or improved screening. Crop species may also produce higher yields on larger cultivars, particularly those in which the vegetative portion of the plant is edible.

Delayed Flowering

In a sizeable number of species, for example, root crops, where the vegetative parts of the plants constitute the crop and the reproductive tissues are discarded, it is advantageous to identify and incorporate transcription factor genes that delay or prevent flowering in order to prevent resources being diverted into reproductive development. For example, overexpression of G1073, G1067, G1667, G2153, G2156, G3399, G3401, G3406, G3459, G3460 or G3556 delays flowering time in transgenic plants. Extending vegetative development with presently disclosed transcription factor genes could thus bring about large increases in yields. Prevention of flowering can help maximize vegetative yields and prevent escape of genetically modified organism (GMO) pollen.

Summary of altered plant characteristics. Members of the G1073 clade of transcription factor polypeptides, which derive from a wide range of plants, have been shown in laboratory and field experiments to confer increased size, abiotic stress tolerance and delayed flowering phenotypes in plants that overexpress these sequences. The invention also provides polynucleotides that encode G1073 clade polypeptides, fragments thereof, conserved domains thereof, paralogs, orthologs, equivalogs, and fragments thereof. These sequences are listed in the Sequence Listing, and due to the high degree of structural similarity to the sequences of the invention, it is expected that many of the sequences for which data have not been generated will also function to increase plant biomass and/or abiotic stress tolerance. The invention also encompasses the complements of the polynucleotides. The polynucleotides are also useful for screening libraries of molecules or compounds for specific binding and for identifying other sequences of G1073 clade member by identifying orthologs having similar sequences, particularly in the conserved domains.

Antisense and Co-Suppression

In addition to expression of the nucleic acids of the invention as gene replacement or plant phenotype modification nucleic acids, the nucleic acids are also useful for sense and anti-sense suppression of expression, e.g., to down-regulate expression of a nucleic acid of the invention, e.g., as a further mechanism for modulating plant phenotype. That is, the nucleic acids of the invention, or subsequences or anti-sense sequences thereof, can be used to block expression of naturally occurring homologous nucleic acids. A variety of sense and anti-sense technologies are known in the art, e.g., as set forth in Lichtenstein and Nellen (1997) *Antisense Technology: A Practical Approach* IRL Press at Oxford University Press, Oxford, U.K. Antisense regulation is also described in Crowley et al. (1985) *Cell* 43: 633-641; Rosenberg et al. (1985) *Nature* 313: 703-706; Preiss et al. (1985) *Nature* 313: 27-32; Melton (1985) *Proc. Natl. Acad. Sci. USA* 82: 144-148; Izant and Weintraub (1985) *Science* 229: 345-352; and Kim and Wold (1985) *Cell* 42: 129-138. Additional methods for antisense regulation are known in the art. Antisense regulation has been used to reduce or inhibit expression of plant genes in, for example in European Patent Publication No. 271988. Antisense RNA may be used to reduce gene expression to produce a visible or biochemical phenotypic change in a plant (Smith et al. (1988) *Nature* 334: 724-726; Smith et al. (1990) *Plant Mol. Biol.* 14: 369-379). In general, sense or anti-sense sequences are introduced into a cell, where they are optionally amplified, for example, by transcription. Such sequences include both simple oligonucleotide sequences and catalytic sequences such as ribozymes.

For example, a reduction or elimination of expression (i.e., a "knock-out") of a transcription factor or transcription factor homolog polypeptide in a transgenic plant, e.g., to modify a plant trait, can be obtained by introducing an antisense construct corresponding to the polypeptide of interest as a cDNA. For antisense suppression, the transcription factor or homolog cDNA is arranged in reverse orientation (with respect to the coding sequence) relative to the promoter sequence in the expression vector. The introduced sequence need not be the full length cDNA or gene, and need not be identical to the cDNA or gene found in the plant type to be transformed. Typically, the antisense sequence need only be capable of hybridizing to the target gene or RNA of interest. Thus, where the introduced sequence is of shorter length, a higher degree of homology to the endogenous transcription factor sequence will be needed for effective antisense suppression. While antisense sequences of various lengths can be utilized, preferably, the introduced antisense sequence in the vector will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous transcription factor gene in the plant cell.

Suppression of endogenous transcription factor gene expression can also be achieved using a ribozyme. Ribozymes are RNA molecules that possess highly specific endoribonuclease activity. The production and use of ribozymes are disclosed in U.S. Pat. No. 4,987,071 and U.S. Pat. No. 5,543,508. Synthetic ribozyme sequences including antisense RNAs can be used to confer RNA cleaving activity on the antisense RNA, such that endogenous mRNA molecules that hybridize to the antisense RNA are cleaved, which in turn leads to an enhanced antisense inhibition of endogenous gene expression.

Vectors in which RNA encoded by a transcription factor or transcription factor homolog cDNA is over-expressed can also be used to obtain co-suppression of a corresponding endogenous gene, for example, in the manner described in U.S. Pat. No. 5,231,020 to Jorgensen. Such co-suppression (also termed sense suppression) does not require that the entire transcription factor cDNA be introduced into the plant cells, nor does it require that the introduced sequence be exactly identical to the endogenous transcription factor gene of interest. However, as with antisense suppression, the suppressive efficiency will be enhanced as specificity of hybridization is increased, e.g., as the introduced sequence is lengthened, and/or as the sequence similarity between the introduced sequence and the endogenous transcription factor gene is increased.

Vectors expressing an untranslatable form of the transcription factor mRNA, e.g., sequences comprising one or more stop codon, or nonsense mutation, can also be used to suppress expression of an endogenous transcription factor, thereby reducing or eliminating its activity and modifying one or more traits. Methods for producing such constructs are described in U.S. Pat. No. 5,583,021. Preferably, such constructs are made by introducing a premature stop codon into the transcription factor gene. Alternatively, a plant trait can be modified by gene silencing using double-stranded RNA (Sharp (1999) *Genes and Development* 13: 139-141). Another method for abolishing the expression of a gene is by insertion mutagenesis using the T-DNA of *Agrobacterium tumefaciens*. After generating the insertion mutants, the mutants can be screened to identify those containing the insertion in a transcription factor or transcription factor homolog gene. Plants containing a single transgene insertion event at the desired gene can be crossed to generate homozygous plants for the mutation. Such methods are well known to those of skill in the art (see for example Koncz et al. (1992) *Methods in Arabidopsis Research*, World Scientific Publishing Co. Pte, Ltd., River Edge N.J.).

Suppression of endogenous transcription factor gene expression can also be achieved using RNA interference-, or RNAi. RNAi is a post-transcriptional, targeted gene-silencing technique that uses double-stranded RNA (dsRNA) to incite degradation of messenger RNA (mRNA) containing the same sequence as the dsRNA (Constans, (2002) *The Scientist* 16:36). Small interfering RNAs, or siRNAs are produced in at least two steps; an endogenous ribonuclease cleaves longer daRNA into shorter, 21-23 nucleotide-long RNAs. The siRNA segments then mediate the degradation of the target mRNA (Zamore, (2001) *Nature Struct. Biol.*, 8:746-50). RNAi has been used for gene function determination in a manner similar to antisense oligonucleotides (Constans, (2002) *The Scientist* 16:36). Expression vectors that continually express siRNAs in transiently and stably transfected cells have been engineered to express small hairpin RNAs (shRNAs), which get processed in vivo into siRNAs-like molecules capable of carrying out gene-specific silencing (Brummelkamp et al., (2002) *Science* 296:550-553, and Paddison, et al. (2002) *Genes & Dev.* 16:948-958). Post-transcriptional gene silencing by double-stranded RNA is discussed in further detail by Hammond et al. (2001) *Nature Rev Gen* 2: 110-119, Fire et al, (1998) *Nature* 391: 806-811 and Timmons and Fire (1993) *Nature* 395: 354.

Alternatively, a plant phenotype can be altered by eliminating an endogenous gene, such as a transcription factor or transcription factor homolog, e.g., by homologous recombination (Kempin et al. (1997) *Nature* 389: 802-803).

A plant trait can also be modified by using the Cre-lox system (for example, as described in U.S. Pat. No. 5,658,772). A plant genome can be modified to include first and second lox sites that are then contacted with a Cre recombinase. If the lox sites are in the same orientation, the intervening DNA sequence between the two sites is excised. If the lox sites are in the opposite orientation, the intervening sequence is inverted.

The polynucleotides and polypeptides of this invention can also be expressed in a plant in the absence of an expression cassette by manipulating the activity or expression level of the endogenous gene by other means, such as, for example, by ectopically expressing a gene by T-DNA activation tagging (Ichikawa et al. (1997) *Nature* 390 698-701; Kakimoto et al. (1996) *Science* 274: 982-985). This method entails transforming a plant with a gene tag containing multiple transcriptional enhancers and once the tag has inserted into the genome, expression of a flanking gene coding sequence becomes deregulated. In another example, the transcriptional machinery in a plant can be modified so as to increase transcription levels of a polynucleotide of the invention (see, for example, PCT Publications WO 96/06166 and WO 98/53057 which describe the modification of the DNA-binding specificity of zinc finger proteins by changing particular amino acids in the DNA-binding motif).

The transgenic plant can also include the machinery necessary for expressing or altering the activity of a polypeptide encoded by an endogenous gene, for example, by altering the phosphorylation state of the polypeptide to maintain it in an activated state.

Transgenic plants (or plant cells, or plant explants, or plant tissues) incorporating the polynucleotides of the invention and/or expressing the polypeptides of the invention can be produced by a variety of well established techniques as described above. Following construction of a vector, most typically an expression cassette, including a polynucleotide, e.g., encoding a transcription factor or transcription factor homolog, of the invention, standard techniques can be used to introduce the polynucleotide into a plant, a plant cell, a plant explant or a plant tissue of interest. Optionally, the plant cell, explant or tissue can be regenerated to produce a transgenic plant.

The plant can be any higher plant, including gymnosperms, monocotyledonous and dicotyledonous plants. Suitable protocols are available for *Leguminosae* (alfalfa, soybean, clover, etc.), *Umbelliferae* (carrot, celery, parsnip), *Crucrferae* (cabbage, radish, rapeseed, broccoli, etc.), *Curcurbitaceae* (melons and cucumber), *Gramineae* (wheat, corn, rice, barley, millet, etc.), *Solanaceae* (potato, tomato, tobacco, peppers, etc.), and various other crops. See protocols described in Ammirato et al., Editors, (1984) *Handbook of Plant Cell Culture Crop Species*, Macmillan Publ. Co., New York N.Y.; Shimamoto et al. (1989) *Nature* 338: 274-276; Fromm et al. (1990) *Bio/Technol* 8: 833-839; and Vasil et al. (1990) *Bio/Technol.* 8: 429-434.

Transformation and regeneration of both monocotyledonous and dicotyledonous plant cells are now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens*-mediated transformation. Transformation means introducing a nucleotide sequence into a plant in a manner to cause stable or transient expression of the sequence.

Successful examples of the modification of plant characteristics by transformation with cloned sequences which serve to illustrate the current knowledge in this field of technology, and which are herein incorporated by reference, include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants are preferably selected using a dominant selectable marker incorporated into the transformation vector. Typically, such a marker will confer antibiotic or herbicide resistance on the transformed plants, and selection of transformants can be accomplished by exposing the plants to appropriate concentrations of the antibiotic or herbicide.

After transformed plants are selected and grown to maturity, those plants showing a modified trait are identified. The modified trait can be any of those traits described above. Additionally, to confirm that the modified trait is due to changes in expression levels or activity of the polypeptide or polynucleotide of the invention can be determined by analyzing mRNA expression using Northern blots, RT-PCR or microarrays, or protein expression using immunoblots or Western blots or gel shift assays.

Integrated Systems for Determining Sequence Identity

In addition to providing compositions and methods to improve plant traits, the present invention may be an integrated system, computer or computer readable medium that comprises an instruction set for determining the identity of one or more sequences in a database. In addition, the instruction set can be used to generate or identify sequences that meet any specified criteria. Furthermore, the instruction set may be used to associate or link certain functional benefits, such improved characteristics, with one or more identified sequence.

For example, the instruction set can include, e.g., a sequence comparison or other alignment program, e.g., an available program such as, for example, the Wisconsin Package Version 10.0, such as BLAST, FASTA, PILEUP, FIND-PATTERNS or the like (GCG, Madison, Wis.). Public sequence databases such as GenBank, EMBL, Swiss-Prot and PIR or private sequence databases such as PHYTOSEQ sequence database (Incyte Genomics,Wilmington, Del.) can be searched.

Alignment of sequences for comparison can be conducted by the local homology algorithm of Smith and Waterman (1981) *Adv. Appl. Math.* 2: 482-489, by the homology alignment algorithm of Needleman and Wunsch (1970) *J. Mol. Biol.* 48: 443-453, by the search for similarity method of Pearson and Lipman (1988) *Proc. Natl. Acad. Sci. USA* 85: 2444-2448, by computerized implementations of these algorithms. After alignment, sequence comparisons between two (or more) polynucleotides or polypeptides are typically performed by comparing sequences of the two sequences over a comparison window to identify and compare local regions of sequence similarity. The comparison window can be a segment of at least about 20 contiguous positions, usually about 50 to about 200, more usually about 100 to about 150 contiguous positions. A description of the method is provided in Ausubel et al. (through 2000) supra).

A variety of methods for determining sequence relationships can be used, including manual alignment and computer assisted sequence alignment and analysis. This later approach is a preferred approach in the present invention, due to the increased throughput afforded by computer assisted methods. As noted above, a variety of computer programs for performing sequence alignment are available, or can be produced by one of skill.

One example algorithm that is suitable for determining percent sequence identity and sequence similarity is the BLAST algorithm, which is described in Altschul et al. (1990) supra. Software for performing BLAST analyses is publicly available, e.g., through the National Library of Medicine's National Center for Biotechnology Information (ncbi.nlm.nih; see at world wide web (www) National Institutes of Health US government (gov) website). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990, 1993) supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff (1992) *Proc. Natl. Acad. Sci. USA* 89: 10915-10919). Unless otherwise indicated, "sequence identity" here refers to the % sequence identity generated from a tblastx using the NCBI version of the algorithm at the default settings using gapped alignments with the filter "off" (see, for example, NIH NLM NCBI website at ncbi.nlm.nih).

In addition to calculating percent sequence identity, the BLAST algorithm also performs a statistical analysis of the similarity between two sequences (see, for example, Karlin and Altschul (1993) *Proc. Natl. Acad. Sci. USA* 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (and, therefore, in this context, homologous) if the smallest sum probability in a comparison of the test nucleic acid to the reference nucleic acid is less than about 0.1, or less than about 0.01, and or even less than about 0.001. An additional example of a useful sequence alignment algorithm is PILEUP. PILEUP creates a multiple sequence alignment from a group of related sequences using progressive, pairwise alignments. The program can align, for example, up to 300 sequences of a maximum length of 5,000 letters.

The integrated system, or computer typically includes a user input interface allowing a user to selectively view one or more sequence records corresponding to the one or more character strings, as well as an instruction set which aligns the one or more character strings with each other or with an additional character string to identify one or more region of sequence similarity. The system may include a link of one or more character strings with a particular phenotype or gene function. Typically, the system includes a user readable output element that displays an alignment produced by the alignment instruction set.

The methods of this invention can be implemented in a localized or distributed computing environment. In a distributed environment, the methods may be implemented on a single computer comprising multiple processors or on a multiplicity of computers. The computers can be linked, e.g. through a common bus, but more preferably the computer(s) are nodes on a network. The network can be a generalized or a dedicated local or wide-area network and, in certain preferred embodiments, the computers may be components of an intra-net or an internet.

Thus, the invention provides methods for identifying a sequence similar or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an inter or intra net) and a query is made against the sequence database using the relevant sequences herein and associated plant phenotypes or gene functions.

Any sequence herein can be entered into the database, before or after querying the database. This provides for both expansion of the database and, if done before the querying step, for insertion of control sequences into the database. The control sequences can be detected by the query to ensure the general integrity of both the database and the query. As noted, the query can be performed using a web browser based interface. For example, the database can be a centralized public database such as those noted herein, and the querying can be done from a remote terminal or computer across an internet or intranet.

Any sequence herein can be used to identify a similar, homologous, paralogous, or orthologous sequence in another plant. This provides means for identifying endogenous sequences in other plants that may be useful to alter a trait of progeny plants, which results from crossing two plants of different strain. For example, sequences that encode an ortholog of any of the sequences herein that naturally occur in a plant with a desired trait can be identified using the sequences disclosed herein. The plant is then crossed with a second plant of the same species but which does not have the desired trait to produce progeny which can then be used in further crossing experiments to produce the desired trait in the second plant. Therefore the resulting progeny plant contains no transgenes; expression of the endogenous sequence may also be regulated by treatment with a particular chemical or other means, such as EMR. Some examples of such compounds well known in the art include: ethylene; cytokinins; phenolic compounds, which stimulate the transcription of the genes needed for infection; specific monosaccharides and acidic environments which potentiate vir gene induction; acidic polysaccharides which induce one or more chromosomal genes; and opines; other mechanisms include light or dark treatment (for a review of examples of such treatments, see, Winans (1992) *Microbiol. Rev.* 56: 12-31; Eyal et al. (1992) *Plant Mol. Biol.* 19:589-599; Chrispeels et al. (2000) *Plant Mol. Biol.* 42: 279-290; Piazza et al. (2002) *Plant Physiol.* 128:1077-1086).

Table 5 lists sequences discovered to be orthologous to a number of representative transcription factors of the present invention. The column headings include the transcription factors listed by (a) the SEQ ID NO: of the ortholog or nucleotide encoding the ortholog; (b) the Sequence Identifier or GenBank Accession Number; (c) the species from which the orthologs to the transcription factors are derived; and (d) the smallest sum probability during by BLAST analysis.

TABLE 5

Paralogs and Orthologs and Other Related Genes of Representative *Arabidopsis* Transcription Factor Genes identified using BLAST

| SEQ ID NO: of Ortholog or Nucleotide Encoding Ortholog | GID No. | Sequence Identifier or Accession Number | Species from Which Ortholog is Derived | Smallest Sum Probability to *Arabidopsis* Polynucleotide Sequence |
|---|---|---|---|---|
| 1 | G1073 | | *Arabidopsis thaliana* | |
| 3 | G1067 | | *Arabidopsis thaliana* | |
| 5 | G2153 | | *Arabidopsis thaliana* | |
| 7 | G2156 | | *Arabidopsis thaliana* | |
| 41 | G1069 | | *Arabidopsis thaliana* | 5e−90** |
| 43 | G1945 | | *Arabidopsis thaliana* | 5e−51** |
| 45 | G2155 | | *Arabidopsis thaliana* | 6e−43** |
| 47 | G1070 | | *Arabidopsis thaliana* | 5e−70** |
| 49 | G2657 | | *Arabidopsis thaliana* | 3e−70† |
| 51 | G1075 | | *Arabidopsis thaliana* | 8e−72** |
| 53 | G1076 | | *Arabidopsis thaliana* | 9e−74** |
| 9 | G3399 | AP004165 | *Oryza sativa* (*japonica* cultivar-group) | 1e−81† |
| 11 | G3407 | AP004635 | *Oryza sativa* | 5e−90† |
| 13 | G3456 | BM525692 | *Glycine max* | 2e−87** |
| 39 | G3556 | | *Oryza sativa* | 7e−67†† |
| 15 | G3459 | C33095_1 | *Glycine max* | 6e−67†† |
| 17 | G3460 | C33095_2 | *Glycine max* | 1e−66* |
| 65 | | BH566718 | *Brassica oleracea* | 1e−129** |
| 67 | | BH685875 | *Brassica oleracea* | 1e−124† |
| | | BZ432677 | *Brassica oleracea* | 1e−113** |
| | | BZ433664 | *Brassica oleracea* | 1e−107† |
| | | BH730050 | *Brassica oleracea* | 1e−104† |
| | | AP004971 | *Lotus corniculatus* var. *japonicus* | 3e−91** |
| | | CC729476 | *Zea mays* | 1e−83** |
| 21 | G3403 | AP004020 | *Oryza sativa* (*japonica* cultivar-group) | 2e−81** |
| | | AAAA01000486 | *Oryza sativa* (*indica* cultivar-group) | 7e−80* |
| | | CB003423 | *Vitis vinifera* | 2e−76* |
| | | CC645378 | *Zea mays* | 4e−75* |
| 23 | G3458 | C32394_2 | *Glycine max* | 9e−73** |
| 25 | G3406 | AL662981 | *Oryza sativa* | 7e−73* |
| | | BQ785950 | *Glycine max* | 3e−73* |
| | | BH975957 | *Brassica oleracea* | 9e−72* |
| | | BQ865858 | *Lactuca sativa* | 7e−72* |
| | | CB891166 | *Medicago truncatula* | 5e−72* |
| | | CF229888 | *Populus x canescens* | 2e−71* |
| | | BQ863249 | *Lactuca sativa* | 2e−71* |
| | | BG134451 | *Lycopersicon esculentum* | 3e−70* |
| 27 | G3405 | AP005653 | *Oryza sativa* (*japonica* cultivar-group) | 1e−69** |
| 29 | G3400 | AP005477 | *Oryza sativa* (*japonica* cultivar-group) | 2e−67* |

TABLE 5-continued

Paralogs and Orthologs and Other Related Genes of Representative *Arabidopsis* Transcription Factor Genes identified using BLAST

| SEQ ID NO: of Ortholog or Nucleotide Encoding Ortholog | GID No. | Sequence Identifier or Accession Number | Species from Which Ortholog is Derived | Smallest Sum Probability to *Arabidopsis* Polynucleotide Sequence |
|---|---|---|---|---|
| 31 | G3404 | AP003526 | *Oryza sativa* (japonica cultivar-group) | 2e−67* |
|  |  | AP004971 | *Lotus corniculatus* var. *japonicus* | 7e−66* |
|  |  | BM110212 | *Solanum tuberosum* | 8e−65* |
|  |  | AC124953 | *Medicago truncatula* | 2e−63* |
| 35 | G3462 | BI321563 | *Glycine max* | 3e−61* |
|  |  | BH660108 | *Brassica oleracea* | 2e−61† |
|  |  | BQ838600 | *Triticum aestivum* | 2e−59* |
|  |  | CD825510 | *Brassica napus* | 7e−58† |
|  |  | BF254863 | *Hordeum vulgare* | 1e−56* |
| 37 | G3401 | AAAA01017331 SC17331 AP004587 | *Oryza sativa* (japonica cultivar-group | 9e−42* |

*Smallest sum probability comparison to G1073
†Smallest sum probability comparison to G1067
**Smallest sum probability comparison to G2153
††Smallest sum probability comparison to 2156

Molecular Modeling

Another means that may be used to confirm the utility and function of transcription factor sequences that are orthologous or paralogous to presently disclosed transcription factors is through the use of molecular modeling software. Molecular modeling is routinely used to predict polypeptide structure, and a variety of protein structure modeling programs, such as "Insight II" (Accelrys, Inc.) are commercially available for this purpose. Modeling can thus be used to predict which residues of a polypeptide can be changed without altering function (Crameri et al. (2003) U.S. Pat. No. 6,521,453). Thus, polypeptides that are sequentially similar can be shown to have a high likelihood of similar function by their structural similarity, which may, for example, be established by comparison of regions of superstructure. The relative tendencies of amino acids to form regions of superstructure (for example, helixes and β-sheets) are well established. For example, O'Neil et al. ((1990) *Science* 250: 646-651) have discussed in detail the helix forming tendencies of amino acids. Tables of relative structure forming activity for amino acids can be used as substitution tables to predict which residues can be functionally substituted in a given region, for example, in DNA-binding domains of known transcription factors and equivalogs. Homologs that are likely to be functionally similar can then be identified.

Of particular interest is the structure of a transcription factor in the region of its conserved domains, such as those identified in Table 1. Structural analyses may be performed by comparing the structure of the known transcription factor around its conserved domain with those of orthologs and paralogs. Analysis of a number of polypeptides within a transcription factor group or clade, including the functionally or sequentially similar polypeptides provided in the Sequence Listing, may also provide an understanding of structural elements required to regulate transcription within a given family.

EXAMPLES

It is to be understood that this invention is not limited to the particular devices, machines, materials and methods described. Although particular embodiments are described, equivalent embodiments may be used to practice the invention.

The invention, now being generally described, will be more readily understood by reference to the following examples, which are included merely for purposes of illustration of certain aspects and embodiments of the present invention and are not intended to limit the invention. It will be recognized by one of skill in the art that a transcription factor that is associated with a particular first trait may also be associated with at least one other, unrelated and inherent second trait which was not predicted by the first trait.

Example I

Full Length Gene Identification and Cloning

Putative transcription factor sequences (genomic or ESTs) related to known transcription factors were identified in the *Arabidopsis thaliana* GenBank database using the tblastn sequence analysis program using default parameters and a P-value cutoff threshold of 4 or 5 or lower, depending on the length of the query sequence. Putative transcription factor sequence hits were then screened to identify those containing particular sequence strings. If the sequence hits contained such sequence strings, the sequences were confirmed as transcription factors.

Alternatively, *Arabidopsis thaliana* cDNA libraries derived from different tissues or treatments, or genomic libraries were screened to identify novel members of a transcription family using a low stringency hybridization approach. Probes were synthesized using gene specific primers in a standard PCR reaction (annealing temperature 60° C.) and labeled with $^{32}P$ dCTP using the High Prime DNA Labeling Kit (Boehringer Mannheim Corp. (now Roche Diagnostics Corp.), Indianapolis, Ind.). Purified radiolabelled probes were added to filters immersed in Church hybridization medium (0.5 M $NaPO_4$ pH 7.0, 7% SDS, 1% w/v bovine serum albumin) and hybridized overnight at 60° C. with shaking. Filters were washed two times for 45 to 60 minutes with 1×SCC, 1% SDS at 60° C.

To identify additional sequence 5' or 3' of a partial cDNA sequence in a cDNA library, 5' and 3' rapid amplification of cDNA ends (RACE) was performed using the MARATHON cDNA amplification kit (Clontech, Palo Alto, Calif.). Generally, the method entailed first isolating poly(A) mRNA, performing first and second strand cDNA synthesis to generate double stranded cDNA, blunting cDNA ends, followed by ligation of the MARATHON Adaptor to the cDNA to form a library of adaptor-ligated ds cDNA.

Gene-specific primers were designed to be used along with adaptor specific primers for both 5' and 3' RACE reactions. Nested primers, rather than single primers, were used to increase PCR specificity. Using 5' and 3' RACE reactions, 5' and 3' RACE fragments were obtained, sequenced and cloned. The process can be repeated until 5' and 3' ends of the full-length gene were identified. Then the full-length cDNA was generated by PCR using primers specific to 5' and 3' ends of the gene by end-to-end PCR.

Example II

Construction of Expression Vectors

The sequence was amplified from a genomic or cDNA library using primers specific to sequences upstream and downstream of the coding region. The expression vector was pMEN20 or pMEN65, which are both derived from pMON316 (Sanders et al. (1987) *Nucleic Acids Res.* 15:1543-1558) and contain the CaMV 35S promoter to express transgenes. To clone the sequence into the vector, both pMEN20 and the amplified DNA fragment were digested separately with SalI and NotI restriction enzymes at 37° C. for 2 hours. The digestion products were subject to electrophoresis in a 0.8% agarose gel and visualized by ethidium bromide staining. The DNA fragments containing the sequence and the linearized plasmid were excised and purified by using a QIAQUICK gel extraction kit (Qiagen, Valencia, Calif.). The fragments of interest were ligated at a ratio of 3:1 (vector to insert). Ligation reactions using T4 DNA ligase (New England Biolabs, Beverly Mass.) were carried out at 16° C. for 16 hours. The ligated DNAs were transformed into competent cells of the *E. coli* strain DH5alpha by using the heat shock method. The transformations were plated on LB plates containing 50 mg/l kanamycin (Sigma Chemical Co. St. Louis Mo.). Individual colonies were grown overnight in five milliliters of LB broth containing 50 mg/l kanamycin at 37° C. Plasmid DNA was purified by using Qiaquick Mini Prep kits (Qiagen, Valencia Calif.).

For the two-component system, two separate constructs are used: pPromoter::LexA-GAL4TA and opLexA:: transcription factor. The first of these (promoter::LexA-GAL4TA) comprised a desired promoter cloned in front of a LexA DNA binding domain fused to a GAL4 activation domain. The construct vector backbone (pMEN48, also known as P5375) also carried a kanamycin resistance marker along with an opLexA::GFP reporter. Transgenic lines were obtained containing this first component and at least one line was selected that showed reproducible expression of the reporter gene in the desired pattern through a number of generations. A homozygous population was established for that line and the population was supertransformed (to produce a supertransformation or "supTfn") with the second construct (opLexA:: transcription factor) carrying the transcription factor of interest cloned behind a LexA operator site. This second construct vector backbone (pMEN53, also known as P5381) also contained a sulfonamide resistance marker.

Example III

Transformation of *Agrobacterium* with the Expression Vector

After the plasmid vector containing the gene was constructed, the vector was used to transform *Agrobacterium tumefaciens* cells expressing the gene products. The stock of *Agrobacterium tumefaciens* cells for transformation was made as described by Nagel et al. (1990) *FEMS Microbiol Letts.* 67: 325-328. *Agrobacterium* strain ABI was grown in 250 ml LB medium (Sigma) overnight at 28° C. with shaking until an absorbance over 1 cm at 600 nm ($A_{600}$) of 0.5-1.0 was reached. Cells were harvested by centrifugation at 4,000×g for 15 minutes at 4° C. Cells were then resuspended in 250 µl chilled buffer (1 mM HEPES, pH adjusted to 7.0 with KOH). Cells were centrifuged again as described above and resuspended in 125 µl chilled buffer. Cells were then centrifuged and resuspended two more times in the same HEPES buffer as described above at a volume of 100 µl and 750 µl, respectively. Resuspended cells were then distributed into 40 µl aliquots, quickly frozen in liquid nitrogen, and stored at −80° C.

*Agrobacterium* cells were transformed with plasmids prepared as described above following the protocol described by Nagel et al. 1990) supra. For each DNA construct to be transformed, 50-100 ng DNA (generally resuspended in 10 mM Tris-HCl, 1 mM EDTA, pH 8.0) was mixed with 40 µl of *Agrobacterium* cells. The DNA/cell mixture was then transferred to a chilled cuvette with a 2 mm electrode gap and subject to a 2.5 kV charge dissipated at 25 µF and 200 µF using a Gene Pulser II apparatus (Bio-Rad, Hercules, Calif.). After electroporation, cells were immediately resuspended in 1.0 ml LB and allowed to recover without antibiotic selection for 2-4 hours at 28° C. in a shaking incubator. After recovery, cells were plated onto selective medium of LB broth containing 100 µg/ml spectinomycin (Sigma) and incubated for 24-48 hours at 28° C. Single colonies were then picked and inoculated in fresh medium. The presence of the plasmid construct was verified by PCR amplification and sequence analysis.

Example IV

Transformation of *Arabidopsis* Plants with *Agrobacterium tumefaciens* with Expression Vector After transformation of *Agrobacterium tumefaciens* with plasmid vectors containing the gene, single *Agrobacterium* colonies were identified, propagated, and used to transform *Arabidopsis* plants. Briefly, 500 ml cultures of LB medium containing 50 mg/l kanamycin were inoculated with the colonies and grown at 28° C. with shaking for 2 days until an optical absorbance at 600 nm wavelength over 1 cm ($A_{600}$) of >2.0 is reached. Cells were then harvested by centrifugation at 4,000×g for 10 minutes, and resuspended in infiltration medium (½× Murashige and Skoog salts (Sigma), 1× Gamborg's B-5 vitamins (Sigma), 5.0% (w/v) sucrose (Sigma), 0.044 µM benzylamino purine (Sigma), 200 µl/l Silwet L-77 (Lehle Seeds)) until an $A_{600}$ of 0.8 was reached.

Prior to transformation, *Arabidopsis thaliana* seeds (ecotype Columbia) were sown at a density of ~10 plants per 4" pot onto Pro-Mix BX potting medium (Hummert International) covered with fiberglass mesh (18 mm×16 mm). Plants were grown under continuous illumination (50-75 µE/m²/second) at 22-23° C. with 65-70% relative humidity. After about 4 weeks, primary inflorescence stems (bolts) are cut off to encourage growth of multiple secondary bolts. After flowering of the mature secondary bolts, plants were prepared for transformation by removal of all siliques and opened flowers.

The pots were then immersed upside down in the mixture of *Agrobacterium* infiltration medium as described above for 30 seconds, and placed on their sides to allow draining into a 1'×2' flat surface covered with plastic wrap. After 24 hours, the plastic wrap was removed and pots are turned upright. The immersion procedure was repeated one week later, for a total of two immersions per pot. Seeds were then collected from each transformation pot and analyzed following the protocol described below.

Example V

Identification of *Arabidopsis* Primary Transformants

Seeds collected from the transformation pots were sterilized essentially as follows. Seeds were dispersed into in a solution containing 0.1% (v/v) Triton X-100 (Sigma) and sterile water and washed by shaking the suspension for 20 minutes. The wash solution was then drained and replaced with fresh wash solution to wash the seeds for 20 minutes with shaking. After removal of the ethanol/detergent solution, a solution containing 0.1% (v/v) Triton X-100 and 30% (v/v) bleach (CLOROX; Clorox Corp. Oakland Calif.) was added to the seeds, and the suspension was shaken for 10 minutes. After removal of the bleach/detergent solution, seeds were then washed five times in sterile distilled water. The seeds were stored in the last wash water at 4° C. for 2 days in the dark before being plated onto antibiotic selection medium (1× Murashige and Skoog salts (pH adjusted to 5.7 with 1M KOH), 1× Gamborg's B-5 vitamins, 0.9% phytagar (Life Technologies), and 50 mg/l kanamycin). Seeds were germinated under continuous illumination (50-75 µE/m²/second) at 22-23° C. After 7-10 days of growth under these conditions, kanamycin resistant primary transformants ($T_1$ generation) were visible and obtained. These seedlings were transferred first to fresh selection plates where the seedlings continued to grow for 3-5 more days, and then to soil (Pro-Mix BX potting medium).

Primary transformants were crossed and progeny seeds ($T_2$) collected; kanamycin resistant seedlings were selected and analyzed. The expression levels of the recombinant polynucleotides in the transformants varies from about a 5% expression level increase to a least a 100% expression level increase. Similar observations are made with respect to polypeptide level expression.

Example VI

Identification of *Arabidopsis* Plants with Transcription Factor Gene Knockouts

The screening of insertion mutagenized *Arabidopsis* collections for null mutants in a known target gene was essentially as described in Krysan et al. (1999) *Plant Cell* 11: 2283-2290. Briefly, gene-specific primers, nested by 5-250 base pairs to each other, were designed from the 5' and 3' regions of a known target gene. Similarly, nested sets of primers were also created specific to each of the T-DNA or transposon ends (the "right" and "left" borders). All possible combinations of gene specific and T-DNA/transposon primers were used to detect by PCR an insertion event within or close to the target gene. The amplified DNA fragments were then sequenced which allows the precise determination of the T-DNA/transposon insertion point relative to the target gene. Insertion events within the coding or intervening sequence of the genes were deconvoluted from a pool comprising a plurality of insertion events to a single unique mutant plant for functional characterization. The method is described in more detail in Yu and Adam, U.S. application Ser. No. 09/177,733 filed Oct. 23, 1998.

Example VII

Identification of Modified Phenotypes in Overexpressing or Knockout Plants

In some instances, expression patterns of the stress-induced genes may be monitored by microarray experiments. In these experiments, cDNAs are generated by PCR and resuspended at a final concentration of ~100 ng/µl in 3×SSC or 150 mM Na-phosphate (Eisen and Brown (1999) *Methods Enzymol.* 303: 179-205). The cDNAs are spotted on microscope glass slides coated with polylysine. The prepared cDNAs are aliquoted into 384 well plates and spotted on the slides using, for example, an x-y-z gantry (OmniGrid) which may be purchased from GeneMachines (Menlo Park, Calif.) outfitted with quill type pins which may be purchased from Telechem International (Sunnyvale, Calif.). After spotting, the arrays are cured for a minimum of one week at room temperature, rehydrated and blocked following the protocol recommended by Eisen and Brown (1999; supra).

Sample total RNA (10 µg) samples are labeled using fluorescent Cy3 and Cy5 dyes. Labeled samples are resuspended in 4×SSC/0.03% SDS/4 µg salmon sperm DNA/2 µg tRNA/50 mM Na-pyrophosphate, heated for 95° C. for 2.5 minutes, spun down and placed on the array. The array is then covered with a glass coverslip and placed in a sealed chamber. The chamber is then kept in a water bath at 62° C. overnight. The arrays are washed as described in Eisen and Brown (1999) supra) and scanned on a General Scanning 3000 laser scanner. The resulting files are subsequently quantified using IMA-GENE, software (BioDiscovery, Los Angeles Calif.).

RT-PCR experiments may be performed to identify those genes induced after exposure to abiotic stresses. Generally, the gene expression patterns from ground plant leaf tissue is examined.

Reverse transcriptase PCR was conducted using gene specific primers within the coding region for each sequence identified. The primers were designed near the 3' region of each DNA binding sequence initially identified.

Total RNA from these ground leaf tissues was isolated using the CTAB extraction protocol. Once extracted total RNA was normalized in concentration across all the tissue types to ensure that the PCR reaction for each tissue received the same amount of cDNA template using the 28S band as reference. Poly(A+) RNA was purified using a modified protocol from the Qiagen OLIGOTEX purification kit batch protocol. cDNA was synthesized using standard protocols. After the first strand cDNA synthesis, primers for Actin 2 were used to normalize the concentration of cDNA across the tissue types. Actin 2 is found to be constitutively expressed in fairly equal levels across the tissue types being investigated.

For RT PCR, cDNA template was mixed with corresponding primers and Taq DNA polymerase. Each reaction consisted of 0.2 µl cDNA template, 2 µl 10× Tricine buffer, 2 µl 10× Tricine buffer and 16.8 µl water, 0.05 µl Primer 1, 0.05 µl, Primer 2, 0.3 µl Taq DNA polymerase and 8.6 µl water.

The 96 well plate is covered with microfilm and set in the thermocycler to start the reaction cycle. By way of illustration, the reaction cycle may comprise the following steps:

Step 1: 93° C. for 3 minutes;
Step 2: 93° C. for 30 seconds;
Step 3: 65° C. for 1 minute;
Step 4: 72° C. for 2 minutes;
Steps 2, 3 and 4 are repeated for 28 cycles;
Step 5: 72° C. for 5 minutes; and
Step 6 4° C.

To amplify more products, for example, to identify genes that have very low expression, additional steps may be performed: The following method illustrates a method that may be used in this regard. The PCR plate is placed back in the thermocycler for 8 more cycles of steps 2-4.

Step 2 93° C. for 30 seconds;
Step 3 65° C. for 1 minute;
Step 4 72° C. for 2 minutes, repeated for 8 cycles; and
Step 5 4° C.

Eight microliters of PCR product and 1.5 µl of loading dye are loaded on a 1.2% agarose gel for analysis after 28 cycles and 36 cycles. Expression levels of specific transcripts are considered low if they were only detectable after 36 cycles of PCR. Expression levels are considered medium or high depending on the levels of transcript compared with observed transcript levels for an internal control such as actin2. Transcript levels are determined in repeat experiments and compared to transcript levels in control (e.g., non-transformed) plants.

Modified phenotypes observed for particular overexpressor plants may include increased biomass, and/or increased or decreased abiotic stress tolerance or resistance. For a particular overexpressor that shows a less beneficial characteristic, such as reduced abiotic stress tolerance or resistance, it may be more useful to select a plant with a decreased expression of the particular transcription factor. For a particular knockout that shows a less beneficial characteristic, such as decreased abiotic stress tolerance, it may be more useful to select a plant with an increased expression of the particular transcription factor.

The germination assays in this example followed modifications of the same basic protocol. Sterile seeds were sown on the conditional media listed below. Plates were incubated at 22° C. under 24-hour light (120-130 µEin/m$^2$/s) in a growth chamber. Evaluation of germination and seedling vigor was conducted 3 to 15 days after planting. The basal media was 80% Murashige-Skoog medium (MS)+vitamins.

For stress experiments conducted with more mature plants, seeds were germinated and grown for seven days on MS+vitamins+1% sucrose at 22° C. and then transferred to cold and heat stress conditions. The plants were either exposed to cold stress (6 hour exposure to 4-8° C.), or heat stress (32° C. was applied for five days, after which the plants were transferred back 22° C. for recovery and evaluated after 5 days relative to controls not exposed to the depressed or elevated temperature).

The salt stress assays were intended to find genes that confer better germination, seedling vigor or growth in high salt. Evaporation from the soil surface causes upward water movement and salt accumulation in the upper soil layer where the seeds are placed. Thus, germination normally takes place at a salt concentration much higher than the mean salt concentration in the whole soil profile. Plants differ in their tolerance to NaCl depending on their stage of development, therefore seed germination, seedling vigor, and plant growth responses were evaluated.

Osmotic stress assays (including NaCl and mannitol assays) were conducted to determine if an osmotic stress phenotype was NaCl-specific or if it was a general osmotic stress related phenotype. Plants tolerant to osmotic stress could also have more tolerance to drought and/or freezing.

For salt and osmotic stress germination experiments, the medium was supplemented with 150 mM NaCl or 300 mM mannitol. Growth regulator sensitivity assays were performed in MS media, vitamins, and either 0.3 µM ABA, 9.4% sucrose, or 5% glucose.

Drought assays were performed to find genes that mediate better plant survival after short-term, severe water deprivation. Ion leakage is measured if needed. Positive osmotic stress tolerance results also support a drought-tolerant phenotype. Soil-based drought screens were performed with *Arabidopsis* plants overexpressing the transcription factors listed in the Sequence Listing, where noted below. Seeds from wild-type *Arabidopsis* plants, or plants overexpressing a polypeptide of the invention, were stratified for three days at 4° C. in 0.1% agarose. Fourteen seeds of each overexpressor or wild-type were then sown in three inch clay pots containing a 50:50 mix of vermiculite:perlite topped with a small layer of MetroMix 200 and grown for fifteen days under 24 hr light. Pots containing wild-type and overexpressing seedlings were placed in flats in random order. Drought stress was initiated by placing pots on absorbent paper for seven to eight days. The seedlings were considered to be sufficiently stressed when the majority of the pots containing wild-type seedlings within a flat had become severely wilted. Pots were then re-watered and survival was scored four to seven days later. Plants were ranked against wild-type controls for each of two criteria: tolerance to the drought conditions and recovery (survival) following re-watering.

At the end of the initial drought period, each pot was assigned a numeric value score depending on the above criteria. A low value was assigned to plants with an extremely poor appearance (i.e., the plants were uniformly brown) and a high value given to plants that were rated very healthy in appearance (i.e., the plants were all green). After the plants were rewatered and incubated an additional four to seven days, the plants were reevaluated to indicate the degree of recovery from the water deprivation treatment.

An analysis was then conducted to determine which plants best survived water deprivation, identifying the transgenes that consistently conferred drought-tolerant phenotypes and their ability to recover from this treatment. The analysis was performed by comparing overall and within-flat tabulations with a set of statistical models to account for variations between batches. Several measures of survival were tabulated, including: (a) the average proportion of plants surviving relative to wild-type survival within the same flat; (b) the median proportion surviving relative to wild-type survival within the same flat; (c) the overall average survival (taken over all batches, flats, and pots); (d) the overall average survival relative to the overall wild-type survival; and (e) the average visual score of plant health before rewatering.

Experiments were performed to identify those transformants that exhibited modified sugar-sensing. For such studies, seeds from transformants were germinated on high sugar-containing media (5% glucose, 9.4% sucrose) that normally partially restrict hypocotyl elongation. Plants with altered sugar sensing may have either longer or shorter hypocotyls than normal plants when grown on this media. Additionally, other plant traits may be varied such as root mass. Sugar sensing assays were intended to find genes involved in sugar sensing by germinating seeds on high concentrations of sucrose and glucose and looking for degrees of hypocotyl elongation. The germination assay on mannitol controlled for responses related to osmotic stress. Sugars are key regulatory molecules that affect diverse processes in higher plants including germination, growth, flowering, senescence, sugar metabolism and photosynthesis. Sucrose is the major transport form of photosynthate and its flux through cells has been shown to affect gene expression and alter storage compound accumulation in seeds (source-sink relationships). Glucose-specific hexose-sensing has also been described in plants and is implicated in cell division and repression of "famine" genes (photosynthetic or glyoxylate cycles).

Temperature stress assays were carried out to find genes that confer better germination, seedling vigor or plant growth under temperature stress (cold, freezing and heat). Temperature stress cold germination experiments were carried out at 8° C. Heat stress germination experiments were conducted at 32° C. to 37° C. for 6 hours of exposure.

Flowering time was measured by the number of rosette leaves present when a visible inflorescence of approximately 3 cm is apparent. Rosette and total leaf number on the progeny stem are tightly correlated with the timing of flowering (Koomneef et al. (1991) *Mol. Gen. Genet.* 229: 57-66). The vernalization response was also measured. For vernalization treatments, seeds were sown to MS agar plates, sealed with micropore tape, and placed in a 4° C. cold room with low light levels for 6-8 weeks. The plates were then transferred to the growth rooms alongside plates containing freshly sown non-vernalized controls. Rosette leaves were counted when a visible inflorescence of approximately 3 cm was apparent.

The transcription factor sequences of the Sequence Listing, or those in the present Tables or Figures, and their equivalogs, can be used to prepare transgenic plants and plants with altered traits. The specific transgenic plants listed below are produced from the sequences of the Sequence Listing, as noted. The Sequence Listing, Table 5 and Example VIII provide exemplary polynucleotide and polypeptide sequences of the invention.

Example VIII

Genes that Confer Significant Improvements to Plants

This example provides experimental evidence for increased biomass and abiotic stress tolerance controlled by the transcription factor polypeptides and polypeptides of the invention.

Experiments were performed to identify those transformants that exhibited a morphological difference relative to wild-type control plants, i.e., a modified structure and/or development characteristics. For such studies, the transformants were observed by eye to identify novel structural or developmental characteristics associated with the ectopic expression of the polynucleotides or polypeptides of the invention. Examples of genes and equivalogs that confer significant improvements to overexpressing plants are noted below. Experimental observations made with regard to specific genes whose expression has been modified in overexpressing plants, and potential applications based on these observations, are also presented.

The transcription factor sequences of the Sequence Listing can be used to prepare transgenic plants with altered traits. From the experimental results of the plate-based physiology assays presented in the tables of this Example, it may be inferred that a representative number of sequences from diverse plant species imparted increased stress tolerance in a range of abiotic stress assays. Observed effects of overexpression on flowering time are also noted in the text below. These comparable effects indicate that sequences found within the G1073 clade of transcription factor polypeptides are functionally related and can be used to confer various types of abiotic stress tolerance in plants. A number of these genes concurrently confer increased biomass and increased tolerance to multiple abiotic stresses.

Results:

As noted below and in previously-performed assays, a representative number of members of the G1073 clade of transcription factor polypeptides, including G1073, G1067, G1069, G2153, G2156, G3456, G3399, G3400, G3401, G3406, G3456, G3459 and G3460, increase abiotic stress tolerance when these sequences are overexpressed.

G1073 (SEQ ID NO: 1 and 2)

We have previously demonstrated that overexpression of G1073 imparts drought tolerance and enhanced yield in 35S::G1073 lines. We have now designated this locus as HERCULES 1 (HRC1).

The aim of this study was to re-assess 35S::G1073 lines and compare its overexpression effects to those of its putative paralogs and orthologs. We also sought to test whether use of a two-component overexpression system would produce any strengthening of the phenotype relative to the use of a 35S direct promoter-fusion.

G1073 overexpression via the two-component system resulted in similar phenotypes to those previously observed with previously performed direct promoter fusion experiments. In both projects, G1073-overexpressing plants exhibited an increase in biomass relative to wild-type control plants along with changes in leaf morphology and a slight to moderate delay in flowering time.

Transgenic plants overexpressing G1073 were substantially larger than wild-type controls, with at least a 60% increase in biomass (FIGS. 6A and 6B, 7A, and 7B). The increased mass of 35S::G1073 transgenic plants was attributed to enlargement of multiple organ types including stems, roots and floral organs; other than the size differences, these organs were not affected in their overall morphology. 35S::G1073 plants exhibited an increase of the width (but not length) of mature leaf organs, produced 2-3 more rosette leaves, and had enlarged cauline leaves in comparison to corresponding wild-type leaves. Overexpression of G1073 resulted in an increase in both leaf mass and leaf area per plant, and leaf morphology (G1073 overexpressors tended to produce more serrated leaves). We also found that root mass was increased in the transgenic plants, and that floral organs were also enlarged (FIG. 7B). An increase of approximately 40% in stem diameter was observed in the transgenic plants. Images from the stem cross-sections of 35S::G1073 plants revealed that cortical cells are large and that vascular bundles contained more cells in the phloem and xylem relative to wild type controls (FIGS. 6A and 6B). Petal size in the 35S::G1073 lines was increased by 40-50% compared to wild type controls. Petal epidermal cells in those same lines were approximately 25-30% larger than those of the control plants. Furthermore, 15-20% more epidermal cells per petal were produced compared to wild type controls. Thus, in petals and stems, the increase in size was associated with an increase in cell size as well as in cell number.

Seed yield was also increased compared to control plants. 35S::G1073 lines showed an increase of at least 70% in seed yield. This increased seed production was associated with an increased number of siliques per plant, rather than seeds per silique.

35S::G1073 two-component lines showed a mild to moderate delay in the onset of flowering and developed larger broader leaves than those of wild type controls. These effects were of intermediate penetrance, being observed, to varying extents in eight of twenty T1 lines.

G1073 functions in both soybean and tomato to increase biomass. In FIG. 9A, the larger soybean plant on the right is overexpressing G1073. Tomato leaves of a number of G1073 overexpressor lines were much larger than those of wild-type tomato plants, as seen in FIG. 9B by comparing the leaves of the overexpressor plant on the left and that from a wild-type plant on the right Our previous studies with 35S direct promoter fusion resulted in plants with greater abiotic stress tolerance and drought tolerance in soil-based assays. As seen in the table below, the two component 35S::G1073 lines also displayed a markedly increased tolerance to high salt and sucrose levels during germination.

As noted in Table 1 and subsequent tables in this example, we have obtained similar morphological and/or physiological phenotypes from overexpression of the related *Arabidopsis* genes (G1067, G1069, G1667, G2153, G2156, G2789), rice (G3399, G3400, G3401, G3406, G3407, G3556) and soy genes (G3456, G3459, G3460), indicating that these genes are likely to be functionally related.

utable to G1073 overexpression indicate that the gene could be used to modify traits such as flowering time and organ size.

G1067 (SEQ ID NO: 3 and 4)

G1067 is a paralog of G1073. Based on our phylogenetic analysis, this gene and G2156 are the most related paralogs of G1073.

G1067 corresponds to ESCAROLA (ESC). Morphological effects of overexpression of this gene expressed under the control of the CaMV 35S promoter, including slow growth, delayed flowering and leaf curling, have been documented by Weigel et al. (2000) *Plant Physiol.* 122: 1003-1013. This study did not consider or report altered sugar sensing or increased abiotic stress tolerance.

The aim of the current study was to re-evaluate the effects of G1067 overexpression using a two component approach.

35S::G1067 direct promoter fusion lines were found to exhibit a variety of deleterious phenotypes. However, a number of lines of transgenic plants overexpressing G11067 were found to be large and had broad leaves.

Overexpression lines were also obtained using the two component expression system, and these lines were generally small and slow growing. The two-component lines were obtained at very low frequency, possibly indicating that high

TABLE 6

*Arabidopsis thaliana* G1073 35S 2-components-supertransformation (supTfn)

| Project type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 301 | ++ | wt | ++ | wt | wt | wt | wt | wt | wt |
| 2-components-supTfn | 304 | ++ | wt | ++ | wt | + | wt | wt | wt | wt |
| 2-components-supTfn | 305 | + | wt | wt | wt | wt | wt | wt | wt | wt |
| 2-components-supTfn | 306 | ++ | wt | ++ | wt | wt | wt | wt | wt | wt |
| 2-components-supTfn | 308 | + | wt | wt | wt | wt | wt | wt | wt | wt |
| 2-components-supTfn | 310 | + | wt | ++ | wt | wt | wt | wt | wt | wt |
| 2-components-supTfn | 311 | ++ | wt | wt | wt | wt | wt | wt | wt | wt |
| 2-components-supTfn | 314 | + | wt | ++ | wt | wt | wt | wt | wt | wt |
| 2-components-supTfn | 319 | + | wt | wt | wt | wt | wt | wt | wt | wt |
| 2-components-supTfn | 320 | + | wt | wt | wt | wt | wt | wt | wt | wt |

+ more tolerant than wild-type control plants
++ much more tolerant than wild-type control plants Utilities The results of this study suggest that G1073 and other members of the G1073 clade can be used to improve drought related stress tolerance and yield under stress conditions when these sequences are overexpressed. The data also confirm our earlier conclusions obtained with G1073 that showed an increase in biomass and modified flowering time when this sequence is overexpressed. The developmental effects attriblevel overexpression produced lethality. It is possible that a higher level of G1067 activity was attained with a two component approach and that this impeded the isolation of transformants.

Of the two-component lines that were obtained, four (#301, 302, 441, 442) of the five lines were notably smaller and slow developing compared to controls. The final line #303 was tiny and arrested growth early in development.

TABLE 7

*Arabidopsis thaliana* G1067 35S 2-components-supertransformation

| Project type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 301 | wt | wt | wt | wt | wt | wt | − | wt | wt |
| 2-components-supTfn | 302 | wt | wt | wt | wt | wt | wt | wt | wt | wt |
| 2-components-supTfn | 441 | wt | wt | wt | ++ | wt | wt | − | wt | + |
| 2-components-supTfn | 442 | wt | wt | wt | + | wt | wt | wt | wt | wt |

The results obtained with these abiotic stress experiments show that members of the G1073 clade, including G1067, are able to confer increased stress tolerance and yield under stress conditions when overexpressed. The undesirable morphological effects associated with G1067 overexpression suggest that plants overexpressing this sequence would benefit from optimization by inducible or tissue-specific regulatory control.

G1069 (SEQ ID NO: 41 and 42)

The sequence of G1069 was obtained from the EU *Arabidopsis* sequencing project, GenBank accession number Z97336, based on its sequence similarity within the conserved domain to other AT-hook related proteins in *Arabidopsis*.

The sequence of G1069 was experimentally determined and the function of G1069 was analyzed using transgenic plants in which G1069 was expressed under the control of the 35 S promoter. Plants overexpressing G1069 showed changes in leaf architecture, reduced overall plant size, and retarded progression through the life cycle. This is a common phenomenon for most transgenic plants in which AT-hook proteins are overexpressed if the gene is predominantly expressed in root in the wild-type background. Indeed, based on analysis of RT-PCR results G1069 was predominantly expressed in roots. To minimize these detrimental effects, G1069 may be overexpressed under an inducible promoter or a tissue specific promoter such as root- or leaf-specific promoter.

G1069 overexpressors tended to be slow developing and bolt later than wild-type controls. A number of lines had broad, short leaves (it is uncertain whether this resulted in an increase in overall biomass). A number of G1069 overexpressing lines showed more tolerance to osmotic stress when they were germinated on high sucrose containing plates. They also showed insensitivity to ABA in a germination assay.

phylogenetic analysis, G2153 is more related to G1069 than the other putative G1073 paralogs.

In our earlier studies, a number of G2153 overexpressing lines were larger, and had broader, flatter leaves than those of wild-type control plants. Some of these lines showed much larger rosettes than wild-type control plants. In the latest experiments, we generated lines for both direct fusion and two component constructs. Lines from both approaches exhibited similar effects. The majority of transformants were small, slow developing and had abnormally shaped leaves. However, a significant proportion of the G2153 overexpressing lines developed enlarged lateral organs (leaves and flowers), particularly at later developmental stages. It is particularly interesting that similar effects on organ growth and stress tolerance have also been obtained with 35S::G1073 and 35S::G2156 lines, suggesting that these sequences are functionally related.

It should be noted that a greater frequency of deleterious phenotypes were seen among the two-component lines, perhaps indicating that these possessed higher levels of G2153 activity than the direct fusion lines.

Tomato plants overexpressing the *A. thaliana* G2153 polypeptide have been found to be significantly larger than wild-type control tomato plants.

Physiology assays with direct fusion lines re-confirmed our earlier observations that 35S::G2153 lines have enhanced tolerance to abiotic stress. In our newest studies, the results of which are presented in the table below, positive phenotypes were seen in NaCl, sucrose, ABA, and cold stress assays. Experiments conducted with the two component system have shown that these overexpressors were also more tolerant to abiotic stress, as presented in the table below.

TABLE 8

*Arabidopsis thaliana* G2153 35S Direct Promoter Fusion and 2-components-supertransformation

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter-fusion | 341 | + | wt | + | ++ | wt | + | wt | wt | + |
| Direct promoter-fusion | 342 | wt | wt | wt | ++ | wt | + | wt | wt | + |
| Direct promoter-fusion | 343 | + | wt | + | ++ | wt | wt | wt | wt | + |
| Direct promoter-fusion | 345 | wt | wt | wt | wt | wt | wt | wt | wt | wt |
| Direct promoter-fusion | 347 | wt | wt | wt | ++ | wt | wt | wt | wt | wt |
| Direct promoter-fusion | 348 | + | + | wt | ++ | wt | wt | wt | wt | wt |
| Direct promoter-fusion | 349 | + | wt | wt | ++ | wt | wt | wt | wt | wt |
| Direct promoter-fusion | 350 | wt | wt | wt | ++ | wt | + | wt | wt | + |
| Direct promoter-fusion | 352 | wt | wt | ++ | ++ | wt | + | wt | wt | + |
| Direct promoter-fusion | 354 | wt | wt | + | ++ | wt | + | wt | wt | wt |
| 2-components-supTfn | 302 | wt | wt | + | wt | wt | wt | wt | wt | wt |
| 2-components-supTfn | 305 | wt | wt | + | wt | wt | wt | wt | wt | + |
| 2-components-supTfn | 308 | wt | wt | wt | wt | wt | wt | wt | wt | + |
| 2-components-supTfn | 361 | + | wt | wt | + | wt | wt | wt | wt | + |
| 2-components-supTfn | 363 | wt | wt | + | wt | wt | wt | wt | wt | + |
| 2-components-supTfn | 365 | wt | wt | + | + | wt | wt | wt | wt | + |
| 2-components-supTfn | 383 | + | wt | wt | wt | wt | wt | wt | wt | wt |
| 2-components-supTfn | 403 | wt | wt | wt | wt | wt | wt | wt | wt | wt |
| 2-components-supTfn | 405 | + | wt | wt | wt | wt | wt | wt | wt | wt |
| 2-components-supTfn | 410 | + | wt | wt | wt | wt | + | wt | wt | ++ |
| 2-components-supTfn | 401 | wt | wt | wt | ++ | wt | wt | wt | wt | + |
| 2-components-supTfn | 406 | wt | wt | wt | ++ | wt | wt | wt | wt | + |
| 2-components-supTfn | 408 | wt | wt | wt | + | wt | wt | wt | wt | + |
| 2-components-supTfn | 411 | wt | wt | + | ++ | wt | wt | wt | wt | + |

These experiments were repeated and only one line showed the ABA insensitive and osmotic stress tolerant phenotypes.

G2153 (SEQ ID NO: 5 and 6)

We have demonstrated that G2153 confers increased tolerance to osmotic stress in overexpressing plants. Based on a Utilities The results obtained with these abiotic stress experiments show that members of the G1073 clade, including G2153, are able to confer increased stress tolerance and yield under stress conditions when overexpressed. G2153 is thus a potential candidate for improvement of drought related stress tolerance in commercial species. Based on the developmental effects observed, the gene could also be used to manipulate organ growth and flowering time.

Undesirable morphological effects that may be associated with overexpression of G2153 suggest that plants overexpressing the sequence would benefit by optimization with inducible or tissue-specific regulatory control.

G2156 (SEQ ID NO: 7 and 8)

G2156 is a paralog to G1073. Based on amino acid sequence, the G2156 and G1067 polypeptides are phylogenetically more closely related to G1073 than the other putative paralogs.

Our earlier studies characterized 35S::G2156 lines as having multiple morphological alterations. A number of *Arabidopsis* lines overexpressing G2156 under the control of the 35S promoter were found be larger, with broader leaves and larger rosettes than wild-type control plants. The aim of this study was to re-examine the effects of G2156 overexpression, particularly with respect to abiotic stress responses.

In recent experiments, we generated lines for both direct fusion and two component constructs. Lines from both approaches exhibited similar effects. The majority of transformants were small, slow developing and had abnormally shaped leaves. However, a significant proportion of the lines developed enlarged lateral organs (leaves and flowers), particularly at later developmental stages. It should be noted that a greater frequency of deleterious phenotypes were seen among the two-component lines, perhaps indicating that these possessed higher levels of G2156 activity than the direct fusion lines.

Physiology performed on the direct fusion and two component lines showed enhanced tolerance in a germination assay on sodium chloride media, and tolerance to other abiotic stress as well.

It is particularly interesting that similar effects on organ growth and stress tolerance have been obtained with 35S::G1073 and 35S::G2153 lines, suggesting that these genes are functionally related.

and osmotic stress tolerant. In a germination assay on ABA containing media, G2789 transgenic seedlings showed enhanced seedling vigor. In a similar germination assay on media containing high concentrations of sucrose, the G2789 overexpressors also showed enhanced seedling vigor. In a repeat experiment on individual lines, all three lines showed the phenotype.

G1667 (SEQ ID NO: 85 and 86)

G1667 is a paralog of G1073. A number of G1667 overexpressing lines were larger than wild-type control plants, with curled and serrated leaves, larger rosette leaves, longer bolts, more secondary bolts, and more siliques present. This phenotype was similar to that observed in plants overexpressing G1073 and other G1073 clade members as noted as follows.

G3456 (SEQ ID NO: 13 and 14)

G3456 is a soy ortholog of G1073. The aim of this project is to determine whether overexpression of G3456 in *Arabidopsis* produces comparable effects to those of G1073 overexpression.

35S::G3456 lines exhibited alterations in overall size, coloration, inflorescence architecture, leaf shape, and flowering time. In particular, at later stages of growth, a significant number of lines developed enlarged leaves and displayed increased biomass relative to wild type controls.

Lines 321-337 at early stages appeared normal. However, 3/17 lines (#329, 334, 335) were slightly small, had short internodes, and displayed curled leaves relative to controls. Later in development, four of seventeen lines (#323, 325, 328, 332) exhibited substantially larger rosettes than controls and also appeared dark in coloration. These plants also showed a slight delay in the onset of flowering.

In lines 341-350 2/10 lines (#348 and 350) displayed noticeably enlarged leaves. All lines were rather dark at late stages and had slightly short inflorescence internodes leading to a somewhat bushy architecture. Occasional plants, such as #349, exhibited floral defe

TABLE 9

Arabidopsis thaliana G2156 35S Direct Promoter Fusion and 2-components-supertransformation

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter-fusion | 421 | + | wt | ++ | wt | wt | wt | wt | wt | wt |
| Direct promoter-fusion | 422 | + | wt | wt | wt | wt | wt | wt | wt | wt |
| Direct promoter-fusion | 424 | ++ | wt | wt | wt | wt | wt | wt | wt | wt |
| Direct promoter-fusion | 425 | + | wt | wt | wt | ++ | wt | wt | wt | + |
| Direct promoter-fusion | 428 | + | wt | wt | wt | wt | wt | wt | wt | wt |
| Direct promoter-fusion | 429 | + | wt | wt | wt | wt | wt | wt | wt | wt |
| Direct promoter-fusion | 431 | wt | wt | wt | wt | wt | wt | wt | wt | wt |
| Direct promoter-fusion | 432 | + | wt | wt | wt | wt | wt | wt | wt | wt |
| Direct promoter-fusion | 434 | + | wt | wt | wt | wt | wt | wt | wt | wt |
| Direct promoter-fusion | 435 | wt | wt | wt | wt | wt | wt | wt | wt | wt |
| 2-components-supTfn | 322 | wt | wt | wt | wt | wt | wt | wt | wt | + |
| 2-components-supTfn | 401 | wt | wt | + | + | wt | wt | wt | wt | wt |
| 2-components-supTfn | 403 | wt | wt | wt | wt | wt | wt | wt | wt | + |

Utilities

Based on the results of our overexpression studies, G1073 and other members of the G1073 clade, including G2156, may be used for improving abiotic stress tolerance in commercial species. Based on the developmental effects observed, the gene could also be used to manipulate organ growth and flowering time.

G2789 (SEQ ID NO: 83 and 84)

G2789 is a paralog of G1073. Overexpression of G2789 in *Arabidopsis* resulted in seedlings that were ABA insensitive For Lines 361-380, all plants were slightly larger and darker than controls at later stages. At early stages, these lines appeared normal. cts.

These developmental effects were similar to those produced in *Arabidopsis* plants overexpressing G1073 or other *Arabidopsis* polypeptides of the G1073 clade.

A majority of the G3456 overexpressors demonstrated increased abiotic stress tolerance (e.g., growth in cold conditions) relative to wild-type control plants, as indicated in the table below.

TABLE 10

*Glycine max* G3456 35S Direct Promoter Fusion

| Project type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter fusion | 324 | wt | wt | wt | wt | wt | wt | wt | wt | wt |
| Direct promoter fusion | 325 | + | wt | wt | wt | wt | wt | wt | wt | + |
| Direct promoter fusion | 326 | + | wt | wt | wt | wt | wt | wt | wt | + |
| Direct promoter fusion | 327 | wt | wt | wt | wt | wt | wt | wt | wt | wt |
| Direct promoter fusion | 328 | wt | wt | wt | wt | wt | wt | wt | wt | + |
| Direct promoter fusion | 331 | wt | wt | wt | wt | wt | wt | wt | wt | + |
| Direct promoter fusion | 332 | wt | wt | wt | wt | wt | wt | wt | wt | + |
| Direct promoter fusion | 333 | wt | wt | wt | wt | wt | wt | wt | wt | wt |
| Direct promoter fusion | 335 | wt | wt | wt | wt | wt | wt | wt | wt | + |
| Direct promoter fusion | 337 | + | wt | wt | + | wt | wt | wt | wt | + |

Utilities.

The results obtained with these abiotic stress experiments show that members of the G1073 clade, including G3456, are able to confer increased stress tolerance and yield under stress conditions when overexpressed. The developmental effects attributable to G3456 overexpression indicate that the gene could be used to modify traits such as flowering time and organ size. The dark coloration exhibited by some of the lines could indicate increased chlorophyll levels; G3456 might therefore also impact photosynthetic capacity, yield, and nutritional value.

G3399 (SEQ ID NO: 9 and 10)

G3399 is a rice ortholog of G1073. Phylogenetic analysis identifies G3399 along with G3400 as being the most closely related rice orthologs of G1073.

The aim of this project was to determine whether overexpression of G3399 in *Arabidopsis* produces comparable effects to those of G1073 overexpression. 35S::G3399 lines were obtained containing either of two different constructs. Both constructs produced similar morphological phenotypes; many of the lines were small at early stages, showed alterations in leaf shape, and had slightly delayed flowering. However a significant number of lines developed enlarged lateral organs-leaves, rosettes and flowers—particularly at later stages, as compared to wild-type control plants.

It is noteworthy that one of the constructs (P21269; SEQ ID NO: 82) contained an amino acid conversion (proline to a glutamine at residue 198, in a conserved domain) relative to the native protein. Lines for this mutated protein showed fewer undesirable morphologies than the wild type version.

The morphologically similar effects caused by overexpression of this rice gene versus G1073 and other *Arabidopsis* paralogs suggest that they likely have related functions.

Four G3399 overexpressor lines demonstrated increased abiotic stress tolerance relative to wild-type control plants, as indicated in the table below.

TABLE 12

*Oryza sativa* (*japonica* cultivar-group) G3399 35S Direct Promoter Fusion

| Project type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter-fusion | 321 | wt | wt | wt | wt | wt | wt | wt | wt | wt |
| Direct promoter-fusion | 322 | wt | wt | wt | wt | wt | wt | wt | wt | wt |
| Direct promoter-fusion | 323 | wt | wt | wt | wt | wt | wt | wt | wt | wt |
| Direct promoter-fusion | 325 | wt | wt | wt | wt | ++ | wt | wt | wt | wt |
| Direct promoter-fusion | 330 | wt | wt | wt | wt | wt | wt | wt | wt | wt |
| Direct promoter-fusion | 331 | wt | wt | wt | wt | wt | wt | wt | wt | wt |
| Direct promoter-fusion | 332 | wt | wt | wt | wt | wt | wt | wt | wt | wt |
| Direct promoter-fusion | 336 | wt | wt | wt | wt | wt | wt | wt | wt | wt |
| Direct promoter-fusion | 338 | wt | wt | wt | wt | + | wt | wt | wt | wt |
| Direct promoter-fusion | 340 | wt | wt | wt | wt | wt | wt | wt | wt | wt |
| Direct promoter-fusion | 347 | wt | wt | wt | wt | wt | wt | wt | wt | + |
| Direct promoter-fusion | 348 | wt | wt | wt | wt | wt | wt | wt | wt | + |
| Direct promoter-fusion | 406 | wt | wt | wt | wt | wt | wt | wt | wt | wt |
| Direct promoter-fusion | 408 | wt | wt | wt | wt | wt | wt | wt | + | wt |
| Direct promoter-fusion | 409 | wt | wt | wt | wt | wt | wt | wt | wt | wt |
| Direct promoter-fusion | 410 | wt | wt | wt | wt | wt | wt | wt | wt | wt |
| Direct promoter-fusion | 412 | wt | wt | wt | wt | wt | + | wt | + | wt |
| Direct promoter-fusion | 413 | wt | wt | wt | wt | wt | wt | wt | wt | wt |
| Direct promoter-fusion | 415 | wt | wt | wt | wt | wt | wt | wt | + | wt |
| Direct promoter-fusion | 416 | wt | wt | wt | wt | wt | wt | wt | wt | wt |
| Direct promoter-fusion | 417 | wt | wt | wt | wt | wt | wt | wt | wt | wt |
| Direct promoter-fusion | 420 | wt | wt | wt | wt | wt | wt | wt | wt | wt |

Utilities

The results obtained with these abiotic stress experiments show that members of the G1073 clade, including G3399, are able to confer increased stress tolerance and yield under stress conditions when overexpressed. Undesirable morphological effects that are at times associated with overexpression of G3399 suggest that plants overexpressing the sequence would benefit by optimization with inducible or tissue-specific regulatory control.

The morphological phenotypes indicate that the gene could be used to modify traits such as organ size and flowering time. This study also identified a specific region of the G3399 protein that might be modified in order to optimize the acquisition of desirable phenotypes.

G3400 (SEQ ID NO: 29 and 30)

G3400 is a rice ortholog of G1073. Phylogenetic analysis identifies G3400 along with G3399 as being the most closely related rice orthologs to G1073. The aim of this project was to determine whether overexpression of G3400 in *Arabidopsis* produces comparable effects to those of G1073 overexpression.

Only a few 35S::G3400 overexpression lines have been obtained thus far. Such a low frequency of transformants suggests that the gene might have lethal effects when overexpressed at high levels. The lines that were obtained were small, slow developing and showed curled leaves. However, at later stages, two of the lines formed rather enlarged leaves and flowers.

It should be noted that the morphologically similar effects caused by overexpression of this rice gene versus G1073 and its *Arabidopsis* paralogs suggest that these sequences likely have related functions.

All of the G3400 overexpressors tested thus far demonstrated increased abiotic stress tolerance relative to wild-type control plants (germination and growth in cold), as indicated in the table below.

TABLE 13

*Oryza sativa* (*japonica* cultivar-group) G3400 35S Direct Promoter Fusion

| Project type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter fusion | 321 | wt | wt | wt | wt | wt | + | wt | wt | + |
| Direct promoter fusion | 322 | wt | wt | wt | wt | wt | + | wt | + | + |
| Direct promoter fusion | 323 | wt | wt | wt | wt | wt | + | wt | wt | + |

Utilities

The results obtained with these abiotic stress experiments show that members of the G1073 clade, including G3400, are able to confer increased stress tolerance and yield under stress conditions when overexpressed. Undesirable morphological effects that may be associated with overexpression of G3400 suggest that plants overexpressing the sequence would benefit by optimization with inducible or tissue-specific regulatory control.

G3401 (SEQ ID NO: 37 and 38)

G3401 is a rice ortholog of G1073. The aim of this project was to determine whether overexpression of G3401 in *Arabidopsis* produces comparable effects to those of G1073 overexpression.

A significant number of 35S::G3401 lines obtained thus far showed a range of developmental changes including reduced size, slow growth, and altered leaf shape. At least one line exhibited slightly enlarged leaves at late stages. A number of the lines, including several showing abiotic stress tolerance, appeared normal at various stages of development.

A majority of the overexpressors demonstrated insensitivity to ABA, and tolerance to a number of abiotic stresses, as indicated in the table below.

TABLE 14

*Oryza sativa* (*japonica* cultivar-group) G3401 35S Direct Promoter Fusion

| Project type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter fusion | 341 | wt | wt | wt | wt | wt | wt | wt | wt | wt |
| Direct promoter fusion | 342 | wt | wt | wt | + | wt | wt | wt | wt | wt |
| Direct promoter fusion | 343 | wt | wt | wt | + | wt | wt | wt | wt | wt |
| Direct promoter fusion | 344 | wt | wt | wt | + | wt | wt | wt | wt | wt |

TABLE 14-continued

Oryza sativa (japonica cultivar-group) G3401 35S Direct Promoter Fusion

| Project type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter fusion | 345 | wt | wt | wt | wt | wt | wt | wt | wt | wt |
| Direct promoter fusion | 346 | wt | wt | + | wt | wt | wt | wt | wt | wt |
| Direct promoter fusion | 347 | + | wt | + | + | wt | wt | wt | wt | wt |
| Direct promoter fusion | 348 | wt | wt | wt | + | wt | wt | wt | wt | wt |
| Direct promoter fusion | 352 | + | wt | + | + | wt | ++ | wt | wt | wt |

Utilities

The results obtained with these abiotic stress experiments show that members of the G1073 clade, including G3401, are able to confer increased tolerance and yield under abiotic stress conditions when these sequences are overexpressed. Undesirable morphological effects that are at times associated with overexpression of G3401 suggest that plants overexpressing the sequence would benefit by optimization with inducible or tissue-specific regulatory control.

G3459 (SEQ ID NO: 15 and 16)

G3459 is a soy ortholog of G1073. Some of the G3459 overexpressors exhibited developmental abnormalities, including contorted leaves, slightly small stature, small rosettes, floral abnormalities and short floral internodes leading to bunched inflorescences. At later stages of growth, a significant number of lines had larger rosettes and broad leaves with more serrations than wild-type control plants. Other lines appeared normal.

A majority of the G3459 overexpressors demonstrated tolerance to high salt and a number of other abiotic stresses, as indicated in the table below.

G3460 (SEQ ID NO: 17 and 18)

G3460 is a soy ortholog of G1073. Phylogenetic analysis based on protein alignments places G3460 in a somewhat distant subclade within the G1073 clade. The aim of this project was to determine whether overexpression of G3460 in Arabidopsis produces comparable effects to those of G1073 overexpression.

Overexpression lines were obtained; the majority of lines displayed a variety of morphological abnormalities including reduced size, slow growth, very delayed flowering, severely curled leaves and floral defects. However, nine out of a total of thirty six T1 lines showed a somewhat different phenotype; these plants were slightly late flowering but developed larger rosettes and extremely enlarged leaves, particularly at later stages of development. This resulted in a very substantial increase in vegetative biomass (possibly greater than that seen in 35S::G1073 Arabidopsis lines).

TABLE 15

Glycine max G3459 35S Direct Promoter Fusion

| Project type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter fusion | 302 | + | wt | wt | wt | wt | wt | wt | wt | wt |
| Direct promoter fusion | 303 | + | wt | wt | wt | wt | wt | wt | wt | wt |
| Direct promoter fusion | 304 | + | wt | wt | wt | wt | wt | − | wt | wt |
| Direct promoter fusion | 306 | + | wt | wt | wt | wt | wt | wt | wt | wt |
| Direct promoter fusion | 309 | + | wt | wt | wt | wt | wt | wt | wt | wt |
| Direct promoter fusion | 324 | wt | wt | wt | wt | + | wt | wt | wt | + |
| Direct promoter fusion | 330 | + | wt | wt | wt | wt | wt | wt | wt | + |
| Direct promoter fusion | 331 | wt | wt | wt | wt | + | wt | wt | wt | wt |
| Direct promoter fusion | 332 | wt | wt | wt | wt | + | wt | wt | wt | + |
| Direct promoter fusion | 333 | wt | wt | wt | wt | + | wt | wt | wt | wt |
| Direct promoter fusion | 310 | wt | wt | wt | wt | wt | wt | wt | wt | wt |
| Direct promoter fusion | 311 | wt | wt | wt | wt | wt | + | wt | wt | + |

Utilities

The results obtained with these abiotic stress experiments show that members of the G1073 clade, including G3459, are able to confer increased stress tolerance and yield under stress conditions when overexpressed. Undesirable morphological effects that are at times associated with overexpression of G3459 suggest that plants overexpressing the sequence would benefit by optimization with inducible or tissue-specific regulatory control.

It is interesting to note that some aspects of the above phenotype, such as the enlarged leaves, were similar to those seen in 35S::G1073 lines. However, other features such as the extremely twisted dark curled leaves seen in the majority of 35S::G3460 lines were not seen in 35S::G1073 transformants.

A majority of the G3460 overexpressors demonstrated tolerance to a number of abiotic stresses, as indicated in the table below.

TABLE 16

Glycine max G3460 35S Direct Promoter Fusion

| Project type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter fusion | 306 | wt | wt | wt | wt | wt | wt | wt | wt | wt |
| Direct promoter fusion | 309 | wt | wt | wt | wt | wt | wt | wt | wt | wt |
| Direct promoter fusion | 310 | wt | wt | wt | wt | + | wt | wt | wt | wt |
| Direct promoter fusion | 323 | wt | wt | wt | wt | wt | wt | wt | wt | wt |
| Direct promoter fusion | 324 | wt | wt | wt | wt | + | wt | wt | wt | wt |
| Direct promoter fusion | 343 | wt | wt | + | wt | wt | wt | wt | wt | wt |
| Direct promoter fusion | 348 | wt | wt | wt | wt | + | wt | + | + | wt |
| Direct promoter fusion | 350 | + | wt | + | wt | wt | wt | wt | wt | + |
| Direct promoter fusion | 351 | wt | wt | wt | wt | + | wt | + | + | + |
| Direct promoter fusion | 353 | wt | wt | wt | wt | wt | + | wt | + | + |

Utilities

The results obtained with these abiotic stress experiments show that members of the G1073 clade, including G3460, are able to confer increased stress tolerance and yield under stress conditions when overexpressed. Undesirable morphological effects that are at times associated with overexpression of G3460 suggest that plants overexpressing the sequence would benefit by optimization with inducible or tissue-specific regulatory control.

G3460 is clearly a candidate for the enhancement of yield and biomass accumulation.

G3406 (SEQ ID NO: 25 and 26)

G3406 is a rice ortholog of G1073. The aim of this project was to determine whether overexpression of G3406 in *Arabidopsis* produces comparable effects to those of G1073 overexpression.

Lines 321-329 may have been slightly small relative to wild-type controls at the rosette stage. At the early flowering stage, lines 361 and 362 may have been slightly late in developing. Other than these observations, the G3406 plants in Table 17 were morphologically indistinguishable from wild-type controls at all other stages of growth.

As seen in Table 17, lines 361 and 362 were less sensitive to ABA and germination in cold conditions than wild type controls. Line 321 was also less sensitive to cold in a growth assay.

able morphological effects associated with overexpression of G3406 suggests that these plants were not strongly overexpressing this sequence, also suggested by the relatively few positive stress assay results.

G3556 (SEQ ID NO: 39 and 40)

G3556 is a rice ortholog of G1073. A number of *Arabidopsis* lines overexpressing G3556 were exhibited broad, curling leaves and were late developing. No physiology results are available at this time.

G2157 (SEQ ID NO: 87 and 88)

Overall summary. Transgenic tomatoes expressing G2157 under the regulation of APETALA 1 (AP1; Mandel at al. (1992a) *Nature* 360: 273-277), *LIPID TRANSFER PROTEIN* 1 (LTP1; Thoma et al. (1994) *Plant Physiol.* 105: 35-45) and *SHOOT MERISTEMLESS* (STM; Long and Barton (1998) *Development* 125: 3027-3035-; Long and Barton (2000) *Dev. Biol.* 218: 341-353) promoters, and a significant increase in plant size was observed. Results with the AP1 and STM promoters were particularly notable as the increased plant size was also associated with increased fruit set in these lines.

G2157 is closely related to a subfamily of transcription factors well characterized in their ability to confer drought tolerance and to increase organ size. Genes within this subfamily have also exhibited deleterious morphological effects as in the overexpression of G2157 in *Arabidopsis*. It has been

TABLE 17

Oryza sativa G3406 35S Direct Promoter Fusion

| Project type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter-fusion | 321 | wt | wt | wt | wt | wt | wt | wt | wt | + |
| Direct promoter-fusion | 323 | wt | wt | wt | wt | wt | wt | wt | wt | wt |
| Direct promoter-fusion | 324 | wt | wt | wt | wt | wt | wt | wt | wt | wt |
| Direct promoter-fusion | 325 | wt | wt | wt | wt | wt | wt | wt | wt | wt |
| Direct promoter-fusion | 326 | wt | wt | wt | wt | wt | wt | wt | wt | wt |
| Direct promoter-fusion | 329 | wt | wt | wt | wt | wt | wt | wt | wt | wt |
| Direct promoter-fusion | 361 | wt | wt | wt | + | wt | + | wt | wt | wt |
| Direct promoter-fusion | 362 | wt | wt | wt | + | wt | + | wt | wt | wt |

Utilities

The results obtained with these abiotic stress experiments show that members of the G1073 clade, including G3406, are able to confer increased stress tolerance and yield under stress conditions when overexpressed. The relative lack of undesirhypothesized that targeted expression of genes in this subfamily could increase the efficacy or penetrance of desirable phenotypes.

In our overexpression studies of G1073, different promoters were used to optimize desired phenotypes. In this analysis, we discovered that localized expression via a promoter specific to young leaf and stem primordia (SUC2) was more effective than a promoter (RbcS3) lacking expression in meristematic tissue. In tomato, a similar result was obtained by expressing G2157 in meristematic and primordial tissues via the STM and AP1 promoters, respectively. G2157 has also been identified as being significantly induced under severe drought conditions. These results are strong evidence that G2157, when expressed in localized tissues in tomatoes, can mechanistically function in a similar fashion to its closely related paralogs.

Genomics discoveries. The complete sequence of G2157 was determined. G2157 is expressed at low to moderate levels throughout the plant. It shows induction by *Fusarium* infection and possibly by auxin. The function of this gene was analyzed using transgenic plants in which G2157 was expressed under the control of the 35S promoter.

Overexpression of G2157 produced distinct changes in leaf development and severely reduced overall plant size and fertility. The most strongly affected 35S::G2157 primary transformants were tiny, slow growing, and developed small dark green leaves that were often curled, contorted, or had serrated margins. A number of these plants arrested growth at a vegetative stage and failed to flower. Lines with a more moderate phenotype produced thin inflorescence stems; the flowers borne on these structures were frequently sterile and failed to open or had poorly formed stamens. Due to such defects, the vast majority of T1 plants produced very few seeds. The progeny of three T1 lines showing a moderately severe phenotype were examined; all three T2 populations, however, displayed wild-type morphology, suggesting that activity of the transgene had been reduced between the generations.

G2157 expression has been assayed using microarrays. Assays in which drought conditions were applied to 6 week old *Arabidopsis* plants resulted in the increase of G2157 transcript approximately two fold above wild type plants, under severe drought conditions.

Summary of phenotype. Transgenic tomatoes expressing G2157 under the regulation of AP1, LTP and STM a significant increase in volume was observed.

TABLE 18

Data Summary for G2157

| Promoter | Volume (m³) Avg ± Std (Count) |
|---|---|
| 35S | 0.31 ± 0.087 (3) |
| AP1 | 0.33 ± 0.068 (3) |
| LTP1 | 0.33 ± 0.054 (3) |
| STM | 0.36 ± 0.114 (2) |
| Wild-type | 0.165 ± 0.005 (277) |

Example IX

Mitigation of Undesirable Morphological Effects by G1073 Clade Polypeptide Overexpression The abiotic stress results shown above provide evidence that members of the G1073 clade of transcription factor polypeptides may be used to create plants with the characteristics of improved yield, performance and/or range. However, overexpression of these clade members may bring about unwanted morphological effects, including smaller plant size. This was observed with many, but not all, of the lines generated in the present study. Since it is often desirable to generate plants with normal or near-normal stature, a reduction or elimination of other morphological characteristics brought about by overexpression of a G1073 clade member under the regulatory control of a constitutive promoter may not always be the best approach to improving stress tolerance.

This present study also included an investigation in the use of alternative promoter or two-component overexpression systems for the purpose of conferring enhanced stress tolerance and eliminating developmental abnormalities such as reduced size that were associated with G1073 constitutive overexpression. In this regard, the present invention also relates to methods and compositions for producing transgenic plants with improved stress performance achieved by altering the expression of G1073 and related sequences with specific promoter-gene combinations or other regulatory means. These combinations may regulate transcription factor expression patterns in a transient, inducible, or organ- or tissue-specific manner. As shown below, this approach may be used to generate plants that are morphologically similar to wild-type control plants that have not been transformed with a polynucleotide encoding G1073 or an equivalog. Thus, the type of regulatory element used to control regulation of the transcription factor gene may be used to alleviate undesirable developmental abnormalities or adverse morphological effects that would otherwise result by overexpressing of the same transcription factor genes with a constitutive promoter such as the 35S promoter.

G1073 (*Arabidopsis*)—Root ARSK1

We have obtained ARSK1::G1073 lines using a two component approach; no consistent effects on morphology were apparent among these transformants and alterations in leaf size were not observed. Thus, either expression from the ARSK1 promoter was too weak or root expression was not sufficient to trigger the alterations in leaf size that are apparent in 35S::G1073 lines.

Interestingly, although ARSK1::G1073 lines showed no clear morphological changes, five out of ten of these lines did exhibit enhanced tolerance to sodium chloride in a plate based germination assay. Two other lines outperformed wild type controls in a cold germination assay. These osmotic stress tolerance phenotypes are of particular interest, since they show that G1073 can provide stress tolerance independently of changes in organ size. Additionally, since ARSK1 is not significantly expressed in shoot tissue, the results suggest that G1073 expression is not required in the shoot in order to achieve stress tolerance.

Morphology Summary

*Arabidopsis* lines in which G1073 was expressed from the ARSK1 promoter (via the two component system) displayed no consistent difference in morphology compared to controls. Twenty T1 lines were examined (341-360); three lines (#342, 346, 357) were noted to be slightly small and slow developing. However the remainder of the lines exhibited wild-type morphology at all stages.

Of the lines submitted for physiological assays, all except line 556 showed segregation on selection plates in the T2 generation that was compatible with the transgene being present at a single locus. Lines 556, showed segregation that was compatible with insertions at multiple loci.

Physiology Summary

Seedlings from five ARSK1::G1073 lines had more seedling vigor when germinated on plates containing sodium chloride. Seedlings from two other lines performed better than wild-type controls in a cold germination assay, and two lines performed better in a drought assay.

TABLE 19

G1073 (Arabidopsis) - Root ARSK1 Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 342 | wt | wt | wt | wt | wt | wt | wt | wt | wt |
| 2-components-supTfn | 344 | wt | wt | wt | wt | wt | wt | wt | wt | wt |
| 2-components-supTfn | 345 | + | wt | wt | wt | wt | wt | wt | wt | wt |
| 2-components-supTfn | 346 | wt | wt | wt | wt | wt | + | wt | wt | wt |
| 2-components-supTfn | 347 | wt | wt | wt | wt | wt | + | wt | wt | wt |
| 2-components-supTfn | 351 | wt | wt | wt | wt | wt | wt | wt | wt | wt |
| 2-components-supTfn | 354 | + | wt | wt | wt | wt | wt | wt | wt | wt |
| 2-components-supTfn | 355 | + | wt | wt | wt | wt | wt | wt | wt | wt |
| 2-components-supTfn | 356 | + | wt | wt | wt | wt | wt | wt | wt | wt |
| 2-components-supTfn | 359 | + | wt | wt | wt | wt | wt | wt | wt | wt |

G1073 (Arabidopsis)—Epidermal CUT1

We have obtained CUT1::G1073 lines using a two component approach; no consistent effects on morphology were apparent among these transformants and alterations in leaf size were not observed. Thus, either expression from the CUT1 promoter was too weak or epidermal expression was not sufficient to trigger the alterations in leaf size that are apparent in 35S::G1073 lines.

Although CUT1::G1073 lines showed no clear morphological changes, three out of ten of these lines did exhibit enhanced tolerance to sodium chloride in a plate based germination assay. Two of these lines also outperformed wild type controls in a sucrose germination assay, whereas the third line germinated better than wild type controls on mannitol media. A fourth CUT1::G1073 line gave a positive result in the sucrose assay alone. Although these osmotic stress tolerance phenotypes were seen in a relatively small number of lines, they are of particular interest, since they suggest that G1073 can provide stress tolerance independently of changes in organ size. Additionally, the CUT1 driver line does not give significant expression in the root, suggesting that G1073 expression is not required in the root in order to achieve such tolerance.

Morphology Summary

Arabidopsis lines that express G1073 from the CUT I promoter (using the two component system; CUT1::LexA; opLexA::G1073) have now been generated. A total of nineteen of lines were obtained (381-399). Some size variation was apparent at early stages of growth, but overall, the plants showed no consistent differences in morphology to controls.

Of the lines submitted for physiological assays, the following showed a segregation on selection plates in the T2 generation that was compatible with the transgene being present at a single locus: 384, 391, 392, 394, 396. Lines 381, 390, 393, 395, 397 showed segregation that was compatible with insertions at multiple loci.

Physiology (Plate Assays) Summary

Three CUT1::G1073 lines showed increased seedling vigor when germinated on plates containing sodium chloride. Of these three lines, seedlings of two lines also performed better than wild-type controls when germinated on sucrose whereas seedlings of the third line had better vigor when germinated on mannitol containing plates. A fourth line showed a better performance in a sucrose germination assay.

TABLE 20

G1073 (Arabidopsis) - Epidermal CUT1 Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 381 | wt | wt | + | wt | wt | wt | wt | wt | wt |
| 2-components-supTfn | 384 | wt | wt | wt | wt | wt | wt | wt | wt | wt |
| 2-components-supTfn | 390 | wt | wt | wt | wt | wt | wt | wt | wt | wt |
| 2-components-supTfn | 391 | wt | wt | wt | wt | wt | wt | wt | wt | wt |
| 2-components-supTfn | 392 | wt | wt | wt | wt | wt | wt | wt | wt | wt |
| 2-components-supTfn | 393 | + | ++ | wt | wt | wt | wt | wt | wt | wt |
| 2-components-supTfn | 394 | + | wt | + | wt | wt | wt | wt | wt | wt |
| 2-components-supTfn | 395 | wt | wt | wt | wt | wt | wt | wt | wt | wt |
| 2-components-supTfn | 396 | + | wt | + | wt | wt | wt | wt | wt | wt |
| 2-components-supTfn | 397 | wt | wt | wt | wt | wt | wt | wt | wt | wt |

G1073 (Arabidopsis)—Vascular SUC2

We have obtained SUC2::G1073 lines using a two component approach; the majority of these lines displayed wild-type morphology, and several lines had increased stress tolerance compared to wild-type control plants. Five of thirteen lines exhibited a slight delay in the onset of flowering, and developed enlarged leaves relative to controls. This effect became particularly apparent at later developmental stages. Similar phenotypes were obtained at a similar frequency in 35S::G1073 lines; thus the SUC2 and 35S promoters produced comparable morphological effects when used in combination with G1073.

Morphology Summary

Two sets of 2-component lines have been obtained (#1081-1088, 1101-1105) for which an opLexA::G1073 construct was supertransformed into a SUC2::LexA-GAL4TA promoter driver line. A number of these lines exhibited enlarged leaves and a slight delay in the onset of flowering, as detailed below:

Lines 1081-1088: all appeared normal at early stages. #1085 and #1088 were slightly late flowering and developed enlarged leaves at later stages. #1082 was also slightly late flowering. The remaining lines showed wild-type morphology at all stages.

Lines 1101-1105: all were slightly small at early stages. #1102 and #1105 were slightly later flowering and #1102 developed enlarged rosette leaves at late stages. The remaining lines all appeared normal later in development.

It should be noted that a direct promoter-fusion construct (P21521) for SUC2::G1073 has also been built, but lines containing that construct have not yet been selected.

Physiology Summary

Three SUC2::G1073 lines showed increased seedling vigor when germinated on plates in cold conditions. Seedlings of two of these lines also performed better than wild-type controls when germinated on mannitol containing plates. A fourth line showed a better performance in a plate-based drought assay.

TABLE 21

G1073 (*Arabidopsis*) - Vascular SUC2 Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 1081 | wt | wt | wt | wt | wt | wt | wt | wt | wt |
| 2-components-supTfn | 1082 | wt | + | wt | wt | wt | + | wt | wt | wt |
| 2-components-supTfn | 1083 | wt | + | wt | wt | wt | + | wt | wt | wt |
| 2-components-supTfn | 1085 | wt | wt | wt | wt | wt | + | wt | wt | wt |
| 2-components-supTfn | 1087 | wt | wt | wt | wt | wt | wt | wt | wt | wt |
| 2-components-supTfn | 1088 | wt | wt | wt | wt | wt | wt | wt | + | wt |
| 2-components-supTfn | 1101 | wt | wt | wt | wt | wt | wt | wt | wt | wt |
| 2-components-supTfn | 1102 | wt | wt | wt | wt | wt | wt | wt | wt | wt |
| 2-components-supTfn | 1103 | wt | wt | wt | wt | wt | wt | wt | wt | wt |
| 2-components-supTfn | 1104 | wt | wt | wt | wt | wt | wt | wt | wt | wt |
| Direct promoter-fusion | 1581 | wt | wt | wt | + | wt | wt | wt | wt | wt |
| Direct promoter-fusion | 1582 | + | wt | wt | + | wt | wt | wt | wt | wt |
| Direct promoter-fusion | 1584 | + | wt | wt | wt | wt | wt | wt | wt | wt |
| Direct promoter-fusion | 1585 | wt | wt | wt | wt | wt | wt | wt | wt | wt |
| Direct promoter-fusion | 1586 | + | wt | wt | + | wt | wt | wt | wt | wt |
| Direct promoter-fusion | 1587 | wt | wt | wt | wt | wt | wt | wt | wt | wt |
| Direct promoter-fusion | 1588 | wt | wt | wt | wt | wt | + | wt | wt | wt |
| Direct promoter-fusion | 1589 | wt | wt | wt | wt | wt | + | wt | wt | wt |
| Direct promoter-fusion | 1590 | wt | wt | wt | wt | wt | + | wt | wt | wt |
| Direct promoter-fusion | 1591 | wt | wt | wt | wt | wt | + | wt | wt | wt |

G1073 (*Arabidopsis*) Leaf RBCS3

We have obtained tissue-specific (leaf) promoter RBCS3::G1073 lines using a two component approach.

Morphology Summary

Lines 541 and 542 may have been marginally late but otherwise showed no obvious morphological differences relative to wild-type controls.

Lines 961-973 were slightly slower growing than wild-type controls, but were otherwise morphologically similar to the controls.

Physiology Summary

Most notably, seedlings of these overexpressors showed increased tolerance to the osmotic stresses of salt and heat in germination assays. Two lines showed increased tolerance to cold in growth assays.

TABLE 22

G1073 (*Arabidopsis*) - Leaf RBCS3 Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 541 | wt | wt | wt | + | wt | wt | + | wt | + |
| 2-components-supTfn | 542 | wt | wt | wt | wt | wt | wt | + | wt | wt |

TABLE 22-continued

G1073 (*Arabidopsis*) - Leaf RBCS3 Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 961 | wt | wt | wt | wt | wt | wt | wt | wt | wt |
| 2-components-supTfn | 962 | wt | wt | wt | wt | wt | wt | wt | wt | wt |
| 2-components-supTfn | 965 | wt | wt | wt | wt | wt | wt | + | wt | + |
| 2-components-supTfn | 966 | wt | wt | wt | wt | wt | wt | + | wt | wt |
| 2-components-supTfn | 967 | + | wt | wt | wt | wt | wt | wt | wt | wt |
| 2-components-supTfn | 968 | + | wt | wt | wt | wt | wt | + | wt | wt |
| 2-components-supTfn | 969 | wt | wt | wt | wt | wt | wt | wt | wt | wt |
| 2-components-supTfn | 973 | + | wt | wt | wt | wt | wt | wt | wt | wt |

G1073 (*Arabidopsis*)—Super Activation (N-GAL4-TA)

We have now isolated lines that overexpress a version of the G1073 protein that has a GAL4 activation domain fused to the N terminus.

Morphology Summary

For the most part, lines were morphologically indistinguishable from wild type controls, with a number of lines having normal or near-normal physiologies. However, there were a small number of plants that showed delayed flowering and changes in leaf shape. In addition, some were observed to be dark in coloration.

Three batches of lines were generated that overexpressed a super-active form of G1073 comprising a GAL4 transactivation domain fused to the N terminus of the protein: lines 841-852, 981-991, and 1441-1460.

The majority of plants in each of the above plantings appeared wild-type; however delayed flowering, and changes in leaf shape were apparent in a small number of the lines in each set. Plants showing this phenotype flowered up to 3-4 weeks after wild type controls (under 24-hour light), were dark in coloration, and had leaves that became curled and twisted (particularly at the late stages of the life cycle).

This above phenotype was observed with the following frequencies:

3/12 lines (846, 851, 852) from the 841-852 set
2/11 (983, 989) lines from the 981-991 set
7/20 (1442, 1443, 1449, 1452, 1453, 1454, 1455) lines from the 1441-1460 set.

Of the plants in this final set, however, only #1442 showed a strong phenotype whereas others displayed relatively mild effects.

It is perhaps noteworthy that in addition to the effects on flowering time and leaf development, a small number of the T1 lines obtained in the second batch (981-991) were noted to be more advanced than wild-type controls at the 7 day stage. However, this effect was not observed in the T2 progeny of any of those lines or in either of the other two sets of T1 plants.

Physiology Summary

Seedlings of two of these superactivated lines showed increased tolerance to ABA, and germinated on plates in cold conditions. Seedlings of two lines also performed better than wild-type controls in a plate-based drought assay. Other lines showed a better performance in a sucrose-based osmotic stress assay, or in growth assays in cold or hot conditions.

TABLE 23

G1073 (*Arabidopsis*) - Super Activation (N-GAL4-TA) Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| GAL4 N-terminus | 842 | wt | wt | wt | wt | wt | wt | + | wt | wt |
| GAL4 N-terminus | 843 | wt | wt | wt | wt | wt | wt | wt | wt | wt |
| GAL4 N-terminus | 849 | wt | wt | wt | wt | wt | wt | wt | wt | wt |
| GAL4 N-terminus | 850 | wt | wt | wt | wt | wt | wt | wt | + | + |
| GAL4 N-terminus | 851 | wt | wt | wt | wt | wt | wt | wt | wt | wt |
| GAL4 N-terminus | 981 | wt | wt | + | + | wt | wt | wt | wt | wt |
| GAL4 N-terminus | 983 | wt | wt | wt | + | wt | wt | wt | + | wt |
| GAL4 N-terminus | 984 | wt | wt | wt | wt | wt | wt | wt | wt | wt |
| GAL4 N-terminus | 985 | wt | wt | wt | wt | wt | wt | wt | wt | wt |
| GAL4 N-terminus | 986 | wt | wt | wt | wt | wt | wt | wt | wt | wt |
| GAL4 N-terminus | 989 | wt | wt | wt | + | wt | wt | wt | wt | wt |

G1073 (*Arabidopsis*)—Super Activation (C-GAL4-TA)

We have now isolated lines that overexpress a version of the G1073 protein that has a GAL4 activation domain fused to the C terminus.

Morphology Summary

At various stages of growth, some of the plants with a GAL4 activation domain fused to the C terminus were somewhat small. However, many of the plants there were more tolerant to abiotic stresses, indicated in the table below, were only slightly smaller than wild-type controls at some stages of growth, and many of the lines were morphologically very similar to wild-type control plants.

Physiology Summary

Most of the lines C-GAL4 superactivated lines tested were more tolerant to osmotic stress in a plate-based severe desiccation assay than wild-type control plants. Two lines were more tolerant to high mannitol.

TABLE 24

G1073 (*Arabidopsis*) - Super Activation (C-GAL4-TA) Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| GAL4 C-terminus | 1542 | wt | wt | wt | wt | wt | wt | wt | + | wt |
| GAL4 C-terminus | 1543 | wt | wt | wt | wt | wt | wt | wt | wt | wt |
| GAL4 C-terminus | 1544 | wt | wt | wt | wt | wt | wt | wt | + | wt |
| GAL4 C-term terminus | 1545 | wt | wt | wt | wt | wt | wt | wt | wt | wt |
| GAL4 C-terminus | 1546 | wt | wt | wt | wt | wt | wt | wt | + | wt |
| GAL4 C-terminus | 1547 | wt | wt | wt | wt | wt | wt | wt | + | wt |
| GAL4 C-terminus | 1551 | wt | + | wt | wt | wt | wt | wt | + | wt |
| GAL4 C-terminus | 1552 | wt | + | wt | wt | wt | wt | wt | + | wt |

G1067 (*Arabidopsis*) Root ARSK1

We have obtained tissue-specific (root) ARSK1::G1067 lines using a two component approach.

The majority (18 out of 26) of these transformants appeared wild type, and displayed no evidence of curled leaves and severe dwarfing. Eight of 26 lines showed size reductions and developed more slowly than controls, to various extents.

In plate based stress assays, four out of ten lines ARSK1::G1067 lines showed enhanced tolerance in a severe dehydration assay. All of these four lines had shown a wild-type phenotype in the morphological screens, demonstrating that G1067 could enhance drought tolerance without producing obvious negative effects on plant size. Three other ARSK1::G1067 lines outperformed wild-type control plants in a high NaCl germination assay.

short rounded leaves and flowered slightly late. At later stages of growth, the leaves became contorted and curled, but in occasional lines leaves appeared broader than those of controls. The appearance of broad leaves, albeit at a low frequency, suggests that G1073 and G1067 might, at least to some extent, be functionally related.

Lines 581-590 showed a slight delay in the onset of flowering (about 1-5 days under 24-hour light).

At early stages of growth, lines 621-629 were slightly small at early stages and had short, round, rather broad leaves. Delayed flowering was not noted in this set of lines. Late in the flowering stage, lines 621-629 had no consistent morphological differences relative to wild-type control plants, except

TABLE 25

ARSK1::G1067 Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 344 | wt | wt | wt | wt | wt | wt | wt | + | wt |
| 2-components-supTfn | 345 | + | wt | wt | wt | wt | wt | wt | wt | wt |
| 2-components-supTfn | 346 | wt | wt | wt | wt | wt | wt | wt | wt | wt |
| 2-components-supTfn | 347 | + | wt | wt | wt | wt | wt | wt | wt | wt |
| 2-components-supTfn | 401 | wt | wt | wt | wt | wt | wt | wt | + | wt |
| 2-components-supTfn | 402 | wt | wt | wt | wt | wt | wt | wt | + | wt |
| 2-components-supTfn | 403 | + | wt | wt | wt | wt | wt | wt | wt | wt |
| 2-components-supTfn | 406 | wt | wt | wt | wt | wt | wt | wt | + | wt |
| 2-components-supTfn | 407 | + | wt | wt | wt | wt | wt | wt | wt | wt |
| 2-components-supTfn | 408 | wt | wt | wt | wt | wt | wt |  |  | wt |

G1067 (*Arabidopsis*) Leaf RBCS3

We have obtained tissue-specific (leaf) promoter RBCS3::G1067 lines using a two component approach.

A number of RBCS3::G1067 lines produced with a two component approach were generally small at early stages, had for lines 622,624, which had slightly broad flat leaves. In later stages of growth there were no consistent differences in morphology between overexpressing lines 621-629 and wild-type control plants.

Several of these lines had greater stress tolerance than wild-type control plants, as seen in the following table.

TABLE 26

RBCS3::G1067 Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 581 | wt | wt | wt | wt | wt | wt | wt | wt | wt |
| 2-components-supTfn | 582 | wt | wt | wt | wt | wt | wt | wt | wt | wt |
| 2-components-supTfn | 586 | wt | wt | wt | wt | wt | wt | wt | wt | wt |
| 2-components-supTfn | 587 | + | wt | wt | wt | wt | wt | wt | wt | wt |
| 2-components-supTfn | 588 | + | wt | wt | wt | wt | wt | wt | wt | wt |
| 2-components-supTfn | 622 | + | wt | wt | wt | wt | wt | wt | wt | wt |
| GAL4 N-terminus | 624 | wt | wt | wt | wt | wt | wt | wt | wt | wt |
| 2-components-supTfn | 627 | + | wt | wt | wt | wt | wt | wt | wt | + |
| 2-components-supTfn | 628 | wt | wt | wt | wt | wt | wt | wt | wt | wt |
| 2-components-supTfn | 629 | wt | wt | wt | wt | wt | wt | wt | wt | wt |

G1067 (*Arabidopsis*) Stress-Inducible RD29A

We have obtained stress-inducible promoter RD29A::G1067 lines using a two component approach.

The majority of these RD29A::LexA;opLexA::G1067) lines in the RD29A line 5 background showed no consistent alterations in morphology relative to controls. A smaller number of the transformants did show a small reduction in size and slightly more rounded leaves than controls. Thus, in these lines, low constitutive expression produced by the driver line could have triggered such effects. However, none of the lines showed the extreme dwarfing and curled leaves seen in 35S::G1067 lines.

Several of these lines had greater stress tolerance than wild-type control plants, particularly in the plate-based severe desiccation assays, as seen in the following table.

G2156 (*Arabidopsis*) Root ARSK1

We have obtained tissue-specific (root) promoter ARSK1::G2156 lines using a two component approach.

Approximately half of the lines from one of these batches displayed a very marginal delay in the onset of flowering, but the majority of lines displayed no obvious differences in growth and development to wild-type controls. Thus, use of a root promoter in combination with G2156 largely eliminated the undesirable morphologies produced by overexpression of that gene.

Several of these lines also had greater stress tolerance than wild-type control plants, particularly in plate-based severe desiccation assays as seen in the following table.

TABLE 27

RD29A::G1067 Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 661 | wt | wt | wt | wt | wt | wt | wt | + | wt |
| 2-components-supTfn | 663 | wt | wt | wt | wt | wt | wt | wt | wt | wt |
| 2-components-supTfn | 664 | wt | wt | wt | wt | wt | wt | wt | + | wt |
| 2-components-supTfn | 668 | + | wt | wt | wt | wt | wt | wt | wt | wt |
| 2-components-supTfn | 704 | + | + | wt | wt | wt | wt | wt | wt | wt |
| 2-components-supTfn | 707 | wt | wt | wt | wt | wt | wt | wt | wt | wt |
| GAL4 N-terminus | 708 | wt | + | wt | wt | wt | wt | wt | + | wt |
| 2-components-supTfn | 710 | wt | + | wt | wt | wt | wt | wt | + | wt |
| 2-components-supTfn | 711 | wt | wt | + | + | wt | + | wt | + | wt |
| 2-components-supTfn | 717 | + | wt | wt | + | wt | wt | wt | + | wt |

TABLE 28

ARSK1::G2156 Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 363 | wt | wt | wt | wt | wt | wt | wt | wt | wt |
| 2-components-supTfn | 364 | wt | wt | wt | wt | wt | wt | wt | wt | wt |
| 2-components-supTfn | 365 | wt | wt | wt | wt | wt | wt | wt | + | wt |
| 2-components-supTfn | 368 | wt | wt | wt | wt | wt | wt | wt | + | wt |
| 2-components-supTfn | 370 | wt | wt | wt | wt | wt | wt | wt | wt | wt |
| 2-components-supTfn | 486 | wt | wt | wt | wt | wt | wt | wt | wt | wt |
| 2-components-supTfn | 488 | wt | wt | wt | wt | wt | wt | wt | + | wt |
| 2-components-supTfn | 490 | wt | wt | wt | wt | wt | wt | wt | wt | wt |
| 2-components-supTfn | 492 | wt | wt | wt | wt | wt | wt | wt | wt | wt |
| 2-components-supTfn | 494 | wt | wt | wt | wt | wt | wt | wt | + | wt |

G2156 (*Arabidopsis*) Leaf RBCS3

We have obtained tissue-specific (leaf) promoter RBCS3::G2156 lines using a two component approach.

At early stages, these plants were slightly small and showed rather rounded leaves. However, at later stages, 50% of the lines developed enlarged leaves and showed increased rosette biomass compare to controls. The majority of lines showing this phenotype also displayed a slight delay in the onset of flowering. We have previously observed large leaves in 35S::G2156 constitutive overexpressors. However, leaf enlargements were seen at lower frequency in the 35S::G2156 study than in the RBCS3::G2156 study. Additionally many of the lines from the 35S::G2156 experiment were very small and had multiple defects; these effects appear to have been avoided by use of the RBCS3 promoter. The increased leaf size seen in the present study was comparable to the effects produced by increased G1073 expression and serves to strengthen the conclusion that the two genes have related roles.

RBCS3 produces expression in relatively mature, photosynthesizing leaf tissue. Thus, G2156 when expressed at a relatively late stage of leaf development produced developmental signals that maintained leaf growth. However, there remains the possibility that G2156 triggered the production of developmental signals in mature leaves that were then transmitted to younger leaf primordia, and committed them to overgrowth at an early stage.

Several of these lines had greater abiotic stress tolerance than wild-type control plants, as seen in the following table.

TABLE 29

RBCS3::G2156 Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 543 | wt | wt | wt | wt | wt | wt | wt | + | wt |
| 2-components-supTfn | 544 | wt | wt | wt | wt | wt | wt | wt | + | wt |
| 2-components-supTfn | 551 | wt | wt | wt | wt | wt | wt | wt | wt | wt |
| 2-components-supTfn | 552 | wt | wt | wt | wt | wt | wt | wt | wt | wt |
| 2-components-supTfn | 553 | wt | wt | wt | wt | wt | wt | wt | wt | wt |
| 2-components-supTfn | 554 | wt | wt | wt | + | wt | wt | wt | wt | wt |
| 2-components-supTfn | 557 | wt | wt | wt | + | wt | wt | wt | wt | wt |
| 2-components-supTfn | 582 | wt | wt | wt | + | wt | wt | wt | wt | wt |
| 2-components-supTfn | 584 | wt | wt | wt | wt | wt | wt | wt | wt | wt |
| 2-components-supTfn | 587 | wt | wt | wt | wt | wt | wt | wt | wt | wt |

G2156 (*Arabidopsis*) Stress-Inducible RD29A

We have obtained stress-inducible promoter RD29A::G2156 lines using a two component approach.

The majority of the two component RD29A::LexA; opLexA::G2156 transformants in the RD29A line 5 background showed no consistent differences in morphology to controls. A smaller number of lines did flower slightly late and developed enlarged leaves later in development. Thus, in these lines, low constitutive expression produced by the driver line could have triggered such effects.

Several of these lines had greater stress tolerance than wild-type control plants, as seen in the following table. Particularly noteworthy were the results obtained showing that a majority of lines were less sensitive in the ABA germination assay, indicating an osmotic stress tolerant phenotype.

TABLE 30

RD29A::G2156- Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 622 | wt | wt | wt | wt | wt | wt | – | wt | wt |
| 2-components-supTfn | 624 | wt | wt | wt | wt | wt | wt | wt | wt | wt |
| 2-components-supTfn | 625 | wt | wt | wt | + | wt | wt | wt | wt | wt |
| 2-components-supTfn | 626 | wt | wt | wt | + | wt | wt | wt | wt | wt |
| 2-components-supTfn | 628 | wt | wt | wt | + | wt | wt | wt | wt | wt |
| 2-components-supTfn | 686 | + | wt | + | wt | wt | wt | wt | wt | wt |
| 2-components-supTfn | 688 | wt | wt | wt | wt | wt | wt | wt | wt | wt |
| 2-components-supTfn | 689 | wt | wt | wt | wt | wt | wt | wt | wt | wt |
| 2-components-supTfn | 690 | wt | wt | wt | + | wt | wt | wt | wt | wt |
| 2-components-supTfn | 692 | wt | wt | + | ++ | wt | wt | wt | wt | wt |

Utilities for G1073 Clade Members Under Non-Constitutive Regulatory Control

The results of these studies with the non-constitutive regulatory control of numerous G1073 clade members indicate that the polynucleotide and polypeptide sequences can be used to improve drought related stress tolerance while maintaining normal or near normal morphology under stress-free or low stress conditions, and improved size and vigor relative to wild-type control plants under conditions of abiotic stress. The data also confirm our conclusions that G1073 and other G1073 clade members may be valuable tools for the purpose of increasing yield, biomass and modifying flowering time.

Analysis of combinations of G1073 clade member with regulatory elements was performed to 1) provide mechanistic insights into G1073 clade member function, and 2) to identify optimized patterns of G1073 clade member expression. Differential expression of G1073 and related sequences has revealed that some degree of osmotic stress tolerance can be obtained without a significant impact on plant or organ size. Specific examples include expression with tissue-specific promoters, including the CUT1 (epidermal-specific), The SUC2 (vascular-specific), the ARSK1 (root-specific), the RBCS3 (leaf specific) promoters, and stress inducible promoters, including the RD29A promoter. Lines that overexpressed a super-active form of G1073 comprising a GAL4 transactivation domain fused to either the N- or the C terminus of the polypeptide were also more tolerant to abiotic stresses, and were generally morphologically similar to wild-type control plants. These transcription factor-regulatory element combinations demonstrate that tissue-specific, inducible and transactivated G1073 clade members can be used to provide abiotic stress tolerance with little or no impact on overall plant growth or yield under low-abiotic stress conditions, and significantly improve yield and vigor in conditions of abiotic stress.

Example X

Identification of Homologous Sequences by Computer Homology Search

This example describes identification of genes that are orthologous to *Arabidopsis thaliana* transcription factors from a computer homology search.

Homologous sequences, including those of paralogs and orthologs from *Arabidopsis* and other plant species, were identified using database sequence search tools, such as the Basic Local Alignment Search Tool (BLAST) (Altschul et al. (1990) supra; and Altschul et al. (1997) *Nucleic Acid Res.* 25: 3389-3402). The tblastx sequence analysis programs were employed using the BLOSUM-62 scoring matrix (Henikoff and Henikoff (1992) *Proc. Natl. Acad. Sci. USA* 89: 10915-10919). The entire NCBI GenBank database was filtered for sequences from all plants except *Arabidopsis thaliana* by selecting all entries in the NCBI GenBank database associated with NCBI taxonomic ID 33090 (Viridiplantae; all plants) and excluding entries associated with taxonomic ID 3701 (*Arabidopsis thaliana*).

These sequences are compared to sequences representing transcription factor genes presented in the Sequence Listing, using the Washington University TBLASTX algorithm (version 2.0a19 MP) at the default settings using gapped alignments with the filter "off". For each transcription factor gene in the Sequence Listing, individual comparisons were ordered by probability score (P-value), where the score reflects the probability that a particular alignment occurred by chance. For example, a score of 3.6e-59 is $3.6 \times 10$-59. In addition to P-values, comparisons were also scored by percentage identity. Percentage identity reflects the degree to which two segments of DNA or protein are identical over a particular length. Examples of sequences so identified are presented in, for example, the Sequence Listing, and Table 5. Paralogous or orthologous sequences were readily identified and available in GenBank by Accession number (Table 5; Sequence Identifier or Accession Number). The percent sequence identity among these sequences can be as low as 49%, or even lower sequence identity.

Candidate paralogous sequences were identified among *Arabidopsis* transcription factors through alignment, identity, and phylogenic relationships. G1067, G2153 and G2156 (SEQ ID NO: 4, 6, and 8, respectively), paralogs of G1073, may be found in the Sequence Listing.

Candidate orthologous sequences were identified from proprietary unigene sets of plant gene sequences in *Zea mays*, *Glycine max* and *Oryza sativa* based on significant homology to *Arabidopsis* transcription factors. These candidates were reciprocally compared to the set of *Arabidopsis* transcription factors. If the candidate showed maximal similarity in the protein domain to the eliciting transcription factor or to a paralog of the eliciting transcription factor, then it was considered to be an ortholog. Identified non-*Arabidopsis* sequences that were shown in this manner to be orthologous to the *Arabidopsis* sequences are provided in, for example, Table 5.

Example XI

Identification of Orthologous and Paralogous Sequences by PCR

Orthologs to *Arabidopsis* genes may identified by several methods, including hybridization, amplification, or bioinformatically. This example describes how one may identify equivalogs to the *Arabidopsis* AP2 family transcription factor CBF 1 (polynucleotide SEQ ID NO: 69, encoded polypeptide SEQ ID NO: 70), which confers tolerance to abiotic stresses (Thomashow et al. (2002) U.S. Pat. No. 6,417,428), and an example to confirm the function of homologous sequences. In this example, orthologs to CBF1 were found in canola (*Brassica napus*) using polymerase chain reaction (PCR).

Degenerate primers were designed for regions of AP2 binding domain and outside of the AP2 (carboxyl terminal domain):

Mol 368 (reverse) 5'-CAY CCN ATH TAY MGN GGN GT-3' (SEQ ID NO: 77)

Mol 378 (forward) 5'-GGN ARN ARC ATN CCY TCN GCC-3' (SEQ ID NO: 78)

(Y: C/T, N: A/C/G/T, H: A/C/T, M: A/C, R: A/G)

Primer Mol 368 is in the AP2 binding domain of CBF1 (amino acid sequence: His-Pro-Ile-Tyr-Arg-Gly-Val) while primer Mol 378 is outside the AP2 domain (carboxyl terminal domain) (amino acid sequence: Met-Ala-Glu-Gly-Met-Leu-Leu-Pro).

The genomic DNA isolated from *B. napus* was PCR-amplified by using these primers following these conditions: an initial denaturation step of 2 minutes at 93° C.; 35 cycles of 93° C. for 1 minute, 55° C. for 1 minute, and 72° C. for 1 minute; and a final incubation of 7 minutes at 72° C. at the end of cycling.

The PCR products were separated by electrophoresis on a 1.2% agarose gel and transferred to nylon membrane and hybridized with the AT CBF1 probe prepared from *Arabidopsis* genomic DNA by PCR amplification. The hybridized products were visualized by colorimetric detection system (Boehringer Mannheim) and the corresponding bands from a similar agarose gel were isolated using the Qiagen Extraction Kit (Qiagen, Valencia Calif.). The DNA fragments were ligated into the TA clone vector from TOPO TA Cloning Kit (Invitrogen Corporation, Carlsbad Calif.) and transformed into *E. coli* strain TOP10 (Invitrogen).

Seven colonies were picked and the inserts were sequenced on an ABI 377 machine from both strands of sense and antisense after plasmid DNA isolation. The DNA sequence was edited by sequencer and aligned with the AtCBF1 by GCG software and NCBI blast searching.

The nucleic acid sequence and amino acid sequence of one canola ortholog found in this manner (bnCBF1; polynucleotide SEQ ID NO: 75 and polypeptide SEQ ID NO: 76) identified by this process is shown in the Sequence Listing.

The aligned amino acid sequences show that the bnCBF1 gene has 88% identity with the *Arabidopsis* sequence in the AP2 domain region and 85% identity with the *Arabidopsis* sequence outside the AP2 domain when aligned for two insertion sequences that are outside the AP2 domain.

Similarly, paralogous sequences to *Arabidopsis* genes, such as CBF1, may also be identified.

Two paralogs of CBF1 from *Arabidopsis thaliana*: CBF2 and CBF3. CBF2 and CBF3 have been cloned and sequenced as described below. The sequences of the DNA SEQ ID NO: 71 and 73 and encoded proteins SEQ ID NO: 72 and 74 are set forth in the Sequence Listing.

A lambda cDNA library prepared from RNA isolated from *Arabidopsis thaliana* ecotype Columbia (Lin and Thomashow (1992) *Plant Physiol.* 99: 519-525) was screened for recombinant clones that carried inserts related to the CBF1 gene (Stockinger et al. (1997) *Proc. Natl. Acad. Sci. USA* 94:1035-1040). CBF1 was $^{32}$P-radiolabeled by random priming (Sambrook et al. supra) and used to screen the library by the plaque-lift technique using standard stringent hybridization and wash conditions (Hajela et al. (1990) *Plant Physiol.* 93:1246-1252; Sambrook et al. supra) 6×SSPE buffer, 60° C. for hybridization and 0.1×SSPE buffer and 60° C. for washes). Twelve positively hybridizing clones were obtained and the DNA sequences of the cDNA inserts were determined. The results indicated that the clones fell into three classes. One class carried inserts corresponding to CBF1. The two other classes carried sequences corresponding to two different homologs of CBF1, designated CBF2 and CBF3. The nucleic acid sequences and predicted protein coding sequences for *Arabidopsis* CBF1, CBF2 and CBF3 are listed in the Sequence Listing (SEQ ID NOs: 69, 71, 73 and SEQ ID NOs: 70, 72, and 74, respectively). The nucleic acid sequences and predicted protein coding sequence for *Brassica napus* CBF ortholog is listed in the Sequence Listing (SEQ ID NOs: 75 and 76, respectively).

A comparison of the nucleic acid sequences of *Arabidopsis* CBF1, CBF2 and CBF3 indicate that they are 83 to 85% identical as shown in Table 31.

TABLE 31

Identity comparison of *Arabidopsis* CBF1, CBF2 and CBF3

| | Percent identity[a] | |
|---|---|---|
| | DNA[b] | Polypeptide |
| cbf1/cbf2 | 85 | 86 |
| cbf1/cbf3 | 83 | 84 |
| cbf2/cbf3 | 84 | 85 |

[a]Percent identity was determined using the Clustal algorithm from the Megalign program (DNASTAR, Inc.).
[b]Comparisons of the nucleic acid sequences of the open reading frames are shown.

Similarly, the amino acid sequences of the three CBF polypeptides range from 84 to 86% identity. An alignment of the three amino acid sequences reveals that most of the differences in amino acid sequence occur in the acidic C-terminal half of the polypeptide. This region of CBF1 serves as an activation domain in both yeast and *Arabidopsis* (not shown).

Residues 47 to 106 of CBF1 correspond to the AP2 domain of the protein, a DNA binding motif that to date, has only been found in plant proteins. A comparison of the AP2 domains of CBF1, CBF2 and CBF3 indicates that there are a few differences in amino acid sequence. These differences in amino acid sequence might have an effect on DNA binding specificity.

Example XII

Transformation of Canola with a Plasmid Containing CBF1, CBF2, or CBF3

After identifying homologous genes to CBF1, canola was transformed with a plasmid containing the *Arabidopsis* CBF1, CBF2, or CBF3 genes cloned into the vector pGA643 (An (1987) *Methods Enzymol.* 253: 292). In these constructs the CBF genes were expressed constitutively under the CaMV 35S promoter. In addition, the CBF1 gene was cloned under the control of the *Arabidopsis* COR15 promoter in the same vector pGA643. Each construct was transformed into *Agrobacterium* strain GV3101. Transformed *Agrobacteria* were grown for 2 days in minimal AB medium containing appropriate antibiotics.

Spring canola (*B. napus* cv. Westar) waa transformed using the protocol of Moloney et al. (1989) *Plant Cell Reports* 8: 238, with some modifications as described. Briefly, seeds were sterilized and plated on half strength MS medium, containing 1% sucrose. Plates were incubated at 24° C. under 60-80 $\mu E/m^2 s$ light using a $_{-16}$ hour light/8 hour dark photoperiod. Cotyledons from 4-5 day old seedlings were collected, the petioles cut and dipped into the *Agrobacterium* solution. The dipped cotyledons were placed on co-cultivation medium at a density of 20 cotyledons/plate and incubated as described above for 3 days. Explants were transferred to the same media, but containing 300 mg/l timentin (SmithKline Beecham, Pa.) and thinned to 10 cotyledons/plate. After 7 days explants were transferred to Selection/Regeneration medium. Transfers were continued every 2-3 weeks (2 or 3 times) until shoots had developed. Shoots were transferred to Shoot-Elongation medium every 2-3 weeks. Healthy looking shoots were transferred to rooting medium. Once good roots had developed, the plants were placed into moist potting soil.

The transformed plants were then analyzed for the presence of the NPTII gene/kanamycin resistance by ELISA, using the ELISA NPTII kit from 5Prime-3Prime Inc. (Boulder, Colo.). Approximately 70% of the screened plants were NPTII positive. Only those plants were further analyzed.

From Northern blot analysis of the plants that were transformed with the constitutively expressing constructs, showed expression of the CBF genes and all CBF genes were capable of inducing the *Brassica napus* cold-regulated gene BN115 (homolog of the *Arabidopsis* COR15 gene). Most of the transgenic plants appear to exhibit a normal growth phenotype. As expected, the transgenic plants are more freezing tolerant than the wild-type control plants. Using the electrolyte leakage of leaves test, the control showed a 50% leakage at −2 to −3° C. Spring canola transformed with either CBF1 or CBF2 showed a −50% leakage at −6 to −7° C. Spring canola transformed with CBF3 shows a 50% leakage at about −10 to −15° C. Winter canola transformed with CBF3 may show a 50% leakage at about −16 to −20° C. Furthermore, if the spring or winter canola are cold acclimated the transformed plants may exhibit a further increase in freezing tolerance of at least −2°.

To test salinity tolerance of the transformed plants, plants were watered with 150 mM NaCl. Plants overexpressing CBF1, CBF2, or CBF3 grew better compared with plants that had not been transformed with CBF1, CBF2, or CBF3.

These results demonstrate that equivalogs of *Arabidopsis* transcription factors can be identified and shown to confer similar functions in non-*Arabidopsis* plant species.

Example XIII

Screen of Plant cDNA library for Sequence Encoding a Transcription Factor DNA Binding Domain that Binds to a Transcription Factor Binding Promoter Element and Demonstration of Protein Transcription Regulation Activity The "one-hybrid" strategy (Li and Herskowitz (1993) *Science* 262: 1870-1874) is used to screen for plant cDNA clones encoding a polypeptide comprising a transcription factor DNA binding domain, a conserved domain. In brief, yeast strains are constructed that contain a lacZ reporter gene with either wild-type or mutant transcription factor binding promoter element sequences in place of the normal UAS (upstream activator sequence) of the GAL4 promoter. Yeast reporter strains are constructed that carry transcription factor binding promoter element sequences as UAS elements are operably linked upstream (5') of a lacZ reporter gene with a minimal GAL4 promoter. The strains are transformed with a plant expression library that contains random cDNA inserts fused to the GAL4 activation domain (GAL4-ACT) and screened for blue colony formation on X-gal-treated filters (X-gal: 5-bromo-4-chloro-3-indolyl-β-D-galactoside; Invitrogen Corporation, Carlsbad Calif.). Alternatively, the strains are transformed with a cDNA polynucleotide encoding a known transcription factor DNA binding domain polypeptide sequence.

Yeast strains carrying these reporter constructs produce low levels of beta-galactosidase and form white colonies on filters containing X-gal. The reporter strains carrying wild-type transcription factor binding promoter element sequences are transformed with a polynucleotide that encodes a polypeptide comprising a plant transcription factor DNA binding domain operably linked to the acidic activator domain of the yeast GAL4 transcription factor, "GAL4-ACT". The clones that contain a polynucleotide encoding a transcription factor DNA binding domain operably linked to GAL4-ACT can bind upstream of the lacZ reporter genes carrying the wild-type transcription factor binding promoter element sequence, activate transcription of the lacZ gene and result in yeast forming blue colonies on X-gal-treated filters.

Upon screening about $2 \times 10^6$ yeast transformants, positive cDNA clones are isolated; i.e., clones that cause yeast strains carrying lacZ reporters operably linked to wild-type transcription factor binding promoter elements to form blue colonies on X-gal-treated filters. The cDNA clones do not cause a yeast strain carrying a mutant type transcription factor binding promoter elements fused to LacZ to turn blue. Thus, a polynucleotide encoding transcription factor DNA binding domain, a conserved domain, is shown to activate transcription of a gene.

Example XIV

Gel Shift Assays

The presence of a transcription factor comprising a DNA binding domain which binds to a DNA transcription factor binding element is evaluated using the following gel shift assay. The transcription factor is recombinantly expressed and isolated from *E. coli* or isolated from plant material. Total soluble protein, including transcription factor, (40 ng) is incubated at room temperature in 10 μl of 1× binding buffer (15 mM HEPES (pH 7.9), 1 mM EDTA, 30 mM KCl, 5% glycerol, 5% bovine serum albumin, 1 mM DTT) plus 50 ng poly(dI-dC):poly(dI-dC) (Pharmacia, Piscataway N.J.) with or without 100 ng competitor DNA. After 10 minutes incubation, probe DNA comprising a DNA transcription factor binding element (1 ng) that has been $^{32}$P-labeled by end-filling (Sambrook et al. (1989) supra) is added and the mixture incubated for an additional 10 minutes. Samples are loaded onto polyacrylamide gels (4% w/v) and fractionated by electrophoresis at 150 V for 2 h (Sambrook et al. supra). The degree of transcription factor-probe DNA binding is visualized using autoradiography. Probes and competitor DNAs are prepared from oligonucleotide inserts ligated into the BamHI site of pUC118 (Vieira et al. (1987) *Methods Enzymol.* 153: 3-11). Orientation and concatenation number of the inserts are determined by dideoxy DNA sequence analysis (Sambrook et al. supra). Inserts are recovered after restriction digestion with EcoRI and HindIII and fractionation on polyacrylamide gels (12% w/v) (Sambrook et al. supra).

Example XV

Cloning of Transcription Factor Promoters

Promoters are isolated from transcription factor genes that have gene expression patterns useful for a range of applications, as determined by methods well known in the art (including transcript profile analysis with cDNA or oligonucleotide microarrays, Northern blot analysis, semi-quantitative or quantitative RT-PCR). Interesting gene expression profiles are revealed by determining transcript abundance for a selected transcription factor gene after exposure of plants to a range of different experimental conditions, and in a range of different tissue or organ types, or developmental stages. Experimental conditions to which plants are exposed for this purpose includes cold, heat, drought, osmotic challenge, and varied hormone concentrations (e.g., ABA). The tissue types and developmental stages include stem, root, flower, rosette leaves, cauline leaves, siliques, germinating seed, and meristematic tissue. The set of expression levels provides a pattern that is determined by the regulatory elements of the gene promoter.

Transcription factor promoters for the genes disclosed herein are obtained by cloning 1.5 kb to 2.0 kb of genomic sequence immediately upstream of the translation start codon for the coding sequence of the encoded transcription factor protein. This region includes the 5'-UTR of the transcription factor gene, which can comprise regulatory elements. The 1.5 kb to 2.0 kb region is cloned through PCR methods, using primers that include one in the 3' direction located at the translation start codon (including appropriate adaptor sequence), and one in the 5' direction located from 1.5 kb to 2.0 kb upstream of the translation start codon (including appropriate adaptor sequence). The desired fragments are PCR-amplified from *Arabidopsis* Col-0 genomic DNA using high-fidelity Taq DNA polymerase to minimize the incorporation of point mutation(s). The cloning primers incorporate two rare restriction sites, such as Not1 and Sfi1, found at low frequency throughout the *Arabidopsis* genome. Additional restriction sites are used in the instances where a Not1 or Sfi1 restriction site is present within the promoter.

The 1.5-2.0 kb fragment upstream from the translation start codon, including the 5'-untranslated region of the transcription factor, is cloned in a binary transformation vector immediately upstream of a suitable reporter gene, or a transactivator gene that is capable of programming expression of a reporter gene in a second gene construct. Reporter genes used include green fluorescent protein (and related fluorescent protein color variants), beta-glucuronidase, and luciferase. Suitable transactivator genes include LexA-GAL4, along with a transactivatable reporter in a second binary plasmid (as disclosed in U.S. patent application Ser. No. 09/958,131, incorporated herein by reference). The binary plasmid(s) is transferred into *Agrobacterium* and the structure of the plasmid confirmed by PCR. These strains are introduced into *Arabidopsis* plants as described in other examples, and gene expression patterns determined according to standard methods know to one skilled in the art for monitoring GFP fluorescence, beta-glucuronidase activity, or luminescence.

Example XVI

Transformation of Dicots

Crop species overexpressing members of the G1073 clade of transcription factor polypeptides (e.g., G2153) have been shown experimentally to produce plants with increased biomass in field trials. This observation indicates that these genes, when overexpressed, will result in larger yields of various plant species, which may be most significant in those plants in which the vegetative portion of the plant is edible. Tomato plants overexpressing the *A. thaliana* G2153 polypeptide have been found to be larger than wild-type control tomato plants.

Thus, transcription factor sequences listed in the Sequence Listing recombined into pMEN20 or pMEN65 expression vectors may be transformed into a plant for the purpose of modifying plant traits. The cloning vector may be introduced into a variety of cereal plants by means well known in the art such as, for example, direct DNA transfer or *Agrobacterium tumefaciens*-mediated transformation. It is now routine to produce transgenic plants using most dicot plants (see Weissbach and Weissbach, (1989) supra; Gelvin et al. (1990) supra; Herrera-Estrella et al. (1983) supra; Bevan (1984) supra; and Klee (1985) supra). Methods for analysis of traits are routine in the art and examples are disclosed above.

Numerous protocols for the transformation of tomato and soy plants have been previously described, and are well known in the art. Gruber et al. ((1993) in *Methods in Plant Molecular Biology and Biotechnology*, p. 89-119, Glick and Thompson, eds., CRC Press, Inc., Boca Raton) describe several expression vectors and culture methods that may be used for cell or tissue transformation and subsequent regeneration. For soybean transformation, methods are described by Miki et al. (1993) in *Methods in Plant Molecular Biology and Biotechnology*, p. 67-88, Glick and Thompson, eds., CRC Press, Inc., Boca Raton; and U.S. Pat. No. 5,563,055, (Townsend and Thomas), issued Oct. 8, 1996.

There are a substantial number of alternatives to *Agrobacterium*-mediated transformation protocols, other methods for the purpose of transferring exogenous genes into soybeans or tomatoes. One such method is microprojectile-mediated transformation, in which DNA on the surface of microprojectile particles is driven into plant tissues with a biolistic device (see, for example, Sanford et al., (1987) *Part. Sci. Technol.* 5:27-37; Christou et al. (1992) *Plant. J.* 2: 275-281; Sanford (1993) *Methods Enzymol.* 217: 483-509; Klein et al. (1987) *Nature* 327: 70-73; U.S. Pat. No. 5,015,580 (Christou et al), issued May 14, 1991; and U.S. Pat. No. 5,322,783 (Tomes et al.), issued Jun. 21, 1994.

Alternatively, sonication methods (see, for example, Zhang et al. (1991) *Bio/Technology* 9: 996-997); direct uptake of DNA into protoplasts using $CaCl_2$ precipitation, polyvinyl alcohol or poly-L-ornithine (see, for example, Hain et al. (1985) *Mol. Gen. Genet.* 199: 161-168; Draper et al., *Plant Cell Physiol.* 23: 451-458 (1982)); liposome or spheroplast fusion (see, for example, Deshayes et al. (1985) *EMBO J.*, 4: 2731-2737; Christou et al. (1987) *Proc. Natl. Acad. Sci. U.S.A.* 84: 3962-3966); and electroporation of protoplasts and whole cells and tissues (see, for example, Donn et al. (1990) in *Abstracts of VIIth International Congress on Plant Cell and Tissue Culture IAPTC*, A2-38: 53; D'Halluin et al (1992) *Plant Cell* 4: 1495-1505; and Spencer et al. (1994)

*Plant Mol. Biol.* 24: 51-61) have been used to introduce foreign DNA and expression vectors into plants.

After a plant or plant cell is transformed (and the latter regenerated into a plant), the transformed plant may be crossed with itself or a plant from the same line, a non-transformed or wild-type plant, or another transformed plant from a different transgenic line of plants. Crossing provides the advantages of producing new and often stable transgenic varieties. Genes and the traits they confer that have been introduced into a tomato or soybean line may be moved into distinct line of plants using traditional backcrossing techniques well known in the art. Transformation of tomato plants may be conducted using the protocols of Koornmeef et al (1986) In *Tomato Biotechnology*: Alan R. Liss, Inc., 169-178, and in U.S. Pat. No. 6,613,962, the latter method described in brief here. Eight day old cotyledon explants are precultured for 24 hours in Petri dishes containing a feeder layer of *Petunia hybrida* suspension cells plated on MS medium with 2% (w/v) sucrose and 0.8% agar supplemented with 10 μM α-naphthalene acetic acid and 4.4 μM 6-benzylaminopurine. The explants are then infected with a diluted overnight culture of *Agrobacterium tumefaciens* containing an expression vector comprising a polynucleotide of the invention for 5-10 minutes, blotted dry on sterile filter paper and cocultured for 48 hours on the original feeder layer plates. Culture conditions are as described above. Overnight cultures of *Agrobacterium tumefaciens* are diluted in liquid MS medium with 2% (w/v/) sucrose, pH 5.7) to an $OD_{600}$ of 0.8.

Following cocultivation, the cotyledon explants are transferred to Petri dishes with selective medium comprising MS medium with 4.56 μM zeatin, 67.3 μM vancomycin, 418.9 μM cefotaxime and 171.6 μM kanamycin sulfate, and cultured under the culture conditions described above. The explants are subcultured every three weeks onto fresh medium. Emerging shoots are dissected from the underlying callus and transferred to glass jars with selective medium without zeatin to form roots. The formation of roots in a kanamycin sulphate-containing medium is a positive indication of a successful transformation.

Transformation of soybean plants may be conducted using the methods found in, for example, U.S. Pat. No. 5,563,055 (Townsend et al., issued Oct. 8, 1996), described in brief here. In this method soybean seed is surface sterilized by exposure to chlorine gas evolved in a glass bell jar. Seeds are germinated by plating on ⅒ strength agar solidified medium without plant growth regulators and culturing at 28° C. with a 16 hour day length. After three or four days, seed may be prepared for cocultivation. The seedcoat is removed and the elongating radicle removed 3-4 mm below the cotyledons.

Overnight cultures of *Agrobacterium tumefaciens* harboring the expression vector comprising a polynucleotide of the invention are grown to log phase, pooled, and concentrated by centrifugation. Inoculations are conducted in batches such that each plate of seed was treated with a newly resuspended pellet of *Agrobacterium*. The pellets are resuspended in 20 ml inoculation medium. The inoculum is poured into a Petri dish containing prepared seed and the cotyledonary nodes are macerated with a surgical blade. After 30 minutes the explants are transferred to plates of the same medium that has been solidified. Explants are embedded with the adaxial side up and level with the surface of the medium and cultured at 22° C. for three days under white fluorescent light. These plants may then be regenerated according to methods well established in the art, such as by moving the explants after three days to a liquid counter-selection medium (see U.S. Pat. No. 5,563,055).

The explants may then be picked, embedded and cultured in solidified selection medium. After one month on selective media transformed tissue becomes visible as green sectors of regenerating tissue against a background of bleached, less healthy tissue. Explants with green sectors are transferred to an elongation medium. Culture is continued on this medium with transfers to fresh plates every two weeks. When shoots are 0.5 cm in length they may be excised at the base and placed in a rooting medium.

Example XVII

Increased Biomass and Abiotic Stress Tolerance in Monocots

Cereal plants such as, but not limited to, corn, wheat, rice, sorghum, or barley, may be transformed with the present polynucleotide sequences, including monocot or dicot-derived sequences such as those presented in Tables 2 or 5, cloned into a vector such as pGA643 and containing a kanamycin-resistance marker, and expressed constitutively under, for example, the CaMV 35S or COR15 promoters. pMEN20 or pMEN65 and other expression vectors may also be used for the purpose of modifying plant traits. For example, pMEN020 may be modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

The cloning vector may be introduced into a variety of cereal plants by means well known in the art including direct DNA transfer or *Agrobacterium tumefaciens*-mediated transformation. The latter approach may be accomplished by a variety of means, including, for example, that of U.S. Pat. No. 5,591,616, in which monocotyledon callus is transformed by contacting dedifferentiating tissue with the *Agrobacterium* containing the cloning vector.

The sample tissues are immersed in a suspension of $3\times10^{-9}$ cells of *Agrobacterium* containing the cloning vector for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants are then analyzed for the presence of the NPTII gene/kanamycin resistance by ELISA, using the ELISA NPTII kit from 5Prime-3Prime Inc. (Boulder, Colo.).

It is also routine to use other methods to produce transgenic plants of most cereal crops (Vasil (1994) *Plant Mol. Biol.* 25: 925-937) such as corn, wheat, rice, sorghum (Cassas et al. (1993) *Proc. Natl. Acad. Sci. USA* 90: 11212-11216), and barley (Wan and Lemeaux (1994) *Plant Physiol.* 104:37-48). DNA transfer methods such as the microprojectile method can be used for corn (Fromm at al. (1990) *Bio/Technol.* 8: 833-839); Gordon-Kamm et al. (1990) *Plant Cell* 2: 603-618; Ishida (1990) *Nature Biotechnol.* 14:745-750), wheat (Vasil et al. (1992) *Bio/Technol.* 10:667-674; Vasil et al. (1993) *Bio/Technol.* 11:1553-1558; Weeks at al. (1993) *Plant Physiol.* 102:1077-1084), and rice (Christou (1991) *Bio/Technol.* 9:957-962; Hiei at al. (1994) *Plant J.* 6:271-282; Aldemita and Hodges (1996) *Planta* 199:612-617; and Hiei at al. (1997) *Plant Mol. Biol.* 35:205-218). For most cereal plants, embryogenic cells derived from immature scutellum tissues are the preferred cellular targets for transformation (Hiei et al. (1997) *Plant Mol. Biol.* 35:205-218; Vasil (1994) *Plant Mol. Biol.* 25; 925-937). For transforming corn embryogenic cells derived from immature scutellar tissue using microprojectile bombardment, the A188XB73 genotype is the preferred genotype (Fromm at al. (1990) *Bio/Technol.* 8: 833-839; Gordon-Kamm et al. (1990) *Plant Cell* 2: 603-618). After microprojectile bombardment the tissues are selected on phosphinothricin to identify the transgenic embryogenic cells (Gordon-Kamm et al. (1990) *Plant Cell* 2: 603-618). Transgenic plants are regenerated by standard corn regeneration techniques (Fromm et al. (1990) *Bio/Technol.* 8: 833-839; Gordon-Kamm et al. (1990) *Plant Cell* 2: 603-618).

Northern blot analysis, RT-PCR or microarray analysis of the regenerated, transformed plants may be used to show expression of G1073 and related genes that are capable of inducing abiotic stress tolerance and larger size.

To verify the ability to confer abiotic stress tolerance, mature plants overexpressing a G1073 or equivalog, or alternatively, seedling progeny of these plants, may be challenged by an osmotic stress, such as drought, heat, high salt, or freezing. Alternatively, these plants may challenged in an osmotic stress condition that may also measure altered sugar sensing, such as a high sugar condition. By comparing wild type and transgenic plants similarly treated, the transgenic plants may be shown to have greater tolerance to abiotic stress.

After a monocot plant or plant cell has been transformed (and the latter regenerated into a plant) and shown to have greater size or tolerance to abiotic stress, or produce greater yield relative to a control plant under the stress conditions, the transformed monocot plant may be crossed with itself or a plant from the same line, a non-transformed or wild-type monocot plant, or another transformed monocot plant from a different transgenic line of plants.

These experiments would demonstrate that members of the G1073 clade of transcription factor polypeptides can be identified and shown to confer larger size, greater yield, and/or greater abiotic stress tolerance in monocots, including tolerance or resistance to multiple stresses.

Example XVIII

Genes that Confer Significant Improvements to Non-*Arabidopsis* Species

The function of specific orthologs of G1073 have been analyzed and may be further characterized and incorporated into crop plants. The ectopic overexpression of these orthologs may be regulated using constitutive, inducible, or tissue specific regulatory elements. Genes that have been examined and have been shown to modify plant traits (including increasing biomass and abiotic stress tolerance) encode members of the G1073 clade of transcription factor polypeptides, such as those found in *Arabidopsis thaliana* (SEQ ID NO: 2, 4, 6, 8, 42, 84 and 86) *Oryza sativa* (SEQ ID NO: 10, 12, 26, 30, and 38), and *Glycine max* (SEQ ID NO: 14, 16, 18, and 40). In addition to these sequences, it is expected that related polynucleotide sequences encoding polypeptides found in the Sequence Listing can also induce altered traits, including increased biomass and abiotic stress tolerance, when transformed into a considerable variety of plants of different species, and including dicots and monocots. The polynucleotide and polypeptide sequences derived from monocots (e.g., the rice sequences) may be used to transform both monocot and dicot plants, and those derived from dicots (e.g., the *Arabidopsis* and soy genes) may be used to transform either group, although it is expected that some of these sequences will function best if the gene is transformed into a plant from the same group as that from which the sequence is derived.

Seeds of these transgenic plants are subjected to germination assays to measure sucrose sensing. Sterile monocot seeds, including, but not limited to, corn, rice, wheat, rye and sorghum, as well as dicots including, but not limited to, soybean and alfalfa, are sown on 80% MS medium plus vitamins with 9.4% sucrose; control media lack sucrose. All assay plates are then incubated at 22° C. under 24-hour light, 120-130 µEin/m$^2$/s, in a growth chamber. Evaluation of germination and seedling vigor is then conducted three days after planting. Overexpressors of these genes may be found to be more tolerant to high sucrose by having better germination, longer radicles, and more cotyledon expansion. These results have indicated that overexpressors of G1073, G1067, G1069, G2153, G2156, G2657, G3401 and G3460 are involved in sucrose-specific sugar sensing; it is expected that structurally similar orthologs of these sequences, including those found in the Sequence Listing, are also involved in sugar sensing, an indication of altered osmotic stress tolerance.

Plants overexpressing the transcription factor sequences of the invention may also be subjected to soil-based drought assays to identify those lines that are more tolerant to water deprivation than wild-type control plants. A number of the lines of plants overexpressing a member of the G1073 clade of transcription factor polypeptides will be significantly larger and greener, with less wilting or desiccation, than wild-type control plants, particularly after a period of water deprivation is followed by rewatering and a subsequent incubation period. The sequence of the G1073 clade member may be overexpressed under the regulatory control of constitutive, tissue specific or inducible promoters, or may comprise a GAL4 transactivation domain fused to either the N- or the C terminus of the polypeptide. The results presented in Example IX indicate that G1073 clade members may confer stress tolerance when they are overexpressed under the regulatory control of non-constitutive promoters or a transactivation domain fused to the clade member without a significant impact on plant morphology. The lines that display useful traits may be selected for further study or commercial development.

Monocotyledonous plants, including rice, corn, wheat, rye, sorghum, barley and others, may be transformed with a plasmid containing a member of the G1073 clade of transcription factor polypeptides. The G1073 clade sequence may include dicot or monocot-derived sequences such as those presented in Table 1 or Table 5. These AT-hook transcription factor genes may be cloned into a vector such as pGA643 and containing a kanamycin-resistance marker, and then expressed constitutively under the CaMV 35S promoter or COR15 promoter.

The cloning vector may be introduced into monocots by, for example, means described in detail in Example XV, including direct DNA transfer or *Agrobacterium tumefaciens*-mediated transformation. The latter approach may be accomplished by a variety of means, including, for example, that of U.S. Pat. No. 5,591,616, in which monocotyledon callus is transformed by contacting dedifferentiating tissue with the *Agrobacterium* containing the cloning vector.

The sample tissues are immersed in a suspension of $3 \times 10^{-9}$ cells of *Agrobacterium* containing the cloning vector for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants are then analyzed for the presence of the NPTII gene/kanamycin resistance by ELISA, using the ELISA NPTII kit from 5Prime-3Prime Inc. (Boulder, Colo.).

Northern blot analysis, RT-PCR or microarray analysis of the regenerated, transformed plants may be used to show expression of a member of the G1073 clade of transcription factor polypeptides that is capable of inducing abiotic stress tolerance.

To verify the ability to confer abiotic stress tolerance, mature plants expressing a monocot-derived equivalog gene, or alternatively, seedling progeny of these plants, may be challenged using methods described in Example VII. By comparing wild type plants and the transgenic plants, the latter are shown be more tolerant to abiotic stress, and/or have increased biomass, as compared to wild type control plants similarly treated.

These experiments demonstrate that a number of representative members of the G1073 clade of transcription factor polypeptides, including G1073, G1067, G2153, G2156, G3399, G3400, G3401, G3406, G3407, G3456, G3459 and G3460, can be identified and shown to increase biomass and improve abiotic stress tolerance, including osmotic stresses such as drought or salt stress. It is expected that the same methods may be applied to identify other useful and valuable members of the clade from a diverse range of species.

All publications and patent applications mentioned in this specification are herein incorporated by reference to the same extent as if each individual publication or patent application was specifically and individually indicated to be incorporated by reference.

The present invention is not limited by the specific embodiments described herein. The invention now being fully described, it will be apparent to one of ordinary skill in the art that many changes and modifications can be made thereto without departing from the spirit or scope of the appended claims. Modifications that become apparent from the foregoing description and accompanying figures fall within the scope of the claims.

What is claimed is:

1. A transgenic plant having greater tolerance to 4° C. to 8° C. than a control plant, wherein said transgenic plant comprises a recombinant polynucleotide encoding a transcription factor polypeptide that has at least 95% amino acid sequence identity to SEQ ID NO: 2;
    wherein expression of the transcription factor polypeptide in the transgenic plant confers to the transgenic plant greater tolerance to 4° C. to 8° C. as compared to the control plant.

2. The transgenic plant of claim 1, wherein the transcription factor polypeptide comprises SEQ ID NO: 2.

3. The transgenic plant of claim 1, wherein the transcription factor polypeptide comprises SEQ ID NO: 80 or SEQ ID NO: 81.

4. A transgenic seed produced from the transgenic plant according to claim 1.

5. A transgenic plant having greater tolerance to 9.4% sucrose than a control plant, wherein said transgenic plant comprises a recombinant polynucleotide encoding a transcription factor polypeptide that has at least 95% amino acid sequence identity to SEQ ID NO: 2;
    wherein expression of the transcription factor polypeptide in the transgenic plant confers to the transgenic plant greater tolerance to 9.4% sucrose as compared to the control plant.

6. The transgenic plant of claim 5, wherein the transcription factor polypeptide comprises SEQ ID NO: 2.

7. The transgenic plant of claim 5, wherein the transcription factor polypeptide comprises SEQ ID NO: 80 or SEQ ID NO: 81.

8. A transgenic seed produced from the transgenic plant according to claim 5.

9. A transgenic plant having greater tolerance to 150 mM NaCl than a control plant, wherein said transgenic plant comprises a recombinant polynucleotide encoding a transcription factor polypeptide that has at least 95% amino acid sequence identity to SEQ ID NO: 2;
    wherein expression of the transcription factor polypeptide in the transgenic plant confers to the transgenic plant greater tolerance to 150 mM NaCl as compared to the control plant.

10. The transgenic plant of claim 9, wherein the transcription factor polypeptide comprises SEQ ID NO: 2.

11. The transgenic plant of claim 9, wherein the transcription factor polypeptide comprises SEQ ID NO: 80 or SEQ ID NO: 81.

12. A transgenic seed produced from the transgenic plant according to 9.

13. A transgenic plant having greater tolerance to seven to eight days of water deprivation than a control plant, wherein said transgenic plant comprises a recombinant polynucleotide encoding a transcription factor polypeptide that has at least 95% amino acid sequence identity to SEQ ID NO: 2;
    wherein expression of the transcription factor polypeptide in the transgenic plant confers to the transgenic plant greater tolerance to seven to eight days of water deprivation as compared to the control plant.

14. The transgenic plant of claim 13, wherein the transcription factor polypeptide comprises SEQ ID NO: 2.

15. The transgenic plant of claim 13, wherein the transcription factor polypeptide comprises SEQ ID NO: 80 or SEQ ID NO: 81.

16. A transgenic seed produced from the transgenic plant according to claim 13.

17. A transgenic plant having more biomass than a control plant, wherein said transgenic plant comprises a recombinant polynucleotide encoding a transcription factor polypeptide that has at least 95% amino acid sequence identity to SEQ ID NO: 2;
    wherein expression of the transcription factor polypeptide in the transgenic plant confers to the transgenic plant greater biomass as compared to the control plant.

18. The transgenic plant of claim 17, wherein the transcription factor polypeptide comprises SEQ ID NO: 2.

19. The transgenic plant of claim 17, wherein the transcription factor polypeptide comprises SEQ ID NO: 80 or SEQ ID NO: 81.

20. A transgenic seed produced from the transgenic plant according to claim 17.

21. A method for producing a transformed plant with greater tolerance to an abiotic stress as compared to a control plant, wherein the abiotic stress is selected from the group consisting of 4° C. to 8° C., 9.4% sucrose, 150 mM NaCl, and seven to eight days of water deprivation, the method steps comprising:
    (a) providing a nucleic acid construct comprising a polynucleotide sequence encoding a transcription factor polypeptide that has at least 95% amino acid sequence identity to SEQ ID NO: 2; and
        wherein the polynucleotide sequence is operably linked to a regulatory element that controls expression of the polynucleotide sequence;
    (b) transforming a target plant with the expression vector to produce the transformed plant; and
    (c) growing the transformed plant comprising the nucleic acid construct;
    wherein the transformed plant has greater tolerance to 4° C. to 8° C., 9.4% sucrose, 150 mM NaCl, or seven to eight days of water deprivation.

22. The method of claim 21, wherein the transcription factor polypeptide comprises SEQ ID NO: 2.

23. The method of claim 21, wherein the transcription factor polypeptide comprises SEQ ID NO: 80 or SEQ ID NO: 81.

24. A transgenic seed produced from the transformed plant produced by the method according to claim 21.

25. The method of claim 21, the method steps further comprising:
    (d) selfing or crossing the transformed plant with itself or another plant, respectively, to produce seed; and
    (e) growing a progeny plant from the seed;
    wherein the progeny plant has greater tolerance to the abiotic stress than the control plant.

26. A transgenic seed produced from the progeny plant produced by the method according to claim 25.

27. A transgenic plant comprising a recombinant polynucleotide encoding SEQ ID NO: 2.

* * * * *

SEQUENCE LISTING

```
<160> NUMBER OF SEQ ID NOS: 99

<210> SEQ ID NO 1
<211> LENGTH: 974
<212> TYPE: DNA
<213> ORGANISM: Arabidopsis thaliana
<220> FEATURE:
<223> OTHER INFORMATION: G1073

<400> SEQUENCE: 1 cccccgacc  tgcctctaca  gagacctgaa  gattccagaa  ccccacctga  tcaaaaataa      60
catggaactt  aacagatctg  aagcagacga  agcaaaggcc  gagaccactc  ccaccggtgg     120
agccaccagc  tcagccacag  cctctggctc  ttcctccgga  cgtcgtccac  gtggtcgtcc     180
tgcaggttcc  aaaaacaaac  ccaaacctcc  gacgattata  actagagata  gtcctaacgt     240
ccttagatca  cacgttcttg  aagtcacctc  cggttcggac  atatccgagg  cagtctccac     300
ctacgccact  cgtcgcggct  gcggcgtttg  cattataagc  ggcacgggtg  cggtcactaa     360
cgtcacgata  cggcaacctg  cggctccggc  tggtggaggt  gtgattaccc  tgcatggtcg     420
gtttgacatt  ttgtctttga  ccggtactgc  gcttccaccg  cctgcaccac  cgggagcagg     480
aggtttgacg  gtgtatctag  ccggaggtca  aggacaagtt  gtaggaggga  atgtggctgg     540
ttcgttaatt  gcttcgggac  cggtagtgtt  gatggctgct  tcttttgcaa  acgcagttta     600
tgataggtta  ccgattgaag  aggaagaaac  cccaccgccg  agaaccaccg  gggtgcagca     660
gcagcagccg  gaggcgtctc  agtcgtcgga  ggttacgggg  agtggggccc  aggcgtgtga     720
gtcaaacctc  caaggtggaa  atggtggagg  aggtgttgct  ttctacaatc  ttggaatgaa     780
tatgaacaat  tttcaattct  ccgggggaga  tatttacggt  atgagcggcg  gtagcggagg     840
aggtggtggc  ggtgcgacta  gacccgcgtt  ttagagtttt  agcgttttgg  tgacacettt     900 tgttgcgttt  gcgtgtttga  cctcaaacta  ctaggctact  agctatagcg  gttgcgaaat     960
gcgaatatta  ggtt                                                          974

<210> SEQ ID NO 2
<211> LENGTH: 270
<212> TYPE: PRT
```

<213> ORGANISM: Arabidopsis thaliana
<220> FEATURE:
<223> OTHER INFORMATION: G1073 polypeptide

<400> SEQUENCE: 2

```
Met Glu Leu Asn Arg Ser Glu Ala Asp Glu Ala Lys Ala Glu Thr Thr
  1               5                  10                  15
Pro Thr Gly Gly Ala Thr Ser Ser Ala Thr Ser Gly Ser Ser Ser
             20                  25                  30
Gly Arg Arg Pro Arg Gly Arg Pro Ala Gly Ser Lys Asn Lys Pro Lys
         35                  40                  45
Pro Pro Thr Ile Ile Thr Arg Asp Ser Pro Asn Val Leu Arg Ser His
     50                  55                  60
Val Leu Glu Val Thr Ser Gly Ser Asp Ile Ser Glu Ala Val Ser Thr
 65                  70                  75                  80
Tyr Ala Thr Arg Arg Gly Cys Gly Val Cys Ile Ile Ser Gly Thr Gly
                 85                  90                  95
Ala Val Thr Asn Val Thr Ile Arg Gln Pro Ala Ala Pro Ala Gly Gly
            100                 105                 110
Gly Val Ile Thr Leu His Gly Arg Phe Asp Ile Leu Ser Leu Thr Gly
        115                 120                 125
Thr Ala Leu Pro Pro Pro Ala Pro Pro Gly Ala Gly Gly Leu Thr Val
    130                 135                 140
Tyr Leu Ala Gly Gly Gln Gly Gln Val Val Gly Gly Asn Val Ala Gly
145                 150                 155                 160
Ser Leu Ile Ala Ser Gly Pro Val Val Leu Met Ala Ala Ser Phe Ala
                165                 170                 175
Asn Ala Val Tyr Asp Arg Leu Pro Ile Glu Glu Glu Thr Pro Pro
            180                 185                 190
Pro Arg Thr Thr Gly Val Gln Gln Gln Gln Pro Glu Ala Ser Gln Ser
        195                 200                 205
Ser Glu Val Thr Gly Ser Gly Ala Gln Ala Cys Glu Ser Asn Leu Gln
    210                 215                 220
Gly Gly Asn Gly Gly Gly Gly Val Ala Phe Tyr Asn Leu Gly Met Asn
225                 230                 235                 240
Met Asn Asn Phe Gln Phe Ser Gly Gly Asp Ile Tyr Gly Met Ser Gly
                245                 250                 255
Gly Ser Gly Gly Gly Gly Gly Ala Thr Arg Pro Ala Phe
            260                 265                 270
```

<210> SEQ ID NO 3
<211> LENGTH: 1473
<212> TYPE: DNA
<213> ORGANISM: Arabidopsis thaliana
<220> FEATURE:
<223> OTHER INFORMATION: G1067

<400> SEQUENCE: 3

```
tctcaagctt ctctctcctt ttttccccat agcacatcag aatcgctaaa tacgactcct      60
atgcaaagaa gaagctactt ctttctcttg ccctaattaa tctacctaac tagggtttcc     120
tcttaccttt catgagagag atcatttaac ataagtcacc ttttttatat cttttgcttc     180
gtctttaatt tagttctgtt cttggtctgt ttctatattt tgtcggcttg cgtaaccgat     240
cacaccttaa tgcttttagct attgtttcct caaaatcatg agtttttgact tctcgatctg     300 agttttcttt ttctctcttt acgctcttct tcacctagct accaatatat gaacgagcag     360
```

-continued

```
gatcaagaat cgagaaattg atttgagctg gcgaataagc agtggtggga tagggaatta      420
gtagatgcgg cggcgatgga aggcggttac gagcaaggcg gtggagcttc tagatacttc      480
cataacctct ttagaccgga gattcaccac caacagcttc aaccgcaggg cgggatcaat      540
cttatcgacc agcatcatca tcagcaccag caacatcaac aacaacaaca accgtcggat      600
gattcaagag aatctgacca ttcaaacaaa gatcatcatc aacagggtcg acccgattca      660
gacccgaata catcaagctc agcaccggga aaacgtccac gtggacgtcc accaggatct      720
aagaacaaag ccaagccacc gatcatagta actcgtgata gccccaacgc gcttagatct      780
cacgttcttg aagtatctcc tggagctgac atagttgaga gtgtttccac gtacgctagg      840
aggagaggga gaggcgtctc cgttttagga ggaaacggca ccgtatctaa cgtcactctc      900
cgtcagccag tcactcctgg aaatggcggt ggtgtgtccg gaggaggagg agttgtgact      960
ttacatggaa ggtttgagat tctttcgcta acggggactg ttttgccacc tcctgcaccg     1020
cctggtgccg gtggtttgtc tatattttta gccggagggc aaggtcaggt ggtcggagga     1080
agcgttgtgg ctccccttat tgcatcagct ccggttatac taatgcggc ttcgttctca      1140 aatgcggttt tcgagagact accgattgag gaggaggaag aagaaggtgg tggtggcgga     1200
ggaggaggag gaggagggcc accgcagatg caacaagctc catcagcatc tccgccgtct     1260
ggagtgaccg tcagggaca gttaggaggt aatgtgggtg gttatgggtt ttctggtgat      1320
cctcatttgc ttggatgggg agctggaaca ccttcaagac caccttttta attgaatttt     1380
aatgtccgga aatttatgtg tttttatcat cttgaggagt cgtctttcct ttgggatatt     1440
tggtgtttaa tgtttagttg atatgcatat ttt                                   1473
```

<210> SEQ ID NO 4
<211> LENGTH: 311
<212> TYPE: PRT
<213> ORGANISM: Arabidopsis thaliana
<220> FEATURE:
<223> OTHER INFORMATION: G1067 polypeptide

<400> SEQUENCE: 4

```
Met Glu Gly Gly Tyr Glu Gln Gly Gly Gly Ala Ser Arg Tyr Phe His
 1               5                  10                  15

Asn Leu Phe Arg Pro Glu Ile His His Gln Leu Gln Pro Gln Gly
            20                  25                  30

Gly Ile Asn Leu Ile Asp Gln His His Gln His Gln Gln His Gln
        35                  40                  45

Gln Gln Gln Gln Pro Ser Asp Asp Ser Arg Glu Ser Asp His Ser Asn
    50                  55                  60

Lys Asp His His Gln Gln Gly Arg Pro Asp Ser Asp Pro Asn Thr Ser
65                  70                  75                  80

Ser Ser Ala Pro Gly Lys Arg Pro Arg Gly Arg Pro Gly Ser Lys
                85                  90                  95

Asn Lys Ala Lys Pro Pro Ile Ile Val Thr Arg Asp Ser Pro Asn Ala
            100                 105                 110

Leu Arg Ser His Val Leu Glu Val Ser Pro Gly Ala Asp Ile Val Glu
        115                 120                 125

Ser Val Ser Thr Tyr Ala Arg Arg Arg Gly Arg Gly Val Ser Val Leu
    130                 135                 140

Gly Gly Asn Gly Thr Val Ser Asn Val Thr Leu Arg Gln Pro Val Thr
145                 150                 155                 160

Pro Gly Asn Gly Gly Gly Val Ser Gly Gly Gly Gly Val Val Thr Leu
```

165                 170                 175
His Gly Arg Phe Glu Ile Leu Ser Leu Thr Gly Thr Val Leu Pro Pro
            180                 185                 190

Pro Ala Pro Pro Gly Ala Gly Gly Leu Ser Ile Phe Leu Ala Gly Gly
        195                 200                 205

Gln Gly Gln Val Val Gly Ser Val Val Ala Pro Leu Ile Ala Ser
    210                 215                 220

Ala Pro Val Ile Leu Met Ala Ala Ser Phe Ser Asn Ala Val Phe Glu
225                 230                 235                 240

Arg Leu Pro Ile Glu Glu Glu Glu Glu Gly Gly Gly Gly Gly
                245                 250                 255

Gly Gly Gly Gly Gly Pro Pro Gln Met Gln Gln Ala Pro Ser Ala Ser
            260                 265                 270

Pro Pro Ser Gly Val Thr Gly Gln Gly Gln Leu Gly Gly Asn Val Gly
        275                 280                 285

Gly Tyr Gly Phe Ser Gly Asp Pro His Leu Leu Gly Trp Gly Ala Gly
    290                 295                 300

Thr Pro Ser Arg Pro Pro Phe
305                 310

<210> SEQ ID NO 5
<211> LENGTH: 1383
<212> TYPE: DNA
<213> ORGANISM: Arabidopsis thaliana
<220> FEATURE:
<223> OTHER INFORMATION: G2153

<400> SEQUENCE: 5
ttcttgctta gtatcattct ttgtcgtgtt cttttaatta accttttgca atttgtcttg      60
tgtttctcac aacacaaaaa cttgtaaaag tgttaaaaaa tcaagatctg aaaaatctta     120
tcaccgcttc taggtttttc agttttttt cttccttttc ctgatctaaa ttaacttata     180
tttcttaggg tttcacttct tgaaacattt aatcagaatt aattaacctc tctagggctt     240
tcatggcgaa tccatggtgg acaggacaag tgaacctatc cggcctcgaa acgacgccgc     300
ctggttcctc tcagttaaag aaaccagatc tccacatctc catgaacatg ccatggact      360 caggtcacaa taatcatcac catcaccaag aagtcgataa caacaacaac gacgacgata     420
gagacaactt gagtggagac gaccacgagc cacgtgaagg agccgtagaa gcccccacgc     480
gccgtccacg tggacgtcct gctggttcca agaacaaacc aaagccaccg atcttcgtca     540
ctcgcgattc tccaaatgct ctcaagagcc atgtcatgga gatcgctagt gggactgacg     600
tcatcgaaac cctagctact tttgctaggc ggcgtcaacg tggcatctgc atcttgagcg     660
gaaatggcac agtggctaac gtcaccctcc gtcaaccctc gaccgctgcc gttgcggcgg     720
ctcctggtgg tgcggctgtt ttggctttac aagggaggtt tgagattctt tctttaaccg     780
gttcttttct gccaggaccg gctccacctg gttccaccgg tttaacgatt tacttagccg     840
gtggtcaagg tcaggttgtt ggaggaagcg tggtgggccc attgatggca gcaggtccgg     900
tgatgctgat cgccgccacg ttctctaacg cgacttacga gagattgcca ttggaggagg     960
aagaggcagc agagagaggc ggtggtggag cagcggagg agtggttccg ggcagctcg     1020 gaggcggagg ttcgccacta agcagcggtg ctggtgagg cgacggtaac caaggacttc     1080
cggtgtataa tatgccggga aatcttgttt ctaatggtgg cagtggtgga ggaggacaga     1140
tgagcggcca agaagcttat ggttgggctc aagctaggtc aggattttaa cgtgcgttaa     1200

-continued

```
aatggttttt aatttacaga agttaacaat aagattataa tgatgtttat tatgatgatg    1260
aaaaccagtc agttgctact tgttactagt gagctatata gtttgtggac attatattat    1320
gttctctctt gactatgatt attatttgct aaatttcact tagctaaaaa aaaaaaaaaa    1380
aaa                                                                  1383
```

```
<210> SEQ ID NO 6
<211> LENGTH: 315
<212> TYPE: PRT
<213> ORGANISM: Arabidopsis thaliana
<220> FEATURE:
<223> OTHER INFORMATION: G2153 polypeptide

<400> SEQUENCE: 6
```

Met Ala Asn Pro Trp Trp Thr Gly Gln Val Asn Leu Ser Gly Leu Glu
1               5                   10                  15

Thr Thr Pro Pro Gly Ser Ser Gln Leu Lys Lys Pro Asp Leu His Ile
            20                  25                  30

Ser Met Asn Met Ala Met Asp Ser Gly His Asn Asn His His His
        35                  40                  45

Gln Glu Val Asp Asn Asn Asn Asp Asp Asp Arg Asp Asn Leu Ser
    50                  55                  60

Gly Asp His Glu Pro Arg Glu Gly Ala Val Glu Ala Pro Thr Arg
65                  70                  75                  80

Arg Pro Arg Gly Arg Pro Ala Gly Ser Lys Asn Lys Pro Lys Pro Pro
            85                  90                  95

Ile Phe Val Thr Arg Asp Ser Pro Asn Ala Leu Lys Ser His Val Met
            100                 105                 110

Glu Ile Ala Ser Gly Thr Asp Val Ile Glu Thr Leu Ala Thr Phe Ala
        115                 120                 125

Arg Arg Arg Gln Arg Gly Ile Cys Ile Leu Ser Gly Asn Gly Thr Val
    130                 135                 140

Ala Asn Val Thr Leu Arg Gln Pro Ser Thr Ala Ala Val Ala Ala Ala
145                 150                 155                 160

Pro Gly Gly Ala Ala Val Leu Ala Leu Gln Gly Arg Phe Glu Ile Leu
                165                 170                 175

Ser Leu Thr Gly Ser Phe Leu Pro Gly Pro Ala Pro Gly Ser Thr
            180                 185                 190

Gly Leu Thr Ile Tyr Leu Ala Gly Gly Gln Gly Gln Val Val Gly Gly
        195                 200                 205

Ser Val Val Gly Pro Leu Met Ala Ala Gly Pro Val Met Leu Ile Ala
    210                 215                 220

Ala Thr Phe Ser Asn Ala Thr Tyr Glu Arg Leu Pro Leu Glu Glu Glu
225                 230                 235                 240

Glu Ala Ala Glu Arg Gly Gly Gly Gly Ser Gly Gly Val Val Pro
                245                 250                 255

Gly Gln Leu Gly Gly Gly Gly Ser Pro Leu Ser Ser Gly Ala Gly Gly
            260                 265                 270

Gly Asp Gly Asn Gln Gly Leu Pro Val Tyr Asn Met Pro Gly Asn Leu
        275                 280                 285

Val Ser Asn Gly Gly Ser Gly Gly Gly Gln Met Ser Gly Gln Glu
    290                 295                 300

Ala Tyr Gly Trp Ala Gln Ala Arg Ser Gly Phe
305                 310                 315

<210> SEQ ID NO 7
<211> LENGTH: 1361
<212> TYPE: DNA
<213> ORGANISM: Arabidopsis thaliana
<220> FEATURE:
<223> OTHER INFORMATION: G2156

<400> SEQUENCE: 7

```
ttttttttcc ctttcctcgt tcaaaaaaag tacttgcaga gtcactcact ctcagtctca      60
gcacatgaat taatttgaag cttccctaga attctttcac atcaattaat acgacaccgt     120
ctcgggtgaa gaatctctcc tctcttgccc taaagcgagt tagggtttaa cacacaaagc     180
ataccttta gatttgtgtc tcttagctct gttttgtcg gcttgtgtaa ccgatcaact      240
caagctattg ctcctcacc tcctgaaatt tgacttctcc aatggatctc aaagtttctc     300
ttatatgaat tctatcttca ccctcacaat atctttatat atgagccca caagaacaag     360
aagagtcagt agatgcggct gccatggacg gtggttacga tcaatccgga ggagcttcta     420
gatactttca aacctcttc aggcctgagc ttcatcacca gcttcaacct cagcctcaac     480
ttcaccctt gcctcagcct cagcctcaac ctcagcctca gcagcagaat tcagatgatg     540
aatctgactc caacaaggat ccgggttccg acccagttac ctctggttca accgggaaac     600
gtccacgtgg acgtcctccg ggatccaaga caagccgaa gccaccggtg atagtgacta     660
gagatagccc caacgtgctt agatctcatg ttcttgaagt ctcatctgga gccgacatag     720
tcgagagcgt taccacttac gctcgcagga gaggaagagg agtctccatt ctcagtggta     780
acggcacggt ggctaacgtc agtctccggc agccggcaac gacagcggct catggggcaa     840
atggtggaac cggaggtgtt gtggctctac atggaaggtt tgagatactt tccctcacag     900
gtacggtgtt gccgccccct gcgccgccag gatccgtgg tctttctatc tttctttccg     960
gcgttcaagg tcaggtgatt ggaggaaacg tggtggctcc gcttgtggct tcgggtccag    1020
tgatactaat ggctgcatcg ttctctaatg caactttcga aaggcttccc cttgaagatg    1080
aaggaggaga aggtggagag ggaggagaag ttggagaggg aggaggagga gaaggtggtc    1140
caccgccggc cacgtcatca tcaccaccat ctggagccgg tcaaggacag ttaagaggta    1200
acatgagtgg ttatgatcag tttgccggtg atcctcattt gcttggttgg ggagccgcag    1260
ccgcagccgc accaccaaga ccagcctttt agaattgaaa attatgtccg taacatagct    1320
gtaaccaaat ttcatttctc aaaattaaaa gaaaaaaaaa a                        1361
```

<210> SEQ ID NO 8
<211> LENGTH: 302
<212> TYPE: PRT
<213> ORGANISM: Arabidopsis thaliana
<220> FEATURE:
<223> OTHER INFORMATION: G2156 polypeptide

<400> SEQUENCE: 8

```
Met Asp Gly Gly Tyr Asp Gln Ser Gly Gly Ala Ser Arg Tyr Phe His
  1               5                  10                  15

Asn Leu Phe Arg Pro Glu Leu His His Gln Leu Gln Pro Gln Pro Gln
             20                  25                  30

Leu His Pro Leu Pro Gln Pro Gln Pro Gln Pro Gln Gln Gln
         35                  40                  45

Asn Ser Asp Asp Glu Ser Asp Ser Asn Lys Asp Pro Gly Ser Asp Pro
         50                  55                  60

Val Thr Ser Gly Ser Thr Gly Lys Arg Pro Arg Gly Arg Pro Pro Gly
 65                  70                  75                  80
```

```
Ser Lys Asn Lys Pro Lys Pro Val Ile Val Thr Arg Asp Ser Pro
                 85                  90                  95
Asn Val Leu Arg Ser His Val Leu Glu Val Ser Ser Gly Ala Asp Ile
                100                 105                 110
Val Glu Ser Val Thr Thr Tyr Ala Arg Arg Gly Arg Gly Val Ser
            115                 120                 125
Ile Leu Ser Gly Asn Gly Thr Val Ala Asn Val Ser Leu Arg Gln Pro
            130                 135                 140
Ala Thr Thr Ala Ala His Gly Ala Asn Gly Gly Thr Gly Gly Val Val
145                 150                 155                 160
Ala Leu His Gly Arg Phe Glu Ile Leu Ser Leu Thr Gly Thr Val Leu
                165                 170                 175
Pro Pro Pro Ala Pro Pro Gly Ser Gly Leu Ser Ile Phe Leu Ser
            180                 185                 190
Gly Val Gln Gly Gln Val Ile Gly Gly Asn Val Val Ala Pro Leu Val
            195                 200                 205
Ala Ser Gly Pro Val Ile Leu Met Ala Ala Ser Phe Ser Asn Ala Thr
        210                 215                 220
Phe Glu Arg Leu Pro Leu Glu Asp Glu Gly Gly Glu Gly Gly Glu Gly
225                 230                 235                 240
Gly Glu Val Gly Glu Gly Gly Gly Glu Gly Pro Pro Ala
                245                 250                 255
Thr Ser Ser Ser Pro Pro Ser Gly Ala Gly Gln Gly Gln Leu Arg Gly
                260                 265                 270
Asn Met Ser Gly Tyr Asp Gln Phe Ala Gly Asp Pro His Leu Leu Gly
                275                 280                 285
Trp Gly Ala Ala Ala Ala Ala Pro Pro Arg Pro Ala Phe
        290                 295                 300

<210> SEQ ID NO 9
<211> LENGTH: 1160
<212> TYPE: DNA
<213> ORGANISM: Oryza sativa
<220> FEATURE:
<223> OTHER INFORMATION: G3399

<400> SEQUENCE: 9
cggtgaggag cgagttgtag aggaggaggg gcaccgatca accgggaagc tggcggccgg    60
gaagtggtgg gagcggccag atgacacggc catggccggg atggaccctg cgggggcgg   120 cgccggcgcc ggcagctcac ggtacttcca ccatctgctc cgaccgcagc agccgtcgcc   180
gctgtcaccg ctgtcgccga catcccatgt caagatggag cactccaaga tgtcacccga   240
caagagcccc gtgggcgagg gagatcacgc gggagggagt ggaagcggcg gcgtcggcgg   300
tgaccaccag ccgtcgtcgt cggccatggt gcccgtcgag ggtggcagcg cagcgccgg   360 cggtagtggc tcgggtgggc cgacgcggcg cccgcgcggg cgcccgcccg ggtccaagaa   420
caagccgaag ccgcccatca tcgtgacgcg cgacagcccg aacgcgctgc actcgcacgt   480
gctcgaggtc gccggcggcg ccgacgtcgt cgactgcgtg gccgagtacg cccgccgccg   540
agggcgcggc gtgtgcgtgc tgagcggcgg cggcgccgtc gtcaacgtgg cgctgcggca   600
gccgggcgcg tcgccgccgg gcagcatggt ggccacgctg cggggccggt tcgagatcct   660
atctctcacg ggcacggtcc tgccgcctcc cgcgccaccc ggcgcgagcg gcctcaccgt   720
gttcctctcc ggcggccagg gccaggtgat cggcggcagc gtggtgggcc cgctggtcgc   780
```

```
cgcggggccc gtcgtcctga tggcggcctc attcgcgaac gccgtgtacg agcggctgcc    840
gctggagggc gaggaagagg aggtcgccgc gcccgccgcc ggaggcgaag cacaagatca    900
agtggcacaa tcagctggac ccccagggca gcaaccggcg gcgtcacagt cctccggcgt    960
gacaggaggc gacggcaccg gcggcgccgg tggcatgtcg ctctacaacc tcgccgggaa   1020
tgtgggaggc tatcagctcc ccggagacaa cttcggaggt tggagcggcg ccggcgccgg   1080
cggagtcagg ccaccgttct gacccatgtc ttagcatcca gttcaaaaat tctccaaatt   1140
aagaattgcg cagtgcaggc                                               1160
```

<210> SEQ ID NO 10
<211> LENGTH: 336
<212> TYPE: PRT
<213> ORGANISM: Oryza sativa
<220> FEATURE:
<223> OTHER INFORMATION: G3399 polypeptide

<400> SEQUENCE: 10

```
Met Ala Gly Met Asp Pro Gly Gly Gly Ala Gly Ala Gly Ser Ser
1               5                   10                  15

Arg Tyr Phe His His Leu Leu Arg Pro Gln Gln Pro Ser Pro Leu Ser
            20                  25                  30

Pro Leu Ser Pro Thr Ser His Val Lys Met Glu His Ser Lys Met Ser
        35                  40                  45

Pro Asp Lys Ser Pro Val Gly Glu Gly Asp His Ala Gly Gly Ser Gly
    50                  55                  60

Ser Gly Gly Val Gly Gly Asp His Gln Pro Ser Ser Ala Met Val
65                  70                  75                  80

Pro Val Glu Gly Gly Ser Gly Ser Ala Gly Gly Ser Gly Ser Gly Gly
                85                  90                  95

Pro Thr Arg Arg Pro Arg Gly Arg Pro Pro Gly Ser Lys Asn Lys Pro
            100                 105                 110

Lys Pro Pro Ile Ile Val Thr Arg Asp Ser Pro Asn Ala Leu His Ser
        115                 120                 125

His Val Leu Glu Val Ala Gly Gly Ala Asp Val Val Asp Cys Val Ala
    130                 135                 140

Glu Tyr Ala Arg Arg Arg Gly Arg Gly Val Cys Val Leu Ser Gly Gly
145                 150                 155                 160

Gly Ala Val Val Asn Val Ala Leu Arg Gln Pro Gly Ala Ser Pro Pro
                165                 170                 175

Gly Ser Met Val Ala Thr Leu Arg Gly Arg Phe Glu Ile Leu Ser Leu
            180                 185                 190

Thr Gly Thr Val Leu Pro Pro Ala Pro Gly Ala Ser Gly Leu
        195                 200                 205

Thr Val Phe Leu Ser Gly Gly Gln Gly Gln Val Ile Gly Gly Ser Val
    210                 215                 220

Val Gly Pro Leu Val Ala Ala Gly Pro Val Val Leu Met Ala Ala Ser
225                 230                 235                 240

Phe Ala Asn Ala Val Tyr Glu Arg Leu Pro Leu Glu Gly Glu Glu Glu
                245                 250                 255

Glu Val Ala Ala Pro Ala Ala Gly Gly Glu Ala Gln Asp Gln Val Ala
            260                 265                 270

Gln Ser Ala Gly Pro Pro Gly Gln Gln Pro Ala Ser Gln Ser Ser
        275                 280                 285

Gly Val Thr Gly Gly Asp Gly Thr Gly Gly Ala Gly Gly Met Ser Leu
```

```
                      290              295              300
Tyr Asn Leu Ala Gly Asn Val Gly Gly Tyr Gln Leu Pro Gly Asp Asn
305                 310                  315                  320

Phe Gly Gly Trp Ser Gly Ala Gly Ala Gly Gly Val Arg Pro Pro Phe
                325                  330                  335

<210> SEQ ID NO 11
<211> LENGTH: 987
<212> TYPE: DNA
<213> ORGANISM: Oryza sativa
<220> FEATURE:
<223> OTHER INFORMATION: G3407

<400> SEQUENCE: 11
tcatcatcat catcacttgc atatcgaatt attaataata tcgaagatgg caggccttga    60
tttgggcacc agctacctcc accaccacca atcactgcat ctccgccacg acgatggcgg   120
cgccggctcc gacgacggcg gccacgacga cctctcgccg gggagcggcg gtggcggcgg   180
gcccagcagc acggccggtg gcgccgggat cggcggcggc gaggtcgtcg ctcgccgccc   240
ccgcggccgc ccgccgggct ccaagaacaa gcccaagccg ccgtgatca tcaccaggga   300 gagcgccaac gcgctcaggg cgcatatcct cgaggtagcc gccggttgcg atgtgttcga   360
ggcgctgacg gcgtacgcgc gccgccggca gcgcggggtg tgcgtgctct cggcggcggg   420
gacagtggcg aacgtcacgc tccggcagcc gcagtcggcg cagcccgggc cggcctcgcc   480
ggcggtggcg acgctgcacg gcaggttcga gatactctcc ctcgcgggct ccttcctgcc   540
cccgcccgcg ccgccgggcg ccaccagcct cgccgcgttc ctcgccggcg ggcaggggca   600
ggtcgtcggt ggcagcgtcg ccggcgcgct catcgcggcg gggcccgtcg tcgtcgtcgc   660
cgcgtcgttc agcaacgtgg cgtacgagag gctgccgctc gaggacggcg acgaggtggt   720
ccccccggcg ccggcaggga gcgaccaggg cggcggcggc agcggcggca tgccaccatt   780
aggcgttgat ccgtcgggcg cgccgccac cggtgggctc ccgttcttca acatgccgtt   840
cgggatgccg ccaatgccgg tggacggcca cgccggctgg cctggcgccg gcgtcgggag   900
gccaccgttc tcatgatgga tggatcccca tattccggcg agcggccggc ggcgaggtgg   960
tcggcaagat tgaagacatg gacatgg                                       987

<210> SEQ ID NO 12
<211> LENGTH: 289
<212> TYPE: PRT
<213> ORGANISM: Oryza sativa
<220> FEATURE:
<223> OTHER INFORMATION: G3407 polypeptide

<400> SEQUENCE: 12

Met Ala Gly Leu Asp Leu Gly Thr Ser Tyr Leu His His Gln Ser
1               5                   10                  15

Leu His Leu Arg His Asp Asp Gly Ala Gly Ser Asp Asp Gly Gly
                20                  25                  30

His Asp Asp Leu Ser Pro Gly Ser Gly Gly Gly Gly Pro Ser Ser
            35                  40                  45

Thr Ala Gly Gly Ala Gly Ile Gly Gly Gly Glu Val Val Ala Arg Arg
        50                  55                  60

Pro Arg Gly Arg Pro Pro Gly Ser Lys Asn Lys Pro Lys Pro Pro Val
65                  70                  75                  80

Ile Ile Thr Arg Glu Ser Ala Asn Ala Leu Arg Ala His Ile Leu Glu
                85                  90                  95
```

```
Val Ala Ala Gly Cys Asp Val Phe Glu Ala Leu Thr Ala Tyr Ala Arg
            100                 105                 110

Arg Arg Gln Arg Gly Val Cys Val Leu Ser Ala Ala Gly Thr Val Ala
        115                 120                 125

Asn Val Thr Leu Arg Gln Pro Gln Ser Ala Gln Pro Gly Pro Ala Ser
    130                 135                 140

Pro Ala Val Ala Thr Leu His Gly Arg Phe Glu Ile Leu Ser Leu Ala
145                 150                 155                 160

Gly Ser Phe Leu Pro Pro Ala Pro Pro Gly Ala Thr Ser Leu Ala
                165                 170                 175

Ala Phe Leu Ala Gly Gly Gln Gly Gln Val Val Gly Gly Ser Val Ala
                180                 185                 190

Gly Ala Leu Ile Ala Ala Gly Pro Val Val Val Ala Ala Ser Phe
                195                 200                 205

Ser Asn Val Ala Tyr Glu Arg Leu Pro Leu Glu Asp Gly Asp Glu Val
    210                 215                 220

Val Pro Pro Ala Pro Ala Gly Ser Asp Gln Gly Gly Gly Ser Gly
225                 230                 235                 240

Gly Met Pro Pro Leu Gly Val Asp Pro Ser Gly Ala Ala Thr Gly
                245                 250                 255

Gly Leu Pro Phe Phe Asn Met Pro Phe Gly Met Pro Pro Met Pro Val
                260                 265                 270

Asp Gly His Ala Gly Trp Pro Gly Ala Gly Val Gly Arg Pro Pro Phe
            275                 280                 285

Ser
```

<210> SEQ ID NO 13
<211> LENGTH: 869
<212> TYPE: DNA
<213> ORGANISM: Glycine max
<220> FEATURE:
<223> OTHER INFORMATION: G3456

<400> SEQUENCE: 13

```
tcgacaactt caacttttgt tatggccaac cggtggtgga ccgggtcggt gggtctagag      60
aactctggcc actcgatgaa aaaccggat ctggggtttt ccatgaacga gagtacggtg     120
acggggaacc atataggaga agaagatgag gacagagaaa acagcgacga gccaagagag    180
ggagctattg acgtcgccac cacgcgccgc cctaggggac gtccaccggg ctccagaaac    240
aagccgaaac cgccgatatt cgtcacccga gacagcccta acgcgctgcg gagccacgtc   300
atggagattg ccgtcggagc cgacatcgcc gactgcgtgg cgcagttcgc tcggaggcgc   360
cagcgcgggg ttccattct cagcggcagc gggaccgtcg tcaacgtcaa tctccggcaa    420
cccacggcac ccggcgccgt catggcgctc acggccgct cgacatcct ctccctcacc     480
ggctcctttc tccctgggcc gtcccctccc ggcgccaccg gctcacaat ctacctcgcc    540
ggaggccagg gcagatcgt cggcggcgga gtggtgggcc cgtcgtggc ggcgggcccc    600
gtattggtaa tggcggctac tttttccaat gctacgtatg aaagattgcc tttagaggat    660
gatgatcagg aacaacacgg cggcggaggc ggaggaggtt cgccgcagga aaaaaccggg    720
ggtcccggcg aggcgtcgtc gtcgatttcg gtttataaca ataatgttcc tccgagttta    780
ggtcttccga atgggcaaca tctgaaccat gaagcttatt cttctccttg gggtcattct    840
cctcatgcca gacctccttt ctaattagc                                      869
```

<210> SEQ ID NO 14
<211> LENGTH: 262
<212> TYPE: PRT
<213> ORGANISM: Glycine max
<220> FEATURE:
<223> OTHER INFORMATION: G3456 polypeptide

<400> SEQUENCE: 14

```
Met Lys Lys Pro Asp Leu Gly Phe Ser Met Asn Glu Ser Thr Val Thr
 1               5                  10                  15

Gly Asn His Ile Gly Glu Glu Asp Glu Asp Arg Glu Asn Ser Asp Glu
            20                  25                  30

Pro Arg Glu Gly Ala Ile Asp Val Ala Thr Thr Arg Arg Pro Arg Gly
        35                  40                  45

Arg Pro Pro Gly Ser Arg Asn Lys Pro Lys Pro Ile Phe Val Thr
 50                  55                  60

Arg Asp Ser Pro Asn Ala Leu Arg Ser His Val Met Glu Ile Ala Val
 65                  70                  75                  80

Gly Ala Asp Ile Ala Asp Cys Val Ala Gln Phe Ala Arg Arg Gln
                85                  90                  95

Arg Gly Val Ser Ile Leu Ser Gly Ser Gly Thr Val Val Asn Val Asn
            100                 105                 110

Leu Arg Gln Pro Thr Ala Pro Gly Ala Val Met Ala Leu His Gly Arg
        115                 120                 125

Phe Asp Ile Leu Ser Leu Thr Gly Ser Phe Leu Pro Gly Pro Ser Pro
    130                 135                 140

Pro Gly Ala Thr Gly Leu Thr Ile Tyr Leu Ala Gly Gly Gln Gly Gln
145                 150                 155                 160

Ile Val Gly Gly Gly Val Val Gly Pro Leu Val Ala Ala Gly Pro Val
                165                 170                 175

Leu Val Met Ala Ala Thr Phe Ser Asn Ala Thr Tyr Glu Arg Leu Pro
            180                 185                 190

Leu Glu Asp Asp Asp Gln Glu Gln His Gly Gly Gly Gly Gly Gly
        195                 200                 205

Ser Pro Gln Glu Lys Thr Gly Gly Pro Gly Glu Ala Ser Ser Ser Ile
    210                 215                 220

Ser Val Tyr Asn Asn Val Pro Pro Ser Leu Gly Leu Pro Asn Gly
225                 230                 235                 240

Gln His Leu Asn His Glu Ala Tyr Ser Ser Pro Trp Gly His Ser Pro
                245                 250                 255

His Ala Arg Pro Pro Phe
            260
```

<210> SEQ ID NO 15
<211> LENGTH: 1596
<212> TYPE: DNA
<213> ORGANISM: Glycine max
<220> FEATURE:
<223> OTHER INFORMATION: G3459

<400> SEQUENCE: 15

```
ctgtcgcgtg ggaaacaaat ggctgcattg tgagttcttt gtccccttca acctcatttc      60
aattctctct ctcccccatt cttacttcac ccgcgccccc tccccgccc gctccgtcc       120 cttttctttc tctgcactcc atctttcttt ccaaaaccca cccttttcta ttcctcttcc     180
tcttcctcct tttcccttct ttttatttcc ttacactcac acatttccc ttaaaataaa      240
```

```
cataaacaaa ccagcactgt tcttgacccc caaaaaaaaa aaatctctac tatttattaa    300
ctatattaat tcctccataa tataatcatt tgttttcctt gttttctgtt ttctcttata    360
atatataacc ttcttttatc tattttttct gttttgcacc ttgtgattgt gagttatatc    420
tatttatatt tatatatcat tctctctctt ttttttggat gtgtctatgg ctggtttgga    480
tttaggaagc gcctcacgct tgttcaaaa ccttcacaga ccagacttgc acttgcaaca    540
aaatttccag cagcaccagg accagcagca ccagcgtgat tggaggagc agaaaactcc    600
tccgaatcac agaatggggg cgccgttcga cgatgatagc gatgatagaa gcccgggcct    660
ggagctcact tcaggtcctg cgacatcgt cggacggcgc ccgcgtggca ggcctcctgg    720
gtcgaagaac aagcctaagc cgcccgtcat aatcacccgg gagagcgcca acacgctgag    780
ggcgcacatc ctcgaggtcg gaagcggctc cgacgtcttc gactgtgtca ccgcgtatgc    840
ccggcggcgc cagcgtggga tctgcgtcct cagtggcagc ggcaccgtca ccaatgtcag    900
tctccggcag cctgcagctg ccggtgccgt cgtcacgctg cacggcaggt tcgagattct    960
ctccctctct ggctcgttcc tcccgccgcc ggctccgccg ggagccacca gcctcacaat   1020
ctacctggcc ggcgggcagg ggcaggttgt cggaggaaac gtcatcggag aattaaccgc   1080
agcagggcca gtaatcgtca tcgcagcgtc gttcaccaac gtggcttacg agaggttacc   1140
cttagaagaa gatgaacaac agcagcaaca acagcagctt cagattcagc acctgcaac    1200
gacgtcgtct caaggaaaca acaacaacaa taaccctttc cccgacccct cttcaggact   1260
tcccttcttc aatttaccac tcaatatgca gaatgttcag ttaccagttg agggttgggc   1320
tgtaaaccct gcttcacgtc cacaaccttt ttgagagttc atgaagatgt tgacggagga   1380
tttatatcac aaaaggcttt atattatttt aaggtcagca aattaatatt catggactac   1440
aacatatata taaactatat gttttttctt cttcttcatg ttattttgtt ttttttcttat   1500
gttgttaatg gatataatat gacatgataa ttattatgta gtctgatttt catctccttg   1560
gaatttata tacttatttc ccctgttaaa aaaaaa                              1596
```

<210> SEQ ID NO 16
<211> LENGTH: 295
<212> TYPE: PRT
<213> ORGANISM: Glycine max
<220> FEATURE:
<223> OTHER INFORMATION: G3459 polypeptide

<400> SEQUENCE: 16

```
Met Ala Gly Leu Asp Leu Gly Ser Ala Ser Arg Phe Val Gln Asn Leu
1               5                   10                  15

His Arg Pro Asp Leu His Leu Gln Gln Asn Phe Gln Gln His Gln Asp
            20                  25                  30

Gln Gln His Gln Arg Asp Leu Glu Glu Gln Lys Thr Pro Pro Asn His
        35                  40                  45

Arg Met Gly Ala Pro Phe Asp Asp Ser Asp Asp Arg Ser Pro Gly
    50                  55                  60

Leu Glu Leu Thr Ser Gly Pro Gly Asp Ile Val Gly Arg Arg Pro Arg
65                  70                  75                  80

Gly Arg Pro Pro Gly Ser Lys Asn Lys Pro Lys Pro Val Ile Ile
                85                  90                  95

Thr Arg Glu Ser Ala Asn Thr Leu Arg Ala His Ile Leu Glu Val Gly
            100                 105                 110

Ser Gly Ser Asp Val Phe Asp Cys Val Thr Ala Tyr Ala Arg Arg Arg
        115                 120                 125
```

```
Gln Arg Gly Ile Cys Val Leu Ser Gly Ser Gly Thr Val Thr Asn Val
    130                 135                 140

Ser Leu Arg Gln Pro Ala Ala Ala Gly Ala Val Val Thr Leu His Gly
145                 150                 155                 160

Arg Phe Glu Ile Leu Ser Leu Ser Gly Ser Phe Leu Pro Pro Pro Ala
                165                 170                 175

Pro Pro Gly Ala Thr Ser Leu Thr Ile Tyr Leu Ala Gly Gly Gln Gly
            180                 185                 190

Gln Val Val Gly Gly Asn Val Ile Gly Glu Leu Thr Ala Ala Gly Pro
        195                 200                 205

Val Ile Val Ile Ala Ala Ser Phe Thr Asn Val Ala Tyr Glu Arg Leu
    210                 215                 220

Pro Leu Glu Glu Asp Glu Gln Gln Gln Gln Gln Gln Leu Gln Ile
225                 230                 235                 240

Gln Pro Pro Ala Thr Thr Ser Ser Gln Gly Asn Asn Asn Asn Asn Asn
                245                 250                 255

Pro Phe Pro Asp Pro Ser Ser Gly Leu Pro Phe Phe Asn Leu Pro Leu
            260                 265                 270

Asn Met Gln Asn Val Gln Leu Pro Val Glu Gly Trp Ala Val Asn Pro
        275                 280                 285

Ala Ser Arg Pro Gln Pro Phe
    290                 295

<210> SEQ ID NO 17
<211> LENGTH: 862
<212> TYPE: DNA
<213> ORGANISM: Glycine max
<220> FEATURE:
<223> OTHER INFORMATION: G3460

<400> SEQUENCE: 17 tatgctggt ttggatttag gaagcgcgtc acgctttgtt cagaatcttc acttaccgga      60
cttgcacttg caacaaaatt accagcaacc ccggcacaag cgcgattcgg aggagcaaga    120
gactcctccg aacccgggaa cagcgctggc gccgttcgac aacgatgatg acaaaagcca    180
gggcctggag ctggcttcag gccctgggga catcgttgga cggcgcccac gcggcagacc    240
ttccgggtcc aagaacaagc cgaagccacc ggtgataatc ccccgggaga gcgccaacac    300
gctgagggcg cacattctcg aggtaggaag cggctccgac gtcttcgact gtgtcaccgc    360
ttatgcgcgg cggcgccagc gcgggatctg cgtcctcagc ggcagtggta ccgtcaccaa    420
tgtcagtctc cggcagcctg cggctgccgg agccgtcgtc aggctgcacg gaaggttcga    480
gattctctct ctctccggct cgttcctccc gccgccggct ccgccgggag ccaccagtct    540
cacaatctac ctcgccggcg ggcagggcca ggtcgtcgga ggaaacgtcg tgggagaatt    600
aaccgcggca gggccagtaa tcgtcatcgc agcatcgttc accaacgtgg cttacgagag    660 gctccccta gaagaagatg aacaacaaca acaacagctt cagattcagt cacccgcaac    720
gacgtcatct caaggaaaca acaacaataa ccctttccct gacccttctt caggacttcc    780
cttcttcaac ttaccactca atatgcagaa tgttcagtta ccaccttttt gagggttcat    840
gaatctgata atatgagact ga                                             862

<210> SEQ ID NO 18
<211> LENGTH: 276
<212> TYPE: PRT
<213> ORGANISM: Glycine max
```

```
<220> FEATURE:
<223> OTHER INFORMATION: G3460 polypeptide

<400> SEQUENCE: 18

Met Ala Gly Leu Asp Leu Gly Ser Ala Ser Arg Phe Val Gln Asn Leu
1               5                   10                  15

His Leu Pro Asp Leu His Leu Gln Gln Asn Tyr Gln Gln Pro Arg His
            20                  25                  30

Lys Arg Asp Ser Glu Glu Gln Glu Thr Pro Pro Asn Pro Gly Thr Ala
        35                  40                  45

Leu Ala Pro Phe Asp Asn Asp Asp Lys Ser Gln Gly Leu Glu Leu
    50                  55                  60

Ala Ser Gly Pro Gly Asp Ile Val Gly Arg Arg Pro Arg Gly Arg Pro
65                  70                  75                  80

Ser Gly Ser Lys Asn Lys Pro Lys Pro Val Ile Ile Thr Arg Glu
                85                  90                  95

Ser Ala Asn Thr Leu Arg Ala His Ile Leu Glu Val Gly Ser Gly Ser
            100                 105                 110

Asp Val Phe Asp Cys Val Thr Ala Tyr Ala Arg Arg Gln Arg Gly
        115                 120                 125

Ile Cys Val Leu Ser Gly Ser Gly Thr Val Thr Asn Val Ser Leu Arg
130                 135                 140

Gln Pro Ala Ala Gly Ala Val Val Arg Leu His Gly Arg Phe Glu
145                 150                 155                 160

Ile Leu Ser Leu Ser Gly Ser Phe Leu Pro Pro Ala Pro Gly
                165                 170                 175

Ala Thr Ser Leu Thr Ile Tyr Leu Ala Gly Gln Gly Gln Val Val
            180                 185                 190

Gly Gly Asn Val Val Gly Glu Leu Thr Ala Ala Gly Pro Val Ile Val
        195                 200                 205

Ile Ala Ala Ser Phe Thr Asn Val Ala Tyr Glu Arg Leu Pro Leu Glu
210                 215                 220

Glu Asp Glu Gln Gln Gln Gln Leu Gln Ile Gln Ser Pro Ala Thr
225                 230                 235                 240

Thr Ser Ser Gln Gly Asn Asn Asn Asn Pro Phe Pro Asp Pro Ser
                245                 250                 255

Ser Gly Leu Pro Phe Phe Asn Leu Pro Leu Asn Met Gln Asn Val Gln
            260                 265                 270

Leu Pro Pro Phe
    275

<210> SEQ ID NO 19
<211> LENGTH: 1064
<212> TYPE: DNA
<213> ORGANISM: Oryza sativa
<220> FEATURE:
<223> OTHER INFORMATION: G3408

<400> SEQUENCE: 19
gtggttttgg ttgattgcta ctctgtgcca tgtcgttctg cgagagggac atgaacaagg      60
agagcatgta ccaagaacgg acgacatgg cggggatacg gttcgcgacg ccgccgctgc     120
ctcagcagca gcagcagcag cagctggtgg agtgcttctc cgacgaggtg acagccgcg      180 ggagtggcgg cgagatgaag gatgccgtgg ggagcgggag tggcagctg gtcgttgttg     240 gtggcgggga tggggcgagc atcgaggtgg cgaagaagag gaggggagg ccgccggggt     300
```

```
ccaagaacaa gccgaagcca cccgtggtga tcacgcggga ggcggagccg gcggcggcga      360
tgcggccgca cgtgatcgag atccccggcg ggcgggacgt cgcggaggcg ctcgcgcggt      420
tctcgagccg tcggaacctc gggatctgcg tgctcgccgg caccggcgcg gtcgccaacg      480
tgtcgctccg ccaccgtca cccggggtcc cgggctcagc tccggctgcg atcgtgttcc       540
acggccggta cgagatcctc tccctgtcgg ccacgttcct gcctccggcc atgtcctccg      600
tggcgcccca ggccgcggtc gccgccgcgg gcctctccat ctcgctcgcc ggcccgcacg      660
gccagatcgt cggcggggcc gtggcaggcc cgctctacgc cgcgaccacc gtcgtggtcg      720
tcgccgccgc cttcaccaac cccaccttcc accgcctccc cgccgacgac gacgcgtcgg      780
tgtccgtctc ggtgtcactc tccggcagcg gcgacgcgga cgaacaccgg ggccaccagc      840
acaaacctga gccgcaagaa ccgcgccaac ttcgacggcc gccaccgcac ctgtcagcag      900
ccgccgccgt ctcagcagca cagccggtgg agccatgcgg cgcgcccatg tacgcctgcc      960
accctcagcc acaggaggtg atgtggccgc cgccggctcg tacgccgcac ccgccgccgc     1020
cgccgccgta ctaatccgac cgaattggta cgccattgcc acat                     1064
```

<210> SEQ ID NO 20
<211> LENGTH: 334
<212> TYPE: PRT
<213> ORGANISM: Oryza sativa
<220> FEATURE:
<223> OTHER INFORMATION: G3408 polypeptide

<400> SEQUENCE: 20

```
Met Ser Phe Cys Glu Arg Asp Met Asn Lys Glu Ser Met Tyr Gln Glu
1               5                   10                  15

Arg Asp Asp Met Ala Gly Ile Arg Phe Ala Thr Pro Pro Leu Pro Gln
            20                  25                  30

Gln Gln Gln Gln Gln Gln Leu Val Glu Cys Phe Ser Asp Glu Val Asp
        35                  40                  45

Ser Arg Gly Ser Gly Gly Glu Met Lys Asp Ala Val Gly Ser Gly Ser
    50                  55                  60

Gly Gln Leu Val Val Val Gly Gly Gly Asp Gly Ala Ser Ile Glu Val
65                  70                  75                  80

Ala Lys Lys Arg Arg Gly Arg Pro Pro Gly Ser Lys Asn Lys Pro Lys
                85                  90                  95

Pro Pro Val Val Ile Thr Arg Glu Ala Glu Pro Ala Ala Ala Met Arg
            100                 105                 110

Pro His Val Ile Glu Ile Pro Gly Gly Arg Asp Val Ala Glu Ala Leu
        115                 120                 125

Ala Arg Phe Ser Ser Arg Arg Asn Leu Gly Ile Cys Val Leu Ala Gly
    130                 135                 140

Thr Gly Ala Val Ala Asn Val Ser Leu Arg His Pro Ser Pro Gly Val
145                 150                 155                 160

Pro Gly Ser Ala Pro Ala Ala Ile Val Phe His Gly Arg Tyr Glu Ile
                165                 170                 175

Leu Ser Leu Ser Ala Thr Phe Leu Pro Ala Met Ser Ser Val Ala
            180                 185                 190

Pro Gln Ala Ala Val Ala Ala Gly Leu Ser Ile Ser Leu Ala Gly
        195                 200                 205

Pro His Gly Gln Ile Val Gly Gly Ala Val Ala Gly Pro Leu Tyr Ala
    210                 215                 220

Ala Thr Thr Val Val Val Val Ala Ala Ala Phe Thr Asn Pro Thr Phe
```

-continued

```
            225                 230                 235                 240
His Arg Leu Pro Ala Asp Asp Ala Ser Val Ser Val Ser Val Ser
                245                 250                 255
Leu Ser Gly Ser Gly Asp Ala Asp Glu His Arg Gly His Gln His Lys
            260                 265                 270
Pro Glu Pro Gln Glu Pro Arg Gln Leu Arg Arg Pro Pro His Leu
        275                 280                 285
Ser Ala Ala Ala Val Ser Ala Ala Gln Pro Val Glu Pro Cys Gly
    290                 295                 300
Ala Pro Met Tyr Ala Cys His Pro Gln Pro Gln Glu Val Met Trp Pro
305                 310                 315                 320
Pro Pro Ala Arg Thr Pro His Pro Pro Pro Pro Pro Tyr
                325                 330

<210> SEQ ID NO 21
<211> LENGTH: 902
<212> TYPE: DNA
<213> ORGANISM: Oryza sativa
<220> FEATURE:
<223> OTHER INFORMATION: G3403

<400> SEQUENCE: 21
tcgaccagtg cattaattgt gcttctcctg gagcagggtc aagctggcga acaggtcgtg      60
gtggtcgggc cccatgggct tgccggagca gccgtccggc tcgtcgggcc ccaaggcgga     120
gctcccggtg ccaaggagc cggaggcgag cccgacgggg ggcgcggcgg cggaccacgc     180
cgacgagaac aacgaatccg gcggcggcga gccgcgggag ggcgccgtgg tggcggcgcc     240
caaccggcgc cccgcggcc gcccgccggg ctccaagaac aagccgaagc cgcccatctt     300
cgtgacgcgc gacagcccca cgcgctgcg cagccacgtc atggaggtgg ccggcggcgc     360
cgacgtcgcc gacgccatcg cgcagttctc cgccgccgc cagcgcggcg tctgcgtgct     420
cagcggcgcc gggacggtcg ccaacgtcgc gctgcgccag ccgtcggcgc ccggcgccgt     480
cgtcgccctg cacggccgct cgagatcct ctccctcacc ggcaccttcc tcccggccc     540 ggcgcctccg ggctccacgg ggctcaccgt ctacctcgcc ggcggccagg gccaggttgt     600
cggcggcagc gtcgtggggt cgctcatcgc cgcgggcccg gtcatggtga tcgcgtccac     660
gttcgccaac gccacctacg agcgcctgcc attggaggaa gagaggagg gctcaggccc     720 gcccatgccc ggcggcgccg agccctcat ggccggcggc cacggcatcg ccgacccttc     780
ggcgctgcca atgttcaacc tgccgccgag caacgggctc ggcggcggcg cgacggtttt     840
cccatgggcg gcgcaccccc gcccaccgta ctgatcgatg caatagcat ggaagattca     900 tt                                                                   902

<210> SEQ ID NO 22
<211> LENGTH: 266
<212> TYPE: PRT
<213> ORGANISM: Oryza sativa
<220> FEATURE:
<223> OTHER INFORMATION: G3403 polypeptide

<400> SEQUENCE: 22

Met Gly Leu Pro Glu Gln Pro Ser Gly Ser Gly Pro Lys Ala Glu
1               5                   10                  15

Leu Pro Val Ala Lys Glu Pro Glu Ala Ser Pro Thr Gly Gly Ala Ala
            20                  25                  30

Ala Asp His Ala Asp Glu Asn Asn Glu Ser Gly Gly Gly Glu Pro Arg
```

```
                35                  40                  45
Glu Gly Ala Val Val Ala Ala Pro Asn Arg Arg Pro Arg Gly Arg Pro
             50                  55                  60

Pro Gly Ser Lys Asn Lys Pro Lys Pro Pro Ile Phe Val Thr Arg Asp
 65                  70                  75                  80

Ser Pro Asn Ala Leu Arg Ser His Val Met Glu Val Ala Gly Gly Ala
                 85                  90                  95

Asp Val Ala Asp Ala Ile Ala Gln Phe Ser Arg Arg Arg Gln Arg Gly
            100                 105                 110

Val Cys Val Leu Ser Gly Ala Gly Thr Val Ala Asn Val Ala Leu Arg
        115                 120                 125

Gln Pro Ser Ala Pro Gly Ala Val Val Ala Leu His Gly Arg Phe Glu
    130                 135                 140

Ile Leu Ser Leu Thr Gly Thr Phe Leu Pro Gly Pro Ala Pro Pro Gly
145                 150                 155                 160

Ser Thr Gly Leu Thr Val Tyr Leu Ala Gly Gln Gly Gln Val Val
                165                 170                 175

Gly Gly Ser Val Val Gly Ser Leu Ile Ala Ala Gly Pro Val Met Val
            180                 185                 190

Ile Ala Ser Thr Phe Ala Asn Ala Thr Tyr Glu Arg Leu Pro Leu Glu
        195                 200                 205

Glu Glu Glu Glu Gly Ser Gly Pro Pro Met Pro Gly Gly Ala Glu Pro
    210                 215                 220

Leu Met Ala Gly Gly His Gly Ile Ala Asp Pro Ser Ala Leu Pro Met
225                 230                 235                 240

Phe Asn Leu Pro Pro Ser Asn Gly Leu Gly Gly Gly Asp Gly Phe
                245                 250                 255

Pro Trp Ala Ala His Pro Arg Pro Pro Tyr
            260                 265

<210> SEQ ID NO 23
<211> LENGTH: 1153
<212> TYPE: DNA
<213> ORGANISM: Glycine max
<220> FEATURE:
<223> OTHER INFORMATION: G3458

<400> SEQUENCE: 23
tcgcccacgc gtccgtacgg ctgcgagaag acgacagaag gggccacttt atttgtctct      60
ctctttccct tccaacctca tcccattccg ttttctctgc agtactcaat tgatcccttt     120 gttttctat tcgttctgag agctttgtgt gtatggccgg catagacttg ggttcagcat      180
cacattttgt tcatcatcgc cttgaacgcc ctgaccttga agacgatgag aaccaacaag     240
accaagacaa caaccttaac aatcacgaag ggcttgacct agttacacca aattcaggtc     300
ctggtgatgt tgttggtcgc aggccaagag aagacctcc aggttcaaag aacaagccaa      360
aaccaccagt tatcatcaca agagagagtg caaacaccct tagggctcac atccttgaag     420
ttagtagtgg ttgtgacgtc tttgaatcgg tcgctaccta tgcaaggaag cgacaaagag     480
ggatctgtgt cctcagtggg agtggcaccg tgaccaacgt gacattgagg cagccggccg     540
cggctggtgc cgtcgtcacg ctgcacggaa ggtttgagat cctctctttg tcaggatcat     600
tcctcccacc tccagctcca ccaggtgcta caagtttgac tgtgttcctt ggtggaggac     660
agggtcaagt ggtgggagga atgttgttg gtcctttggt ggcttctggg cctgttattg      720
ttattgcttc atctttact aatgtagcat atgagaggtt gcctttggat gaagatgaat       780
```

-continued

```
ctatgcagat gcaacaaggg caatcatcag ctggtgatgg tagcggtgac catggtggtg    840
gagttagtaa taactctttt ccggatccgt cttccgggct tccattcttc aatttgccac    900
taaacatgcc tcagttacct gttgatggtt gggctggcaa ctctggtgga aggcaatctt    960
actgatccag agtctttggg ggcacaaagg tgagaagttg aattgatctc atatatattg   1020
gtcttctcta atctttcctc tgaatattgc ttgtgaagaa gtactgattt ttctattgaa   1080
gaaatcgttt gtttggctag gtttgttgta aggacgatca gtttctagga acaactgtaa   1140
aacgttttct ctt                                                      1153

<210> SEQ ID NO 24
<211> LENGTH: 270
<212> TYPE: PRT
<213> ORGANISM: Glycine max
<220> FEATURE:
<223> OTHER INFORMATION: G3458 polypeptide

<400> SEQUENCE: 24

Met Ala Gly Ile Asp Leu Gly Ser Ala Ser His Phe Val His His Arg
1               5                   10                  15

Leu Glu Arg Pro Asp Leu Glu Asp Asp Glu Asn Gln Gln Asp Gln Asp
                20                  25                  30

Asn Asn Leu Asn Asn His Glu Gly Leu Asp Leu Val Thr Pro Asn Ser
            35                  40                  45

Gly Pro Gly Asp Val Val Gly Arg Arg Pro Arg Gly Arg Pro Pro Gly
        50                  55                  60

Ser Lys Asn Lys Pro Lys Pro Pro Val Ile Ile Thr Arg Glu Ser Ala
65                  70                  75                  80

Asn Thr Leu Arg Ala His Ile Leu Glu Val Ser Ser Gly Cys Asp Val
                85                  90                  95

Phe Glu Ser Val Ala Thr Tyr Ala Arg Lys Arg Gln Arg Gly Ile Cys
            100                 105                 110

Val Leu Ser Gly Ser Gly Thr Val Thr Asn Val Thr Leu Arg Gln Pro
        115                 120                 125

Ala Ala Ala Gly Ala Val Val Thr Leu His Gly Arg Phe Glu Ile Leu
130                 135                 140

Ser Leu Ser Gly Ser Phe Leu Pro Pro Ala Pro Pro Gly Ala Thr
145                 150                 155                 160

Ser Leu Thr Val Phe Leu Gly Gly Gln Gly Gln Val Val Gly Gly
                165                 170                 175

Asn Val Val Gly Pro Leu Val Ala Ser Gly Pro Val Ile Val Ile Ala
            180                 185                 190

Ser Ser Phe Thr Asn Val Ala Tyr Glu Arg Leu Pro Leu Asp Glu Asp
        195                 200                 205

Glu Ser Met Gln Met Gln Gln Gly Gln Ser Ser Ala Gly Asp Gly Ser
    210                 215                 220

Gly Asp His Gly Gly Val Ser Asn Asn Ser Phe Pro Asp Pro Ser
225                 230                 235                 240

Ser Gly Leu Pro Phe Phe Asn Leu Pro Leu Asn Met Pro Gln Leu Pro
                245                 250                 255

Val Asp Gly Trp Ala Gly Asn Ser Gly Gly Arg Gln Ser Tyr
            260                 265                 270

<210> SEQ ID NO 25
<211> LENGTH: 918
```

```
<212> TYPE: DNA
<213> ORGANISM: Oryza sativa
<220> FEATURE:
<223> OTHER INFORMATION: G3406

<400> SEQUENCE: 25
atggcaggtc tcgacctcgg caccgccgcg acgcgctacg tccaccagct ccaccacctc      60
caccccgacc tccagctgca gcacagctac gccaagcagc acgagccgtc cgacgacgac     120
cccaacggca gcggcggcgg cggcaacagc aacggcgggc cgtacgggga ccatgacggc     180
gggtcctcgt cgtcaggtcc tgccaccgac ggcgcggtcg gcgggcccgg cgacgtggtg     240
gcgcgccggc cgcggggggcg cccgcctggc tccaagaaca agccgaagcc gccggtgatc     300
atcacgcggg agagcgccaa cacgctcgcg cccacatcc tggaggtcgg gagcggctgc      360
gacgtgttcg agtgcgtctc cacgtacgcg cgccggcggc agcgcggcgt gtgcgtgctg     420
agcggcagcg gcgtggtcac caacgtgacg ctgcgtcagc cgtcggcgcc cgcgggcgcc     480
gtcgtgtcgc tgcacgggag gttcgagatc ctgtcgctct cgggctcctt cctcccgccg     540
ccggctcccc ccggcgccac cagcctcacc atcttcctcg ccgggggcca gggacaggtc     600
gtcggcggca acgtcgtcgg cgcgctctac gccgcgggcc cggtcatcgt catcgcggcg     660
tccttcgcca acgtcgccta cgagcgcctc ccactggagg aggaggaggc gccgccgccg     720
caggccggcc tgcagatgca gcagcccggc ggcggcgccg atgctggtgg catgggtggc     780
gcgttcccgc cggacccgtc tgccgccggc ctcccgttct tcaacctgcc gctcaacaac     840
atgcccggtg gcggcggctc acagctccct cccggcgccg acggccatgg ctgggccggc     900
gcacggccac cgttctga                                                    918

<210> SEQ ID NO 26
<211> LENGTH: 305
<212> TYPE: PRT
<213> ORGANISM: Oryza sativa
<220> FEATURE:
<223> OTHER INFORMATION: G3406 polypeptide

<400> SEQUENCE: 26

Met Ala Gly Leu Asp Leu Gly Thr Ala Ala Thr Arg Tyr Val His Gln
1               5                   10                  15

Leu His His Leu His Pro Asp Leu Gln Leu Gln His Ser Tyr Ala Lys
            20                  25                  30

Gln His Glu Pro Ser Asp Asp Pro Asn Gly Ser Gly Gly Gly Gly
        35                  40                  45

Asn Ser Asn Gly Gly Pro Tyr Gly Asp His Asp Gly Gly Ser Ser Ser
    50                  55                  60

Ser Gly Pro Ala Thr Asp Gly Ala Val Gly Gly Pro Gly Asp Val Val
65                  70                  75                  80

Ala Arg Arg Pro Arg Gly Arg Pro Pro Gly Ser Lys Asn Lys Pro Lys
                85                  90                  95

Pro Pro Val Ile Ile Thr Arg Glu Ser Ala Asn Thr Leu Arg Ala His
            100                 105                 110

Ile Leu Glu Val Gly Ser Gly Cys Asp Val Phe Glu Cys Val Ser Thr
        115                 120                 125

Tyr Ala Arg Arg Arg Gln Arg Gly Val Cys Val Leu Ser Gly Ser Gly
    130                 135                 140

Val Val Thr Asn Val Thr Leu Arg Gln Pro Ser Ala Pro Ala Gly Ala
145                 150                 155                 160
```

```
Val Val Ser Leu His Gly Arg Phe Glu Ile Leu Ser Leu Ser Gly Ser
                165                 170                 175

Phe Leu Pro Pro Pro Ala Pro Pro Gly Ala Thr Ser Leu Thr Ile Phe
            180                 185                 190

Leu Ala Gly Gly Gln Gly Gln Val Val Gly Gly Asn Val Val Gly Ala
        195                 200                 205

Leu Tyr Ala Ala Gly Pro Val Ile Val Ile Ala Ala Ser Phe Ala Asn
    210                 215                 220

Val Ala Tyr Glu Arg Leu Pro Leu Glu Glu Glu Ala Pro Pro Pro
225                 230                 235                 240

Gln Ala Gly Leu Gln Met Gln Gln Pro Gly Gly Ala Asp Ala Gly
                245                 250                 255

Gly Met Gly Gly Ala Phe Pro Pro Asp Pro Ser Ala Ala Gly Leu Pro
            260                 265                 270

Phe Phe Asn Leu Pro Leu Asn Asn Met Pro Gly Gly Gly Ser Gln
                275                 280                 285

Leu Pro Pro Gly Ala Asp Gly His Gly Trp Ala Gly Ala Arg Pro Pro
    290                 295                 300

Phe
305

<210> SEQ ID NO 27
<211> LENGTH: 1013
<212> TYPE: DNA
<213> ORGANISM: Oryza sativa
<220> FEATURE:
<223> OTHER INFORMATION: G3405

<400> SEQUENCE: 27
ctagctaatt gattgctagc ttgcaaggat ggatccggtc acggcatcaa tacacggtca      60
ccatcttcct ccaccgttca cacccgcga cttccatcac catctccagc agcagcagca     120
ccagctgcat ctcaagaccg aggatgacca aggcggcggc actccgggtg tcttcggcag     180
ccgcggcacc aagcgcgacc acgacgacga cgagaacagt ggcaacgcc atggaagcgg      240 tggtgacggc ggtgacctcg cgctggtacc ccctcgggt ggcgggccgg acggcgccgg      300
gagcgagagc gccacgcgcc gcccgagggg acgcccggcg gggtccaaga acaagccgaa     360
gccaccgatc atcatcacca gggacagcgc caacacgctc cggacgcacg tcatggaggt     420
ggccggcggc tgcgacatct ccgagagcat caccacgttc gcgcgacgcc ggcagcgcgg     480
ggtttgcgtg ctcagcggcg ccggcaccgt cactaacgtc acgctgcggc agcccgcatc     540
gcagggagcg gtcgttgcgc tccacggccg gttcgagata ctctccctct ccggctcctt     600 cctccccgccg cccgccccgc cggaggccac ggggctcacc gtctacctgg ccggaggcca     660
gggccaggtc gtgggcggca gcgtcgtcgg cgcgctgacc gcggctgggc ctgtggtgat     720
aatggcggcc tctttttgcga acgcggtgta cgagcggctg ccgttggagg acgacgagct     780
actggcggct caagggcaag ccgacagcgc tgggttgctc gccgcggggc agcaagcggc     840
gcagctcgcc ggcggggccg tcgatccaag cctcttccaa ggactaccac caaacctact     900
cggaaacgtg cagctgccgc cggaagccgc ctacggatgg aaccctggag ccggcggtgg     960
ccgcccggcg ccgttctgag atggatcgat tccgcgacag caacgcagca tag           1013

<210> SEQ ID NO 28
<211> LENGTH: 316
<212> TYPE: PRT
<213> ORGANISM: Oryza sativa
```

<220> FEATURE:
<223> OTHER INFORMATION: G3405 polypeptide

<400> SEQUENCE: 28

| | | | | | | | | | | | | | | | |
|---|---|---|---|---|---|---|---|---|---|---|---|---|---|---|---|
| Met | Asp | Pro | Val | Thr | Ala | Ser | Ile | His | Gly | His | His | Leu | Pro | Pro | Pro |
| 1 | | | | 5 | | | | | 10 | | | | | 15 | |
| Phe | Asn | Thr | Arg | Asp | Phe | His | His | Leu | Gln | Gln | Gln | Gln | His | Gln | |
| | | | 20 | | | | | 25 | | | | | 30 | | |
| Leu | His | Leu | Lys | Thr | Glu | Asp | Gln | Gly | Gly | Thr | Pro | Gly | Val | | |
| | | | 35 | | | | 40 | | | | | 45 | | | |
| Phe | Gly | Ser | Arg | Gly | Thr | Lys | Arg | Asp | His | Asp | Asp | Glu | Asn | Ser | |
| | 50 | | | | | 55 | | | | | 60 | | | | |
| Gly | Asn | Gly | His | Gly | Ser | Gly | Gly | Asp | Gly | Gly | Asp | Leu | Ala | Leu | Val |
| 65 | | | | | 70 | | | | | 75 | | | | | 80 |
| Pro | Pro | Ser | Gly | Gly | Gly | Pro | Asp | Gly | Ala | Gly | Ser | Glu | Ser | Ala | Thr |
| | | | | 85 | | | | | 90 | | | | | 95 | |
| Arg | Arg | Pro | Arg | Gly | Arg | Pro | Ala | Gly | Ser | Lys | Asn | Lys | Pro | Lys | Pro |
| | | | 100 | | | | | 105 | | | | | 110 | | |
| Pro | Ile | Ile | Ile | Thr | Arg | Asp | Ser | Ala | Asn | Thr | Leu | Arg | Thr | His | Val |
| | | | 115 | | | | | 120 | | | | | 125 | | |
| Met | Glu | Val | Ala | Gly | Gly | Cys | Asp | Ile | Ser | Glu | Ser | Ile | Thr | Thr | Phe |
| | 130 | | | | | 135 | | | | | 140 | | | | |
| Ala | Arg | Arg | Arg | Gln | Arg | Gly | Val | Cys | Val | Leu | Ser | Gly | Ala | Gly | Thr |
| 145 | | | | | 150 | | | | | 155 | | | | | 160 |
| Val | Thr | Asn | Val | Thr | Leu | Arg | Gln | Pro | Ala | Ser | Gln | Gly | Ala | Val | Val |
| | | | | 165 | | | | | 170 | | | | | 175 | |
| Ala | Leu | His | Gly | Arg | Phe | Glu | Ile | Leu | Ser | Leu | Ser | Gly | Ser | Phe | Leu |
| | | | 180 | | | | | 185 | | | | | 190 | | |
| Pro | Pro | Pro | Ala | Pro | Pro | Glu | Ala | Thr | Gly | Leu | Thr | Val | Tyr | Leu | Ala |
| | | | 195 | | | | | 200 | | | | | 205 | | |
| Gly | Gly | Gln | Gly | Gln | Val | Val | Gly | Ser | Val | Val | Gly | Ala | Leu | Thr | |
| | 210 | | | | | 215 | | | | | 220 | | | | |
| Ala | Ala | Gly | Pro | Val | Val | Ile | Met | Ala | Ala | Ser | Phe | Ala | Asn | Ala | Val |
| 225 | | | | | 230 | | | | | 235 | | | | | 240 |
| Tyr | Glu | Arg | Leu | Pro | Leu | Glu | Asp | Asp | Glu | Leu | Leu | Ala | Ala | Gln | Gly |
| | | | | 245 | | | | | 250 | | | | | 255 | |
| Gln | Ala | Asp | Ser | Ala | Gly | Leu | Leu | Ala | Ala | Gly | Gln | Gln | Ala | Ala | Gln |
| | | | 260 | | | | | 265 | | | | | 270 | | |
| Leu | Ala | Gly | Gly | Ala | Val | Asp | Pro | Ser | Leu | Phe | Gln | Gly | Leu | Pro | Pro |
| | | | 275 | | | | | 280 | | | | | 285 | | |
| Asn | Leu | Leu | Gly | Asn | Val | Gln | Leu | Pro | Pro | Glu | Ala | Ala | Tyr | Gly | Trp |
| | 290 | | | | | 295 | | | | | 300 | | | | |
| Asn | Pro | Gly | Ala | Gly | Gly | Gly | Arg | Pro | Ala | Pro | Phe | | | | |
| 305 | | | | | 310 | | | | | 315 | | | | | |

<210> SEQ ID NO 29
<211> LENGTH: 1143
<212> TYPE: DNA
<213> ORGANISM: Oryza sativa
<220> FEATURE:
<223> OTHER INFORMATION: G3400

<400> SEQUENCE: 29
ctctgcaggt gaggtgaggt gaggggtggg atcgagggat cgagaagctg gcggcgagca      60
agtggtggga gcgcgccgat gagggcgcca tggccgggat ggatcccacc ggcggcggtg     120

-continued

```
gcggcggcgg cgtggcggcg cactacctac acatgctccg cgcgcagcag caccagccac    180
tgtccccggc aggtgacgtc aaggcggagc ggtccatgct gtcgccggat gagagccccg    240
gcgcggacgc cgacctagga tcggaccacc cgacgtcgtc ggccatggtg gcggcggagg    300
acagcggcgg cggcagcggt tcgggtggcc cgatgcggcg ccccgcggg aggccgctgg     360
gctccaagaa caagcccaag ccgcccatca tcgtgacgcg ggacagcccc aacgcgttcc    420
actcccacgt cctcgaggtc gccgcgggaa ccgacatcgt cgagtgcgtc tgcgagttcg    480
cgcgccgccg cggccgcggc gtctccgtgc tcagcggtgg cggcgccgtc gccaacgtcg    540
cgctccgcca gccaggcgcg tcgccccgg gcagcctggt cgccaccatg cgcggccagt     600
tcgagatcct gtccctcacg ggcaccgtcc tcccgccgcc cgcgccgccc agcgccagcg    660
gcctcaccgt cttcctctcc ggcgggcagg gccaggtggt cggcgggagc gtggccggcc    720
agctcatcgc cgcggggcca gtcttcctca tggccgcctc gttcgccaat gccgtctacg    780
agcgtctgcc actcgatggg gaggatccgg aggcagaggc tgccgccgcc accctcccg     840
gcgatgcggc gcagccaacc ggcccaccac caccgcagca gcagcccaca gcctcgcagt    900
cctctgaggt gaccgccggt gacggcggcg cggcggcgg tctcggcatg tatcttggag     960
gccatgtggg atcctaccag cagcagcagc agcaacttcc cggaccagga gacaacttcg   1020
gtagctggag cggcagcatc aggccgccgc cattctgatc caaacacctc aaatcaagct   1080
ctcccccaac aacgccatgc atgtctaaat cctcacaaga ttcactccaa gaagacgaag   1140
ctg                                                                  1143
```

<210> SEQ ID NO 30
<211> LENGTH: 322
<212> TYPE: PRT
<213> ORGANISM: Oryza sativa
<220> FEATURE:
<223> OTHER INFORMATION: G3400 polypeptide

<400> SEQUENCE: 30

```
Met Ala Gly Met Asp Pro Thr Gly Gly Gly Gly Gly Gly Gly Val Ala
1               5                   10                  15

Ala His Tyr Leu His Met Leu Arg Ala Gln Gln His Gln Pro Leu Ser
            20                  25                  30

Pro Ala Gly Asp Val Lys Ala Glu Arg Ser Met Leu Ser Pro Asp Glu
        35                  40                  45

Ser Pro Gly Ala Asp Ala Asp Leu Gly Ser Asp His Pro Thr Ser Ser
    50                  55                  60

Ala Met Val Ala Ala Glu Asp Ser Gly Gly Ser Gly Ser Gly Gly
65                  70                  75                  80

Pro Met Arg Arg Pro Arg Gly Arg Pro Leu Gly Ser Lys Asn Lys Pro
                85                  90                  95

Lys Pro Pro Ile Ile Val Thr Arg Asp Ser Pro Asn Ala Phe His Ser
            100                 105                 110

His Val Leu Glu Val Ala Ala Gly Thr Asp Ile Val Glu Cys Val Cys
        115                 120                 125

Glu Phe Ala Arg Arg Arg Gly Arg Gly Val Ser Val Leu Ser Gly Gly
    130                 135                 140

Gly Ala Val Ala Asn Val Ala Leu Arg Gln Pro Gly Ala Ser Pro Pro
145                 150                 155                 160

Gly Ser Leu Val Ala Thr Met Arg Gly Gln Phe Glu Ile Leu Ser Leu
                165                 170                 175
```

```
Thr Gly Thr Val Leu Pro Pro Ala Pro Pro Ser Ala Ser Gly Leu
            180                 185                 190

Thr Val Phe Leu Ser Gly Gly Gln Gly Gln Val Val Gly Ser Val
        195                 200                 205

Ala Gly Gln Leu Ile Ala Ala Gly Pro Val Phe Leu Met Ala Ala Ser
    210                 215                 220

Phe Ala Asn Ala Val Tyr Glu Arg Leu Pro Leu Asp Gly Glu Asp Pro
225                 230                 235                 240

Glu Ala Glu Ala Ala Ala Thr Pro Pro Gly Asp Ala Ala Gln Pro
                245                 250                 255

Thr Gly Pro Pro Pro Gln Gln Pro Thr Ala Ser Gln Ser Ser
            260                 265                 270

Glu Val Thr Ala Gly Asp Gly Gly Gly Gly Leu Gly Met Tyr
            275                 280                 285

Leu Gly Gly His Val Gly Ser Tyr Gln Gln Gln Gln Gln Leu Pro
    290                 295                 300

Gly Pro Gly Asp Asn Phe Gly Ser Trp Ser Gly Ser Ile Arg Pro Pro
305                 310                 315                 320

Pro Phe
```

<210> SEQ ID NO 31
<211> LENGTH: 1152
<212> TYPE: DNA
<213> ORGANISM: Oryza sativa
<220> FEATURE:
<223> OTHER INFORMATION: G3404

<400> SEQUENCE: 31

```
accgtgagag agggagacag atggatccgg tgacggcggc ggcggcgcat gggggtgggc      60
accaccacca ccaccacttc ggagcgccac cggtggcggc gttccaccac cacccgttcc     120
accacgcgg cggggcgcac taccggcgg cgttccagca gtttcaggag gagcagcagc      180
agcttgtggc ggcggcggcg gcggctggtg ggatggcgaa gcaggagctg gtggatgaga     240
gcaacaacac catcaacagc ggcgggagca acgggagcgg cggggaggag cagaggcagc     300
agtccgggga ggagcagcac cagcaagggg cggcggcgcc ggtggtgatc cggcgtccca     360
ggggccgccc cgccggctcc aagaacaagc ccaagcctcc ggtcatcatc acgcgcgaca     420
gcgccagcgc gctgcgggcg cacgtcctcg aggtcgcctc cgggtgcgac ctcgtcgaca     480
gcgtcgccac gttcgcgcgc cgccgccagg tcggtgtctg cgtgctcagc gccaccggcg     540
ccgtcaccaa cgtctccgtc cggcagcccg gcgcgggccc cggcgccgtc gtcaacctca     600
ccggccgctt cgacatcctc tcgctgtccg gctccttcct cccgccgccg gcgcctcccct    660
ccgccaccgg cctcaccgtc tacgtctccg gcggccaggg gcaggtcgtg ggcggcacgg     720
tcgccggacc gctcatcgcc gtcggccccg tcgtcatcat ggccgcctcg ttcgggaacg     780
ccgcctacga gcgcctcccg ctcgaggacg acgagccgcc gcagcacatg gcgggcggcg     840
gccagtcctc gccgccgccg ccgccgctgc cattaccacc acaccagcag ccgattcttc     900
aagaccatct gccacacaac ctgatgaacg gaatccacct cccggcgac gccgcctacg      960
gctggaccag cggcggcggc ggcggcggcc gcgggcgcc gtactgatca acatcgatct     1020
cgccggagag aaaaaaaatg gaggagaagg atcggagcga ccgtgcatg gtgtaggatg      1080
aattaagcta agagttaatt tcttcttccg cctttgctaa tcatgatgct ctcgtgttgt    1140
ttaatctgtg gc                                                        1152
```

```
<210> SEQ ID NO 32
<211> LENGTH: 328
<212> TYPE: PRT
<213> ORGANISM: Oryza sativa
<220> FEATURE:
<223> OTHER INFORMATION: G3404 polypeptide

<400> SEQUENCE: 32
```

| | | | | | | | | | | | | | | | |
|---|---|---|---|---|---|---|---|---|---|---|---|---|---|---|---|
| Met | Asp | Pro | Val | Thr | Ala | Ala | Ala | His | Gly | Gly | Gly | His | His | His | |
| 1 | | | | 5 | | | | | 10 | | | | | 15 | |
| His | His | His | Phe | Gly | Ala | Pro | Pro | Val | Ala | Ala | Phe | His | His | His | Pro |
| | | | 20 | | | | | 25 | | | | | 30 | | |
| Phe | His | His | Gly | Gly | Gly | Ala | His | Tyr | Pro | Ala | Ala | Phe | Gln | Gln | Phe |
| | | | 35 | | | | | 40 | | | | | 45 | | |
| Gln | Glu | Glu | Gln | Gln | Gln | Leu | Val | Ala | Ala | Ala | Ala | Ala | Gly | Gly | |
| | 50 | | | | | 55 | | | | | 60 | | | | |
| Met | Ala | Lys | Gln | Glu | Leu | Val | Asp | Glu | Ser | Asn | Asn | Thr | Ile | Asn | Ser |
| 65 | | | | | 70 | | | | | 75 | | | | | 80 |
| Gly | Gly | Ser | Asn | Gly | Ser | Gly | Gly | Glu | Glu | Arg | Gln | Gln | Ser | Gly | |
| | | | | 85 | | | | | 90 | | | | | 95 | |
| Glu | Glu | Gln | His | Gln | Gln | Gly | Ala | Ala | Ala | Pro | Val | Val | Ile | Arg | Arg |
| | | | 100 | | | | | 105 | | | | | 110 | | |
| Pro | Arg | Gly | Arg | Pro | Ala | Gly | Ser | Lys | Asn | Lys | Pro | Lys | Pro | Pro | Val |
| | | | 115 | | | | | 120 | | | | | 125 | | |
| Ile | Ile | Thr | Arg | Asp | Ser | Ala | Ser | Ala | Leu | Arg | Ala | His | Val | Leu | Glu |
| | | | 130 | | | | | 135 | | | | | 140 | | |
| Val | Ala | Ser | Gly | Cys | Asp | Leu | Val | Asp | Ser | Val | Ala | Thr | Phe | Ala | Arg |
| 145 | | | | | 150 | | | | | 155 | | | | | 160 |
| Arg | Arg | Gln | Val | Gly | Val | Cys | Val | Leu | Ser | Ala | Thr | Gly | Ala | Val | Thr |
| | | | | 165 | | | | | 170 | | | | | 175 | |
| Asn | Val | Ser | Val | Arg | Gln | Pro | Gly | Ala | Gly | Pro | Gly | Ala | Val | Val | Asn |
| | | | | 180 | | | | | 185 | | | | | 190 | |
| Leu | Thr | Gly | Arg | Phe | Asp | Ile | Leu | Ser | Leu | Ser | Gly | Ser | Phe | Leu | Pro |
| | | | 195 | | | | | 200 | | | | | 205 | | |
| Pro | Pro | Ala | Pro | Pro | Ser | Ala | Thr | Gly | Leu | Thr | Val | Tyr | Val | Ser | Gly |
| | 210 | | | | | 215 | | | | | 220 | | | | |
| Gly | Gln | Gly | Gln | Val | Val | Gly | Gly | Thr | Val | Ala | Gly | Pro | Leu | Ile | Ala |
| 225 | | | | | 230 | | | | | 235 | | | | | 240 |
| Val | Gly | Pro | Val | Val | Ile | Met | Ala | Ala | Ser | Phe | Gly | Asn | Ala | Ala | Tyr |
| | | | | 245 | | | | | 250 | | | | | 255 | |
| Glu | Arg | Leu | Pro | Leu | Glu | Asp | Asp | Glu | Pro | Pro | Gln | His | Met | Ala | Gly |
| | | | 260 | | | | | 265 | | | | | 270 | | |
| Gly | Gly | Gln | Ser | Ser | Pro | Pro | Pro | Pro | Leu | Pro | Leu | Pro | Pro | His | |
| | | 275 | | | | | 280 | | | | | 285 | | | |
| Gln | Gln | Pro | Ile | Leu | Gln | Asp | His | Leu | Pro | His | Asn | Leu | Met | Asn | Gly |
| | | 290 | | | | | 295 | | | | | 300 | | | |
| Ile | His | Leu | Pro | Gly | Asp | Ala | Ala | Tyr | Gly | Trp | Thr | Ser | Gly | Gly | Gly |
| 305 | | | | | 310 | | | | | 315 | | | | | 320 |
| Gly | Gly | Gly | Arg | Ala | Ala | Pro | Tyr | | | | | | | | |
| | | | | 325 | | | | | | | | | | | |

```
<210> SEQ ID NO 33
<211> LENGTH: 987
<212> TYPE: DNA
<213> ORGANISM: Oryza sativa
<220> FEATURE:
```

<223> OTHER INFORMATION: G3407

<400> SEQUENCE: 33

```
tcatcatcat catcacttgc atatcgaatt attaataata tcgaagatgg caggccttga      60
tttgggcacc agctacctcc accaccacca atcactgcat ctccgccacg acgatggcgg     120
cgccggctcc gacgacggcg ccacgacga cctctcgccg gggagcggcg gtggcggcgg     180
gcccagcagc acgccggtg cgccgggat cggcggcggc gaggtcgtcg ctcgccgccc     240
ccgcggccgc ccgccgggct ccaagaacaa gcccaagccg ccggtgatca tcaccaggga     300
gagcgccaac gcgctcaggg cgcatatcct cgaggtagcc gccggttgcg atgtgttcga     360
ggcgctgacg gcgtacgcgc gccgccggca gcgcggggtg tgcgtgctct cggcggcggg     420
gacagtggcg aacgtcacgc tccggcagcc gcagtcggcg cagcccgggc cggcctcgcc     480
ggcggtggcg acgctgcacg gcaggttcga gatactctcc ctcgcgggct ccttcctgcc     540
cccgcccgcg ccgccgggcg ccaccagcct cgccgcgttc ctcgccggcg ggcaggggca     600
ggtcgtcggt ggcagcgtcg ccggcgcgct catcgcggcg gggcccgtcg tcgtcgtcgc     660
cgcgtcgttc agcaacgtgg cgtacgagag gctgccgctc gaggacgcg acgaggtggt     720
ccccccggcg ccggcaggga cgaccaggg cggcggcggc agcggcggca tgccaccatt     780
aggcgttgat ccgtcgggcg cgccgccac cggtgggctc ccgttcttca acatgccgtt     840
cgggatgccg ccaatgccgg tggacggcca cgccggctgg cctggcgccg cgtcgggag     900
gccaccgttc tcatgatgga tggatcccca tattccggcg agcggccggc ggcgaggtgg     960
tcggcaagat tgaagacatg gacatgg                                         987
```

<210> SEQ ID NO 34
<211> LENGTH: 289
<212> TYPE: PRT
<213> ORGANISM: Oryza sativa
<220> FEATURE:
<223> OTHER INFORMATION: G3407 polypeptide

<400> SEQUENCE: 34

```
Met Ala Gly Leu Asp Leu Gly Thr Ser Tyr Leu His His Gln Ser
  1               5                  10                  15

Leu His Leu Arg His Asp Asp Gly Ala Gly Ser Asp Asp Gly Gly
                 20                  25                  30

His Asp Asp Leu Ser Pro Gly Ser Gly Gly Gly Gly Pro Ser Ser
             35                  40                  45

Thr Ala Gly Gly Ala Gly Ile Gly Gly Glu Val Val Ala Arg Arg
         50                  55                  60

Pro Arg Gly Arg Pro Pro Gly Ser Lys Asn Lys Pro Lys Pro Val
 65                  70                  75                  80

Ile Ile Thr Arg Glu Ser Ala Asn Ala Leu Arg Ala His Ile Leu Glu
                 85                  90                  95

Val Ala Ala Gly Cys Asp Val Phe Glu Ala Leu Thr Ala Tyr Ala Arg
                100                 105                 110

Arg Arg Gln Arg Gly Val Cys Val Leu Ser Ala Ala Gly Thr Val Ala
             115                 120                 125

Asn Val Thr Leu Arg Gln Pro Gln Ser Ala Gln Pro Gly Pro Ala Ser
         130                 135                 140

Pro Ala Val Ala Thr Leu His Gly Arg Phe Glu Ile Leu Ser Leu Ala
145                 150                 155                 160

Gly Ser Phe Leu Pro Pro Pro Ala Pro Pro Gly Ala Thr Ser Leu Ala
```

```
                165                 170                 175
Ala Phe Leu Ala Gly Gly Gln Gly Gln Val Val Gly Gly Ser Val Ala
            180                 185                 190
Gly Ala Leu Ile Ala Ala Gly Pro Val Val Val Ala Ala Ser Phe
            195                 200                 205
Ser Asn Val Ala Tyr Glu Arg Leu Pro Leu Glu Asp Gly Asp Glu Val
            210                 215                 220
Val Pro Pro Ala Pro Ala Gly Ser Asp Gln Gly Gly Gly Ser Gly
225                 230                 235                 240
Gly Met Pro Pro Leu Gly Val Asp Pro Ser Gly Ala Ala Thr Gly
            245                 250                 255
Gly Leu Pro Phe Phe Asn Met Pro Phe Gly Met Pro Met Pro Val
            260                 265                 270
Asp Gly His Ala Gly Trp Pro Gly Ala Gly Val Gly Arg Pro Pro Phe
            275                 280                 285
Ser
```

<210> SEQ ID NO 35
<211> LENGTH: 1611
<212> TYPE: DNA
<213> ORGANISM: Glycine max
<220> FEATURE:
<223> OTHER INFORMATION: G3462

<400> SEQUENCE: 35

```
ccacgcgtcc gcactctaag gtacttcccc actgttccca tttatgcccc gtactagtct      60
gacccttttta gtggcataga ttgaggtaca attacaaaag catattaccc gtatcgtatc     120
ctttctgcta caaccacccc gaaacacact gcgttttttt tgtgtcaaac ttcaaccggg     180
gctttcttac ttctcttctc ttcaacttttt tagtgttttt tttttttttt tctcgtgtcg     240
ggtccttgag cttctatttg tttatttatt tccggcagcg agttgagtta attttcgtgt     300
catagtctca attaggtgga tgtgacttgt gtggttaggg tttacatgca aaaacgcatg     360
tgcttcgggt ctaattcatc ctgaaacaag gttttgggac agagatctga atatttcaag     420
ctatctattt tgtttctcta tctagaaggt tttgagaaat caaagatggc gaatagatgg     480
tgggctggga atgtgggaat gataagagag caagagttga tggaaaacag caacaacaac     540
aacaacaaca acaacgctac tactactaca ccgacgacga ggagcaacag caacactaac     600
gcgaacacca acaccaacac gaccgaggaa gaggtgagca gggataacgg agaggaccag     660
aaccaaaacc tcggcagcca cgaagggtcg gagcccggaa gcagcggtcg gaggccacgt     720
ggcaggccag cggggtccaa gaacaagccc aagccgccca tagtcataat ttttttaagc     780
cccaacgcgc tccgaagcca cgtcctggaa atcgcctccg gccgcgatgt cgccgagagc     840
atcgccgcct tcgccaaccg ccgccaccgt ggcgtgtcgg tcctcagcgg gagtggcatt     900
gtagccaacg tcactctccg ccagcccgcc gccccgccg gcgtcataac cctccacggg     960
aggttcgaga tactctccct ctcgggtgcc tttttgccgt cccctcgcc gtccggcgcc    1020
accggactga ccgtctacct agccggcggg caggggcagg ttgtcggcgg caacgtggcg    1080
ggctctctcg tcgcctccgg accggtgatg gtgatcgccg ccactttcgc taatgccact    1140
tatgagaggt tgcctctgga ggatgatcaa ggtgaggagg aaatgcaagt gcagcagcag    1200
cagcagcagc agcaacagca gcagcagcag cagcagcaac aacaatctca aggtttgggg    1260
gaacaggttt caatgcctat gtataatttg cctcctaatt tgctacacaa tggtcagaac    1320
```

```
atgcctcatg atgtgttctg gggagctcca cctcgccctc ctccttcctt ctgatcaccc    1380
ttgccaatat gatcatgtct ttaatctctc actgacttgc gaattaagta ctatgttaat    1440
taatttctca cggttttctc tgcaagcata gctagctagc tagcaaggtt agttattagg    1500
atggttttgt taatttgtgc ttcttagaga ctcgagtcaa gtagatgatg ttcttatctt    1560
taatatactt tgtagtacta ctggtttgtt tattgttttt tttaaaaaaa a              1611
```

```
<210> SEQ ID NO 36
<211> LENGTH: 302
<212> TYPE: PRT
<213> ORGANISM: Glycine max
<220> FEATURE:
<223> OTHER INFORMATION: G3462 polypeptide

<400> SEQUENCE: 36
```

Met Ala Asn Arg Trp Trp Ala Gly Asn Val Gly Met Ile Arg Glu Gln
1               5                   10                  15

Glu Leu Met Glu Asn Ser Asn Asn Asn Asn Asn Asn Asn Asn Ala Thr
            20                  25                  30

Thr Thr Thr Pro Thr Thr Arg Ser Asn Ser Asn Thr Asn Ala Asn Thr
        35                  40                  45

Asn Thr Asn Thr Thr Glu Glu Val Ser Arg Asp Asn Gly Glu Asp
 50                  55                  60

Gln Asn Gln Asn Leu Gly Ser His Glu Gly Ser Glu Pro Gly Ser Ser
65                  70                  75                  80

Gly Arg Arg Pro Arg Gly Arg Pro Ala Gly Ser Lys Asn Lys Pro Lys
                85                  90                  95

Pro Pro Ile Val Ile Ile Phe Leu Ser Pro Asn Ala Leu Arg Ser His
            100                 105                 110

Val Leu Glu Ile Ala Ser Gly Arg Asp Val Ala Glu Ser Ile Ala Ala
        115                 120                 125

Phe Ala Asn Arg Arg His Arg Gly Val Ser Val Leu Ser Gly Ser Gly
    130                 135                 140

Ile Val Ala Asn Val Thr Leu Arg Gln Pro Ala Ala Pro Ala Gly Val
145                 150                 155                 160

Ile Thr Leu His Gly Arg Phe Glu Ile Leu Ser Leu Ser Gly Ala Phe
                165                 170                 175

Leu Pro Ser Pro Ser Pro Ser Gly Ala Thr Gly Leu Thr Val Tyr Leu
            180                 185                 190

Ala Gly Gly Gln Gly Gln Val Val Gly Asn Val Ala Gly Ser Leu
        195                 200                 205

Val Ala Ser Gly Pro Val Met Val Ile Ala Ala Thr Phe Ala Asn Ala
    210                 215                 220

Thr Tyr Glu Arg Leu Pro Leu Glu Asp Asp Gln Gly Glu Glu Glu Met
225                 230                 235                 240

Gln Val Gln Gln Gln Gln Gln Gln Gln Gln Gln Gln Gln Gln Gln
                245                 250                 255

Gln Gln Gln Gln Ser Gln Gly Leu Gly Glu Val Ser Met Pro Met
            260                 265                 270

Tyr Asn Leu Pro Pro Asn Leu Leu His Asn Gly Gln Asn Met Pro His
        275                 280                 285

Asp Val Phe Trp Gly Ala Pro Pro Arg Pro Pro Ser Phe
    290                 295                 300

```
<210> SEQ ID NO 37
```

<211> LENGTH: 1003
<212> TYPE: DNA
<213> ORGANISM: Oryza sativa
<220> FEATURE:
<223> OTHER INFORMATION: G3401

<400> SEQUENCE: 37

```
ggatatatag gccgcaggta gaagctggcg agccggtggt gggacgaggg gcggctcagc      60
ctgccggtga cagccgccga cccatccctc ggccttggca caacgacac caccggcgcc     120
ggtgacgacg acatggcgtc caaggagcca agcggcgacc acgaccacga gatgaacggg     180
accagcgccg gggcggcga gcccaaggac ggcgcggtgg tgaccggccg caaccggcgc     240
ccccgcggac ggccgccggg ctccaagaac aagcccaagc cgcccatctt cgtgacgcgg     300
gacagcccga acgcgctgcg cagccacgtc atggaggtgg ccggcggcgc cgatgtcgcc     360
gagtccatcg cgcacttcgc gcggcggcgg cagcgcggcg tctgcgtgct cagcggggcc     420
ggcaccgtga ccgacgtggc cctgcgccag ccggccgcgc cgagcgccgt ggtggcgctc     480
cgtgggcggt tcgagatcct gtccctgacg gggacgttcc tgccggggcc ggcgccgccg     540
ggctccaccg gctgaccgt gtacctcgcc ggcgggcagg ggcaggtggt gggcggcagc     600
gtggtgggga cgctcaccgc ggcggggccg gtcatggtga tcgcctccac cttcgccaac     660
gccacctacg agaggctgcc gctggatcag gaggaggag aagcagcggc aggcggcatg     720
atggcgccgc cgccactcat ggccggcgcc gccgatccac tacttttcgg cggggaatg     780
cacgacgccg ggcttgctgc atggcaccat gcccgccctc cgccgccgcc gccctactag     840
ctctctagct agattaatta attaagcttc atgaattaaa tccttgctta attaattggc     900
atatatat actcacatga tatatatgat caacaagcta tatatagcta gccagctcga     960
gctaattaat taacaaaagg tgagccaata taatgcaaga tcg                     1003
```

<210> SEQ ID NO 38
<211> LENGTH: 235
<212> TYPE: PRT
<213> ORGANISM: Oryza sativa
<220> FEATURE:
<223> OTHER INFORMATION: G3401 polypeptide

<400> SEQUENCE: 38

```
Met Ala Ser Lys Glu Pro Ser Gly Asp His Asp His Glu Met Asn Gly
  1               5                  10                  15

Thr Ser Ala Gly Gly Gly Glu Pro Lys Asp Gly Ala Val Val Thr Gly
             20                  25                  30

Arg Asn Arg Arg Pro Arg Gly Arg Pro Pro Gly Ser Lys Asn Lys Pro
         35                  40                  45

Lys Pro Pro Ile Phe Val Thr Arg Asp Ser Pro Asn Ala Leu Arg Ser
     50                  55                  60

His Val Met Glu Val Ala Gly Gly Ala Asp Val Ala Glu Ser Ile Ala
 65                  70                  75                  80

His Phe Ala Arg Arg Arg Gln Arg Gly Val Cys Val Leu Ser Gly Ala
                 85                  90                  95

Gly Thr Val Thr Asp Val Ala Leu Arg Gln Pro Ala Ala Pro Ser Ala
            100                 105                 110

Val Val Ala Leu Arg Gly Arg Phe Glu Ile Leu Ser Leu Thr Gly Thr
        115                 120                 125

Phe Leu Pro Gly Pro Ala Pro Gly Ser Thr Gly Leu Thr Val Tyr
    130                 135                 140
```

```
Leu Ala Gly Gly Gln Gly Gln Val Val Gly Gly Ser Val Val Gly Thr
145                 150                 155                 160

Leu Thr Ala Ala Gly Pro Val Met Val Ile Ala Ser Thr Phe Ala Asn
                165                 170                 175

Ala Thr Tyr Glu Arg Leu Pro Leu Asp Gln Glu Glu Glu Ala Ala
            180                 185                 190

Ala Gly Gly Met Met Ala Pro Pro Leu Met Ala Gly Ala Ala Asp
        195                 200                 205

Pro Leu Leu Phe Gly Gly Met His Asp Ala Gly Leu Ala Ala Trp
    210                 215                 220

His His Ala Arg Pro Pro Pro Pro Pro Tyr
225                 230                 235

<210> SEQ ID NO 39
<211> LENGTH: 803
<212> TYPE: DNA
<213> ORGANISM: Oryza sativa
<220> FEATURE:
<223> OTHER INFORMATION: G3556

<400> SEQUENCE: 39
tcgacgggat ggggagcatc gacggccact cgctgcagca gcatcagggg tactcccacg      60
gcggcggcgc ggggagggagc aacgaggagg aggaggcgtc gccgccgccc ggcggtggct    120
cggctacggg gtcggcgggc cgccggccga gggggaggcc gccgggctcc aagaacaagc    180
cgaagccgcc cgtcgtggtg acgcgggaga gccccaacgc gatgcgttcc cacgtgctgg    240
agatcgccag cggcgccgac atcgtcgagg ccatcgcggg cttctcccgc cgcaggcagc    300
gcggcgtctc cgtgctcagc gggagcggcg ccgtcaccaa cgtcacgctc cggcagcccg    360
cggggactgg ggccgccgcc gtcgcgctgc ggggaggtt cgagatattg tccatgtctg    420
gcgccttcct cccggcgccg gcgccgcag gggccacggg gctcgccgtg tacctcgccg    480
gcgggcaggg gcaggtggtg ggtgggagcg tcatggggga gctgatcgcg tcgggccccg    540
tcatggtgat cgcggccacg ttcggcaacg ccacgtacga gaggctgccg ctggaccagg    600
aaggcgagga gggcgccgtg ctgtccgggt cggagggcgc cgccgcgcag atggagcagc    660
agagcagcgg aggcgccgtc gtgccccccgc cgatgtacgc cgccgtccag cagacgccgc    720
cgcacgacat gttcgggcag tgggggcatg cagcggtggc tcggccgccg ccgacatcgt    780
tctagcactg gcaccggtta att                                           803

<210> SEQ ID NO 40
<211> LENGTH: 258
<212> TYPE: PRT
<213> ORGANISM: Oryza sativa
<220> FEATURE:
<223> OTHER INFORMATION: G3556 polypeptide

<400> SEQUENCE: 40

Met Gly Ser Ile Asp Gly His Ser Leu Gln Gln His Gln Gly Tyr Ser
1               5                   10                  15

His Gly Gly Gly Ala Gly Gly Ser Asn Glu Glu Glu Ala Ser Pro
            20                  25                  30

Pro Pro Gly Gly Gly Ser Ala Thr Gly Ser Ala Gly Arg Arg Pro Arg
        35                  40                  45

Gly Arg Pro Pro Gly Ser Lys Asn Lys Pro Lys Pro Pro Val Val Val
    50                  55                  60

Thr Arg Glu Ser Pro Asn Ala Met Arg Ser His Val Leu Glu Ile Ala
```

```
                65                  70                  75                  80
Ser Gly Ala Asp Ile Val Glu Ala Ile Ala Gly Phe Ser Arg Arg Arg
                    85                  90                  95

Gln Arg Gly Val Ser Val Leu Ser Gly Ser Gly Ala Val Thr Asn Val
            100                 105                 110

Thr Leu Arg Gln Pro Ala Gly Thr Gly Ala Ala Val Ala Leu Arg
        115                 120                 125

Gly Arg Phe Glu Ile Leu Ser Met Ser Gly Ala Phe Leu Pro Ala Pro
    130                 135                 140

Ala Pro Pro Gly Ala Thr Gly Leu Ala Val Tyr Leu Ala Gly Gly Gln
145                 150                 155                 160

Gly Gln Val Val Gly Gly Ser Val Met Gly Glu Leu Ile Ala Ser Gly
                165                 170                 175

Pro Val Met Val Ile Ala Ala Thr Phe Gly Asn Ala Thr Tyr Glu Arg
            180                 185                 190

Leu Pro Leu Asp Gln Glu Gly Glu Glu Gly Ala Val Leu Ser Gly Ser
        195                 200                 205

Glu Gly Ala Ala Ala Gln Met Glu Gln Gln Ser Ser Gly Gly Ala Val
    210                 215                 220

Val Pro Pro Pro Met Tyr Ala Ala Val Gln Gln Thr Pro Pro His Asp
225                 230                 235                 240

Met Phe Gly Gln Trp Gly His Ala Ala Val Ala Arg Pro Pro Thr
                245                 250                 255

Ser Phe

<210> SEQ ID NO 41
<211> LENGTH: 1116
<212> TYPE: DNA
<213> ORGANISM: Arabidopsis thaliana
<220> FEATURE:
<223> OTHER INFORMATION: G1069

<400> SEQUENCE: 41
ttggaaccct agaggccttt caagcaaatc atcagggtaa caatttcttg atctttcttt      60
ttagcgaatt tccagttttt ggtcaatcat ggcaaaccct tggtggacga accagagtgg     120
tttagcgggc atggtggacc attcggtctc tcaggccat caccaaaacc atcaccacca     180
aagtcttctt accaaaggag atcttggaat agccatgaat cagagccaag acaacgacca     240
agacgaagaa gatgatccta gagaaggagc cgttgaggtg gtcaaccgta gaccaagagg     300
tagaccacca ggatccaaaa acaaacccaa agctccaatc tttgtgacaa gagacagccc     360
caacgcactc cgtagccatg tcttggagat ctccgacggc agtgacgtcg ccgacacaat     420
cgctcacttc tcaagacgca ggcaacgcgg cgtttgcgtt ctcagcggga caggctcagt     480
cgctaacgtc accctccgcc aagccgccgc accaggaggt gtggtctctc tccaaggcag     540
gtttgaaatc ttatctttaa ccggtgcttt cctccctgga ccttccccac ccgggtcaac     600
cggtttaacg gtttacttag ccggggtcca gggtcaggtc gttggaggta gcgttgtagg     660
cccactctta gccataggggt cggtcatggt gattgctgct actttctcta acgctactta     720
tgagagattg cccatggaag aagaggaaga cggtggcggc tcaagacaga ttcacggagg     780
cggtgactca ccgcccagaa tcggtagtaa cctgcctgat ctatcaggga tggccgggcc     840 aggctcacaat atgccgccgc atctgattcc aaatggggct ggtcagctag ggcacgaacc     900
atatacatgg gtccacgcaa gaccaccttta ctgactcagt gagccatttc tatatataat     960
```

```
ggtctatata aataaatata tagatgaata taagcaagca atttgaggta gtctattaca    1020
aagcttttgc tctggttgga aaataaata agtatcaaag ctttgtttgt tcttaatgga    1080
aatatagagc ttgggaaggt agaaagagac gacatt                             1116
```

<210> SEQ ID NO 42
<211> LENGTH: 281
<212> TYPE: PRT
<213> ORGANISM: Arabidopsis thaliana
<220> FEATURE:
<223> OTHER INFORMATION: G1069 polypeptide

<400> SEQUENCE: 42

```
Met Ala Asn Pro Trp Trp Thr Asn Gln Ser Gly Leu Ala Gly Met Val
1               5                   10                  15

Asp His Ser Val Ser Ser Gly His His Gln Asn His His His Gln Ser
                20                  25                  30

Leu Leu Thr Lys Gly Asp Leu Gly Ile Ala Met Asn Gln Ser Gln Asp
            35                  40                  45

Asn Asp Gln Asp Glu Glu Asp Asp Pro Arg Glu Gly Ala Val Glu Val
50                  55                  60

Val Asn Arg Arg Pro Arg Gly Arg Pro Pro Gly Ser Lys Asn Lys Pro
65                  70                  75                  80

Lys Ala Pro Ile Phe Val Thr Arg Asp Ser Pro Asn Ala Leu Arg Ser
                85                  90                  95

His Val Leu Glu Ile Ser Asp Gly Ser Asp Val Ala Asp Thr Ile Ala
            100                 105                 110

His Phe Ser Arg Arg Arg Gln Arg Gly Val Cys Val Leu Ser Gly Thr
        115                 120                 125

Gly Ser Val Ala Asn Val Thr Leu Arg Gln Ala Ala Ala Pro Gly Gly
130                 135                 140

Val Val Ser Leu Gln Gly Arg Phe Glu Ile Leu Ser Leu Thr Gly Ala
145                 150                 155                 160

Phe Leu Pro Gly Pro Ser Pro Pro Gly Ser Thr Gly Leu Thr Val Tyr
                165                 170                 175

Leu Ala Gly Val Gln Gly Gln Val Val Gly Gly Ser Val Val Gly Pro
            180                 185                 190

Leu Leu Ala Ile Gly Ser Val Met Val Ile Ala Ala Thr Phe Ser Asn
        195                 200                 205

Ala Thr Tyr Glu Arg Leu Pro Met Glu Glu Glu Asp Gly Gly Gly
210                 215                 220

Ser Arg Gln Ile His Gly Gly Asp Ser Pro Pro Arg Ile Gly Ser
225                 230                 235                 240

Asn Leu Pro Asp Leu Ser Gly Met Ala Gly Pro Gly Tyr Asn Met Pro
                245                 250                 255

Pro His Leu Ile Pro Asn Gly Ala Gly Gln Leu Gly His Glu Pro Tyr
            260                 265                 270

Thr Trp Val His Ala Arg Pro Pro Tyr
        275                 280
```

<210> SEQ ID NO 43
<211> LENGTH: 1130
<212> TYPE: DNA
<213> ORGANISM: Arabidopsis thaliana
<220> FEATURE:
<223> OTHER INFORMATION: G1945

<400> SEQUENCE: 43

-continued

```
atttcccaaa gggatttacg aaaagtccct ctcctctatc atctctttat tcaccccata      60
ccaacaacct ctacatcttc ttcttcttct tcctcctctt ttattttctt tttaaatcat     120
ttacacaaaa atccaaagac aaatctgaaa tctctaataa acaaatccat aaaataagaa     180
aaacaaagat gaaaggtgaa tacagagagc aaaagagtaa cgaaatgttt ccaagcttc      240 ctcatcatca acaacaacag caacaacaac aacaacaaca ctctcttacc tctcacttcc     300
acctctcctc caccgtaacc cccaccgtcg atgactcctc catcgaagtg gtccgacgtc     360
cacgtggcag accaccaggt tccaaaaaca aacctaaacc accgtcttc gtcacacgtg      420 acaccgaccc tcctatgagt ccttacatcc tcgaagttcc ttcaggaaac gacgtcgtcg     480
aagccatcaa ccgtttctgc cgccgtaaat ccatcggagt ctgcgtcctt agtggctctg     540
gctctgtagc taacgtcact ttacgtcagc catcaccggc agctcttggc tctaccataa     600
ctttccatgg aaagtttgat ctcctctccg tctccgcaac gtttctccct cctccgcctc     660
gtacttcctt gtctcctccc gtttctaact tcttcaccgt ctctctcgct ggacctcaag     720
gacaaatcat cggagggttc gtcgctggtc cacttatttc ggcaggaaca gtttacgtca     780
tcgccgcaag tttcaacaac ccttcttatc accggttacc ggcggaagaa gagcaaaaac     840
actcggcggg gacaggggaa agagagggac aatctccgcc ggtctctggt ggcggtgaag     900
agtcaggaca gatggcggga gtggaggag agtcgtgtgg ggtatcaatg tacagttgcc      960
acatgggtgg ctctgatgtt atttgggccc ctacagccag agctccaccg ccatactaac    1020
caatccttct ttcacaaatc tctttctttc tttttttgtt ttttttttgtt ttgggttagg    1080 atgaatcaag aaactagggt ttttttttttt tttttttaaa aaaaaaaaa                1130
```

<210> SEQ ID NO 44
<211> LENGTH: 276
<212> TYPE: PRT
<213> ORGANISM: Arabidopsis thaliana
<220> FEATURE:
<223> OTHER INFORMATION: G1945 polypeptide

<400> SEQUENCE: 44

```
Met Lys Gly Glu Tyr Arg Glu Gln Lys Ser Asn Glu Met Phe Ser Lys
1               5                   10                  15

Leu Pro His His Gln Gln Gln Gln Gln Gln Gln Gln Gln His Ser
            20                  25                  30

Leu Thr Ser His Phe His Leu Ser Ser Val Thr Pro Thr Val Asp
        35                  40                  45

Asp Ser Ser Ile Glu Val Val Arg Arg Pro Gly Arg Pro Gly
    50                  55                  60

Ser Lys Asn Lys Pro Lys Pro Val Phe Val Thr Arg Asp Thr Asp
65                  70                  75                  80

Pro Pro Met Ser Pro Tyr Ile Leu Glu Val Pro Ser Gly Asn Asp Val
                85                  90                  95

Val Glu Ala Ile Asn Arg Phe Cys Arg Arg Lys Ser Ile Gly Val Cys
            100                 105                 110

Val Leu Ser Gly Ser Gly Ser Val Ala Asn Val Thr Leu Arg Gln Pro
        115                 120                 125

Ser Pro Ala Ala Leu Gly Ser Thr Ile Thr Phe His Gly Lys Phe Asp
    130                 135                 140

Leu Leu Ser Val Ser Ala Thr Phe Leu Pro Pro Pro Arg Thr Ser
145                 150                 155                 160
```

-continued

```
Leu Ser Pro Pro Val Ser Asn Phe Phe Thr Val Ser Leu Ala Gly Pro
            165                 170                 175

Gln Gly Gln Ile Ile Gly Gly Phe Val Ala Gly Pro Leu Ile Ser Ala
        180                 185                 190

Gly Thr Val Tyr Val Ile Ala Ala Ser Phe Asn Asn Pro Ser Tyr His
    195                 200                 205

Arg Leu Pro Ala Glu Glu Gln Lys His Ser Ala Gly Thr Gly Glu
210                 215                 220

Arg Glu Gly Gln Ser Pro Val Ser Gly Gly Glu Glu Ser Gly
225                 230                 235                 240

Gln Met Ala Gly Ser Gly Glu Ser Cys Gly Val Ser Met Tyr Ser
            245                 250                 255

Cys His Met Gly Gly Ser Asp Val Ile Trp Ala Pro Thr Ala Arg Ala
            260                 265                 270

Pro Pro Pro Tyr
        275
```

<210> SEQ ID NO 45
<211> LENGTH: 1050
<212> TYPE: DNA
<213> ORGANISM: Arabidopsis thaliana
<220> FEATURE:
<223> OTHER INFORMATION: G2155

<400> SEQUENCE: 45

```
ctcatatata ccaaccaaac ctctctctgc atctttatta acacaaaatt ccaaaagatt      60
aaatgttgtc gaagctccct acacagcgac acttgcacct ctctccctcc tctccctcca     120
tggaaaccgt cgggcgtcca cgtggcagac ctcgaggttc caaaaacaaa cctaaagctc     180
caatctttgt caccattgac cctcctatga gtccttacat cctcgaagtg ccatccggaa     240
acgatgtcgt tgaagcccta aaccgtttct gccgcggtaa agccatcggc ttttgcgtcc     300
tcagtggctc aggctccgtt gctgatgtca ctttgcgtca gccttctccg gcagctcctg     360
gctcaaccat tactttccac ggaaagttcg atcttctctc tgtctccgcc actttcctcc     420
ctcctctacc tcctacctcc ttgtcccctc ccgtctccaa tttcttcacc gtctctctcg     480
ccggacctca ggggaaagtc atcggtggat tcgtcgctgg tcctctcgtt gccgccggaa     540
ctgtttactt cgtcgccact agtttcaaga acccttccta tcaccggtta cctgctacgg     600
aggaagagca agaaaactcg gcggaagggg aagaggaggg acaatcgccg ccggtctctg     660
gaggtggtgg agagtcgatg tacgtgggtg gctctgatgt catttgggat cccaacgcca     720
aagctccatc gccgtactga ccacaaatcc atctcgttca aactagggtt tcttcttctt     780
tagatcatca agaatcaaca aaaagattgc atttttagat tctttgtaat atcataattg     840
actcactctt taatctctct atcacttctt ctttagcttt ttctgcagtg tcaaacttca     900
catatttgta gtttgatttg actatcccca agttttgtat tttatcatac aaattttttgc    960
ctgtctctaa tggttgtttt ttcgtttgta taatcttatg cattgtttat tggagctcca    1020
gagattgaat gtataatata atggtttaat                                     1050
```

<210> SEQ ID NO 46
<211> LENGTH: 225
<212> TYPE: PRT
<213> ORGANISM: Arabidopsis thaliana
<220> FEATURE:
<223> OTHER INFORMATION: G2155 polypeptide

<400> SEQUENCE: 46

```
Met Leu Ser Lys Leu Pro Thr Gln Arg His Leu His Leu Ser Pro Ser
1               5                   10                  15

Ser Pro Ser Met Glu Thr Val Gly Arg Pro Arg Gly Arg Pro Arg Gly
            20                  25                  30

Ser Lys Asn Lys Pro Lys Ala Pro Ile Phe Val Thr Ile Asp Pro Pro
        35                  40                  45

Met Ser Pro Tyr Ile Leu Glu Val Pro Ser Gly Asn Asp Val Val Glu
    50                  55                  60

Ala Leu Asn Arg Phe Cys Arg Gly Lys Ala Ile Gly Phe Cys Val Leu
65                  70                  75                  80

Ser Gly Ser Gly Ser Val Ala Asp Val Thr Leu Arg Gln Pro Ser Pro
                85                  90                  95

Ala Ala Pro Gly Ser Thr Ile Thr Phe His Gly Lys Phe Asp Leu Leu
            100                 105                 110

Ser Val Ser Ala Thr Phe Leu Pro Pro Leu Pro Pro Thr Ser Leu Ser
        115                 120                 125

Pro Pro Val Ser Asn Phe Phe Thr Val Ser Leu Ala Gly Pro Gln Gly
    130                 135                 140

Lys Val Ile Gly Gly Phe Val Ala Gly Pro Leu Val Ala Ala Gly Thr
145                 150                 155                 160

Val Tyr Phe Val Ala Thr Ser Phe Lys Asn Pro Ser Tyr His Arg Leu
                165                 170                 175

Pro Ala Thr Glu Glu Glu Gln Arg Asn Ser Ala Glu Gly Glu Glu
            180                 185                 190

Gly Gln Ser Pro Pro Val Ser Gly Gly Gly Glu Ser Met Tyr Val
            195                 200                 205

Gly Gly Ser Asp Val Ile Trp Asp Pro Asn Ala Lys Ala Pro Ser Pro
    210                 215                 220

Tyr
225

<210> SEQ ID NO 47
<211> LENGTH: 1295
<212> TYPE: DNA
<213> ORGANISM: Arabidopsis thaliana
<220> FEATURE:
<223> OTHER INFORMATION: G1070

<400> SEQUENCE: 47
tcgaccagct tggatttcgt tgttcatcat tactactctc tttcttcttc tagctagcta      60
gttttgacag caaataaga agcaaaaaaa aggtcaacta aaaaagatct gttcttagat      120
cactctcttc ttcttttttt gatccaattc caccattgaa tcatagatca tggatccagt      180
acaatctcat ggatcacaaa gctctctacc tcctcctttc cacgcaagag actttcaatt      240
acatcttcaa caacagcaac aagagttctt cctccaccat caccagcaac aagaaaacca      300
aaccgatggt gaccaacaag gaggatcagg aggaaaccga caaatcaaga tggatcgtga      360
agagacaagc gacaacatag acaacatagc taacaacagc ggtagtgaag gtaaagacat      420
agatatacac ggtggttcag gagaaggagg tggtggctcc ggaggagatc atcagatgac      480
aagaagacca agaggaagac cagcgggatc caagaacaaa ccaaaccacc gattatcat      540 cacacgggac agcgcaaacg cgcttagaac ccacgtgatg gagatcggag atggctgcga      600
cttagtcgaa agcgttgcca cttttgcacg aagacgccaa cgcggcgttt gcgttatgag      660
cggtactgga aatgttacta acgtcactat acgtcagcct ggatctcatc cttctcctgg      720
```

-continued

```
ctcggtagtt agtcttcacg gaaggttcga gattctatct ctctcaggat ctttttctccc      780
tcctccggct cctcctacag ccaccggatt gagtgtttac ctcgctggag gacaaggaca      840
ggtggttgga ggaagcgtag ttggtccgtt gttatgtgct ggtcctgtcg ttgtcatggc      900
tgcgtctttt agcaatgcgg cgtacgaaag gttgccttta gaggaagatg agatgcagac      960
gccggttcat ggcggaggag gaggaggatc attggagtcg ccgccaatga tgggacaaca     1020
actgcaacat cagcaacaag ctatgtcagg tcatcaaggg ttaccaccta atcttcttgg     1080
ttcggttcag ttgcagcagc aacatgatca gtcttattgg tcaacgggac gaccaccgta     1140
ttgatcaaat atacacacac actcataatc gttgctagct agctaacgat gaatcatgag     1200
tttagtggat atatatatga ttaaaagagg ttagcttatg aacattaata agagtttgga     1260
ttctatcgag cttcattatg tttgggtcat cgttc                                1295
```

<210> SEQ ID NO 48
<211> LENGTH: 324
<212> TYPE: PRT
<213> ORGANISM: Arabidopsis thaliana
<220> FEATURE:
<223> OTHER INFORMATION: G1070 polypeptide

<400> SEQUENCE: 48

```
Met Asp Pro Val Gln Ser His Gly Ser Gln Ser Ser Leu Pro Pro Pro
1               5                   10                  15

Phe His Ala Arg Asp Phe Gln Leu His Leu Gln Gln Gln Gln Gln Glu
            20                  25                  30

Phe Phe Leu His His His Gln Gln Arg Asn Gln Thr Asp Gly Asp
        35                  40                  45

Gln Gln Gly Gly Ser Gly Asn Arg Gln Ile Lys Met Asp Arg Glu
    50                  55                  60

Glu Thr Ser Asp Asn Ile Asp Asn Ile Ala Asn Asn Ser Gly Ser Glu
65                  70                  75                  80

Gly Lys Asp Ile Asp Ile His Gly Gly Ser Glu Gly Gly Gly
                85                  90                  95

Ser Gly Gly Asp His Gln Met Thr Arg Arg Pro Arg Gly Arg Pro Ala
            100                 105                 110

Gly Ser Lys Asn Lys Pro Lys Pro Pro Ile Ile Thr Arg Asp Ser
        115                 120                 125

Ala Asn Ala Leu Arg Thr His Val Met Glu Ile Gly Asp Gly Cys Asp
    130                 135                 140

Leu Val Glu Ser Val Ala Thr Phe Ala Arg Arg Gln Arg Gly Val
145                 150                 155                 160

Cys Val Met Ser Gly Thr Gly Asn Val Thr Asn Val Thr Ile Arg Gln
                165                 170                 175

Pro Gly Ser His Pro Ser Pro Gly Ser Val Val Ser Leu His Gly Arg
            180                 185                 190

Phe Glu Ile Leu Ser Leu Ser Gly Ser Phe Leu Pro Pro Ala Pro
        195                 200                 205

Pro Thr Ala Thr Gly Leu Ser Val Tyr Leu Ala Gly Gly Gln Gly Gln
    210                 215                 220

Val Val Gly Gly Ser Val Val Gly Pro Leu Leu Cys Ala Gly Pro Val
225                 230                 235                 240

Val Val Met Ala Ala Ser Phe Ser Asn Ala Ala Tyr Glu Arg Leu Pro
                245                 250                 255
```

-continued

```
Leu Glu Glu Asp Glu Met Gln Thr Pro Val His Gly Gly Gly Gly
            260                 265                 270
Gly Ser Leu Glu Ser Pro Pro Met Met Gly Gln Gln Leu Gln His Gln
        275                 280                 285
Gln Gln Ala Met Ser Gly His Gln Gly Leu Pro Asn Leu Leu Gly
    290                 295                 300
Ser Val Gln Leu Gln Gln Gln His Asp Gln Ser Tyr Trp Ser Thr Gly
305                 310                 315                 320
Arg Pro Pro Tyr

<210> SEQ ID NO 49
<211> LENGTH: 1020
<212> TYPE: DNA
<213> ORGANISM: Arabidopsis thaliana
<220> FEATURE:
<223> OTHER INFORMATION: G2657

<400> SEQUENCE: 49
tcaatacggt ggccgacccg tagaccaata ctgctgatca ttctgttgtg gcggtggcaa      60
ctgaaccgaa ccaagaagat tcggtggtag tccttgagcc gccgccatag ctgccatagc     120
ttgttgctgt cccatcatcg ggggagatcc cattccacca ccacctcctc ctcctccacc     180
gcctccttga actggcgtct gcatctcatc ttcttccaaa ggcagccttt cgtacgccgc     240
attgctaaaa gaagccgcca taaccaccac aggacccgaa cacaacaaag gtcccaccac     300
actacctcca cgacctgcc cttgtcctcc ggctaggtaa acgcttagtc cggtggctgc      360
aggcggcgca ggcggaggca agaaagatcc cgaaagagag aggatttcaa accggccgtg     420
aaggctaacc accgagccag gtggcgatcc aggctgacgt atagtgacgt tagtaacgct     480
tcctgtaccg ctcataacgc aaacgcctct ttggcggcgt ctagcgaacg tagccataca     540
gtcaactatg tcacatccgt ctcctatctc catgacgtga gttcgaagcg cgtttgcgct     600
gtctcttgtt atgattattg gagctttagg tttgttcttg gatcctgctg gtcttcctct     660
tggccttctt gtcatctgtt ctccacttcc tccaccaccg cttcctcctt ctcctccgtg     720
taaactcatc tctttacctt cgctaccgct gttggtatta gcgatgttgt ccatgttatc     780
gcttgtctct tcgcgatcca tcttgataga tctattcaat attgaccctc cttgctgctc     840
gtgatcttga tcaaggtttc tttgtggttg ctgatgatgg tggagaaaga actgttgttg     900
ttgttgttgt tgatgttgtt gttgatgttg ttgttgttgt tgaagatgta attggaaatc     960
tctagcatgg aaaggaggag gaagagagct ttgtgatcca tgagattgaa ctggatccat    1020

<210> SEQ ID NO 50
<211> LENGTH: 339
<212> TYPE: PRT
<213> ORGANISM: Arabidopsis thaliana
<220> FEATURE:
<223> OTHER INFORMATION: G2657 polypeptide

<400> SEQUENCE: 50

Met Asp Pro Val Gln Ser His Gly Ser Gln Ser Ser Leu Pro Pro Pro
1               5                   10                  15
Phe His Ala Arg Asp Phe Gln Leu His Leu Gln Gln Gln Gln Gln His
            20                  25                  30
Gln Gln Gln His Gln Gln Gln Gln Gln Gln Phe Phe Leu His His
        35                  40                  45
His Gln Gln Pro Gln Arg Asn Leu Asp Gln Asp His Glu Gln Gln Gly
    50                  55                  60
```

```
Gly Ser Ile Leu Asn Arg Ser Ile Lys Met Asp Arg Glu Glu Thr Ser
 65                  70                  75                  80

Asp Asn Met Asp Asn Ile Ala Asn Thr Asn Ser Gly Ser Glu Gly Lys
                 85                  90                  95

Glu Met Ser Leu His Gly Gly Glu Gly Gly Ser Gly Gly Gly Gly Ser
            100                 105                 110

Gly Glu Gln Met Thr Arg Arg Pro Arg Gly Arg Pro Ala Gly Ser Lys
        115                 120                 125

Asn Lys Pro Lys Ala Pro Ile Ile Ile Thr Arg Asp Ser Ala Asn Ala
130                 135                 140

Leu Arg Thr His Val Met Glu Ile Gly Asp Gly Cys Asp Ile Val Asp
145                 150                 155                 160

Cys Met Ala Thr Phe Ala Arg Arg Arg Gln Arg Gly Val Cys Val Met
                165                 170                 175

Ser Gly Thr Gly Ser Val Thr Asn Val Thr Ile Arg Gln Pro Gly Ser
            180                 185                 190

Pro Pro Gly Ser Val Val Ser Leu His Gly Arg Phe Glu Ile Leu Ser
        195                 200                 205

Leu Ser Gly Ser Phe Leu Pro Pro Ala Pro Pro Ala Ala Thr Gly
210                 215                 220

Leu Ser Val Tyr Leu Ala Gly Gly Gln Gly Gln Val Val Gly Gly Ser
225                 230                 235                 240

Val Val Gly Pro Leu Leu Cys Ser Gly Pro Val Val Met Ala Ala
                245                 250                 255

Ser Phe Ser Asn Ala Ala Tyr Glu Arg Leu Pro Leu Glu Glu Asp Glu
                260                 265                 270

Met Gln Thr Pro Val Gln Gly Gly Gly Gly Gly Gly Gly Gly Gly Gly
            275                 280                 285

Gly Met Gly Ser Pro Met Met Gly Gln Gln Ala Met Ala Ala
        290                 295                 300

Met Ala Ala Ala Gln Gly Leu Pro Pro Asn Leu Leu Gly Ser Val Gln
305                 310                 315                 320

Leu Pro Pro Pro Gln Gln Asn Asp Gln Gln Tyr Trp Ser Thr Gly Arg
                325                 330                 335

Pro Pro Tyr

<210> SEQ ID NO 51
<211> LENGTH: 1084
<212> TYPE: DNA
<213> ORGANISM: Arabidopsis thaliana
<220> FEATURE:
<223> OTHER INFORMATION: G1075

<400> SEQUENCE: 51
tttgtgtttg gtgctggcat ggctggtctc gatctaggca caacttctcg ctacgtccac      60
aacgtcgatg gtggcggcgg cggacagttc accaccgaca accaccacga agatgacggt     120
ggcgctggag gaaaccacca tcatcaccat cataatcata atcaccatca aggtttagat     180
ttaatagctt ctaatgataa ctctggacta ggcggcggtg gaggaggagg gagcggtgac     240
ctcgtcatgc gtcggccacg tggccgtcca gctggatcga agaacaaacc gaagccgccg     300
gtgattgtca cgcgcgagag cgcaaacact cttagggctc acattcttga agttggaagt     360
ggctgcgacg ttttcgaatg tatctccact tacgctcgtc ggagacagcg cgggatttgc     420 gtttatccg  ggacgggaac cgtcactaac gtcagcatcc gtcagcctac ggcggccgga     480
```

-continued

```
gctgttgtga ctctgcgggg tactttttgag attctttccc tctccggatc ttttcttccg      540
ccacctgctc ctccaggggc gactagcttg acgatattcc tcgctggagc tcaaggacag      600
gtcgtcggag gtaacgtagt tggtgagtta atggcggcgg ggccggtaat ggtcatggca      660
gcgtctttta caaacgtggc ttacgaaagg ttgcctttgg acgagcatga ggagcacttg      720
caaagtggcg gcggcggagg tggagggaat atgtactcgg aagccactgg cggtggcgga      780
gggttgcctt tctttaattt gccgatgagt atgcctcaga ttggagttga agttggcag       840 gggaatcacg ccggcgccgg tagggctccg ttttagcaat ttaagaaact ttaattgttt      900
tttccacttt tttgtttttc tccgaatttt atgaaattat gatttaagaa aaaaaacgat      960
attgttcatg tattgaccct cttactgcat ggtttcttct attgggttaa ttggctagct     1020
cataagaatt gtttaatttg gttattgtca tcaaatttgc ccacatataa agcttctagc     1080
aaat                                                                  1084
```

<210> SEQ ID NO 52
<211> LENGTH: 285
<212> TYPE: PRT
<213> ORGANISM: Arabidopsis thaliana
<220> FEATURE:
<223> OTHER INFORMATION: G1075 polypeptide

<400> SEQUENCE: 52

```
Met Ala Gly Leu Asp Leu Gly Thr Thr Ser Arg Tyr Val His Asn Val
1               5                  10                  15

Asp Gly Gly Gly Gly Gly Gln Phe Thr Thr Asp Asn His His Glu Asp
                20                  25                  30

Asp Gly Gly Ala Gly Gly Asn His His His His His Asn His Asn
            35                  40                  45

His His Gln Gly Leu Asp Leu Ile Ala Ser Asn Asp Asn Ser Gly Leu
        50                  55                  60

Gly Gly Gly Gly Gly Gly Ser Gly Asp Leu Val Met Arg Arg Pro
65                  70                  75                  80

Arg Gly Arg Pro Ala Gly Ser Lys Asn Lys Pro Lys Pro Pro Val Ile
                85                  90                  95

Val Thr Arg Glu Ser Ala Asn Thr Leu Arg Ala His Ile Leu Glu Val
                100                 105                 110

Gly Ser Gly Cys Asp Val Phe Glu Cys Ile Ser Thr Tyr Ala Arg Arg
            115                 120                 125

Arg Gln Arg Gly Ile Cys Val Leu Ser Gly Thr Gly Thr Val Thr Asn
        130                 135                 140

Val Ser Ile Arg Gln Pro Thr Ala Ala Gly Ala Val Val Thr Leu Arg
145                 150                 155                 160

Gly Thr Phe Glu Ile Leu Ser Leu Ser Gly Ser Phe Leu Pro Pro Pro
                165                 170                 175

Ala Pro Pro Gly Ala Thr Ser Leu Thr Ile Phe Leu Ala Gly Ala Gln
                180                 185                 190

Gly Gln Val Val Gly Gly Asn Val Val Gly Glu Leu Met Ala Ala Gly
            195                 200                 205

Pro Val Met Val Met Ala Ala Ser Phe Thr Asn Val Ala Tyr Glu Arg
        210                 215                 220

Leu Pro Leu Asp Glu His Glu Glu His Leu Gln Ser Gly Gly Gly Gly
225                 230                 235                 240

Gly Gly Gly Asn Met Tyr Ser Glu Ala Thr Gly Gly Gly Gly Gly Leu
```

```
                    245                 250                 255
Pro Phe Phe Asn Leu Pro Met Ser Met Pro Gln Ile Gly Val Glu Ser
            260                 265                 270

Trp Gln Gly Asn His Ala Gly Ala Gly Arg Ala Pro Phe
        275                 280                 285

<210> SEQ ID NO 53
<211> LENGTH: 1342
<212> TYPE: DNA
<213> ORGANISM: Arabidopsis thaliana
<220> FEATURE:
<223> OTHER INFORMATION: G1076

<400> SEQUENCE: 53
attttagtct tcctataact tcttctcaat cctctctcat atcttttttc ttagtttaaa      60
tttcaataaa atagaaaaaa acatatacaa atctacagag aagagaagct ttattttaat     120
cttgtgtgtg tgtgtgtgtt ttatataatt tttattttt ttcaaattaa aatctcttct     180
ttgcttttga tgtgggcatg gctggtcttg atctaggcac agcttttcgt tacgttaatc     240
accagctcca tcgtcccgat ctccaccttc accacaattc ctcctccgat gacgtcactc     300
ccggagccgg gatgggtcat ttcaccgtcg acgacgaaga caacaacaac aaccatcaag     360
gtcttgactt agcctctggt ggaggatcag gaagctctgg aggaggagga ggtcacggcg     420
ggggaggaga cgtcgttggt cgtcgtccac gtggcagacc accgggatcc aagaacaaac     480
cgaaacctcc ggtaattatc acgcgcgaga gcgcaaacac tctaagagct cacattcttg     540
aagtaacaaa cggctgcgat gttttcgact gcgttgcgac ttatgctcgt cggagacagc     600
gagggatctg cgttctgagc ggtagcgaaa cggtcacgaa cgtcagcata cgtcagccat     660
ctgcggctgg agcggttgtg acgctacaag gaacgttcga gattctttct ctctccggat     720
cgtttcttcc tcctccggca cctcccggag caacagagttt gacaattttc ttagccggag     780
gacaaggtca ggtggttgga ggaagcgttg tgggtgagct tacggcggct ggaccggtga     840
ttgtgattgc agcttcgttt actaatgttg cttatgagag acttccttta aagaagatg     900 agcagcagca acagcttgga ggaggatcta acggcggagg taatttgttt ccggaggtgg     960
cagctggagg aggaggagga cttccgttct taatttacc gatgaatatg caaccaaatg    1020
tgcaacttcc ggtggaaggt tggccgggga attccggtgg aagaggtcct ttctgatgtg    1080
tatatattga taatcattat atatataccg gcggagaagc ttttccggcg aagaatttgc    1140
gagagtgaag aaaggttaga aaagctttta atggactaat gaatttcaaa ttatcatcgt    1200
gatttcggac attgtcttgt tcatcatgtt aagcttaggt ttattttttg tcgtttgtag    1260
aattttatgt ttgaatcctt ttttttttct gtgaaactct attgtgttcg tctgcgaagg    1320
aaaaaaaaat tctcaaaaaa aa                                            1342

<210> SEQ ID NO 54
<211> LENGTH: 292
<212> TYPE: PRT
<213> ORGANISM: Arabidopsis thaliana
<220> FEATURE:
<223> OTHER INFORMATION: G1076 polypeptide

<400> SEQUENCE: 54

Met Ala Gly Leu Asp Leu Gly Thr Ala Phe Arg Tyr Val Asn His Gln
1               5                   10                  15

Leu His Arg Pro Asp Leu His Leu His His Asn Ser Ser Ser Asp Asp
            20                  25                  30
```

-continued

```
Val Thr Pro Gly Ala Gly Met Gly His Phe Thr Val Asp Asp Glu Asp
         35                  40                  45
Asn Asn Asn Asn His Gln Gly Leu Asp Leu Ala Ser Gly Gly Gly Ser
 50                  55                  60
Gly Ser Ser Gly Gly Gly Gly His Gly Gly Gly Asp Val Val
 65                  70                  75                  80
Gly Arg Arg Pro Arg Gly Arg Pro Pro Gly Ser Lys Asn Lys Pro Lys
                 85                  90                  95
Pro Pro Val Ile Ile Thr Arg Glu Ser Ala Asn Thr Leu Arg Ala His
                100                 105                 110
Ile Leu Glu Val Thr Asn Gly Cys Asp Val Phe Asp Cys Val Ala Thr
            115                 120                 125
Tyr Ala Arg Arg Gln Arg Gly Ile Cys Val Leu Ser Gly Ser Gly
        130                 135                 140
Thr Val Thr Asn Val Ser Ile Arg Gln Pro Ser Ala Ala Gly Ala Val
145                 150                 155                 160
Val Thr Leu Gln Gly Thr Phe Glu Ile Leu Ser Leu Ser Gly Ser Phe
                165                 170                 175
Leu Pro Pro Pro Ala Pro Pro Gly Ala Thr Ser Leu Thr Ile Phe Leu
                180                 185                 190
Ala Gly Gly Gln Gly Gln Val Val Gly Gly Ser Val Val Gly Glu Leu
            195                 200                 205
Thr Ala Ala Gly Pro Val Ile Val Ile Ala Ala Ser Phe Thr Asn Val
210                 215                 220
Ala Tyr Glu Arg Leu Pro Leu Glu Glu Asp Glu Gln Gln Gln Gln Leu
225                 230                 235                 240
Gly Gly Gly Ser Asn Gly Gly Asn Leu Phe Pro Glu Val Ala Ala
                245                 250                 255
Gly Gly Gly Gly Gly Leu Pro Phe Phe Asn Leu Pro Met Asn Met Gln
                260                 265                 270
Pro Asn Val Gln Leu Pro Val Glu Gly Trp Pro Gly Asn Ser Gly Gly
            275                 280                 285
Arg Gly Pro Phe
        290

<210> SEQ ID NO 55
<211> LENGTH: 983
<212> TYPE: DNA
<213> ORGANISM: Arabidopsis thaliana
<220> FEATURE:
<223> OTHER INFORMATION: G280

<400> SEQUENCE: 55
aagttaatat gagaataatg agaaaaccac tttcccaaat tgcttttttaa aatccctcct      60
cacacagatt ccttccttca tcacctcaca cactctctac gcttgacatg gccttcgatc     120
tccaccatgg ctcagcttca gatacgcatt catcagaact ccgtcgtttt tctctcccac     180
cttatcctca gatgataatg gaagcgattg agtccttgaa cgataagaac ggctgcaaca     240
aaacgacgat tgctaagcac atcgagtcga ctcaacaaac tctaccgccg tcacacatga     300
cgctgctcag ctaccatctc aaccagatga agaaaccgg tcagctaatc atggtgaaga     360
acaattatat gaaaccagat ccagatgctc ctcctaagcg tggtcgtggc cgtcctccga     420
agcagaagac tcaggccgaa tctgacgccg ctgctgctgc tgttgttgct gccaccgtcg     480
tctctacaga tccgcctaga tctcgtggcc gtccaccgaa gccgaaagat ccatcggagc     540
```

```
ctccccagga gaaggtcatt accggatctg gaaggccacg aggacgacca ccgaagagac    600
cgagaacaga ttcggagacg gttgctgcgc cggaaccggc agctcaggcg acaggtgagc    660
gtaggggacg tgggagacct ccgaaggtga agccgacggt ggttgctccg gttgggtgct    720
gaattaatcg gtacttatgc aatttcggaa tctttagtta ctgaaaaatg gaatctctta    780
gagagtaaga gagtgcttta atttagctta attagattta tttggatttc tttcagtatt    840
tggattgtaa actttagaat ttgtgtgtgt gttgttgctt agtcctgaga taagatataa    900
cattagcgac tgtgtattat tattattact gcattgtgtt atgtgaaact ttgttctctt    960
gttgaaaaaa aaaaaaaaaa aaa                                           983
```

<210> SEQ ID NO 56
<211> LENGTH: 204
<212> TYPE: PRT
<213> ORGANISM: Arabidopsis thaliana
<220> FEATURE:
<223> OTHER INFORMATION: G280 polypeptide

<400> SEQUENCE: 56

```
Met Ala Phe Asp Leu His His Gly Ser Ala Ser Asp Thr His Ser Ser
 1               5                  10                  15

Glu Leu Pro Ser Phe Ser Leu Pro Pro Tyr Pro Gln Met Ile Met Glu
            20                  25                  30

Ala Ile Glu Ser Leu Asn Asp Lys Asn Gly Cys Asn Lys Thr Thr Ile
        35                  40                  45

Ala Lys His Ile Glu Ser Thr Gln Gln Thr Leu Pro Pro Ser His Met
    50                  55                  60

Thr Leu Leu Ser Tyr His Leu Asn Gln Met Lys Lys Thr Gly Gln Leu
65                  70                  75                  80

Ile Met Val Lys Asn Asn Tyr Met Lys Pro Asp Pro Asp Ala Pro Pro
                85                  90                  95

Lys Arg Gly Arg Gly Arg Pro Pro Lys Gln Lys Thr Gln Ala Glu Ser
           100                 105                 110

Asp Ala Ala Ala Ala Val Val Ala Ala Thr Val Val Ser Thr Asp
       115                 120                 125

Pro Pro Arg Ser Arg Gly Arg Pro Pro Lys Pro Lys Asp Pro Ser Glu
   130                 135                 140

Pro Pro Gln Glu Lys Val Ile Thr Gly Ser Gly Arg Pro Arg Gly Arg
145                 150                 155                 160

Pro Pro Lys Arg Pro Arg Thr Asp Ser Glu Thr Val Ala Ala Pro Glu
                165                 170                 175

Pro Ala Ala Gln Ala Thr Gly Glu Arg Arg Gly Arg Gly Arg Pro Pro
            180                 185                 190

Lys Val Lys Pro Thr Val Val Ala Pro Val Gly Cys
        195                 200
```

<210> SEQ ID NO 57
<211> LENGTH: 1964
<212> TYPE: DNA
<213> ORGANISM: Arabidopsis thaliana
<220> FEATURE:
<223> OTHER INFORMATION: G1367

<400> SEQUENCE: 57

```
tccttccaca aaactttttt aattttatct gaaaaattaa acaaccgaa acaaaaaaaa     60 aaaactaaaa atcaaaaatc tcatcacctt ccttgctctg tattttttct ctctcactaa   120
```

-continued

```
atcctccatg gatccttctc tctctgcaac caatgatcct catcatcctc ctcctcctca      180
gttcacatct ttccctcctt tcaccaacac caacccctt gcctctccaa accacccctt      240
cttcaccgga cccaccgccg tcgcgccgcc aaacaacatc catctctatc aagcagctcc      300
tccgcagcag ccacaaacat ctccagttcc tcctcatcca tctatttccc accctcctta      360
ctctgacatg atttgcacgg cgattgcagc gttaaacgaa ccagatgggt caagcaagca      420
agctatttcg aggtacatag agagaattta cactgggatt cctactgctc atggagcttt      480
gttgacacac catctcaaga cttttgaagac cagtgggatt cttgtcatgg ttaagaaatc      540
ttacaagctt gcttctactc ctcctcctcc tcctcctact agtgtagctc ctagtcttga      600
acctcccaga tctgatttca tagtcaacga gaaccaacct ttacctgatc cggttttggc      660
ttcttctact cctcagacta ttaaacgtgg tcgtggtcga cctccaaaag ctaaaccaga      720
tgttgttcaa cctcaacctc tgactaatgg aaaactcacc tgggaacaga gtgaattacc      780
tgtctctcga ccagaggaga tacagataca gccgccacag ttaccgttac agccacagca      840
gccggttaag agaccgccgg tcgtcctag aaaagatgga acttcgccga cggtgaagcc      900
agctgcttct gtttccggtg tgtggagac tgtgaaacga agaggtagac ctccgagtgg      960
aagagctgct gggagggaga gaaagcctat agtagtctca gctccagctt cagtgttccc     1020
gtatgttgct aatggtggtg ttagacgccg agggagacca aagagagttg acgctggtgg     1080
tgcttcctct gttgctccac caccaccacc accaactaac gtagagagtg gaggagagga     1140
ggttgcagtc aagaaacgag gaagaggacg gcctcctaag attggaggtg ttatcaggaa     1200
gcctatgaag ccgatgagaa gctttgctcg tactggaaaa cccgtaggaa gacccagaaa     1260
gaatgcggtc tcagtgggag cttctggacg acaagatggt gactatggag aactgaagaa     1320
gaagtttgag ttgtttcaag cgagagctaa ggatattgta attgtgttga atccgagat      1380
aggaggaagt ggaaatcaag cagtggttca agccatacag gacctggaag ggatagcaga     1440
gacaacaaac gagccaaagc acatggaaga agtgcagctg ccagacgagg aacaccttga     1500
aaccgaacca gaagcagagg gtcaaggaca gacagaagca gaggcaatgc aagaagctct     1560
gttctaaaga taaagccttg acataaaaag ctagcaagtg gtgggtttac ttgttgtgtg     1620
ttacatgaaa ttttttaatct tataagggtg tttgcaggaa aaaacaaaa agaacaatgt     1680
gatgaactga tgatgatgat tgtgtctcta accaaacaac aaggagaggt agggtaatgt     1740
ctgtaaagtg aattaggatg ttaccattgt tcatgcttcc catctctctc catcgtccat     1800
atctgtgtag gcagctttgt tctttgttcc ctcgtgtttt ttttagactg ttgtgtctct     1860
tattctattt tgtctcctta ggcttttag gagttgttgt tgatgtttat caaaaacgct     1920
tatgtaattt ttatgaccac ttctactttt tatgatggtt tctt                      1964
```

<210> SEQ ID NO 58
<211> LENGTH: 479
<212> TYPE: PRT
<213> ORGANISM: Arabidopsis thaliana
<220> FEATURE:
<223> OTHER INFORMATION: G1367 polypeptide

<400> SEQUENCE: 58

```
Met Asp Pro Ser Leu Ser Ala Thr Asn Asp Pro His His Pro Pro Pro
1               5                   10                  15

Pro Gln Phe Thr Ser Phe Pro Pro Phe Thr Asn Thr Asn Pro Phe Ala
            20                  25                  30
```

-continued

```
Ser Pro Asn His Pro Phe Phe Thr Gly Pro Thr Ala Val Ala Pro Pro
         35                  40                  45

Asn Asn Ile His Leu Tyr Gln Ala Ala Pro Gln Gln Pro Gln Thr
50              55                  60

Ser Pro Val Pro His Pro Ser Ile Ser His Pro Pro Tyr Ser Asp
65              70                  75                  80

Met Ile Cys Thr Ala Ile Ala Ala Leu Asn Glu Pro Asp Gly Ser Ser
             85                  90                  95

Lys Gln Ala Ile Ser Arg Tyr Ile Glu Arg Ile Tyr Thr Gly Ile Pro
             100                 105                 110

Thr Ala His Gly Ala Leu Leu Thr His His Leu Lys Thr Leu Lys Thr
             115                 120                 125

Ser Gly Ile Leu Val Met Val Lys Lys Ser Tyr Lys Leu Ala Ser Thr
             130                 135                 140

Pro Pro Pro Pro Pro Thr Ser Val Ala Pro Ser Leu Glu Pro Pro
145                 150                 155                 160

Arg Ser Asp Phe Ile Val Asn Glu Asn Gln Pro Leu Pro Asp Pro Val
                 165                 170                 175

Leu Ala Ser Ser Thr Pro Gln Thr Ile Lys Arg Gly Arg Gly Arg Pro
             180                 185                 190

Pro Lys Ala Lys Pro Asp Val Val Gln Pro Gln Pro Leu Thr Asn Gly
             195                 200                 205

Lys Leu Thr Trp Glu Gln Ser Glu Leu Pro Val Ser Arg Pro Glu Glu
             210                 215                 220

Ile Gln Ile Gln Pro Gln Leu Pro Leu Gln Pro Gln Gln Pro Val
225                 230                 235                 240

Lys Arg Pro Pro Gly Arg Pro Arg Lys Asp Gly Thr Ser Pro Thr Val
                 245                 250                 255

Lys Pro Ala Ala Ser Val Ser Gly Gly Val Glu Thr Val Lys Arg Arg
             260                 265                 270

Gly Arg Pro Pro Ser Gly Arg Ala Ala Gly Arg Glu Arg Lys Pro Ile
             275                 280                 285

Val Val Ser Ala Pro Ala Ser Val Phe Pro Tyr Val Ala Asn Gly Gly
             290                 295                 300

Val Arg Arg Arg Gly Arg Pro Lys Arg Val Asp Ala Gly Gly Ala Ser
305                 310                 315                 320

Ser Val Ala Pro Pro Pro Pro Thr Asn Val Glu Ser Gly Gly
             325                 330                 335

Glu Glu Val Ala Val Lys Lys Arg Gly Arg Gly Arg Pro Pro Lys Ile
             340                 345                 350

Gly Gly Val Ile Arg Lys Pro Met Lys Pro Met Arg Ser Phe Ala Arg
             355                 360                 365

Thr Gly Lys Pro Val Gly Arg Pro Arg Lys Asn Ala Val Ser Val Gly
             370                 375                 380

Ala Ser Gly Arg Gln Asp Gly Asp Tyr Gly Glu Leu Lys Lys Lys Phe
385                 390                 395                 400

Glu Leu Phe Gln Ala Arg Ala Lys Asp Ile Val Ile Val Leu Lys Ser
                 405                 410                 415

Glu Ile Gly Gly Ser Gly Asn Gln Ala Val Val Gln Ala Ile Gln Asp
             420                 425                 430

Leu Glu Gly Ile Ala Glu Thr Thr Asn Glu Pro Lys His Met Glu Glu
             435                 440                 445

Val Gln Leu Pro Asp Glu Glu His Leu Glu Thr Glu Pro Glu Ala Glu
```

```
              450                 455                 460
Gly Gln Gly Gln Thr Glu Ala Glu Ala Met Gln Glu Ala Leu Phe
465                 470                 475

<210> SEQ ID NO 59
<211> LENGTH: 1878
<212> TYPE: DNA
<213> ORGANISM: Arabidopsis thaliana
<220> FEATURE:
<223> OTHER INFORMATION: G2787

<400> SEQUENCE: 59
tctcagagca aaaacaaaa  aaaagaaaa  aaaaccta  aatctaaatc tcaccttcca       60
cctctgtctt tttttttt   gttcttttt  tttttttac tgtatcttct cttctctttg      120
ctctgcaaaa atctcacatc catggatcca tctcttggtg atcctcatca tcctcctcag      180 ttcaccccctt ttcctcattt tcccacctcc aatcatcatc ctttaggacc aaatccgtac    240
aataaccatg tcgtcttcca accgcagccg caaacgcaaa cgcaaatccc gcaaccgcag      300
atgtttcagt tatctccaca tgtttcaatg ccccacccctc cttactccga atgatttgc     360 gctgcgattg cggcgttaaa cgaaccggat ggttcgagca agatggcaat ttcgagatac      420
atcgagagat gttacaccgg tttaacttct gctcatgctg ctttgttgac tcaccatctc      480
aagactttga agaccagtgg tgttctttct atggttaaga aatcttacaa aattgctggt      540
tcttctactc ctcctgctag tgtagctgtt gctgctgctg ccgccgctca aggtctcgat      600
gttcccagat ctgagattct ccattcaagt aacaacgatc ccatggcttc tggctctgct      660
tctcagcctc tgaaacgagg tcgtggtcgt cctcctaagc ctaaacctga atctcaacca      720
caaccactac agcaacttcc accgaccaat caagtccagg ctaacggaca gccaatctgg      780
gaacagcagc aagttcaatc acctgttccg gttccgactc cggttacaga gtcggcgaag      840
agaggacctg tcgtccaag gaagaacggt tctgctgctc ctgctactgc accaatcgtt      900
caagcttcgg ttatggctgg aattatgaaa cgtagaggta gaccaccggg tcgtcgagct      960
gctgggagac agaggaagcc caaatccgtt tcttctactg cctctgtgta tccttatgtt     1020
gctaatggtg ctagacgcag aggaaggcct aggagagttg ttgacccctag cagtattgtt    1080 agtgttgctc cagtaggtgg tgaaaatgtg cagcggttg cgccagggat gaagcgtgga     1140
cgtggacgac cacctaagat tggtggtgtt atcagtaggc ttattatgaa gcctaagaga    1200
ggacgaggac gtcctgtagg tagacccaga aagattggaa catcagtcac gactgggaca    1260
caagattctg agaactcaa  gaagaagttt gatatttttc aagagaaagt gaaagaaatt    1320
gtgaaggtgt tgaaggatgg agttacaagt gagaatcaag cagtggtgca agccataaaa     1380
gatctggaag cactaacagt gacggagacc gttgagccac aagttatgga agaagtgcag    1440
ccagaggaga ctgcagcacc acagactgaa gctcaacaaa ctgaagctgc tgagacacaa    1500
ggaggacaag aagaaggaca agaaagagaa ggagaaacac agacccagac agaagcagag    1560
gcaatgcaag aagctctgtt ctgaagaata ataatgatct agaaaacaac ctagacataa    1620
tagccttggt gtttggcgtt aggagtgttt ttttttagtt gttttaggtg ttggaatcgc    1680
atcttaaatt atataaaaat ctataaggaa ttttaatttt tctaggtttt gttgtctgca    1740
gaagaagaaa tagtagactc gttaatggtg ttgttgtcgg tgtgtctta accaaaccat      1800 aagacgtggc tgtaaattag cgatgttct agtcttccat ctttaataat ctcttattgc     1860
gtctgtgcct tgtttttt                                                   1878
```

```
<210> SEQ ID NO 60
<211> LENGTH: 480
<212> TYPE: PRT
<213> ORGANISM: Arabidopsis thaliana
<220> FEATURE:
<223> OTHER INFORMATION: G2787 polypeptide

<400> SEQUENCE: 60
```

| | | | | | | | | | | | | | | | |
|---|---|---|---|---|---|---|---|---|---|---|---|---|---|---|---|
| Met | Asp | Pro | Ser | Leu | Gly | Asp | Pro | His | His | Pro | Gln | Phe | Thr | Pro | |
| 1 | | | | 5 | | | | | 10 | | | | | 15 | |
| Phe | Pro | His | Phe | Pro | Thr | Ser | Asn | His | His | Pro | Leu | Gly | Pro | Asn | Pro |
| | | | 20 | | | | | 25 | | | | | 30 | | |
| Tyr | Asn | Asn | His | Val | Val | Phe | Gln | Pro | Gln | Pro | Gln | Thr | Gln | Thr | Gln |
| | | | 35 | | | | | 40 | | | | | 45 | | |
| Ile | Pro | Gln | Pro | Gln | Met | Phe | Gln | Leu | Ser | Pro | His | Val | Ser | Met | Pro |
| | 50 | | | | | 55 | | | | | 60 | | | | |
| His | Pro | Pro | Tyr | Ser | Glu | Met | Ile | Cys | Ala | Ala | Ile | Ala | Ala | Leu | Asn |
| 65 | | | | | 70 | | | | | 75 | | | | | 80 |
| Glu | Pro | Asp | Gly | Ser | Ser | Lys | Met | Ala | Ile | Ser | Arg | Tyr | Ile | Glu | Arg |
| | | | | 85 | | | | | 90 | | | | | 95 | |
| Cys | Tyr | Thr | Gly | Leu | Thr | Ser | Ala | His | Ala | Ala | Leu | Leu | Thr | His | His |
| | | | 100 | | | | | 105 | | | | | 110 | | |
| Leu | Lys | Thr | Leu | Lys | Thr | Ser | Gly | Val | Leu | Ser | Met | Val | Lys | Lys | Ser |
| | | | | 115 | | | | | 120 | | | | | 125 | |
| Tyr | Lys | Ile | Ala | Gly | Ser | Ser | Thr | Pro | Pro | Ala | Ser | Val | Ala | Val | Ala |
| | | 130 | | | | | 135 | | | | | 140 | | | |
| Ala | Ala | Ala | Ala | Gln | Gly | Leu | Asp | Val | Pro | Arg | Ser | Glu | Ile | Leu | |
| 145 | | | | | 150 | | | | | 155 | | | | | 160 |
| His | Ser | Ser | Asn | Asn | Asp | Pro | Met | Ala | Ser | Gly | Ser | Ala | Ser | Gln | Pro |
| | | | | 165 | | | | | 170 | | | | | 175 | |
| Leu | Lys | Arg | Gly | Arg | Gly | Arg | Pro | Pro | Lys | Pro | Lys | Pro | Glu | Ser | Gln |
| | | | 180 | | | | | 185 | | | | | 190 | | |
| Pro | Gln | Pro | Leu | Gln | Gln | Leu | Pro | Pro | Thr | Asn | Gln | Val | Gln | Ala | Asn |
| | | | | 195 | | | | | 200 | | | | | 205 | |
| Gly | Gln | Pro | Ile | Trp | Glu | Gln | Gln | Val | Gln | Ser | Pro | Val | Pro | Val | |
| | | 210 | | | | | 215 | | | | | 220 | | | |
| Pro | Thr | Pro | Val | Thr | Glu | Ser | Ala | Lys | Arg | Gly | Pro | Gly | Arg | Pro | Arg |
| 225 | | | | | 230 | | | | | 235 | | | | | 240 |
| Lys | Asn | Gly | Ser | Ala | Ala | Pro | Ala | Thr | Ala | Pro | Ile | Val | Gln | Ala | Ser |
| | | | | 245 | | | | | 250 | | | | | 255 | |
| Val | Met | Ala | Gly | Ile | Met | Lys | Arg | Arg | Gly | Arg | Pro | Pro | Gly | Arg | Arg |
| | | | 260 | | | | | 265 | | | | | 270 | | |
| Ala | Ala | Gly | Arg | Gln | Arg | Lys | Pro | Lys | Ser | Val | Ser | Ser | Thr | Ala | Ser |
| | | | | 275 | | | | | 280 | | | | | 285 | |
| Val | Tyr | Pro | Tyr | Val | Ala | Asn | Gly | Ala | Arg | Arg | Gly | Arg | Pro | Arg | |
| | | 290 | | | | | 295 | | | | | 300 | | | |
| Arg | Val | Val | Asp | Pro | Ser | Ser | Ile | Val | Ser | Val | Ala | Pro | Val | Gly | Gly |
| 305 | | | | | 310 | | | | | 315 | | | | | 320 |
| Glu | Asn | Val | Ala | Ala | Val | Ala | Pro | Gly | Met | Lys | Arg | Gly | Arg | Gly | Arg |
| | | | | 325 | | | | | 330 | | | | | 335 | |
| Pro | Pro | Lys | Ile | Gly | Gly | Val | Ile | Ser | Arg | Leu | Ile | Met | Lys | Pro | Lys |
| | | | 340 | | | | | 345 | | | | | 350 | | |
| Arg | Gly | Arg | Gly | Arg | Pro | Val | Gly | Arg | Pro | Arg | Lys | Ile | Gly | Thr | Ser |
| | | | | 355 | | | | | 360 | | | | | 365 | |

| | | | | | | | | | | | |
|---|---|---|---|---|---|---|---|---|---|---|---|
|Val|Thr|Thr|Gly|Thr|Gln|Asp|Ser|Gly|Glu|Leu|Lys Lys Lys Phe Asp|
| |370| | | |375| | | |380| | |

Ile Phe Gln Glu Lys Val Lys Glu Ile Val Lys Val Leu Lys Asp Gly
385             390                 395                 400

Val Thr Ser Glu Asn Gln Ala Val Val Gln Ala Ile Lys Asp Leu Glu
                405                 410                 415

Ala Leu Thr Val Thr Glu Thr Val Glu Pro Gln Val Met Glu Glu Val
            420                 425                 430

Gln Pro Glu Glu Thr Ala Ala Pro Gln Thr Glu Ala Gln Gln Thr Glu
        435                 440                 445

Ala Ala Glu Thr Gln Gly Gly Gln Glu Gly Gln Glu Arg Glu Gly
    450                 455                 460

Glu Thr Gln Thr Gln Thr Glu Ala Glu Ala Met Gln Glu Ala Leu Phe
465                 470                 475                 480

<210> SEQ ID NO 61
<211> LENGTH: 1772
<212> TYPE: DNA
<213> ORGANISM: Arabidopsis thaliana
<220> FEATURE:
<223> OTHER INFORMATION: G3045

<400> SEQUENCE: 61

```
ttacattcca tccgctaact tctggacctc gtcaattgct gttactgctt gtttcaactt      60
agctgcagct tccttcactt tcttttgctg caacattttt catttcgta  acttatcatc     120
agattctttc tttttagttg aaatgaatcc attttaatta actaatcaaa tgaccattca     180
attccatctt ctaggctata cgacataatc taacaattct gttgacttgc tagtatcctt     240
tgtgctccac acaacataat gtctaaatca aattgatgca gggatacagt aatgtttacg     300
aaaaaccatt atagaagcta agtggggata gttcacttac taagagtgcg gttctttttct    360
tgagatctcc gacgtttgca gctaccggtg ccactgaagt gctctttttgt tcatgcatag    420
aaaacccgac tttgacataa gtatacacac agttgtataa gcatggttat gtcttacatg    480
aactcttgta gatattgact caaatgaaat gataatgact aaccaaatag atttcaagaa     540
atacaccaaa tccagatact atacacatct tttcaaaata ttacgaatca tttcaaattc     600
tgcagaacct aaaattaacc agatttgaga ccaccagaga caaataacat acaactctaa     660
acttttttcca ctatatatgc agaacaaaca gtcaagaaca accgtataat tggtatatac    720
cttttgttaa aattatacat taagcattgt tatgtctaac atgaactaaa cacttgtgaa     780
atttatttgg actcaaatta catgataact tcttaccaaa tagaccaatc actttcactt     840
ccacattata caaaaaaaga tttaatgaaa tacaccaaaa tccagataag atgcacatct     900
tttcaaagaa attcgaata atatcagata cttcacactc acaatagacc acatttgaga     960
caaataaaga cattactctg aactttatct actatatgca gaagaaacag tcaagaagaa    1020
caatattaaa taagacattt tcccaaaata caccaaaatc cagataagat acacatttttt  1080
ctaaaaatac ggggaatttc agatactgca atcctaaaag tagaccacat ttgagaccag    1140
agtcaaataa gacattaccc tgaattattt ccacactata cagaacaaac agtcaagaac    1200
aatcatataa ttggtatcag accatttcta aatttctttt gacattttgt gaataaagat    1260
aatgaaatta aagagaaaca taccttccta gtcctgcgca caggctgtgc agctacttcg    1320
acagtaggtt tccttccacg tctcttagct ggagccacca cagttctgc tggaacagtt    1380
gcagccgcca cgtcatcttt ctttggcctc cctcgttttc tagaaccctc tccagtagca    1440
```

-continued

| | |
|---|---|
| gtagtaacca cagccgccgt tacagtcgac ctctttgccc taccacgttt cttcacagcc | 1500 |
| gccgccacag acgtagaagg aacagcctga gctacgtttc ttttcggacg accacttggt | 1560 |
| ttagtactcg ccttcgcaga aacggcaccg atttgggaag agtcagattt agcctttggc | 1620 |
| ggtcgaccac gaccgcgttt ctgagaagca gtatcagtag ctgagacgcc ggtggcatcc | 1680 |
| gtttgaggtt tgttgccaga cgcatctcca ggtgtaccgg atcttggaac ttcggaacca | 1740 |
| gacgcgggag gagtaagagc tgttttcgcc at | 1772 |

<210> SEQ ID NO 62
<211> LENGTH: 189
<212> TYPE: PRT
<213> ORGANISM: Arabidopsis thaliana
<220> FEATURE:
<223> OTHER INFORMATION: G3045 polypeptide

<400> SEQUENCE: 62

Met Ala Lys Thr Ala Leu Thr Pro Pro Ala Ser Gly Ser Glu Val Pro
1               5                   10                  15

Arg Ser Gly Thr Pro Gly Asp Ala Ser Gly Asn Lys Pro Gln Thr Asp
            20                  25                  30

Ala Thr Gly Val Ser Ala Thr Asp Thr Ala Ser Gln Lys Arg Gly Arg
        35                  40                  45

Gly Arg Pro Pro Lys Ala Lys Ser Asp Ser Ser Gln Ile Gly Ala Val
    50                  55                  60

Ser Ala Lys Ala Ser Thr Lys Pro Ser Gly Arg Pro Lys Arg Asn Val
65                  70                  75                  80

Ala Gln Ala Val Pro Ser Thr Ser Val Ala Ala Val Lys Lys Arg
                85                  90                  95

Gly Arg Ala Lys Arg Ser Thr Val Thr Ala Ala Val Val Thr Thr Ala
            100                 105                 110

Thr Gly Glu Gly Ser Arg Lys Arg Gly Arg Pro Lys Lys Asp Asp Val
        115                 120                 125

Ala Ala Ala Thr Val Pro Ala Glu Thr Val Val Ala Pro Ala Lys Arg
    130                 135                 140

Arg Gly Arg Lys Pro Thr Val Glu Val Ala Ala Gln Pro Val Arg Arg
145                 150                 155                 160

Thr Arg Lys Val Cys Phe Ser Leu Ile Ser Leu Ser Leu Phe Thr Lys
                165                 170                 175

Cys Gln Lys Lys Phe Arg Asn Gly Leu Ile Pro Ile Ile
            180                 185

<210> SEQ ID NO 63
<211> LENGTH: 534
<212> TYPE: DNA
<213> ORGANISM: Lycopersicon esculentum
<220> FEATURE:
<223> OTHER INFORMATION: BG134451

<400> SEQUENCE: 63

| | |
|---|---|
| ggtgaatctg acagtgatgc tggtgcaagt tctggaggcg gagctcccaa tcgccgtcct | 60 |
| cgaggccgtc cgcctggatc taaaaataag cccaagcctc caatcatcgt gacgagagat | 120 |
| acgcctaacg cactccgatc tcacgtgctt gaagtttcga ccgatgttga tatcatggaa | 180 |
| agtatctcca attacgcaag gcggagaggg agaggtgttt gtattcttag tggtagcggc | 240 |
| acagttacca acgtcaacct tcgtcagcct gctgcaagtg tagtcacact ccacggacgt | 300 |
| ttcgaaatac ttagcctctc aggtacggtg cttcctccgc ctgcaccgcc cgcctccagt | 360 |

```
gggatctcta tattttatc aggtggacaa ggacaagtgg ttggaggatc cgttgtaggg      420
cctttgatcg catcaggtcc agtcgtctta atggctgcct cttttgctaa tgctgtattt      480
gaacgacttc ccttggagga agatgatgag gctcctgcta atgttcctac taca           534
```

<210> SEQ ID NO 64
<211> LENGTH: 178
<212> TYPE: PRT
<213> ORGANISM: Lycopersicon esculentum
<220> FEATURE:
<223> OTHER INFORMATION: polypeptide encoded by BG134451

<400> SEQUENCE: 64

```
Gly Glu Ser Asp Ser Asp Ala Gly Ala Ser Gly Gly Gly Ala Pro
1               5                   10                  15

Asn Arg Arg Pro Arg Gly Arg Pro Gly Ser Lys Asn Lys Pro Lys
                20                  25                  30

Pro Pro Ile Ile Val Thr Arg Asp Thr Pro Asn Ala Leu Arg Ser His
            35                  40                  45

Val Leu Glu Val Ser Thr Asp Val Asp Ile Met Glu Ser Ile Ser Asn
50                  55                  60

Tyr Ala Arg Arg Arg Gly Arg Gly Val Cys Ile Leu Ser Gly Ser Gly
65                  70                  75                  80

Thr Val Thr Asn Val Asn Leu Arg Gln Pro Ala Ala Ser Val Val Thr
                85                  90                  95

Leu His Gly Arg Phe Glu Ile Leu Ser Leu Ser Gly Thr Val Leu Pro
            100                 105                 110

Pro Pro Ala Pro Pro Ala Ser Ser Gly Ile Ser Ile Phe Leu Ser Gly
        115                 120                 125

Gly Gln Gly Gln Val Val Gly Gly Ser Val Val Gly Pro Leu Ile Ala
130                 135                 140

Ser Gly Pro Val Val Leu Met Ala Ala Ser Phe Ala Asn Ala Val Phe
145                 150                 155                 160

Glu Arg Leu Pro Leu Glu Glu Asp Asp Glu Ala Pro Ala Asn Val Pro
                165                 170                 175

Thr Thr
```

<210> SEQ ID NO 65
<211> LENGTH: 747
<212> TYPE: DNA
<213> ORGANISM: Brassica oleracea
<220> FEATURE:
<223> OTHER INFORMATION: BH566718

<400> SEQUENCE: 65

```
ggaagctctt tcgccgcttc ttcctcatcc aaaggtaatc tctcataagt cgcattagaa      60
aacgtggcag cgattagcat caccggacca gcagccatca atgccccac cacgcttcct      120 ccaacaacct gaccttgacc accagctaag taaatagtta aaccagtgga tccaggtgga      180
gccggtccag gtaagaaaga accgttagaa gaaagaatct caaacctccc ttgtaacgcc      240
aatacagccg caccaccagg ggcagctgca acgggagcca ctgatggttg acggagtgtg      300
acgttagcca ccgtgccgtt accgctcaag atgcagatgc cacgtggcg ccgcctagcg       360 aaagtagcta gggtttctat gacatcagtc ccactagcga tctccatgac atggctcttg      420
agagcgtttg gagaatcacg cgtgacaaag attggtggct tggtttgtt cttggaacca       480 gcaggacgtc cacgtggtcg gcgcgtggga gcttccacgg ctccttcacg tggctcgcgg      540
```

```
tcgtcgccgc tcaagttgtc tctatcgtct tcgttgttgt tgttggtgtt gacttcttgg    600
tgatgatgat ggtggttgtt atgacctgag accatggcca tgttcatgga gatgtggaga    660
tctggtgtct ttaactgaga ggaactcggc ggcgtcgttt cgagactgga gagattcact    720
tgtcctgtcc accatggatt tcgcatt                                        747
```

<210> SEQ ID NO 66
<211> LENGTH: 248
<212> TYPE: PRT
<213> ORGANISM: Brassica oleracea
<220> FEATURE:
<223> OTHER INFORMATION: polypeptide encoded by BH566718

<400> SEQUENCE: 66

```
Met Arg Asn Pro Trp Trp Thr Gly Gln Val Asn Leu Ser Ser Leu Glu
1               5                   10                  15

Thr Thr Pro Pro Ser Ser Ser Gln Leu Lys Thr Pro Asp Leu His Ile
            20                  25                  30

Ser Met Asn Met Ala Met Val Ser Gly His Asn Asn His His His
        35                  40                  45

His Gln Glu Val Asn Thr Asn Asn Asn Glu Asp Asp Arg Asp Asn
    50                  55                  60

Leu Ser Gly Asp Asp Arg Glu Pro Arg Glu Gly Ala Val Glu Ala Pro
65                  70                  75                  80

Thr Arg Arg Pro Arg Gly Arg Pro Ala Gly Ser Lys Asn Lys Pro Lys
                85                  90                  95

Pro Pro Ile Phe Val Thr Arg Asp Ser Pro Asn Ala Leu Lys Ser His
            100                 105                 110

Val Met Glu Ile Ala Ser Gly Thr Asp Val Ile Glu Thr Leu Ala Thr
        115                 120                 125

Phe Ala Arg Arg Arg Gln Arg Gly Ile Cys Ile Leu Ser Gly Asn Gly
    130                 135                 140

Thr Val Ala Asn Val Thr Leu Arg Gln Pro Ser Val Ala Pro Val Ala
145                 150                 155                 160

Ala Ala Pro Gly Gly Ala Ala Val Leu Ala Leu Gln Gly Arg Phe Glu
                165                 170                 175

Ile Leu Ser Leu Thr Gly Ser Phe Leu Pro Gly Pro Ala Pro Pro Gly
            180                 185                 190

Ser Thr Gly Leu Thr Ile Tyr Leu Ala Gly Gly Gln Gly Gln Val Val
        195                 200                 205

Gly Gly Ser Val Val Gly Ala Leu Met Ala Ala Gly Pro Val Met Leu
    210                 215                 220

Ile Ala Ala Thr Phe Ser Asn Ala Thr Tyr Glu Arg Leu Pro Leu Asp
225                 230                 235                 240

Glu Glu Glu Ala Ala Lys Glu Leu
                245
```

<210> SEQ ID NO 67
<211> LENGTH: 620
<212> TYPE: DNA
<213> ORGANISM: Brassica oleracea
<220> FEATURE:
<223> OTHER INFORMATION: BH685875

<400> SEQUENCE: 67

```
accgcatttg agaaggaagc agctactagt ataaccggag ctgatgcaac aagtggagcc    60
```

-continued

```
acaacgcttc ccccaaccac ctgaccttgc ccaccggata gaaatattga caaaccacca      120
gcacctggcg gtgcgggtgg tggcaaaacg gttcccgtta gcgaaagaat ctcaaacctt      180
ccatgtaaag tcacaactcc tcctcctccg gctccaccac cgctatttcc gggagtgact      240
ggctgacgaa gagtgacgtt agaaacggtg ccgtttcctc ctaaaacgga gacccctctc      300
cctctccgcc tagcgtaagt ggacacacac tcaactatgt cagctccagg agatacttca      360
aggacgtgag atctaagcgc attggggcta tcgcgcgtga ctatgatcgg tggcttagct      420
ttgttcttag atcccggtgg acgtccacgt ggacgtttcc caggtgctga gcttgatgta      480
gccgggtctg aatcgggtag acccggttga tgatgatcct tgtttgagtg atcagattct      540
cttgaatcat ccgacgggtg gtgttgttgc tgctggtggt gttgctggtg atgatgctgg      600
tcaaaaaaga tgatcccgcc                                                  620
```

<210> SEQ ID NO 68
<211> LENGTH: 206
<212> TYPE: PRT
<213> ORGANISM: Brassica oleracea
<220> FEATURE:
<223> OTHER INFORMATION: polypeptide encoded by BH685875

<400> SEQUENCE: 68

```
Gly Gly Ile Ile Phe Phe Asp Gln His His Gln Gln His His Gln
1               5                   10                  15

Gln Gln Gln His His Pro Ser Asp Asp Ser Arg Glu Ser Asp His Ser
                20                  25                  30

Asn Lys Asp His His Gln Pro Gly Leu Pro Asp Ser Asp Pro Ala Thr
            35                  40                  45

Ser Ser Ser Ala Pro Gly Lys Arg Pro Arg Gly Arg Pro Pro Gly Ser
        50                  55                  60

Lys Asn Lys Ala Lys Pro Pro Ile Ile Val Thr Arg Asp Ser Pro Asn
65                  70                  75                  80

Ala Leu Arg Ser His Val Leu Glu Val Ser Pro Gly Ala Asp Ile Val
                85                  90                  95

Glu Cys Val Ser Thr Tyr Ala Arg Arg Arg Gly Arg Gly Val Ser Val
                100                 105                 110

Leu Gly Gly Asn Gly Thr Val Ser Asn Val Thr Leu Arg Gln Pro Val
            115                 120                 125

Thr Pro Gly Asn Ser Gly Gly Ala Gly Gly Gly Val Val Thr
        130                 135                 140

Leu His Gly Arg Phe Glu Ile Leu Ser Leu Thr Gly Thr Val Leu Pro
145                 150                 155                 160

Pro Pro Ala Pro Pro Gly Ala Gly Gly Leu Ser Ile Phe Leu Ser Gly
                165                 170                 175

Gly Gln Gly Gln Val Val Gly Gly Ser Val Val Ala Pro Leu Val Ala
            180                 185                 190

Ser Ala Pro Val Ile Leu Val Ala Ala Ser Phe Ser Asn Ala
        195                 200                 205
```

<210> SEQ ID NO 69
<211> LENGTH: 929
<212> TYPE: DNA
<213> ORGANISM: Arabidopsis thaliana
<220> FEATURE:
<223> OTHER INFORMATION: CBF1   G40

<400> SEQUENCE: 69

```
cttgaaaaag aatctacctg aaaagaaaaa aagagagag agatataaat agctttacca      60
agacagatat actatctttt attaatccaa aaagactgag aactctagta actacgtact    120
acttaaacct tatccagttt cttgaaacag agtactctga tcaatgaact cattttcagc    180
tttttctgaa atgtttggct ccgattacga gcctcaaggc ggagattatt gtccgacgtt    240
ggccacgagt tgtccgaaga aaccggcggg ccgtaagaag tttcgtgaga ctcgtcaccc    300
aatttacaga ggagttcgtc aaagaaactc cggtaagtgg gtttctgaag tgagagagcc    360
aaacaagaaa accaggattt ggctcgggac tttccaaacc gctgagatgg cagctcgtgc    420
tcacgacgtc gctgcattag ccctccgtgg ccgatcagca tgtctcaact cgctgactc    480
ggcttggcgg ctacgaatcc cggagtcaac atgcgccaag gatatccaaa agcggctgc    540
tgaagcggcg ttggcttttc aagatgagac gtgtgatacg acgaccacga atcatggcct    600
ggacatggag gagacgatgg tggaagctat ttatacaccg aacagagcg aaggtgcgtt    660
ttatatggat gaggagacaa tgtttgggat gccgactttg ttggataata tggctgaagg    720
catgcttta ccgccgccgt ctgttcaatg gaatcataat tatgacggcg aaggagatgg    780
tgacgtgtcg ctttggagtt actaatattc gatagtcgtt tccattttg tactatagtt    840
tgaaaatatt ctagttcctt tttttagaat ggttccttca tttatttta ttttattgtt    900
gtagaaacga gtggaaaata attcaatac                                      929
```

<210> SEQ ID NO 70  
<211> LENGTH: 213  
<212> TYPE: PRT  
<213> ORGANISM: Arabidopsis thaliana  
<220> FEATURE:  
<223> OTHER INFORMATION: CBF1 G40 polypeptide
<400> SEQUENCE: 70

```
Met Asn Ser Phe Ser Ala Phe Ser Glu Met Phe Gly Ser Asp Tyr Glu
  1               5                  10                  15

Pro Gln Gly Gly Asp Tyr Cys Pro Thr Leu Ala Thr Ser Cys Pro Lys
                 20                  25                  30

Lys Pro Ala Gly Arg Lys Lys Phe Arg Glu Thr Arg His Pro Ile Tyr
             35                  40                  45

Arg Gly Val Arg Gln Arg Asn Ser Gly Lys Trp Val Ser Glu Val Arg
         50                  55                  60

Glu Pro Asn Lys Lys Thr Arg Ile Trp Leu Gly Thr Phe Gln Thr Ala
 65                  70                  75                  80

Glu Met Ala Ala Arg Ala His Asp Val Ala Ala Leu Ala Leu Arg Gly
                 85                  90                  95

Arg Ser Ala Cys Leu Asn Phe Ala Asp Ser Ala Trp Arg Leu Arg Ile
            100                 105                 110

Pro Glu Ser Thr Cys Ala Lys Asp Ile Gln Lys Ala Ala Ala Glu Ala
            115                 120                 125

Ala Leu Ala Phe Gln Asp Glu Thr Cys Asp Thr Thr Thr Thr Asn His
        130                 135                 140

Gly Leu Asp Met Glu Glu Thr Met Val Glu Ala Ile Tyr Thr Pro Glu
145                 150                 155                 160

Gln Ser Glu Gly Ala Phe Tyr Met Asp Glu Glu Thr Met Phe Gly Met
                165                 170                 175

Pro Thr Leu Leu Asp Asn Met Ala Glu Gly Met Leu Leu Pro Pro Pro
            180                 185                 190

Ser Val Gln Trp Asn His Asn Tyr Asp Gly Glu Gly Asp Gly Asp Val
```

Ser Leu Trp Ser Tyr
    210

<210> SEQ ID NO 71
<211> LENGTH: 803
<212> TYPE: DNA
<213> ORGANISM: Arabidopsis thaliana
<220> FEATURE:
<223> OTHER INFORMATION: CBF2  G41

<400> SEQUENCE: 71

```
ctgatcaatg aactcatttt ctgccttttc tgaaatgttt ggctccgatt acgagtctcc      60
ggtttcctca ggcggtgatt acagtccgaa gcttgccacg agctgcccca agaaaccagc     120
gggaaggaag aagtttcgtg agactcgtca cccaatttac agaggagttc gtcaaagaaa     180
ctccggtaag tgggtgtgtg agttgagaga gccaaacaag aaaacgagga tttggctcgg     240
gactttccaa accgctgaga tggcagctcg tgctcacgac gtcgccgcca tagctctccg     300
tggcagatct gcctgtctca atttcgctga ctccggcttgg cggctacgaa tcccggaatc     360
aacctgtgcc aaggaaatcc aaaaggcggc ggctgaagcc gcgttgaatt ttcaagatga     420
gatgtgtcat atgacgacgg atgctcatgg tcttgacatg gaggagacct tggtggaggc     480
tatttatacg ccggaacaga gccaagatgc gtttatatg gatgaagagg cgatgttggg     540
gatgtctagt ttgttggata acatggccga agggatgctt ttaccgtcgc cgtcggttca     600
atggaactat aattttgatg tcgagggaga tgatgacgtg tccttatgga gctattaaaa     660
ttcgattttt atttccattt ttggtattat agcttttat acatttgatc ctttttaga     720
atggatcttc ttcttttttt ggttgtgaga acgaatgta aatggtaaaa gttgttgtca     780
aatgcaaatg tttttgagtg cag                                            803
```

<210> SEQ ID NO 72
<211> LENGTH: 207
<212> TYPE: PRT
<213> ORGANISM: Arabidopsis thaliana
<220> FEATURE:
<223> OTHER INFORMATION: CBF2  G41 polypeptide

<400> SEQUENCE: 72

Met Phe Gly Ser Asp Tyr Glu Ser Pro Val Ser Ser Gly Gly Asp Tyr
1               5                   10                  15

Ser Pro Lys Leu Ala Thr Ser Cys Pro Lys Lys Pro Ala Gly Arg Lys
            20                  25                  30

Lys Phe Arg Glu Thr Arg His Pro Ile Tyr Arg Gly Val Arg Gln Arg
        35                  40                  45

Asn Ser Gly Lys Trp Val Cys Glu Leu Arg Glu Pro Asn Lys Lys Thr
    50                  55                  60

Arg Ile Trp Leu Gly Thr Phe Gln Thr Ala Glu Met Ala Ala Arg Ala
65                  70                  75                  80

His Asp Val Ala Ala Ile Ala Leu Arg Gly Arg Ser Ala Cys Leu Asn
                85                  90                  95

Phe Ala Asp Ser Ala Trp Arg Leu Arg Ile Pro Glu Ser Thr Cys Ala
            100                 105                 110

Lys Glu Ile Gln Lys Ala Ala Ala Glu Ala Ala Leu Asn Phe Gln Asp
        115                 120                 125

Glu Met Cys His Met Thr Thr Asp Ala His Gly Leu Asp Met Glu Glu
    130                 135                 140

-continued

```
Thr Leu Val Glu Ala Ile Tyr Thr Pro Glu Gln Ser Gln Asp Ala Phe
145                 150                 155                 160

Tyr Met Asp Glu Glu Ala Met Leu Gly Met Ser Ser Leu Leu Asp Asn
                165                 170                 175

Met Ala Glu Gly Met Leu Leu Pro Ser Pro Ser Val Gln Trp Asn Tyr
            180                 185                 190

Asn Phe Asp Val Glu Gly Asp Asp Val Ser Leu Trp Ser Tyr
        195                 200                 205
```

<210> SEQ ID NO 73
<211> LENGTH: 908
<212> TYPE: DNA
<213> ORGANISM: Arabidopsis thaliana
<220> FEATURE:
<221> NAME/KEY: misc_feature
<222> LOCATION: (851)..(851)
<223> OTHER INFORMATION: n is a, c, g, or t
<220> FEATURE:
<223> OTHER INFORMATION: CBF3 G42

<400> SEQUENCE: 73

```
cctgaactag aacagaaaga gagagaaact attatttcag caaaccatac caacaaaaaa      60
gacagagatc ttttagttac cttatccagt ttcttgaaac agagtactct tctgatcaat     120
gaactcattt tctgcttttt ctgaaatgtt tggctccgat tacgagtctt cggtttcctc     180
aggcggtgat tatattccga cgcttgcgag cagctgcccc aagaaaccgg cgggtcgtaa     240
gaagtttcgt gagactcgtc acccaatata cagaggagtt cgtcggagaa actccggtaa     300
gtgggtttgt gaggttagag aaccaaacaa gaaaacaagg atttggctcg aacatttca     360
aaccgctgag atggcagctc gagctcacga cgttgccgct ttagcccttc gtggccgatc     420
agcctgtctc aatttcgctg actcggcttg gagactccga atcccggaat caacttgcgc     480
taaggacatc caaaaggcgg cggctgaagc tcgcttggcg tttcaggatg agatgtgtga     540
tgcgacgacg gatcatggct tcgacatgga ggagacgttg gtggaggcta tttacacggc     600
ggaacagagc gaaaatgcgt tttatatgca cgatgaggcg atgtttgaga tgccgagttt     660
gttggctaat atggcagaag gatgcttttt gccgcttccg tccgtacagt ggaatcataa     720
tcatgaagtc gacggcgatg atgacgacgt atcgttatgg agttattaaa actcagatta     780
ttatttccat ttttagtacg atacttttta ttttattatt attttttagat cctttttag     840
aatggaatct ncattatgtt tgtaaaactg agaacgagt gtaaattaaa ttgattcagt     900
ttcagtat                                                             908
```

<210> SEQ ID NO 74
<211> LENGTH: 216
<212> TYPE: PRT
<213> ORGANISM: Arabidopsis thaliana
<220> FEATURE:
<223> OTHER INFORMATION: CBF3 G42 polypeptide

<400> SEQUENCE: 74

```
Met Asn Ser Phe Ser Ala Phe Ser Glu Met Phe Gly Ser Asp Tyr Glu
1               5                   10                  15

Ser Ser Val Ser Ser Gly Gly Asp Tyr Ile Pro Thr Leu Ala Ser Ser
                20                  25                  30

Cys Pro Lys Lys Pro Ala Gly Arg Lys Lys Phe Arg Glu Thr Arg His
            35                  40                  45

Pro Ile Tyr Arg Gly Val Arg Arg Arg Asn Ser Gly Lys Trp Val Cys
```

```
                        50                    55                      60
Glu Val Arg Glu Pro Asn Lys Lys Thr Arg Ile Trp Leu Gly Thr Phe
 65                      70                  75                      80

Gln Thr Ala Glu Met Ala Ala Arg Ala His Asp Val Ala Ala Leu Ala
                     85                  90                      95

Leu Arg Gly Arg Ser Ala Cys Leu Asn Phe Ala Asp Ser Ala Trp Arg
                    100                 105                 110

Leu Arg Ile Pro Glu Ser Thr Cys Ala Lys Asp Ile Gln Lys Ala Ala
                115                 120                 125

Ala Glu Ala Ala Leu Ala Phe Gln Asp Glu Met Cys Asp Ala Thr Thr
            130                 135                 140

Asp His Gly Phe Asp Met Glu Glu Thr Leu Val Glu Ala Ile Tyr Thr
145                 150                 155                 160

Ala Glu Gln Ser Glu Asn Ala Phe Tyr Met His Asp Glu Ala Met Phe
                165                 170                 175

Glu Met Pro Ser Leu Leu Ala Asn Met Ala Glu Gly Met Leu Leu Pro
            180                 185                 190

Leu Pro Ser Val Gln Trp Asn His Asn His Glu Val Asp Gly Asp Asp
        195                 200                 205

Asp Asp Val Ser Leu Trp Ser Tyr
    210                 215

<210> SEQ ID NO 75
<211> LENGTH: 632
<212> TYPE: DNA
<213> ORGANISM: Brassica napus
<220> FEATURE:
<223> OTHER INFORMATION: bnCBF1

<400> SEQUENCE: 75
cacccgatat accggggagt tcgtctgaga aagtcaggta agtgggtgtg tgaagtgagg      60
gaaccaaaca agaaatctag aatttggctt ggaactttca aaacagctga gatggcagct    120
cgtgctcacg acgtcgctgc cctagccctc cgtggaagag cgcctgcctc aattatgcg     180 gactcggctt ggcggctccg catcccggag acaacctgcc acaaggatat ccagaaggct    240
gctgctgaag ccgcattggc ttttgaggct gagaaaagtg atgtgacgat gcaaaatggc    300
cagaacatgg aggagacgac ggcggtggct tctcaggctg aagtgaatga cacgacgaca    360
gaacatggca tgaacatgga ggaggcaacg gcagtggctt ctcaggctga ggtgaatgac    420
acgacgacgg atcatggcgt agacatggag gagacaatgg tggaggctgt ttttactggg    480
gaacaaagtg aagggtttaa catggcgaag gagtcgacgg tggaggctgc tgttgttacg    540
gaggaaccga gcaaaggatc ttacatggac gaggagtgga tgctcgagat gccgaccttg    600
ttggctgata tggcagaagg gatgctcctg cc                                  632

<210> SEQ ID NO 76
<211> LENGTH: 208
<212> TYPE: PRT
<213> ORGANISM: Brassica napus
<220> FEATURE:
<223> OTHER INFORMATION: bnCBF1 polypeptide

<400> SEQUENCE: 76

His Pro Ile Tyr Arg Gly Val Arg Leu Arg Lys Ser Gly Lys Trp Val
  1                   5                  10                  15

Cys Glu Val Arg Glu Pro Asn Lys Lys Ser Arg Ile Trp Leu Gly Thr
                 20                  25                  30
```

```
Phe Lys Thr Ala Glu Met Ala Ala Arg Ala His Asp Val Ala Ala Leu
         35                  40                  45
Ala Leu Arg Gly Arg Gly Ala Cys Leu Asn Tyr Ala Asp Ser Ala Trp
     50                  55                  60
Arg Leu Arg Ile Pro Glu Thr Thr Cys His Lys Asp Ile Gln Lys Ala
 65                  70                  75                  80
Ala Ala Glu Ala Ala Leu Ala Phe Glu Ala Gly Lys Ser Asp Val Thr
                 85                  90                  95
Met Gln Asn Gly Gln Asn Met Glu Thr Thr Ala Val Ala Ser Gln
                100                 105                 110
Ala Glu Val Asn Asp Thr Thr Thr Glu His Gly Met Asn Met Glu Glu
            115                 120                 125
Ala Thr Ala Val Ala Ser Gln Ala Glu Val Asn Asp Thr Thr Thr Asp
        130                 135                 140
His Gly Val Asp Met Glu Glu Thr Met Val Glu Ala Val Phe Thr Gly
145                 150                 155                 160
Glu Gln Ser Glu Gly Phe Asn Met Ala Lys Glu Ser Thr Val Glu Ala
                165                 170                 175
Ala Val Val Thr Glu Glu Pro Ser Lys Gly Ser Tyr Met Asp Glu Glu
            180                 185                 190
Trp Met Leu Glu Met Pro Thr Leu Leu Ala Asp Met Ala Glu Gly Met
        195                 200                 205

<210> SEQ ID NO 77
<211> LENGTH: 20
<212> TYPE: DNA
<213> ORGANISM: artificial sequence
<220> FEATURE:
<223> OTHER INFORMATION: Artificial sequence
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<223> OTHER INFORMATION: Mol 368 reverse primer

<400> SEQUENCE: 77
cayccnatht aymgnggngt                                              20

<210> SEQ ID NO 78
<211> LENGTH: 21
<212> TYPE: DNA
<213> ORGANISM: artificial sequence
<220> FEATURE:
<223> OTHER INFORMATION: Artificial sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
```

```
<220> FEATURE:
<221> NAME/KEY: misc_feature
<222> LOCATION: (18)..(18)
<223> OTHER INFORMATION: n is a, c, g, or t
<220> FEATURE:
<223> OTHER INFORMATION: Mol 378 forward primer

<400> SEQUENCE: 78
ggnarnarca tnccytcngc c                                              21

<210> SEQ ID NO 79
<211> LENGTH: 8
<212> TYPE: PRT
<213> ORGANISM: Arabidopsis thaliana
<220> FEATURE:
<221> NAME/KEY: misc_feature
<222> LOCATION: (7)..(7)
<223> OTHER INFORMATION: Xaa can be any naturally occurring amino acid
<220> FEATURE:
<223> OTHER INFORMATION: AT-hook domain consensus sequence

<400> SEQUENCE: 79

Arg Pro Arg Gly Arg Pro Xaa Gly
1               5

<210> SEQ ID NO 80
<211> LENGTH: 17
<212> TYPE: PRT
<213> ORGANISM: Arabidopsis thaliana
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<223> OTHER INFORMATION: Second conserved domain consensus sequence

<400> SEQUENCE: 80

Pro Xaa Xaa Xaa Xaa Xaa Leu Xaa Xaa Tyr Xaa Xaa Gly Xaa Xaa Gly
1               5                   10                  15

Gln

<210> SEQ ID NO 81
<211> LENGTH: 17
<212> TYPE: PRT
<213> ORGANISM: Arabidopsis thaliana
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(15)
```

```
<223> OTHER INFORMATION: Xaa can be any naturally occurring amino acid
<220> FEATURE:
<223> OTHER INFORMATION: Second conserved domain consensus sequence

<400> SEQUENCE: 81

Pro Xaa Xaa Xaa Xaa Xaa Leu Xaa Xaa Phe Xaa Xaa Gly Xaa Xaa Gly
1               5                   10                  15

Gln

<210> SEQ ID NO 82
<211> LENGTH: 1157
<212> TYPE: DNA
<213> ORGANISM: Artificial sequence
<220> FEATURE:
<223> OTHER INFORMATION: Artificial sequence
<220> FEATURE:
<223> OTHER INFORMATION: P21269

<400> SEQUENCE: 82
ggtgaggagc gagttgtaga ggaggaggga caccgatcaa ccgggaagct ggcggccggg      60
aagtggtggg agcggccaga tgacacggcc atggccggga tggaccctgg cggggggggc    120
gccggcgccg gcagctcacg gtacttccac catctgctcc gaccgcagca gccgtcgccg    180
ctgtcaccgc tgtcgccgac atcccatgtc aagatggagc actccaagat gtcacccgac    240
aagagccccg tgggcgaggg agatcacgcg ggagggagtg gaagcggcgg cgtcggcggt    300
gaccaccagc cgtcgtcgtc ggccatggtg cccgtcgagg gtggcagcgg cagcgccggc    360
ggtagtggct cgggtgggcc gacgcggcgc cgcgcgggc gcccgcccgg gtccaagaac     420
aagccgaagc cgcccatcat cgtgacgcgc gacagcccga acgcgctgca ctcgcacgtg    480
ctcgaggtcg ccggcggcgc cgacgtcgtc gactgcgtgg ccgagtacgc ccgccgccga    540
gggcgcggcg tgtgcgtgct gagcggcggc ggcgccgtcg tcaacgtggc gctgcggcag    600
ccgggcgcgt cgccgccggg cagcatggtg gccacgctgc ggggccggtt cgagatccta    660
tctctcacgg gcacggtcct gcagcctccc gcgccacccg gcgcgagcgg cctcaccgtg    720
ttcctctccg gcggccaggg ccaggtgatc ggcggcagcg tggtgggccc gctggtcgcc    780
gcggggcccg tcgtcctgat ggcggcctca ttcgcgaacg ccgtgtacga gcggctgccg    840
ctggagggcg aggaagagga ggtcgccgcg ccgccgccg gaggcgaagc acaagatcaa     900
gtggcacaat cagctggacc cccagggcag caaccggcgg cgtcacagtc ctccggcgtg    960
acaggaggcg acggcaccgg cggcgccggt ggcatgtcgc tctacaacct cgccgggaat   1020
gtgggaggct atcagctccc cggagacaac ttcggaggtt ggagcggcgc cggcgccggc   1080
ggagtcaggc caccgttctg acccatgtct tagcatccag ttcaaaaatt ctccaaatta   1140
agaattgcgc agtgcag                                                   1157

<210> SEQ ID NO 83
<211> LENGTH: 1040
<212> TYPE: DNA
<213> ORGANISM: Arabidopsis thaliana
<220> FEATURE:
<223> OTHER INFORMATION: G2789

<400> SEQUENCE: 83
ctttagggac accaaatcta ttcaacctaa aagccttctt ttcccctata ttgaccaact       60
ttttagcgaa tcagaagagg aatggatgag gtatctcgtt ctcatacacc gcaatttcta     120
tcaagtgatc atcagcacta tcaccatcaa aacgctggac gacaaaaacg cggcagagaa     180
```

```
gaagaaggag ttgaacccaa caatataggg gaagacctag ccacctttcc ttccggagaa      240
gagaatatca agaagagaag gccacgtggc agacctgctg gttccaagaa caaacccaaa      300
gcaccaatca tagtcactcg cgactccgcg aacgccttca gatgtcacgt catggagata      360
accaacgcct gcgatgtaat ggaaagccta gccgtcttcg ctagacgccg tcagcgtggc      420
gtttgcgtct tgaccggaaa cggggccgtt acaaacgtca ccgttagaca acctggcgga      480
ggcgtcgtca gtttacacgg acggtttgag attctttctc tctcgggttc gtttcttcct      540
ccaccggcac caccagctgc gtctggttta aaggtttact tagccggtgg tcaaggtcaa      600
gtgatcggag gcagtgtggt gggaccgctt acggcatcaa gtccggtggt cgttatggca      660
gcttcatttg gaaacgcatc ttacgagagg ctgccactag aggaggagga ggaaactgaa      720
agagaaatag atggaaacgc ggctagggcg attggaacgc aaacgcagaa acagttaatg      780
caagatgcga catcgtttat tgggtcgccg tcgaatttaa ttaactctgt ttcgttgcca      840
ggtgaagctt attggggaac gcaacgaccg tctttctaag ataatatcat tgataatata      900
agtttcgtct tcttattctt tttcactttt tacctttttc actttcttag gttttgtttt      960
aacgtttgat taatacctga aggttttttgg aaaattttcg atcggataaa aggatttatg     1020
ttgcgagccg aaacgcggcc                                                 1040
```

<210> SEQ ID NO 84
<211> LENGTH: 265
<212> TYPE: PRT
<213> ORGANISM: Arabidopsis thaliana
<220> FEATURE:
<223> OTHER INFORMATION: G2789 polypeptide

<400> SEQUENCE: 84

```
Met Asp Glu Val Ser Arg Ser His Thr Pro Gln Phe Leu Ser Ser Asp
1               5                   10                  15

His Gln His Tyr His His Gln Asn Ala Gly Arg Gln Lys Arg Gly Arg
            20                  25                  30

Glu Glu Glu Gly Val Glu Pro Asn Asn Ile Gly Glu Asp Leu Ala Thr
        35                  40                  45

Phe Pro Ser Gly Glu Glu Asn Ile Lys Lys Arg Arg Pro Arg Gly Arg
    50                  55                  60

Pro Ala Gly Ser Lys Asn Lys Pro Lys Ala Pro Ile Ile Val Thr Arg
65                  70                  75                  80

Asp Ser Ala Asn Ala Phe Arg Cys His Val Met Glu Ile Thr Asn Ala
                85                  90                  95

Cys Asp Val Met Glu Ser Leu Ala Val Phe Ala Arg Arg Arg Gln Arg
            100                 105                 110

Gly Val Cys Val Leu Thr Gly Asn Gly Ala Val Thr Asn Val Thr Val
        115                 120                 125

Arg Gln Pro Gly Gly Gly Val Val Ser Leu His Gly Arg Phe Glu Ile
    130                 135                 140

Leu Ser Leu Ser Gly Ser Phe Leu Pro Pro Ala Pro Pro Ala Ala
145                 150                 155                 160

Ser Gly Leu Lys Val Tyr Leu Ala Gly Gln Gly Gln Val Ile Gly
                165                 170                 175

Gly Ser Val Val Gly Pro Leu Thr Ala Ser Ser Pro Val Val Met
            180                 185                 190

Ala Ala Ser Phe Gly Asn Ala Ser Tyr Glu Arg Leu Pro Leu Glu Glu
        195                 200                 205
```

```
Glu Glu Glu Thr Glu Arg Glu Ile Asp Gly Asn Ala Ala Arg Ala Ile
    210                 215                 220

Gly Thr Gln Thr Gln Lys Gln Leu Met Gln Asp Ala Thr Ser Phe Ile
225                 230                 235                 240

Gly Ser Pro Ser Asn Leu Ile Asn Ser Val Ser Leu Pro Gly Glu Ala
                245                 250                 255

Tyr Trp Gly Thr Gln Arg Pro Ser Phe
            260                 265

<210> SEQ ID NO 85
<211> LENGTH: 938
<212> TYPE: DNA
<213> ORGANISM: Arabidopsis thaliana
<220> FEATURE:
<223> OTHER INFORMATION: G1667

<400> SEQUENCE: 85
```

| | | | | | |
|---|---|---|---|---|---|
| tcgacccatc | cctactcctc | acaatcattc | ttttggtgtc | tctaccattt | aataattcac | 60 |
| caaaatctcc | ttacttaaac | tcacaaactc | ctcacaaatt | ttctgaatct | ttcagttgaa | 120 |
| catataacaa | cattcataac | aatggctgga | ggtacagctc | taactccaac | ctctgtagga | 180 |
| tccaagtctg | ttccaatgag | gaaccatgaa | gcaacagaga | gaggcaacac | caacaacaac | 240 |
| ctgagagcat | tacccaaagc | cgtccaaccg | gtttcatcaa | tcgaaggaga | gatggctaag | 300 |
| aggccacgtg | gcagacccgc | tggctccaag | aacaaaccca | aaccaccaat | cattgtgact | 360 |
| cacgacagtc | caaattccct | cagagctaac | gccgttgaga | tcagctcagg | ttgtgacatc | 420 |
| tgtgagactt | atcggatttt | gcaagaagg | aaacagagag | gtctctgcat | tctcagtgcc | 480 |
| aatggttgtg | tcaccaatgt | gacattaagg | caaccagctt | catcaggagc | aattgtcaca | 540 |
| ttacacggac | gttacgagat | cctctcattg | cttggatcaa | tcttgcctcc | accagcacca | 600 |
| cttggaataa | ctggtctgac | catttactta | gccggacctc | aaggacaggt | tgttggtgga | 660 |
| ggagtggttg | gtgggctaat | cgcatctggt | cctgttgttc | tcatggctgc | atctttcatg | 720 |
| aatgctgttt | tgatcgtctc | tcctatggat | gatgatgaag | ctgcctctat | gcagaaccag | 780 |
| cagtactacc | agaatggaag | atcccgtcct | ttagatgaca | ttcatggact | gcctcaaaat | 840 |
| ctgctcacta | atggaaactc | ggcttctgat | atctactctt | gggggccttg | gaatcaaaga | 900 |
| taaatgtgtc | tgtaggttga | gagagaaccg | taagtctg | | | 938 |

```
<210> SEQ ID NO 86
<211> LENGTH: 253
<212> TYPE: PRT
<213> ORGANISM: Arabidopsis thaliana
<220> FEATURE:
<223> OTHER INFORMATION: G1667 polypeptide

<400> SEQUENCE: 86

Met Ala Gly Gly Thr Ala Leu Thr Pro Thr Ser Val Gly Ser Lys Ser
1               5                   10                  15

Val Pro Met Arg Asn His Glu Ala Thr Glu Arg Gly Asn Thr Asn Asn
                20                  25                  30

Asn Leu Arg Ala Leu Pro Lys Ala Val Gln Pro Val Ser Ser Ile Glu
            35                  40                  45

Gly Glu Met Ala Lys Arg Pro Arg Gly Arg Pro Ala Gly Ser Lys Asn
        50                  55                  60

Lys Pro Lys Pro Pro Ile Ile Val Thr His Asp Ser Pro Asn Ser Leu
65                  70                  75                  80
```

-continued

Arg Ala Asn Ala Val Glu Ile Ser Ser Gly Cys Asp Ile Cys Glu Thr
                85                  90                  95

Leu Ser Asp Phe Ala Arg Arg Lys Gln Arg Gly Leu Cys Ile Leu Ser
            100                 105                 110

Ala Asn Gly Cys Val Thr Asn Val Thr Leu Arg Gln Pro Ala Ser Ser
        115                 120                 125

Gly Ala Ile Val Thr Leu His Gly Arg Tyr Glu Ile Leu Ser Leu Leu
    130                 135                 140

Gly Ser Ile Leu Pro Pro Ala Pro Leu Gly Ile Thr Gly Leu Thr
145                 150                 155                 160

Ile Tyr Leu Ala Gly Pro Gln Gly Gln Val Gly Gly Val Val
                165                 170                 175

Gly Gly Leu Ile Ala Ser Gly Pro Val Val Leu Met Ala Ser Phe
            180                 185                 190

Met Asn Ala Val Phe Asp Arg Leu Pro Met Asp Asp Glu Ala Ala
        195                 200                 205

Ser Met Gln Asn Gln Gln Tyr Tyr Gln Asn Gly Arg Ser Arg Pro Leu
    210                 215                 220

Asp Asp Ile His Gly Leu Pro Gln Asn Leu Leu Thr Asn Gly Asn Ser
225                 230                 235                 240

Ala Ser Asp Ile Tyr Ser Trp Gly Pro Trp Asn Gln Arg
                245                 250

<210> SEQ ID NO 87
<211> LENGTH: 1496
<212> TYPE: DNA
<213> ORGANISM: Arabidopsis thaliana
<220> FEATURE:
<223> OTHER INFORMATION: G2157

<400> SEQUENCE: 87
tcttttgatt ttaacctttt ttcagtagca agccaaaaaa aaaaaacaga caaagaagtt      60
ccttttatga taaaggtatg atgatagcaa acaaatgata cccccatgtc ttgtgtgtct     120
gcttcatgca acatgttggt ttggatttgg ttaatctaaa agtttaagat aaggttttcg     180
gattctcttc ctgtcttgta atagtttctt gtcggagagc catcaacacc aacttcaaca     240
aaaaaaacaa gaaaagaaa aagattctct ttctcgtttt atttccatta gagaagaaaa      300
aaagaatggc gaatccttgg tgggtaggga atgttgcgat cggtggagtt gagagtccag     360
tgacgtcatc agctccttct ttgcaccaca gaaacagtaa caacaacaac ccaccgacta     420
tgactcgttc ggatccaaga ttggaccatg acttcaccac caacaacagt ggaagcccta     480
atacccagac tcagagccaa gaagaacaga acagcagaga cgagcaacca gctgttgaac     540
ccggatccgg atccgggtct acgggtcgtc gtcctagagg tagacctcct ggttccaaga     600
acaaaccaaa gagtccagtt gttgttacca agaaaagccc taactctctc cagagccatg     660
ttcttgagat tgctacggga gctgacgtgg cggaaagctt aaacgccttt gctcgtagac     720
gcggccgggg cgtttcggtg ctgagcggta gtggtttggt tactaatgtt actctgcgtc     780
agcctgctgc atccggtgga gttgttagtt tacgtggtca gtttgagatc ttgtctatgt     840
gtggggcttt tcttcctacg tctggctctc ctgctgcagc cgctggttta accatttact     900
tagctggagc tcaaggtcaa gttgtgggag gtggagttgc tggcccgctt attgcctctg     960
gacccgttat tgtgatagct gctacgtttt gcaatgccac ttatgagagg ttaccgattg    1020
aggaagaaca acagcaagag cagccgcttc aactagaaga tggaagaag cagaaagaag    1080

```
agaatgatga taacgagagt gggaataacg gaaacgaagg atcgatgcag ccgccgatgt   1140
ataatatgcc tcctaatttt atcccaaatg gtcatcaaat ggctcaacac gacgtgtatt   1200
ggggtggtcc tccgcctcgt gctcctcctt cgtattgatt agttagatag cggtggttg    1260 gtgcgttctt tttactggaa tgattatatt ttccattagg atggttaggc ttttgtttat   1320
taaagctatc aagtttcttt ttttttttacg gataattcgg atgacaatta gctagtgttt   1380
gtttgtttgt tttgtggcgg cttttctgac ttgactattt tgatcgcgga tagctttgta   1440
tgaaagtgaa ttgattgtag aatcgtcttt tgaattttga tgttggaaaa aaccaa       1496
```

<210> SEQ ID NO 88
<211> LENGTH: 310
<212> TYPE: PRT
<213> ORGANISM: Arabidopsis thaliana
<220> FEATURE:
<223> OTHER INFORMATION: G2157 polypeptide

<400> SEQUENCE: 88

```
Met Ala Asn Pro Trp Trp Val Gly Asn Val Ala Ile Gly Gly Val Glu
 1               5                  10                  15

Ser Pro Val Thr Ser Ser Ala Pro Ser Leu His His Arg Asn Ser Asn
            20                  25                  30

Asn Asn Asn Pro Pro Thr Met Thr Arg Ser Asp Pro Arg Leu Asp His
        35                  40                  45

Asp Phe Thr Thr Asn Asn Ser Gly Ser Pro Asn Thr Gln Thr Gln Ser
    50                  55                  60

Gln Glu Glu Gln Asn Ser Arg Asp Glu Gln Pro Ala Val Glu Pro Gly
65                  70                  75                  80

Ser Gly Ser Gly Ser Thr Gly Arg Arg Pro Arg Gly Arg Pro Pro Gly
                85                  90                  95

Ser Lys Asn Lys Pro Lys Ser Pro Val Val Thr Lys Glu Ser Pro
            100                 105                 110

Asn Ser Leu Gln Ser His Val Leu Glu Ile Ala Thr Gly Ala Asp Val
        115                 120                 125

Ala Glu Ser Leu Asn Ala Phe Ala Arg Arg Gly Arg Gly Val Ser
    130                 135                 140

Val Leu Ser Gly Ser Gly Leu Val Thr Asn Val Thr Leu Arg Gln Pro
145                 150                 155                 160

Ala Ala Ser Gly Gly Val Val Ser Leu Arg Gly Gln Phe Glu Ile Leu
                165                 170                 175

Ser Met Cys Gly Ala Phe Leu Pro Thr Ser Gly Ser Pro Ala Ala Ala
            180                 185                 190

Ala Gly Leu Thr Ile Tyr Leu Ala Gly Ala Gln Gly Gln Val Val Gly
        195                 200                 205

Gly Gly Val Ala Gly Pro Leu Ile Ala Ser Gly Pro Val Ile Val Ile
    210                 215                 220

Ala Ala Thr Phe Cys Asn Ala Thr Tyr Glu Arg Leu Pro Ile Glu Glu
225                 230                 235                 240

Glu Gln Gln Gln Glu Gln Pro Leu Gln Leu Glu Asp Gly Lys Lys Gln
                245                 250                 255

Lys Glu Glu Asn Asp Asp Asn Glu Ser Gly Asn Asn Gly Asn Glu Gly
            260                 265                 270

Ser Met Gln Pro Pro Met Tyr Asn Met Pro Pro Asn Phe Ile Pro Asn
        275                 280                 285

Gly His Gln Met Ala Gln His Asp Val Tyr Trp Gly Gly Pro Pro Pro
```

```
                 290                 295                 300

Arg Ala Pro Pro Ser Tyr
305                 310

<210> SEQ ID NO 89
<211> LENGTH: 317
<212> TYPE: PRT
<213> ORGANISM: Arabidopsis thaliana
<220> FEATURE:
<223> OTHER INFORMATION: G596 protein

<400> SEQUENCE: 89

Met Asp Gln Val Ser Arg Ser Leu Pro Pro Phe Leu Ser Arg Asp
1               5                  10                  15

Leu His Leu His Pro His His Gln Phe Gln His Gln Gln Gln Gln
                20                  25                  30

Gln Gln Asn His Gly His Asp Ile Asp Gln His Arg Ile Gly Gly Leu
            35                  40                  45

Lys Arg Asp Arg Asp Ala Asp Ile Asp Pro Asn Glu His Ser Ser Ala
50                  55                  60

Gly Lys Asp Gln Ser Thr Pro Gly Ser Gly Glu Ser Gly Gly
65                  70                  75                  80

Gly Gly Gly Asp Asn His Ile Thr Arg Arg Pro Arg Gly Arg Pro Ala
                85                  90                  95

Gly Ser Lys Asn Lys Pro Lys Pro Ile Ile Ile Thr Arg Asp Ser
                100                 105                 110

Ala Asn Ala Leu Lys Ser His Val Met Glu Val Ala Asn Gly Cys Asp
            115                 120                 125

Val Met Glu Ser Val Thr Val Phe Ala Arg Arg Arg Gln Arg Gly Ile
130                 135                 140

Cys Val Leu Ser Gly Asn Gly Ala Val Thr Asn Val Thr Ile Arg Gln
145                 150                 155                 160

Pro Ala Ser Val Pro Gly Gly Ser Ser Val Val Asn Leu His Gly
                165                 170                 175

Arg Phe Glu Ile Leu Ser Leu Ser Gly Ser Phe Leu Pro Pro Ala
            180                 185                 190

Pro Pro Ala Ala Ser Gly Leu Thr Ile Tyr Leu Ala Gly Gly Gln Gly
            195                 200                 205

Gln Val Val Gly Gly Ser Val Val Gly Pro Leu Met Ala Ser Gly Pro
        210                 215                 220

Val Val Ile Met Ala Ala Ser Phe Gly Asn Ala Ala Tyr Glu Arg Leu
225                 230                 235                 240

Pro Leu Glu Glu Asp Asp Gln Glu Glu Gln Thr Ala Gly Ala Val Ala
                245                 250                 255

Asn Asn Ile Asp Gly Asn Ala Thr Met Gly Gly Gly Thr Gln Thr Gln
            260                 265                 270

Thr Gln Thr Gln Gln Gln Gln Gln Gln Leu Met Gln Asp Pro Thr
        275                 280                 285

Ser Phe Ile Gln Gly Leu Pro Pro Asn Leu Met Asn Ser Val Gln Leu
            290                 295                 300

Pro Ala Glu Ala Tyr Trp Gly Thr Pro Arg Pro Ser Phe
305                 310                 315

<210> SEQ ID NO 90
<211> LENGTH: 265
<212> TYPE: PRT
```

<213> ORGANISM: Oryza sativa
<220> FEATURE:
<223> OTHER INFORMATION: BAB64709 protein

<400> SEQUENCE: 90

| Met | Ala | Asp | Glu | Gly | Ser | Ser | Arg | Ala | Glu | Leu | Ile | Glu | Ala | Ser | Pro |
| 1 | | | | 5 | | | | | 10 | | | | | 15 | |

| Ala | Pro | Ala | Leu | Asp | Leu | Pro | Ser | Pro | Pro | Arg | Lys | Pro | Arg | Gly | Arg |
| | | | 20 | | | | | 25 | | | | | 30 | | |

| Pro | Leu | Gly | Ser | Lys | Asn | Lys | Pro | Lys | Pro | Val | Val | Val | Thr | Arg | |
| | | 35 | | | | | 40 | | | | | 45 | | | |

| Glu | Ser | Glu | Ala | Ala | Met | Arg | Pro | Val | Val | Leu | Glu | Leu | Gly | Ala | Gly |
| | 50 | | | | | 55 | | | | | 60 | | | | |

| Cys | Glu | Val | Ala | Ala | Ala | Val | Ala | Ala | Phe | Ala | Arg | Arg | Arg | Arg | Val |
| 65 | | | | | 70 | | | | | 75 | | | | | 80 |

| Gly | Val | Ser | Val | Leu | Cys | Gly | Arg | Gly | Thr | Val | Ala | Ala | Val | Thr | Leu |
| | | | | 85 | | | | | 90 | | | | | 95 | |

| Arg | Leu | Pro | Thr | Ser | Pro | Pro | Ala | Ala | Val | Lys | Leu | His | Gly | Arg | Phe |
| | | | | 100 | | | | | 105 | | | | | 110 | |

| Glu | Val | Leu | Ser | Leu | Ser | Gly | Thr | Val | Leu | Pro | Ser | Ala | Ala | Gly | Glu |
| | | | 115 | | | | | 120 | | | | | 125 | | |

| Gly | Ala | Ala | Pro | Pro | Pro | Phe | Ser | Val | Ser | Leu | Ala | Gly | Ala | Gly | |
| | 130 | | | | | 135 | | | | | 140 | | | | |

| Gly | Gln | Val | Ile | Gly | Gly | Thr | Leu | Ala | Gly | Glu | Met | Thr | Thr | Ala | Asp |
| 145 | | | | | 150 | | | | | 155 | | | | | 160 |

| Gly | Leu | Val | Val | Val | Ala | Ala | Thr | Phe | Gly | Ser | Ala | Glu | Val | His | Arg |
| | | | | 165 | | | | | 170 | | | | | 175 | |

| Leu | Pro | Ala | Asp | Glu | Asp | Asp | Glu | Ala | Thr | Gly | Ser | Arg | Gly | Gly | Glu |
| | | | 180 | | | | | 185 | | | | | 190 | | |

| Glu | Arg | Arg | His | Pro | Gln | Gln | Gln | Pro | Pro | Gln | Thr | Val | Ala | Ala | Thr |
| | | 195 | | | | | 200 | | | | | 205 | | | |

| Ser | Ala | Val | Asp | Val | Gly | Leu | Leu | Gly | Tyr | Gly | Gly | Val | Gly | Val | |
| | 210 | | | | | 215 | | | | | 220 | | | | |

| Ala | Gly | Gly | Ala | Ser | Gly | Gly | Gln | Val | Gly | Arg | His | Gln | Gln | Gln | Gln |
| 225 | | | | | 230 | | | | | 235 | | | | | 240 |

| Gln | Gln | Ala | Glu | Met | Val | Leu | Trp | Ala | Gln | Ser | Pro | Gly | Ser | Val | Gly |
| | | | | 245 | | | | | 250 | | | | | 255 | |

| Pro | Ala | His | Pro | Ala | Thr | Ser | Arg | Tyr | |
| | | | 260 | | | | | 265 | |

<210> SEQ ID NO 91
<211> LENGTH: 348
<212> TYPE: PRT
<213> ORGANISM: Arabidopsis thaliana
<220> FEATURE:
<223> OTHER INFORMATION: G1071 protein

<400> SEQUENCE: 91

| Met | Asp | Arg | Arg | Asp | Ala | Met | Gly | Leu | Ser | Gly | Ser | Gly | Ser | Tyr | Tyr |
| 1 | | | | 5 | | | | | 10 | | | | | 15 | |

| Ile | His | Arg | Gly | Leu | Ser | Gly | Ser | Gly | Pro | Thr | Phe | His | Gly | Ser | |
| | | | 20 | | | | | 25 | | | | | 30 | | |

| Pro | Gln | Gln | Gln | Gln | Gly | Leu | Arg | His | Leu | Pro | Asn | Gln | Asn | Ser | Pro |
| | | | | 35 | | | | | 40 | | | | | 45 | |

| Phe | Gly | Ser | Gly | Ser | Thr | Gly | Phe | Gly | Ser | Pro | Ser | Leu | His | Gly | Asp |
| | 50 | | | | | 55 | | | | | 60 | | | | |

-continued

```
Pro Ser Leu Ala Thr Ala Ala Gly Gly Ala Gly Ala Leu Pro His His
65                  70                  75                  80

Ile Gly Val Asn Met Ile Ala Pro Pro Pro Ser Glu Thr Pro
                85                  90                  95

Met Lys Arg Lys Arg Gly Arg Pro Arg Lys Tyr Gly Gln Asp Gly Ser
            100                 105                 110

Val Ser Leu Ala Leu Ser Ser Ser Val Ser Thr Ile Thr Pro Asn
        115                 120                 125

Asn Ser Asn Lys Arg Gly Arg Gly Arg Pro Pro Gly Ser Gly Lys Lys
    130                 135                 140

Gln Arg Met Ala Ser Val Gly Glu Leu Met Pro Ser Ser Ser Gly Met
145                 150                 155                 160

Ser Phe Thr Pro His Val Ile Ala Val Ser Ile Gly Glu Asp Ile Ala
                165                 170                 175

Ser Lys Val Ile Ala Phe Ser Gln Gln Gly Pro Arg Ala Ile Cys Val
            180                 185                 190

Leu Ser Ala Ser Gly Ala Val Ser Thr Ala Thr Leu Ile Gln Pro Ser
        195                 200                 205

Ala Ser Pro Gly Ala Ile Lys Tyr Glu Gly Arg Phe Glu Ile Leu Ala
    210                 215                 220

Leu Ser Thr Ser Tyr Ile Val Ala Thr Asp Gly Ser Phe Arg Asn Arg
225                 230                 235                 240

Thr Gly Asn Leu Ser Val Ser Leu Ala Ser Pro Asp Gly Arg Val Ile
                245                 250                 255

Gly Gly Ala Ile Gly Gly Pro Leu Ile Ala Ser Pro Val Gln Val
            260                 265                 270

Ile Val Gly Ser Phe Ile Trp Ala Ala Pro Lys Ile Lys Ser Lys Lys
        275                 280                 285

Arg Glu Glu Glu Ala Ser Glu Val Val Gln Glu Thr Asp Asp His His
    290                 295                 300

Val Leu Asp Asn Asn Asn Thr Ile Ser Pro Val Pro Gln Gln Gln
305                 310                 315                 320

Pro Asn Gln Asn Leu Ile Trp Ser Thr Gly Ser Arg Gln Met Asp Met
                325                 330                 335

Arg His Ala His Ala Asp Ile Asp Leu Met Arg Gly
            340                 345
```

<210> SEQ ID NO 92
<211> LENGTH: 347
<212> TYPE: PRT
<213> ORGANISM: Pisum sativum
<220> FEATURE:
<223> OTHER INFORMATION: T06584 protein

<400> SEQUENCE: 92

```
Met Asp Gly Arg Glu Ala Met Ala Phe Ser Gly Gly Pro Gly Ser Tyr
1               5                   10                  15

Tyr Leu His Arg Gly Val Glu Ala Ala Gly Ser Gly Ser Gly Gly
            20                  25                  30

Phe Gln Val Pro Pro Gly Phe Arg Ala Leu Pro Asn Asn Gly Ile Ile
        35                  40                  45

Ala Gln Pro Asn Val Arg Ala Gln Gly Gly Asn Gly Asp Thr Ser Ser
    50                  55                  60

Met Phe Ser Leu Glu Pro Gln Ser His Ala Asp Phe Asn His Asp Ile
65                  70                  75                  80
```

```
Ser Val Gly Ala Ser Gly Ala Pro Ser Ser Glu Pro Val Lys Lys
                85                  90                  95

Lys Arg Gly Arg Pro Arg Lys Tyr Gly Pro Asp Gly Ser Val Ser Leu
                100                 105                 110

Lys Leu Thr Pro Met Ser Ala Pro Ala Asn Ser Thr Gln Asp Ser Gly
            115                 120                 125

Thr Pro Ser Glu Lys Arg Gly Arg Gly Arg Pro Arg Gly Ser Gly Arg
        130                 135                 140

Lys Gln Gln Leu Ala Ala Leu Gly Asp Trp Met Thr Ser Ser Ala Gly
145                 150                 155                 160

Leu Ala Phe Ser Pro His Val Ile Thr Ile Ala Ala Gly Glu Asp Ile
                165                 170                 175

Ala Ala Lys Leu Leu Leu Ser Gln Gln Arg Pro Arg Ala Leu Cys
                180                 185                 190

Ile Leu Ser Gly Thr Gly Ile Ala Ser Lys Val Thr Leu Arg Gln Pro
                195                 200                 205

Ala Ser Thr Asn Ala Gly Val Thr Tyr Glu Gly Lys Phe Gln Ile Leu
            210                 215                 220

Ser Leu Ser Gly Ser Tyr Leu Val Ser Glu Asp Gly Gly Pro Thr Asn
225                 230                 235                 240

Arg Thr Gly Gly Ile Ser Val Ser Leu Ser Ser Arg Asp Gly His Val
                245                 250                 255

Ile Gly Gly Ser Val Ala Met Leu Ile Ala Gly Ser Pro Ile Gln Leu
                260                 265                 270

Val Val Cys Ser Phe Val Tyr Gly Gly Ser Lys Val Lys Thr Lys
            275                 280                 285

Gln Gly Met Ile Thr Asn Gly Glu Ser Ser Glu Pro His Asn Asp Asn
        290                 295                 300

Leu Gly Ser Pro Ala Ser Ala Pro Pro Asp Gln Asn Tyr Ile Ser Ser
305                 310                 315                 320

Pro Thr Gly Met Trp Pro Gly Ser Gln Pro Ser Asp Met Lys Ser Ala
                325                 330                 335

Pro Ala His Thr Gly Ile Asp Leu Thr Arg Gly
                340                 345

<210> SEQ ID NO 93
<211> LENGTH: 300
<212> TYPE: PRT
<213> ORGANISM: Antirrhinum majus
<220> FEATURE:
<223> OTHER INFORMATION: CAA10643 protein

<400> SEQUENCE: 93

Met Glu Gln Pro Asn Asn Asp Gly Asn Asn Gly Gly Ser Cys Tyr Arg
1               5                   10                  15

Pro Gln Leu Pro Asn Gln Ser Pro Pro Ala Asn Gly Val Pro Asn Ser
                20                  25                  30

Thr Thr Thr Asn Ser Thr His Ser Pro Pro Asn Glu Ser Val Lys Arg
            35                  40                  45

Lys Arg Gly Arg Pro Arg Lys Tyr Gly Thr Pro Glu Gln Ala Ala Ala
        50                  55                  60

Ala Lys Arg Leu Ser Ala Pro Lys Lys Arg Asp Ser Ala Ser Gly Val
65                  70                  75                  80

Ala Ser Val Ser Ser Ala Ser Lys Lys Ser Pro Leu Ala Ala Leu
                85                  90                  95
```

```
Gly Asn Met Gly Gln Ser Phe Ser Pro His Ile Ile Thr Val Ala Ala
                100                 105                 110

Gly Glu Asp Val Gly Gln Lys Ile Met Met Phe Val Gln Gln Ser Lys
            115                 120                 125

Arg Glu Ile Cys Val Ile Ser Ala Ser Gly Ser Val Ser Ser Ala Ser
        130                 135                 140

Leu Arg Gln Gln Ala Ser Ser Gly Ser Val Thr Tyr Glu Gly Arg
145                 150                 155                 160

Phe Asp Ile Leu Ser Leu Ser Gly Ser Phe Ile His Ala Glu Phe Gly
                165                 170                 175

Gly Arg Thr Gly Gly Leu Ser Val Cys Leu Ser Ser Asp Gly Gln
            180                 185                 190

Ile Ile Gly Gly Gly Val Gly Gly Pro Leu Thr Ala Ala Ala Thr Ile
        195                 200                 205

Gln Val Ile Val Gly Thr Phe Val Val Glu Thr Lys Lys Asp Ala Asn
    210                 215                 220

Val Glu Ala Ala Ala Ser Gly Lys Ser Pro Ser Pro Asn Gly Gly Ala
225                 230                 235                 240

Ser Ala Pro Gly Leu Ser Phe Arg Ser Pro Ala Asp Ser Gly Ile Gln
                245                 250                 255

Met Gly Gly Gly Asn Pro Phe Leu Ile Gln Asn Arg Thr Met His
            260                 265                 270

Met Thr Pro Met Glu Trp Ile Gly Ser Ala Asp His Gly Met His Gln
        275                 280                 285

Ser Pro Glu Asn Gly Asp Tyr Asp His Ile Pro Asp
    290                 295                 300

<210> SEQ ID NO 94
<211> LENGTH: 405
<212> TYPE: PRT
<213> ORGANISM: Oryza sativa
<220> FEATURE:
<223> OTHER INFORMATION: AAK00433 protein

<400> SEQUENCE: 94

Met Glu Ala Lys Asp Val Ser Pro Leu Val Thr Val Pro Pro Ala Pro
1               5                   10                  15

Ala Ala Ala Ala Pro Pro Ala Ala Ala Pro Ala Pro Pro Pro Ser
            20                  25                  30

Gln Pro Pro Pro Pro Leu Pro Phe Ala Gln Gln Ala Pro Pro Pro
        35                  40                  45

Ala Ala Asn Pro Ala Ala Ala Pro Met Arg Leu Ser Phe Asp Gln Met
    50                  55                  60

Ala Gly Lys Ala Pro Gly Gly Glu Gln Gln His His His Pro Gly
65                  70                  75                  80

Pro Met Leu Tyr Ala Ala Ala Pro Ala Gly Gly Ala Pro Pro
                85                  90                  95

Gln Gly Gly Asn Val Met Gly Met Gly Glu Leu Met Arg Lys Lys Arg
            100                 105                 110

Gly Arg Pro Arg Lys Tyr Ala Pro Asp Gly Ser Met Ala Leu Ala Leu
        115                 120                 125

Ala Pro Ile Ser Ser Ala Ser Gly Gly Ala Ala Pro Pro Pro Pro
    130                 135                 140

Pro Gly His Gln Pro His Gly Phe Ser Ile Ser Ser Pro Ala Ser Asp
145                 150                 155                 160
```

```
Pro Asn Ala Lys Arg Arg Gly Arg Pro Pro Gly Ser Gly Lys Lys Lys
                165                 170                 175

Gln Phe Glu Ala Leu Gly Ser Trp Gly Ile Ala Phe Thr Pro His Ile
            180                 185                 190

Leu Thr Val Lys Ala Gly Glu Asp Val Ala Ser Lys Ile Met Ala Phe
        195                 200                 205

Ser Gln Gln Gly Pro Arg Thr Val Cys Ile Leu Ser Ala Asn Gly Ala
    210                 215                 220

Ile Ser Asn Val Thr Leu Arg Gln Pro Ala Thr Ser Gly Gly Leu Val
225                 230                 235                 240

Thr Tyr Glu Gly Arg Phe Glu Ile Ile Ser Leu Ser Gly Ser Phe Leu
                245                 250                 255

Leu Ala Glu Asp Gly Asp Thr Arg Ser Arg Thr Gly Gly Leu Ser Val
            260                 265                 270

Ala Leu Ala Gly Ser Asp Gly Arg Val Leu Gly Gly Cys Val Ala Gly
        275                 280                 285

Met Leu Met Ala Ala Thr Pro Val Gln Val Val Ala Ser Phe Ile
    290                 295                 300

Ala Glu Gly Lys Lys Ser Lys Pro Val Glu Thr Arg Lys Val Glu Pro
305                 310                 315                 320

Met Ser Ala Pro Pro Gln Met Ala Thr Tyr Val Pro Ala Pro Val Ala
                325                 330                 335

Ser Pro Pro Ser Glu Gly Thr Ser Ser Gly Ser Ser Asp Asp Ser Gly
            340                 345                 350

Ser Pro Ile Asn His Ser Gly Met Pro Tyr Asn His Ser Gly Gln Gln
        355                 360                 365

Gln Gln His Gln His Gln His Met Pro Pro Ala Tyr Ala Ser Gly
    370                 375                 380

Gly Trp Ser Leu Ser Ala His His Gln Asn Arg His Asp Ser Asp Met
385                 390                 395                 400

Lys Met Met Ser Asn
                405

<210> SEQ ID NO 95
<211> LENGTH: 354
<212> TYPE: PRT
<213> ORGANISM: Arabidopsis thaliana
<220> FEATURE:
<223> OTHER INFORMATION: G1072 protein

<400> SEQUENCE: 95

Met Glu Thr Ser Asp Arg Ile Ser Pro Gly Gly Gly Ile Gly Ala Glu
1               5                   10                  15

Val Pro Ser Ala Tyr His Met Ala Pro Arg Pro Ser Asp Ser Pro Ala
                20                  25                  30

Asn Gln Phe Met Met Glu Thr Ser Asp Arg Ile Ser Pro Gly Gly Gly
            35                  40                  45

Ile Gly Ala Glu Val Pro Ser Ala Tyr His Met Ala Pro Arg Pro Ser
        50                  55                  60

Asp Ser Pro Ala Asn Gln Phe Met Gly Leu Ser Leu Pro Pro Met Glu
65                  70                  75                  80

Ala Pro Met Pro Ser Ser Gly Glu Ala Ser Gly Lys Lys Arg Arg Gly
                85                  90                  95

Arg Pro Arg Lys Tyr Glu Ala Asn Gly Ala Pro Leu Pro Ser Ser Ser
                100                 105                 110
```

```
Val Pro Leu Val Lys Lys Arg Val Arg Gly Lys Leu Asn Gly Phe Asp
            115                 120                 125

Met Lys Lys Met His Lys Thr Ile Gly Phe His Ser Ser Gly Glu Arg
130                 135                 140

Phe Gly Val Gly Gly Val Gly Gly Val Gly Ser Asn Phe Thr
145                 150                 155                 160

Pro His Val Ile Thr Val Asn Thr Gly Glu Asp Ile Thr Met Arg Ile
                165                 170                 175

Ile Ser Phe Ser Gln Gln Gly Pro Arg Ala Ile Cys Ile Leu Ser Ala
                180                 185                 190

Asn Gly Val Ile Ser Asn Val Thr Leu Arg Gln Pro Asp Ser Cys Gly
                195                 200                 205

Gly Thr Leu Thr Tyr Glu Gly Arg Phe Glu Ile Leu Ser Leu Ser Gly
            210                 215                 220

Ser Phe Met Glu Thr Glu Asn Gln Gly Ser Lys Gly Arg Ser Gly Gly
225                 230                 235                 240

Met Ser Val Ser Leu Ala Gly Pro Asp Gly Arg Val Val Gly Gly
                245                 250                 255

Val Ala Gly Leu Leu Ile Ala Ala Thr Pro Ile Gln Val Val Val Gly
                260                 265                 270

Ser Phe Ile Thr Ser Asp Gln Gln Asp His Gln Lys Pro Arg Lys Gln
                275                 280                 285

Arg Val Glu His Ala Pro Ala Ala Val Met Ser Val Pro Pro Pro
290                 295                 300

Ser Pro Pro Pro Ala Ala Ser Val Phe Ser Pro Thr Asn Pro Asp
305                 310                 315                 320

Arg Glu Gln Pro Pro Ser Ser Phe Gly Ile Ser Ser Trp Thr Asn Gly
                325                 330                 335

Gln Asp Met Pro Arg Asn Ser Ala Thr Asp Ile Asn Ile Ser Leu Pro
                340                 345                 350

Val Asp

<210> SEQ ID NO 96
<211> LENGTH: 386
<212> TYPE: PRT
<213> ORGANISM: Arabidopsis thaliana
<220> FEATURE:
<223> OTHER INFORMATION: G1068 protein

<400> SEQUENCE: 96

Met Asp Ser Arg Glu Ile His His Gln Gln Gln Gln Gln Gln Gln
1               5                   10                  15

Gln Gln Gln Gln Gln Gln Gln Gln His Leu Gln Gln Gln Gln
            20                  25                  30

Pro Pro Gly Met Leu Met Ser His His Asn Ser Tyr Asn Arg Asn
                35                  40                  45

Pro Asn Ala Ala Ala Val Leu Met Gly His Asn Thr Ser Thr Ser
        50                  55                  60

Gln Ala Met His Gln Arg Leu Pro Phe Gly Gly Ser Met Ser Pro His
65                  70                  75                  80

Gln Pro Gln Gln His Gln Tyr His His Pro Gln Pro Gln Gln Gln Ile
                85                  90                  95
```

-continued

```
Asp Gln Lys Thr Leu Glu Ser Leu Gly Phe Pro Thr Ser Pro Leu Pro
            100                 105                 110

Ser Ala Ser Asn Ser Tyr Gly Gly Asn Glu Gly Gly Gly Gly
            115                 120                 125

Asp Ser Ala Gly Ala Asn Ala Asn Ser Ser Asp Pro Pro Ala Lys Arg
            130                 135                 140

Asn Arg Gly Arg Pro Pro Gly Ser Gly Lys Lys Gln Leu Asp Ala Leu
145                 150                 155                 160

Gly Gly Thr Gly Gly Val Gly Phe Thr Pro His Val Ile Glu Val Lys
                165                 170                 175

Thr Gly Glu Asp Ile Ala Thr Lys Ile Leu Ala Phe Thr Asn Gln Gly
                180                 185                 190

Pro Arg Ala Ile Cys Ile Leu Ser Ala Thr Gly Ala Val Thr Asn Val
                195                 200                 205

Met Leu Arg Gln Ala Asn Asn Ser Asn Pro Thr Gly Thr Val Lys Tyr
        210                 215                 220

Glu Gly Arg Phe Glu Ile Ile Ser Leu Ser Gly Ser Phe Leu Asn Ser
225                 230                 235                 240

Glu Ser Asn Gly Thr Val Thr Lys Thr Gly Asn Leu Ser Val Ser Leu
                245                 250                 255

Ala Gly His Glu Gly Arg Ile Val Gly Gly Cys Val Asp Gly Met Leu
                260                 265                 270

Val Ala Gly Ser Gln Val Gln Val Ile Val Gly Ser Phe Val Pro Asp
                275                 280                 285

Gly Arg Lys Gln Lys Gln Ser Ala Gly Arg Ala Gln Asn Thr Pro Glu
        290                 295                 300

Pro Ala Ser Ala Pro Ala Asn Met Leu Ser Phe Gly Gly Val Gly Gly
305                 310                 315                 320

Pro Gly Ser Pro Arg Ser Gln Gly Gln Gln His Ser Ser Glu Ser Ser
                325                 330                 335

Glu Glu Asn Glu Ser Asn Ser Pro Leu His Arg Arg Ser Asn Asn Asn
                340                 345                 350

Asn Ser Asn Asn His Gly Ile Phe Gly Asn Ser Thr Pro Gln Pro Leu
                355                 360                 365

His Gln Ile Pro Met Gln Met Tyr Gln Asn Leu Trp Pro Gly Asn Ser
        370                 375                 380

Pro Gln
385

<210> SEQ ID NO 97
<211> LENGTH: 9
<212> TYPE: PRT
<213> ORGANISM: artificial sequence
<220> FEATURE:
<223> OTHER INFORMATION: artificial sequence
<220> FEATURE:
<223> OTHER INFORMATION: conserved nine amino acid peptide

<400> SEQUENCE: 97

Lys Arg Pro Arg Gly Arg Pro Lys Lys
1               5

<210> SEQ ID NO 98
<211> LENGTH: 9
<212> TYPE: PRT
<213> ORGANISM: Arabidopsis thaliana
<220> FEATURE:
<223> OTHER INFORMATION: conserved nine amino acid peptide
```

```
<400> SEQUENCE: 98

Arg Arg Pro Arg Gly Arg Pro Ala Gly
1               5

<210> SEQ ID NO 99
<211> LENGTH: 34
<212> TYPE: PRT
<213> ORGANISM: Arabidopsis thaliana
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (15)..(17)
<223> OTHER INFORMATION: Xaa can be any naturally occurring amino acid
      and Xaa (15) is 1 or 2 residues
<220> FEATURE:
<221> NAME/KEY: misc_feature
<222> LOCATION: (19)..(23)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be Y or F
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid

<400> SEQUENCE: 99

Gly Xaa Phe Xaa Ile Leu Ser Xaa Xaa Gly Xaa Xaa Leu Pro Xaa Xaa
1               5                   10                  15

Xaa Pro Xaa Xaa Xaa Xaa Xaa Leu Xaa Xaa Xaa Xaa Gly Xaa Xaa
            20                  25                  30

Gly Gln
```